United States Patent
Azzedine et al.

(10) Patent No.: US 9,546,402 B2
(45) Date of Patent: *Jan. 17, 2017

(54) DIAGNOSIS OF HEREDITARY SPASTIC PARAPLEGIAS (HSP) BY DETECTION OF A MUTATION IN THE KIAA1840 GENE OR PROTEIN

(71) Applicant: Institute National de la Sante et de la Recherche Medicale (INSERM), Paris (FR)

(72) Inventors: Hamid Azzedine, Bagneux (FR); Alexis Brice, Paris (FR); Giovanni Stevanin, Sevran (FR); Filippo Santorelli, Naple (IT); Paola Denora, Rome (IT)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/206,840

(22) Filed: Mar. 12, 2014

(65) Prior Publication Data

US 2014/0308665 A1   Oct. 16, 2014
US 2016/0348172 A9   Dec. 1, 2016

Related U.S. Application Data

(60) Division of application No. 13/567,790, filed on Aug. 6, 2012, now Pat. No. 8,728,727, which is a continuation of application No. 12/440,644, filed as application No. PCT/IB2007/003535 on Sep. 11, 2007, now abandoned.

(51) Int. Cl.
*C07H 21/04* (2006.01)
*C12Q 1/68* (2006.01)

(52) U.S. Cl.
CPC ....... *C12Q 1/6883* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| | | | | |
|---|---|---|---|---|
| 8,728,727 B2* | 5/2014 | Azzedine | ............ | C12Q 1/6883 435/6.1 |
| 2007/0184444 A1* | 8/2007 | Abbas | .................... | C07K 14/47 435/6.14 |

OTHER PUBLICATIONS

Stevanin et al. (Nature Genetics, vol. 39, No. 3, pp. 366-372, Mar. 2007).*

* cited by examiner

*Primary Examiner* — Jeanine A Goldberg
(74) *Attorney, Agent, or Firm* — B. Aaron Schulman, Esq.; Stites & Harbison, PLLC

(57) ABSTRACT

An ex vivo method of diagnosing or predicting an hereditary spastic paraplegias (HSP) in a subject is provided which comprises detecting a mutation in the KIAA1840 gene or protein (spatacsin), wherein that mutation is indicative of an hereditary spastic paraplegias (HSP).

16 Claims, 17 Drawing Sheets

Figure 2:
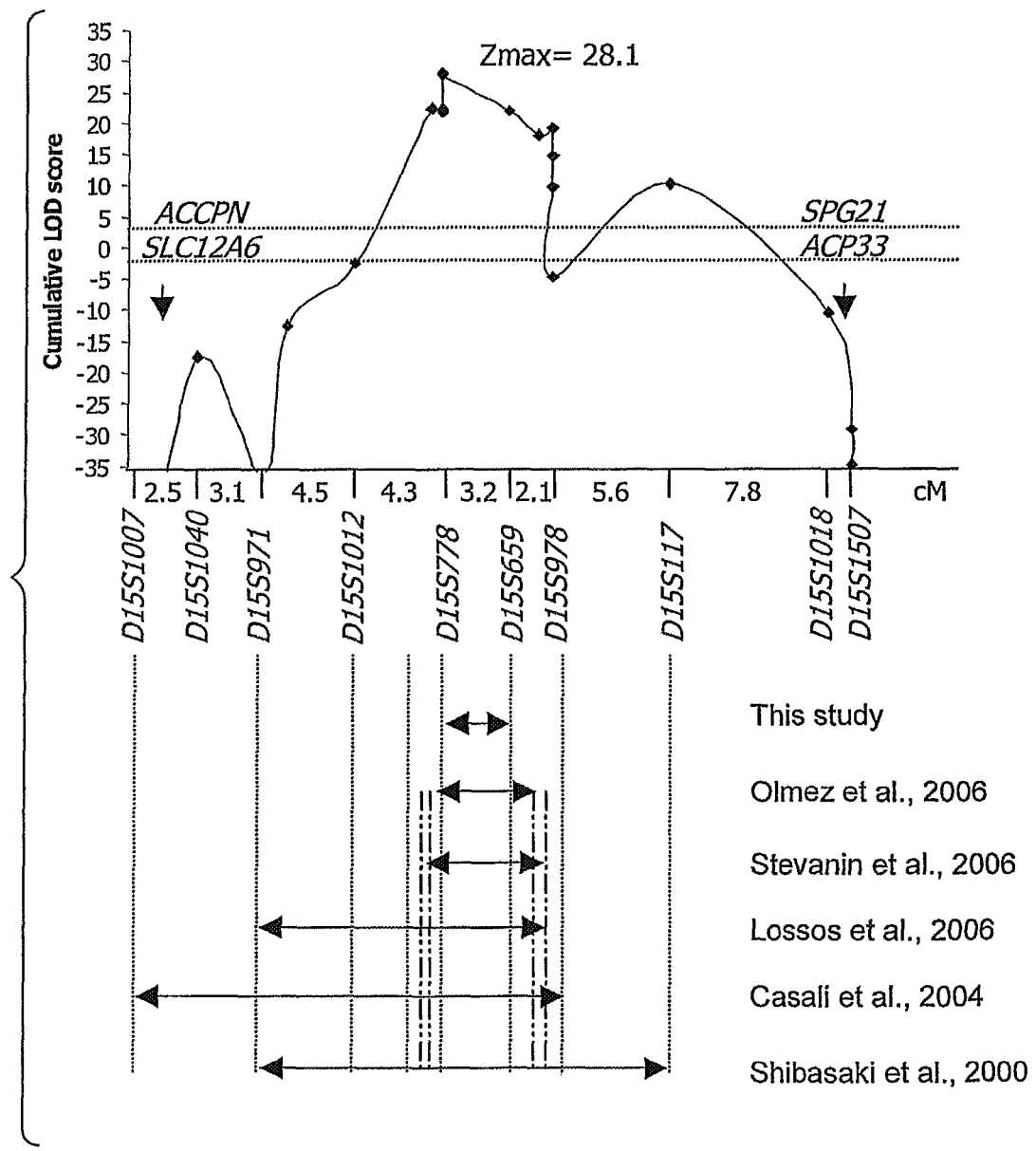

| MAP Location (cM)* | MARKERS | OS | MP | PE | FSP 75 | FSP 221 | FSP 343 | FSP 386 | FSP 393 | FSP 400 | FSP 446 | FSP 515 | FSP 670 | FSP 672 | FSP 732 | FSP 754 | SAL 1608 | SUM |
|---|---|---|---|---|---|---|---|---|---|---|---|---|---|---|---|---|---|---|
| 25.86 | D15S1007 | -4.79 | 0.60 | 0.50 | 1.30 | -8.97 | 1.33 | -7.33 | -19.48 | 2.60 | -3.84 | 0.78 | -7.23 | -4.45 | -2.67 | -4.58 | -0.17 | -56.30 |
| 28.35 | D15S1040 | 0.97 | 0.60 | 0.60 | 1.33 | -1.10 | 1.33 | -3.91 | -7.02 | 2.60 | 1.53 | 0.84 | -0.04 | -1.67 | -3.14 | -5.36 | -5.10 | -17.56 |
| 31.46 | D15S971 | 1.33 | 0.60 | 0.60 | 1.32 | -5.63 | 1.33 | -7.57 | -19.57 | 2.60 | 1.92 | 0.82 | -7.23 | -4.69 | 1.69 | -5.36 | 1.45 | -36.39 |
| 32.58 | D15S1042 | 1.33 | 0.60 | 0.60 | 1.32 | -8.09 | 1.33 | -8.90 | -12.21 | 2.60 | 1.93 | 0.82 | 2.21 | 0.81 | 1.70 | -0.01 | 1.45 | -12.52 |
| 35.95 | D15S1012 | 1.33 | 0.60 | 0.60 | 1.32 | -3.84 | 1.33 | 1.93 | -19.59 | 2.60 | 1.68 | 0.83 | 2.80 | 2.00 | 1.73 | 0.60 | 1.47 | -2.60 |
| 39.72 | D15S1044 | 1.33 | 0.60 | 0.60 | 1.32 | -1.82 | 1.33 | 1.93 | 1.80 | 2.60 | 1.87 | 0.84 | 3.08 | 2.56 | 1.79 | 0.89 | 1.50 | 22.23 |
| 40.25 | D15S214 | 1.33 | 0.60 | 0.60 | 1.33 | -2.26 | 1.33 | 1.93 | 1.81 | 2.60 | 1.93 | 0.85 | 3.08 | 2.60 | 1.80 | 0.92 | 1.50 | 21.94 |
| 40.25 | D15S129 | 1.33 | 0.60 | 0.60 | 1.33 | -2.27 | 1.25 | 1.93 | 1.81 | 2.60 | 1.93 | 0.85 | 3.08 | 2.60 | 1.80 | 0.92 | 1.50 | 21.85 |
| 40.25 | D15S994 | 1.33 | 0.60 | 0.60 | 1.33 | -1.89 | 1.33 | 1.93 | 1.81 | 2.60 | 1.93 | 0.85 | 3.08 | 2.60 | 1.80 | 0.92 | 1.50 | 22.31 |
| 40.25 | D15S968 | 1.33 | 0.60 | 0.60 | 1.33 | -2.31 | 1.33 | 1.93 | 1.81 | 2.60 | 1.93 | 0.85 | 3.08 | 2.60 | 1.80 | 0.92 | 1.50 | 21.89 |
| 40.25 | D15S514 | 1.33 | 0.60 | 0.60 | 1.33 | -2.37 | 1.33 | 1.93 | 1.81 | 2.60 | 1.93 | 0.85 | 3.08 | 2.60 | 1.80 | 0.92 | 1.50 | 21.84 |
| 40.25 | D15S779 | 1.33 | 0.60 | 0.60 | 1.33 | -2.39 | 1.33 | 1.93 | 1.81 | 2.60 | 1.93 | 0.85 | 3.08 | 2.60 | 1.80 | 0.92 | 1.50 | 21.82 |
| 40.25 | D15S780 | 1.33 | 0.60 | 0.60 | 1.33 | -2.41 | 1.33 | 1.93 | 1.81 | 2.60 | 1.93 | 0.85 | 3.08 | 2.60 | 1.80 | 0.92 | 1.50 | 21.74 |
| 40.25 | D15S515 | 1.33 | 0.60 | 0.60 | 1.33 | -1.80 | 1.33 | 1.87 | 1.81 | 2.60 | 1.93 | 0.85 | 3.08 | 2.60 | 1.80 | 0.92 | 1.50 | 22.27 |
| 40.25 | D15S778 | 1.33 | 0.60 | 0.60 | 1.33 | -2.49 | 1.33 | 1.78 | 1.81 | 2.60 | 1.93 | 0.85 | 3.08 | 2.60 | 1.80 | 0.92 | 1.50 | 21.72 |
| 40.25 | D15S784 | 1.33 | 0.60 | 0.60 | 1.33 | 3.81 | 1.33 | 1.93 | 1.81 | 2.60 | 1.93 | 0.85 | 3.08 | 2.60 | 1.80 | 0.92 | 1.50 | 28.02 |
| 40.25 | D15S783 | 1.33 | 0.60 | 0.60 | 1.33 | 3.85 | 1.33 | 1.93 | 1.81 | 2.60 | 1.93 | 0.85 | 3.08 | 2.60 | 1.80 | 0.92 | 1.50 | 28.06 |
| 40.25 | D15S781 | 1.33 | 0.60 | 0.60 | 1.33 | 3.85 | 1.33 | 1.93 | 1.81 | 2.60 | 1.93 | 0.85 | 3.08 | 2.60 | 1.80 | 0.92 | 1.50 | 28.06 |
| 40.25 | D15S182 | 1.33 | 0.60 | 0.60 | 1.33 | 3.85 | 1.33 | 1.93 | 1.81 | 2.60 | 1.93 | 0.85 | 3.08 | 2.60 | 1.80 | 0.92 | 1.50 | 28.06 |
| 40.25 | D15S537 | 1.33 | 0.60 | 0.60 | 1.33 | 3.85 | 1.33 | 1.93 | 1.81 | 2.60 | 1.93 | 0.85 | 3.08 | 2.60 | 1.80 | 0.92 | 1.50 | 28.06 |
| 40.25 | D15S516 | 1.33 | 0.60 | 0.60 | 1.33 | 3.85 | 1.33 | 1.93 | 1.80 | 2.60 | 1.86 | 0.84 | 3.08 | 2.60 | 1.80 | 0.92 | 1.50 | 27.97 |
| 40.25 | D15S517 | 1.33 | 0.60 | 0.60 | 1.33 | 3.85 | 1.33 | 1.93 | 1.80 | 2.60 | 1.84 | 0.83 | 3.08 | 2.45 | 1.80 | 0.90 | 1.49 | 27.69 |
| 40.25 | D15S1508 | 1.33 | 0.60 | 0.60 | 1.33 | 3.85 | 1.33 | 1.93 | 1.80 | 2.55 | 1.93 | 0.82 | 3.08 | -3.30 | 1.80 | 0.89 | 1.49 | 22.01 |
| 43.47 | D15S659 | 1.33 | 0.60 | 0.60 | 1.33 | 3.85 | 1.33 | 1.93 | 1.80 | 2.53 | 1.92 | 0.81 | 3.07 | -0.52 | 1.79 | 0.88 | 1.48 | 18.18 |
| 44.9 | D15S132 | 1.33 | 0.16 | 0.60 | 1.33 | 3.85 | 1.33 | 1.93 | 1.81 | -3.59 | 1.91 | 0.81 | 3.08 | -2.81 | 1.79 | 0.87 | 1.48 | 19.13 |
| 45.62 | D15S161 | 1.33 | -0.75 | 0.60 | 1.32 | 3.85 | 1.33 | 1.93 | 1.81 | 0.58 | 1.91 | 0.81 | 3.08 | -2.78 | 1.79 | 0.87 | 1.48 | 19.04 |
| 45.62 | D15S1039 | 1.33 | -0.85 | 0.60 | 1.32 | 3.85 | 1.33 | 1.93 | 1.81 | 0.56 | 1.91 | 0.81 | 3.08 | -2.81 | 1.79 | 0.87 | 1.48 | 14.83 |
| 45.62 | D15S143 | 1.33 | -0.97 | 0.60 | 1.32 | 3.85 | 1.33 | 1.93 | 1.81 | -3.50 | 1.91 | 0.81 | 3.07 | -1.48 | 1.79 | 0.87 | 1.48 | 9.77 |
| 45.62 | D15S123 | 1.33 | -1.05 | 0.60 | 1.32 | -2.45 | 1.33 | 1.93 | 1.81 | -3.50 | 1.91 | 0.81 | 3.07 | -0.72 | 1.79 | 0.87 | 1.48 | -4.72 |
| 45.62 | D15S978 | 1.33 | -5.70 | 0.60 | 1.32 | -2.45 | 1.33 | -6.66 | 1.81 | -5.49 | -3.82 | 0.80 | 2.37 | 0.97 | 1.77 | 0.87 | 1.47 | 10.26 |
| 51.21 | D15S117 | 1.30 | -0.47 | 0.52 | 1.08 | 1.49 | 1.19 | -0.77 | 1.63 | -0.13 | 0.49 | 0.84 | -0.34 | 0.44 | 1.80 | 0.93 | 1.50 | -10.61 |
| 59.05 | D15S1018 | 1.10 | -0.19 | 0.40 | 0.14 | 0.96 | 0.34 | -8.67 | -4.74 | -5.62 | -1.50 | 0.82 | -12.05 | -2.25 | 1.80 | 0.92 | 1.50 | -29.25 |
| 60.17 | D15S108 | 1.08 | -0.17 | 0.39 | -1.91 | -2.51 | -0.64 | -4.97 | -3.41 | -6.34 | -3.02 | 0.82 | -11.06 | -2.25 | 1.80 | 0.92 | 1.50 | -34.83 |
| 60.17 | D15S1507 | 1.08 | -0.17 | 0.39 | -4.10 | -2.51 | -0.67 | -6.51 | -4.70 | -6.34 | | | | | | | | |

FAMILIES

FIG.1

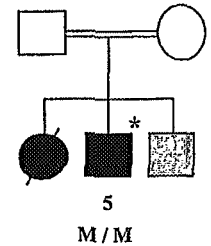
FSP831 (Portugal)
*Exon 3: c.529_533 delATATT, p.I177_F178>S177delfsX178*
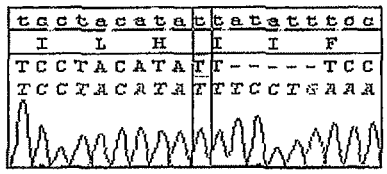
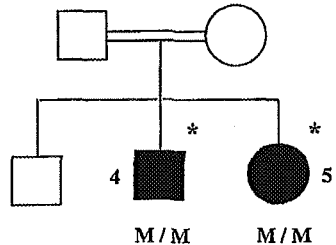
FSP792 (Morocco)
*Exon 32: c.6100 C>T, p.R2034X*
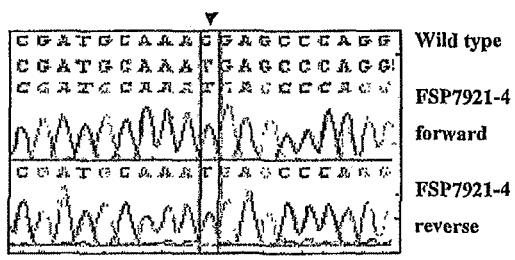
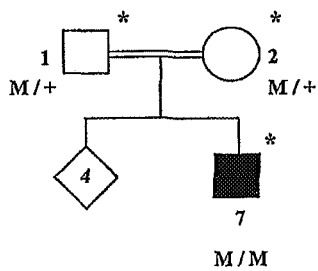
FSP845 (Morocco)
*Exon 32: c.6100 C>T, p.R2034X*
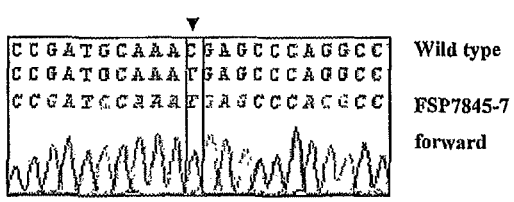
TUN9 (Tunisia)
*Exon 32: c.6100 c>t p.R2034X*
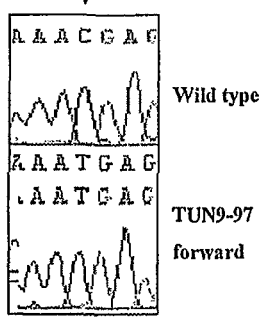
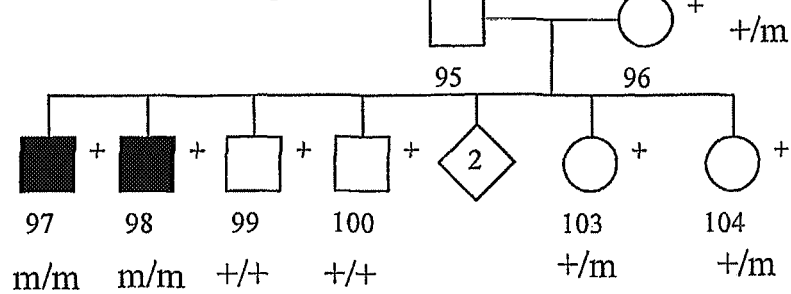
FIG.10

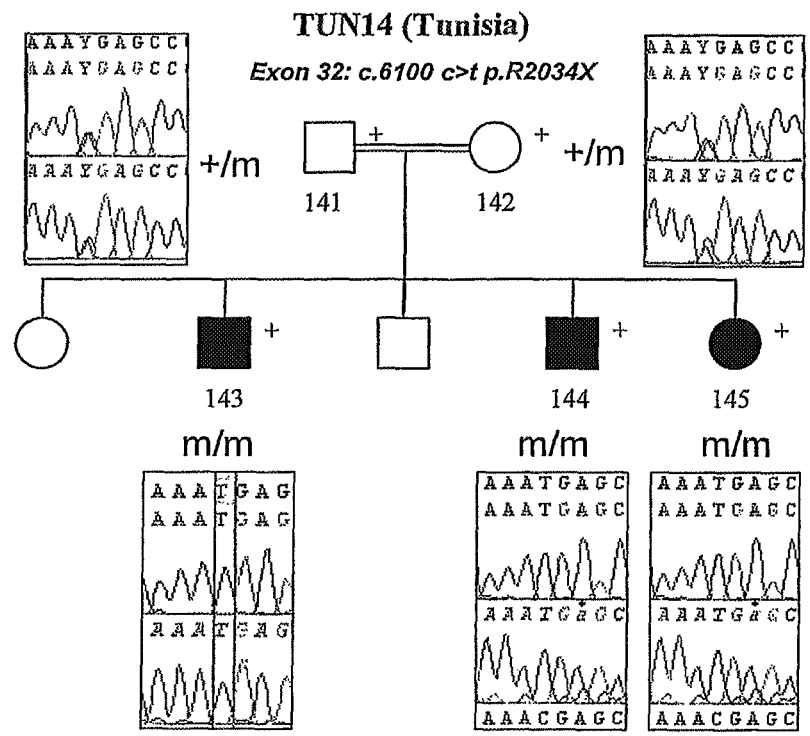
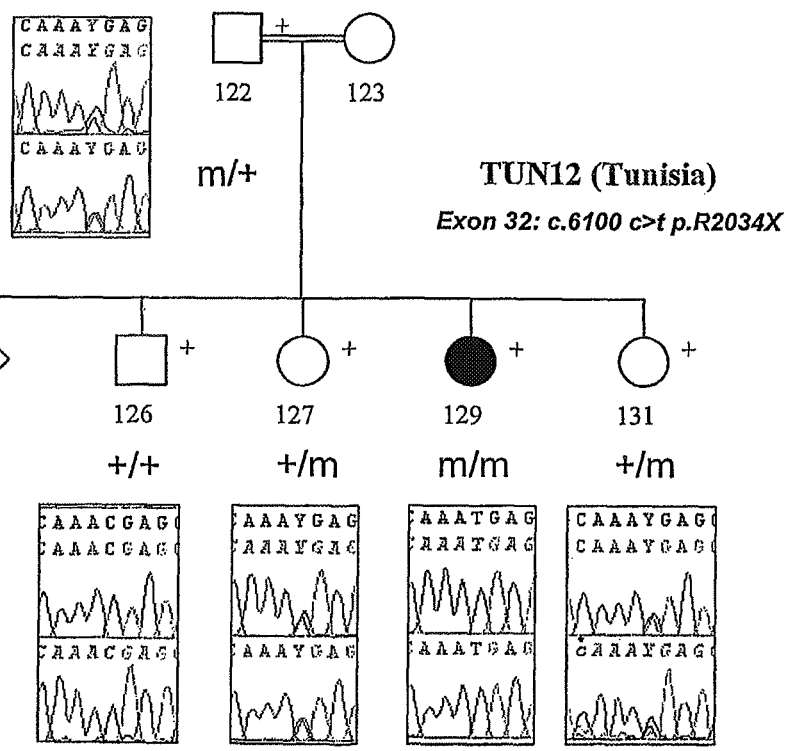
FIG.11

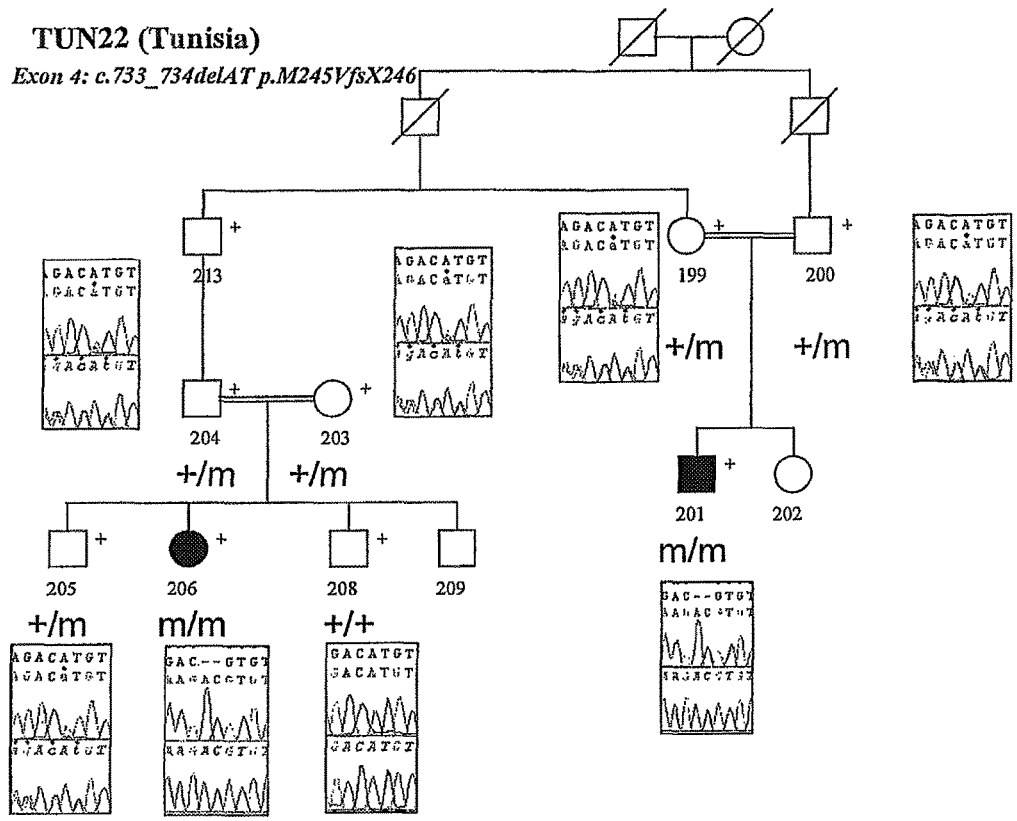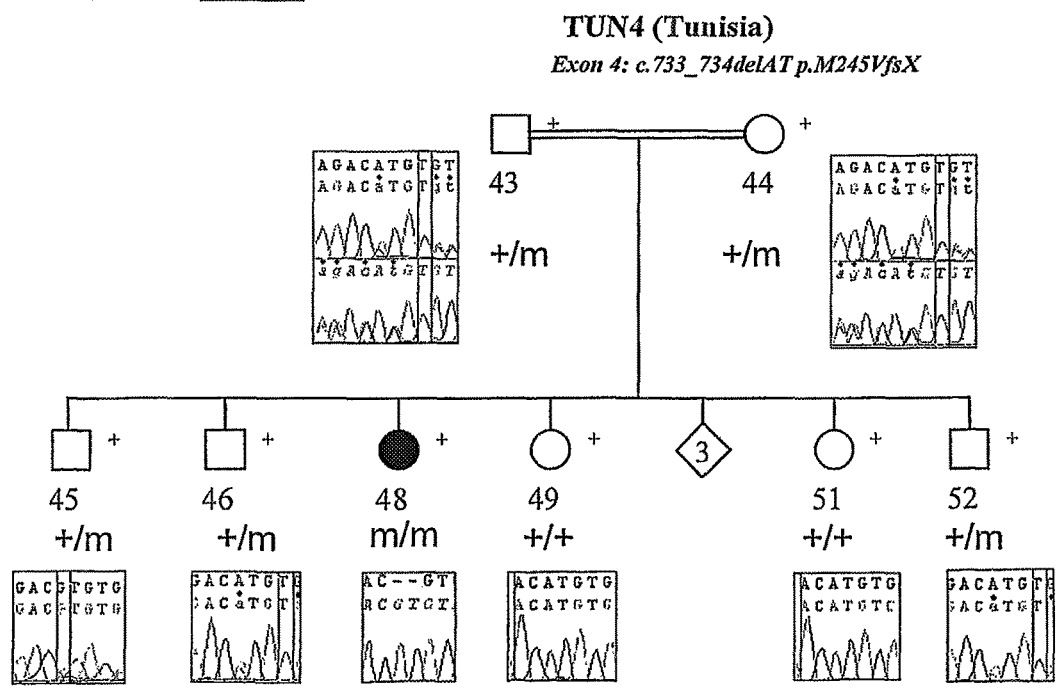
FIG.12

FSP920 (Japan)
*Exon36: c.6737_6740delTTGA; p.I2246_E2247>S2246fsX2260*
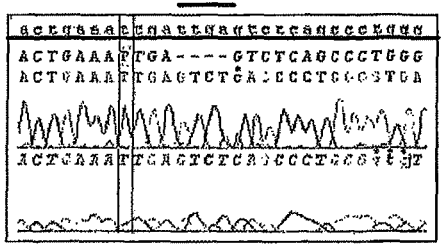
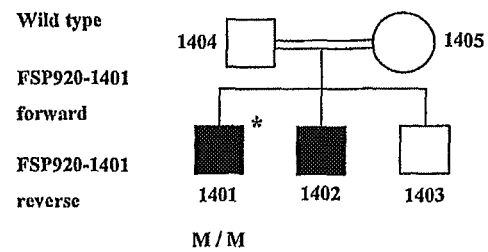
ITA1 (Trukey)
*Exon32: c.6091C>T; p.R2031X*
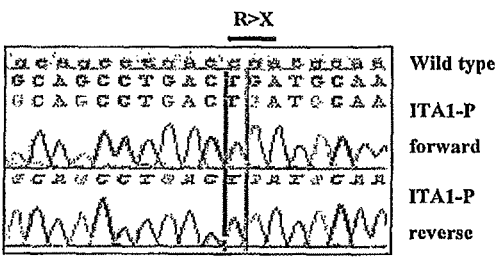
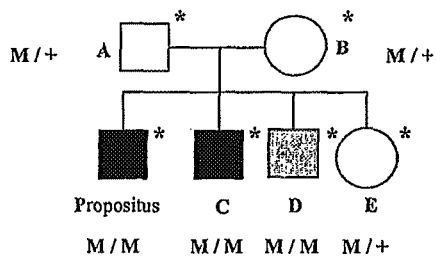
FSP838 (Saudi-Arabia)
*Exon 30: c.5769 delT, p.S1923RfsX1950*
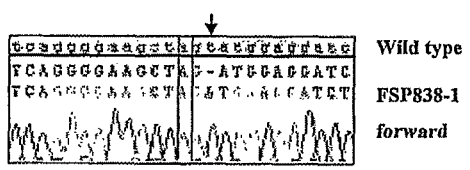
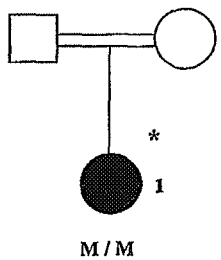
SPD199 (Turkey)
*Exon 4: c.704_705delAT, p.H235RfsX246*
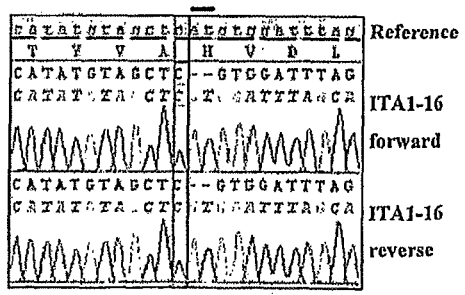
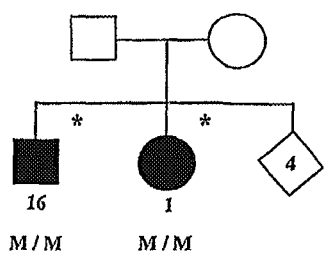
FIG.14

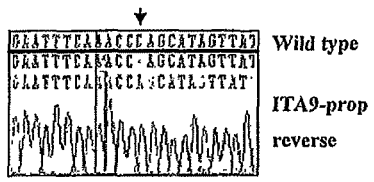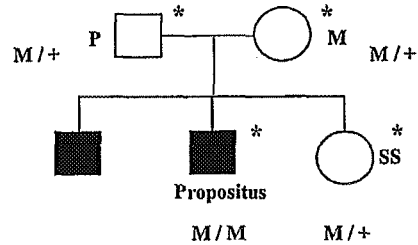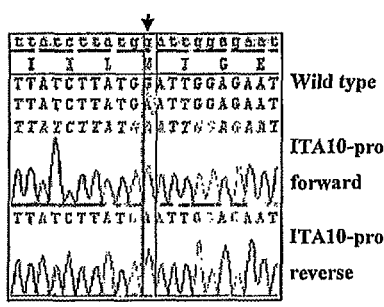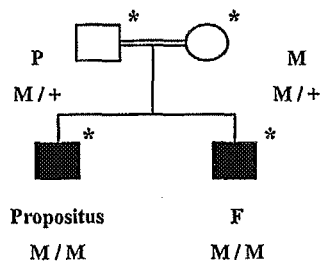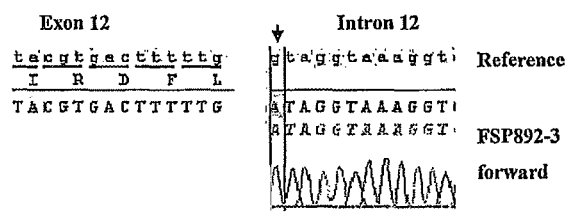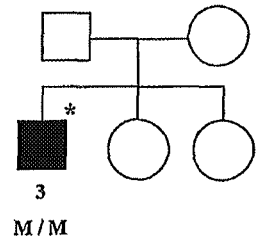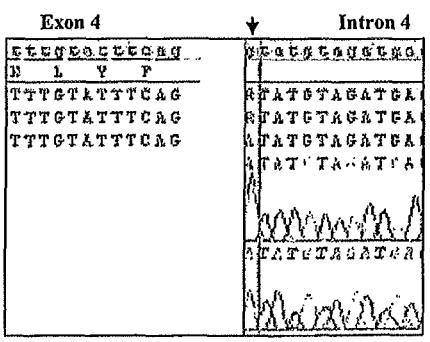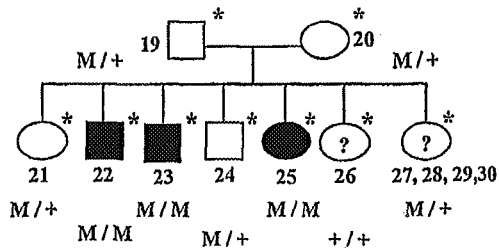
FIG.15

ITA17 (Brazil)

*Exon 3: c.529_533 delATATT, p.I177_F178>S177fsX178*
*Exon 22: c.3741_3742insA, p.P1248fsX1264*

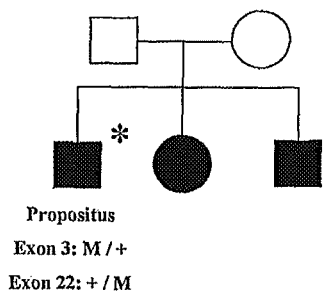

Propositus
Exon 3: M / +
Exon 22: + / M

FSP830 (Portugal)

*Exon 6: c.1282 A>T, p.K428X*
*Intron 34: c.6477+4 A>G, r.?*

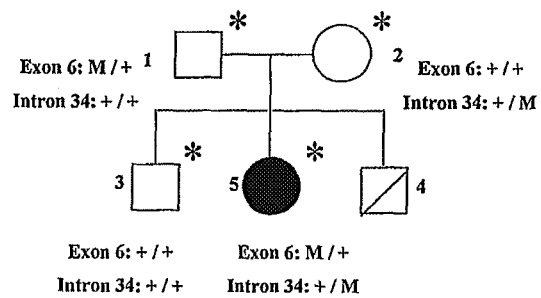

Exon 6: M / +   1    Exon 6: + / +
Intron 34: + / +        Intron 34: + / M

Exon 6: + / +     Exon 6: M / +
Intron 34: + / +  Intron 34: + / M

FSP522 (France)

*Exon 7: c.1471_1472delCT, p.L491DfsX556*
*Exon 30: c.5532_5533delCA, p.S1844SfsX1857*

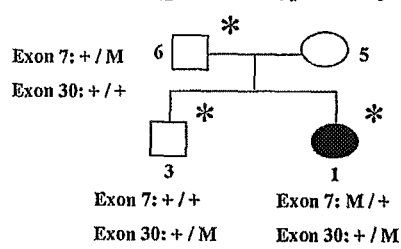

Exon 7: + / M  6          5
Exon 30: + / +

Exon 7: + / +     Exon 7: M / +
Exon 30: + / M    Exon 30: + / M

SAL646 (France)

*Exon 8: c.1668delT, p.F556LfsX577*
*Exon 36: c.6739_6742delGAGT, p.E2247_S2248>L2247fsX2260*

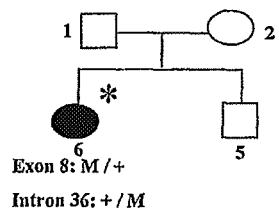

Exon 8: M / +
Intron 36: + / M

ITA16SB (Italy)

*Exon 8: c.1679C>G, p.S560X*
*Exon 31: c.5870C>G, p.S1957X*

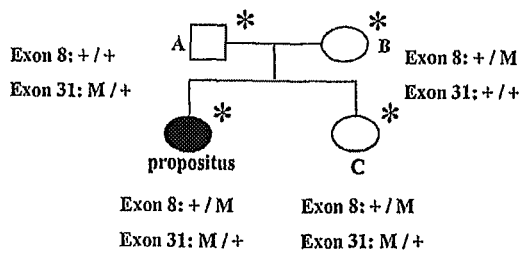

Exon 8: + / +   A          B   Exon 8: + / M
Exon 31: M / +                  Exon 31: + / + propositus                C
Exon 8: + / M      Exon 8: + / M
Exon 31: M / +     Exon 31: M / +

DKD (Italy)

*Exon 8: c.1692delA, p.V564VfsX577*
*Exon 31: c.5982_5983insCTCT, p.L1995LfsX2000*

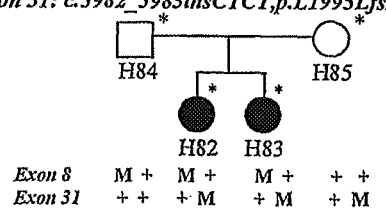

H84                H85
        H82  H83

Exon 8   M +   M +   M +   + +
Exon 31  + +   + M   + M   + M

FIG.16

FSP683 (France)
*Exon 10: c.1951C>T, R651X*
*Exon 31: c.5989_5992delCTGT,p.L1997_Y1998>M1997fsX2056*

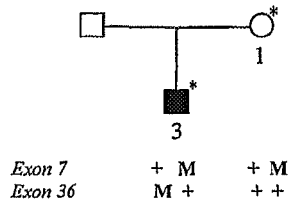

| | | |
|---|---|---|
| Exon 7 | + M | + M |
| Exon 36 | M + | + + |

ITA28VAC (Italy)
*Exon 10: c.1951C>T; p.R651X*
*Exon 13: c.2444G>T, p.R815M and/or r.?*

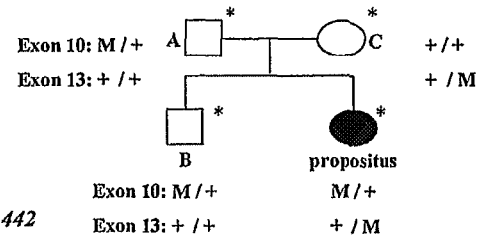

Exon 10: M / +   A       C   + / +
Exon 13: + / +              + / M

B        propositus
         Exon 10: M / +   M / +
         Exon 13: + / +   + / M

ITA16 (Brazil)
*Intron 13: c.2444+1G>C, r.?*
*Exon 25: c.4307_4308 delAA, p.Q1436RfsX1442*

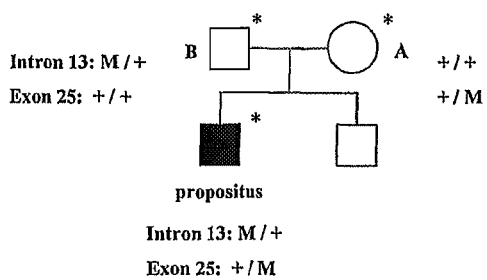

Intron 13: M / +   B       A   + / +
Exon 25: + / +                 + / M propositus
         Intron 13: M / +
         Exon 25: + / M

ITA 14 (Italy)
*Exon 15: c.2833 A>G, p.R945X*
*Exon 38: c.6857 C>T, p.R2286X*

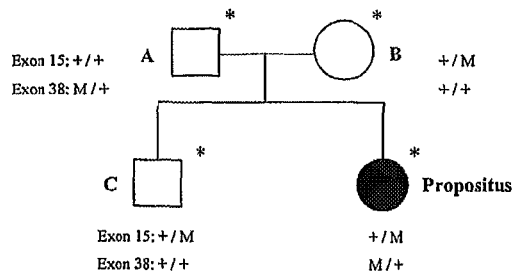

Exon 15: + / +   A       B   + / M
Exon 38: M / +               + / +

C             Propositus
         Exon 15: + / M    + / M
         Exon 38: + / +    M / +

ITA8 (Germany)
*Exon 17: c.3075_3076insA, p.E1026RfsX2029*
*Exon 30: c.5471 C>T, p.R1824X*

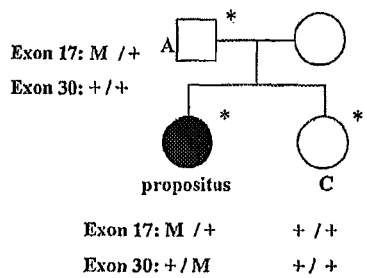

Exon 17: M / +   A
Exon 30: + / + propositus    C
Exon 17: M / +   + / +
Exon 30: + / M   + / +

FSP398 (Israel)
*Exon 25: c.4307_4308delAA, p.Q1436RfsX1442*
*Exon 31: c.5986_5987insT, p.C1996LfsX1999*

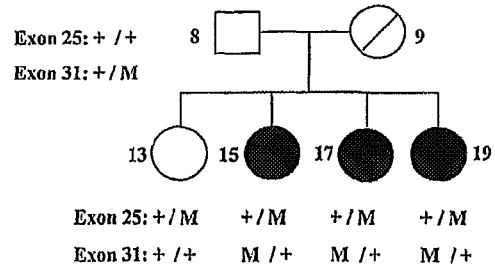

Exon 25: + / +   8       9
Exon 31: + / M 13    15    17    19
Exon 25: + / M   + / M   + / M   + / M
Exon 31: + / +   M / +   M / +   M / +

FIG.17

DIAGNOSIS OF HEREDITARY SPASTIC PARAPLEGIAS (HSP) BY DETECTION OF A MUTATION IN THE KIAA1840 GENE OR PROTEIN

CROSS-REFERENCE TO RELATED APPLICATIONS

This application is a divisional application of U.S. application Ser. No. 13/567,790, filed Aug. 6, 2012, which is a continuation application of U.S. application Ser. No. 12/440,644, filed Jan. 4, 2010, which was a 371 application of PCT/IB2007/003535, filed Sep. 11, 2007, all of said applications incorporated herein by reference.

The invention relates to the identification of mutations in the KIAA1840 gene or protein, associated with a hereditary spastic paraplegias (HSP), and to diagnostic applications that benefit from this identification.

Hereditary spastic paraplegias (HSP) are genetically heterogeneous Mendelian disorders characterized by weakness, spasticity and loss of vibratory sense in the lower limbs (Harding et al. 1983 and Tallaksen et al. 2001). They reveal themselves clinically through difficulties in walking possibly evolving into total paralysis of both legs. The physiopathology of this set of diseases is, to date, relatively undocumented; however, anatomopathological data make it possible to conclude that the attack is limited to the pyramidal tracts responsible for voluntary motricity in the spinal cord (Reid, 1997). The incidence of HSPs, which remains difficult to estimate because of rare epidemiological studies and the considerable clinical variability, varies from 0.9:100000 in Denmark, 3 to 9.6:100000 in certain regions of Spain (Polo et al., 1991) or 14:100000 in Norway (Skre, 1974) (approximately 3:100000 in France). Various clinical and genetic forms of HSP exist. The so-called "pure" HSPs, which correspond to isolated spasticity of the lower limbs, are clinically distinguished from the "complex" HSPs, for which the spasticity of the legs is associated with other clinical signs of neurological or non-neurological type (Bruyn et al., 1991).

Although forms of HSP have been recognized for over a century, new phenotypes are regularly described, demonstrating wide clinical heterogeneity. Genetically, autosomal dominant (AD), autosomal recessive (AR) and X-linked inheritance are observed and almost 32 genetic loci have been identified, but only 12 genes have been cloned (Flink et al. 2006). According to the putative roles of these genes, mitochondrial function, protein folding and axonal transport have been implicated in the dying back of pyramidal tract axons in these disorders.

The most common forms of AD-HSP, accounting for about 40-50% of cases, are caused by mutations in the SPG4 and SPG3A genes that encode for spastin and atlastin, respectively (Hazan et al. 1990, Zhao et al. 2001 and international patent application WO 01/18198). In contrast to AD forms, no major gene accounts for AR-HSP, which is less common and more varied in clinical presentation, implying greater genetic heterogeneity. The four AR-HSP genes cloned so far, encoding for paraplegin (SPG7, MIM#607259 (OMIM database, www.ncbi.nlm.nih.gov/entrez/query.fcgi?db=OMIM)), (Casari et al. 1998) spartin (SPG20; MIM#275900), (Patel et al. 2002) and maspardin (SPG21, MIM 248900) (Simpson et al. 2003) as well as the gene responsible for the related spastic ataxia of Charlevoix Saguenay (ARSACS, MIM#270550) (Engert et al. 2000) probably represent less than 5% of all cases (Fink et al. 2003).

A very common form of AR-HSP associates spastic paraplegia, mental or cognitive deficit and thin corpus callosum (Winner et al. 2005). The majority of the families appear to be linked to SPG11 on chromosome 15, which was the third AR-HSP locus to be identified (Martinez et al. 1999). This entity is particularly prevalent in Japan (Shibasaki et al. 2000), but is also found in North-America, the Middle-East and Europe (Martinez et al 1999 and Lossos et al. 2006 and Casali et al. 2004 and Winner et al. 2004 and Stevanin et al. 2006). The typical clinical features of SPG11 consist of early-onset spastic paraplegia (usually <20 years), urinary bladder dysfunction, deep sensory deficits in the legs and cognitive impairment that progress insidiously to severe functional disability over a period of 10-20 years. Some patients also develop arm involvement, dysarthria, contractures and muscle atrophy. Auxiliary studies frequently identify a thin corpus callosum (TCC) with white matter lesions and variable cerebral cortical atrophy on magnetic resonance imaging (MRI), variable cortical and thalamic glucose hypometabolism on positron emission tomography and predominantly axonal motor or sensorimotor peripheral neuropathy on nerve conduction studies (Winner et al. 2004).

Linkage to chromosome 15q has been reported so far in 31 families in which the patients presented with the typical SPG11 phenotype. In the initial study, a maximum multipoint combined LOD score of 3.14 was detected in seven AR-HSP families in a region between D15S1007 and D15S1012, although patients from only 2 kindreds of North-American and Italian ancestries presented with a TCC (Martinez et al. 1999). A second study reported a group of 10 out of 13 Japanese families with a homogeneous phenotype of AR-HSP-TCC with a cumulative LOD score of 9.68 in the D15S971 to D15S117 interval (Shibasaki et al. 2000). Casali et al. also reported 5 Italian kindreds that showed significant linkage (Z=3.35) to the interval flanked by markers D15S1007 and D15S978 (Casali et al. 2004). More recently, the analysis of 8 additional kindreds (Z=11.5) including 3 large consanguineous families, allowed the locus to be restricted by the inventors to the 6 cM interval between markers D15S1044 and D15S143 (Lossos et al. 2006 and Stevanin et al. 2006) a region that did not overlap with the interval defined in the originally mapped families (Martinez et al. 1999), therefore showing genetic heterogeneity among families linked to 15q and more closely resembling the locus for amyotrophic lateral sclerosis ALS5 (Hentati et al, 1998). It is of note that in the work published by Martinez et al (1999), only 2 of 8 pedigrees presented with the typical SPG11 phenotype with TCC and patients from these 2 families were linked to a larger region on chromosome 15 overlapping the region described in recent reports (Lossos et al. 2006 and Stevanin et al. 2006). More recently, the SPG11 locus was further refined to the 4.6 cM region (according to the Marschfield genetic map, http://research.marshfieldclinic.org/genetics/GeneticResearch/compMaps.asp) between markers D15S968-D15S132 (Olmez et al, 2006) confirming the results of the inventors (FIG. 2).

Figure 6:
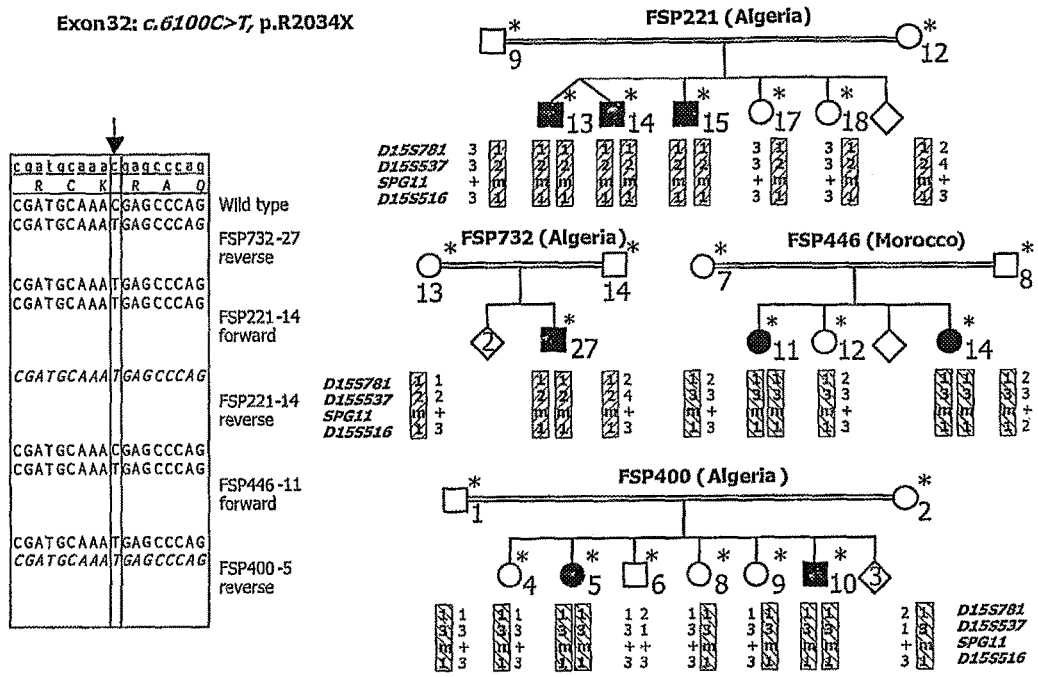
Figure 7:
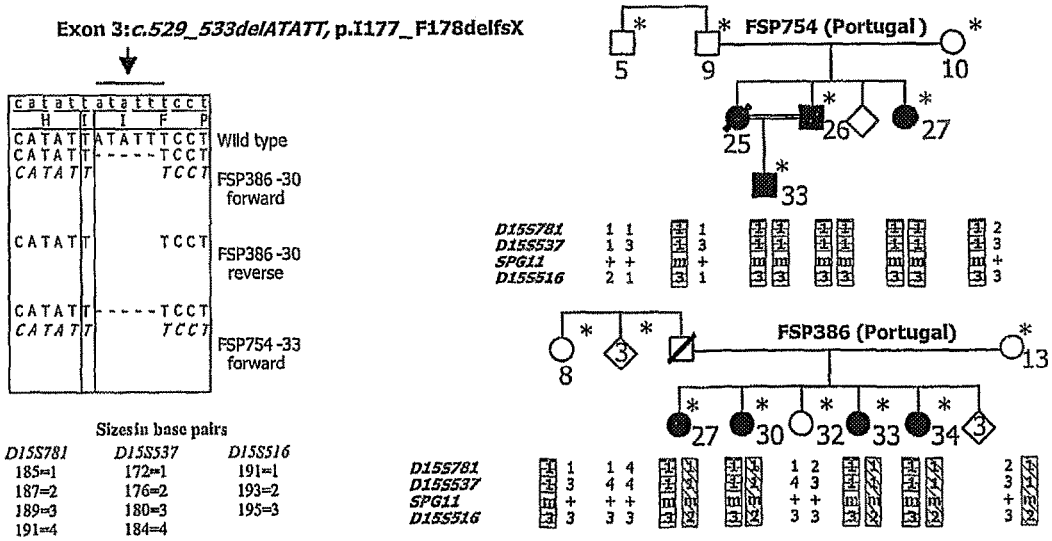
Figure 8:
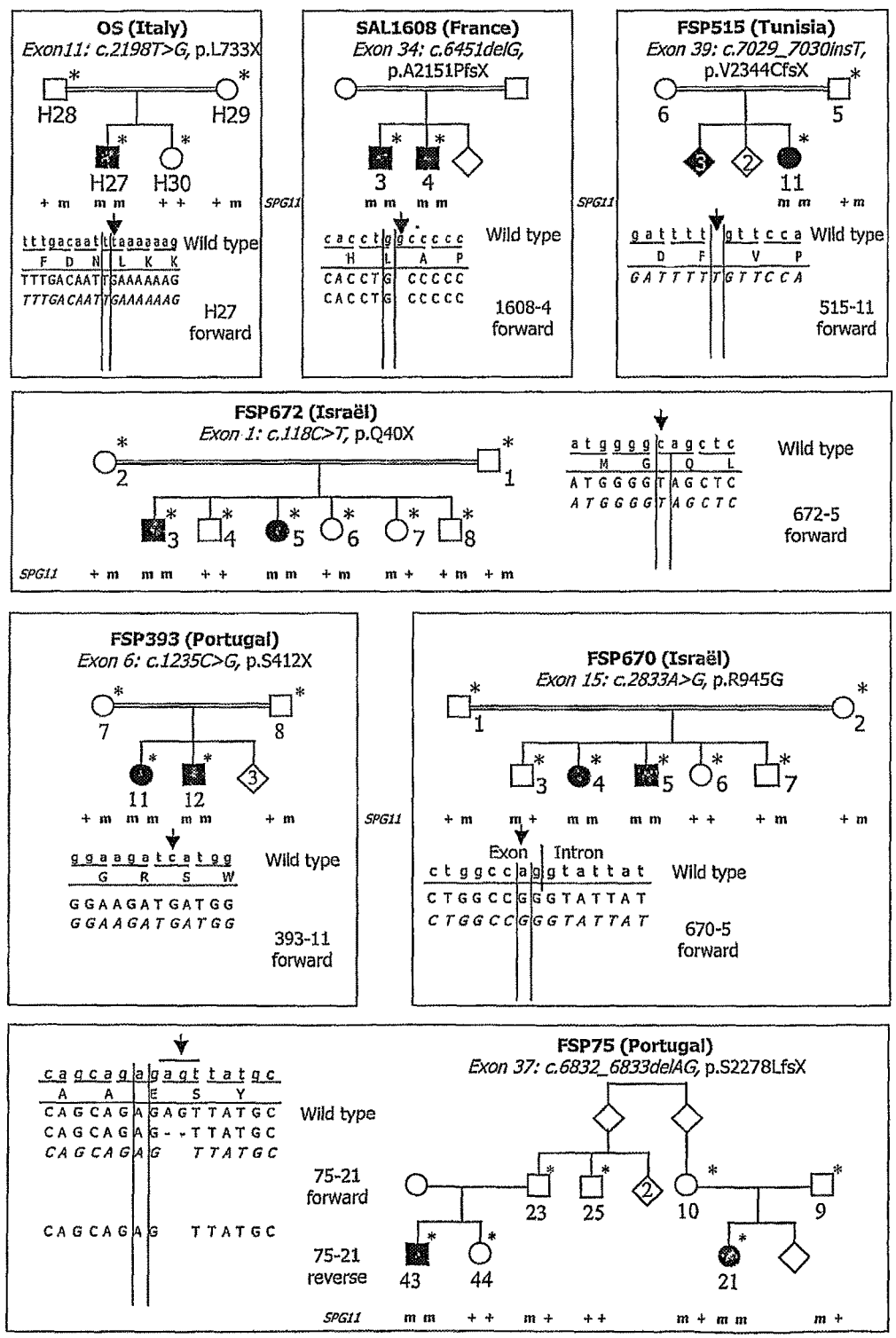
Figure 9:
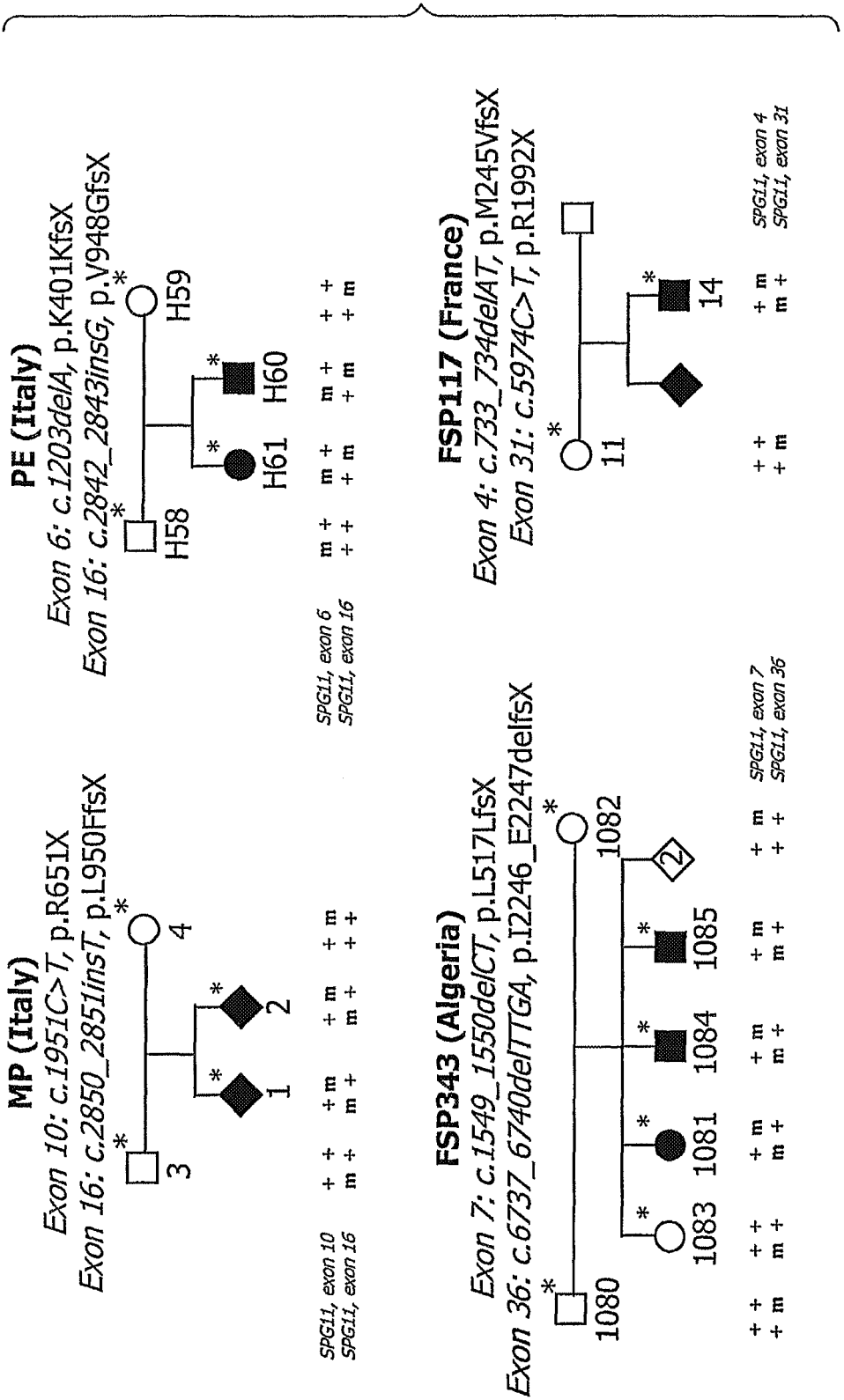
Figure 13:
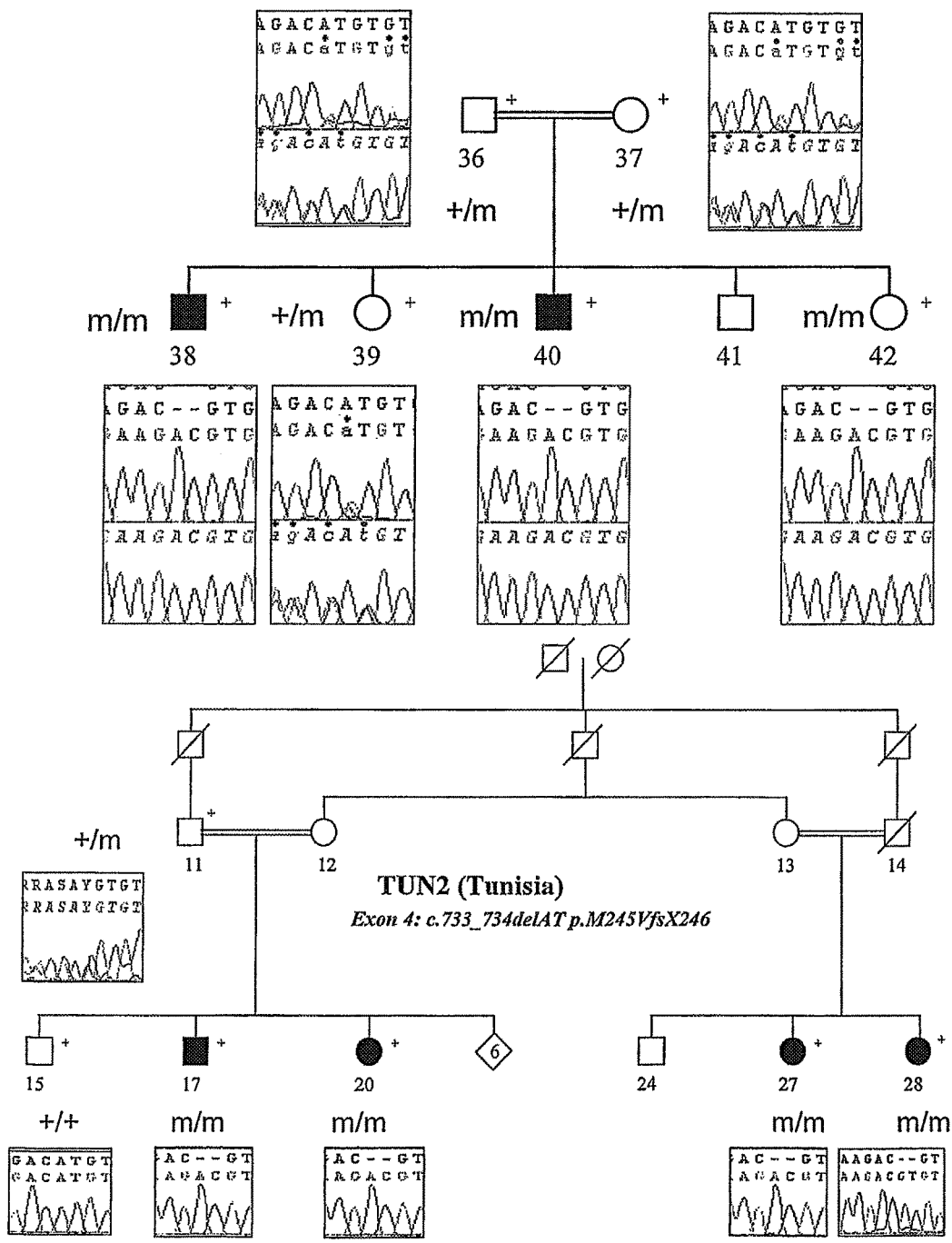

The inventors have now identified the gene responsible for the most frequent form of Autosomal Recessive Hereditary Spastic Paraplegia (AR-HSP). They have indeed demonstrated that the disease is caused by mutations in the KIAA1840 gene (also known as FLJ21439), affecting the spatacsin protein expression (Stevanin et al., 2007). This is supported by four pieces of evidence. First, the inventors have excluded 17 out of about 40 genes assigned to the SPG11 candidate interval after significant reduction of its size to the 3.2 cM interval (according to the Marschfield genetic map) between markers D15S778 and D15S659 (FIGS. 1 to 4). The analysis of 2 of these genes has been reported previously (Stevanin et al, 2006). Secondly, the inventors have identified 43 different mutations segregating in 47 families (FIGS. 5 to 9), 16 of which linked previously to the SPG11 locus with a highly significant 28.1 maximal combined lod score (FIGS. 1 and 2), 8 of them already published as linked (Casali et al, 2004; Lossos et al, 2006 and Stevanin et al, 2006). Thirdly, the inventors have identified mutations, absent in at least 140 control chromosomes, that were all, leading to abnormal splicing of the messenger RNA and/or leading to a truncated protein. Finally, the inventors have demonstrated that all mutated families, except 2 in which magnetic resonance imaging could not be performed (TUN2 and TUN14), presented with the typical AR-HSP-TCC phenotype. In addition, several of these families shared the same mutation with similar surrounding haplotypes when they came from the same geographical origins, suggesting regional founder effects (FIGS. 6 and 7). Mutations in KIAA1840 affected 47 of 91 AR-HSP-TCC families in the study carried out by the inventors making this genetic entity very frequent among AR-HSP-TCC (75% was estimated in a previous study, Stevanin et al, 2006). The invention therefore provides the identification of the major gene responsible of AR-HSP-TCC and probably of AR-HSPs in general and opens thereby new opportunities to improve diagnosis and genetic counseling of said disease. Moreover, the invention also provides a mean to improve the medical care management of patient affected with said disease. In addition, since most patients with spastic paraplegia have isolated forms, it is conceivable that this new gene could account for a small proportion of these patients as well. Indeed, in Europe, due to the small size of the families, recessively inherited diseases are often found in apparently isolated cases.

A first aspect of the invention thus relates to the identification of mutations in the KIAA1840 gene or protein, associated with a hereditary spastic paraplegias (HSP), and to diagnostic application that benefits from this identification.

A second aspect of the invention relates to an isolated nucleic acid, specifically hybridizable to a region of KIAA1840 gene sequence that contains a mutation selected from the group consisting of the substitutions: c.6100C>T, c.2198T>G, c. 118C>T, c. 1235C>G, c.2833A>G, c.1951C>T, c.869+1G>A, c. 1679C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T and c.5974C>T, the deletions: c.529-533delATATT, c.6451delG, c.6832_6833 delAG, c.1203delA, c.1549_1550 delCT, c.6737_6740 delTTGA, c.1471_1472 delCT, c.1692delA, c.2716delC, c.1668delT, c.704_705 delAT, c.5989_5992 delCTGT, c.5532_5533delCA, c.5769delT, c.6739_6742delGAGT, c.4307_4308delAA and c.733_734delAT, and the insertions: c.7029_7030insT, c.2850_2851insT, c.3741_3742insA, c.5982_5983insCTCT, c.5986_5987insT, c.3075_3076insA and c.2842_2843insG.

Such an isolated nucleic acid can be used as a primer or probe.

More preferentially the invention relates to an isolated nucleic acid, which comprises a KIAA1840 gene sequence that contains one or several mutation(s) selected from the group consisting of the substitutions: c.6100C>T, c.2198T>G, c.118C>T, c.1235C>G, c.2833A>G, c.1951C>T, c.869+1G>A, c. 1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T c.5974C>T, the deletions: c.529-533delATATT, c.6451delG, c.6832_6833 delAG, c.1203delA, c.1549_1550 delCT, c.6737_6740 delTTGA, c.1471_1472 delCT, c.1692delA, c.2716delC, c.1668delT, c.704_705 delAT, c.5989_5992 delCTGT, c.5532_5533delCA, c.5769delT, c.6739_6742delGAGT, c.4307_4308delAA c.733_734delAT, and the insertions: c.7029_7030insT, c.2850_2851insT, c.3741_3742insA, c.5982_5983insCTCT, c.5986_5987insT, c.3075_3076insA c.2842_2843insG or a sequence complementary thereto.

Another aspect of the invention relates to an isolated polypeptide which comprises the amino acid sequence of KIAA1840 containing one or several mutation(s) selected from the group consisting of p.Q40X, p.I177_F178delfsX178, p.H235RfsX246, p.M245VfsX246, p.K401KfsX415, p.S412X, p.K428X, p.L491DfsX556, p.L517LfsX556, p.F556LfsX577, p.S560X, p.V564VfsX577, p.R651X, p.L733X, p.R815M, p.W899X, p.Q906SfsX920, p.R945G, p.R945GfsX950, p.L950FfsX953, p.V948GfsX953, p.E1026RfsX1029, p.P1248TfsX1264, p.Q1436RfsX1442, p.R1824X, p.S1844SfsX1857, p.S1923RfsX1950, p.S1957X, p.R1992X, p.L1995LfsX2000, p.C1996LfsX1999, p.L1997_1998 delfsX2056, p.R2031X, p.R2034X, p.A2151PfsX2172, p.I2246_E2247delfsX2260, p.E2247_S2248delfsX2260, p.S2278LfsX2338, p.R2286X and p.V2344CfsX2349.

Another aspect of the invention relates to an isolated monoclonal or polyclonal antibody that specifically recognizes a KIAA1840 protein containing a mutation selected from the group consisting of p.Q40X, p.I177_F178delfsX178, p.H235RfsX246, p.M245VfsX246, p.K401KfsX415, p.S412X, p.K428X, p.L491DfsX556, p.L517LfsX556, p.F556LfsX577, p.S560X, p.V564VfsX577, p.R651X, p.L733X, p.R815M, p.W899X, p.Q906SfsX920, p.R945G, p.R945GfsX950, p.L950FfsX953, p.V948GfsX953, p.E1026RfsX1029, p.P1248TfsX1264, p.Q1436RfsX1442, p.R1824X, p.S1844SfsX1857, p.S1923RfsX1950, p.S1957X, p.R1992X, p.L1995LfsX2000, p.C1996LfsX1999, p.L1997_1998 delfsX2056, p.R2031X, p.R2034X, p.A2151PfsX2172, p.I2246_E2247delfsX2260, p.E2247_S2248delfsX2260, p.S2278LfsX2338, p.R2286X and p.V2344CfsX2349.

Another aspect of the present invention relates to the use of a monoclonal or polyclonal antibody recognizing the wild type protein to identify truncated forms of the protein.

DEFINITIONS

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

As used herein, the term "oligonucleotide" refers to a nucleic acid, generally of at least 10, preferably at least 15, and more preferably at least 20 nucleotides, preferably no more than 100 nucleotides, still preferably no more than 70 nucleotides, and which is hybridizable to a KIAA1840 genomic DNA, cDNA, or mRNA. Oligonucleotides can be labelled according to any technique known in the art, such as with radiolabels, fluorescent labels, enzymatic labels, sequence tags, etc. A labelled oligonucleotide may be used as a probe to detect the presence of a mutated KIAA1840 nucleic acid. Alternatively, oligonucleotides (one or both of which may be labelled) can be used for amplifying a KIAA1840 nucleic acid, for instance by PCR (Saiki et al., 1988), to detect the presence of a mutation. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A nucleic acid molecule is "hybridizable" or "hybridizes" to another nucleic acid molecule, such as a cDNA, genomic DNA, or RNA, when a single stranded form of the nucleic acid molecule can anneal to the other nucleic acid molecule under the appropriate conditions of temperature and solution ionic strength (Sambrook et al., 1989).

The conditions of temperature and ionic strength determine the "stringency" of the hybridization. For preliminary screening for homologous nucleic acids, low stringency hybridization conditions, corresponding to a Tm (melting temperature) of 55° C., can be used, e.g., 5×SSC, 0.1% SDS, 0.25% milk, and no formamide; or 30 formamide, 5×SSC, 0.5% SDS). Moderate stringency hybridization conditions correspond to a higher Tm, e.g., 40% formamide, with 5× or 6×SCC. High stringency hybridization conditions correspond to the highest Tm, e.g., 50% formamide, 5× or 6×SCC. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., 1989, 9.50-9.51). For hybridization with shorter nucleic acids, i.e., oligonucleotides, the position of mismatches becomes more important, and the length of the oligonucleotide determines its specificity (see Sambrook et al., 1989 II.7-11.8). A minimum length for a hybridizable nucleic acid is at least about 10 nucleotides, preferably at least about 15 nucleotides, and more preferably the length is at least about 20 nucleotides.

In a specific embodiment, the term "standard hybridization conditions" refers to a Tm of 55° C., and utilizes conditions as set forth above. In a preferred embodiment, the Tm is 60° C. In a more preferred embodiment, the Tm is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, an "amplification primer" is an oligonucleotide for amplification of a target sequence by extension of the oligonucleotide after hybridization to the target sequence or by ligation of multiple oligonucleotides which are adjacent when hybridized to the target sequence. At least a portion of the amplification primer hybridizes to the target. This portion is referred to as the target binding sequence and it determines the target-specificity of the primer. In addition to the target binding sequence, certain amplification methods require specialized non-target binding sequences in the amplification primer. These specialized sequences are necessary for the amplification reaction to proceed and typically serve to append the specialized sequence to the target. For example, the amplification primers used in Strand Displacement Amplification (SDA) include a restriction endonuclease recognition site 5' to the target binding sequence (U.S. Pat. No. 5,455,166 and U.S. Pat. No. 5,270,184). Nucleic Acid Based Amplification (NASBA), self-sustaining sequence replication (3SR) and transcription based amplification primers require an RNA polymerase promoter linked to the target binding sequence of the primer. Linking such specialized sequences to a target binding sequence for use in a selected amplification reaction is routine in the art. In contrast, amplification methods such as PCR which do not require specialized sequences at the ends of the target, generally employ amplification primers consisting of only target binding sequence.

As used herein, the terms "primer" and "probe" refer to the function of the oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer. It will therefore be appreciated that any of the target binding sequences disclosed herein for amplification, detection or quantisation of KIAA1840 may be used either as hybridization probes or as target binding sequences in primers for detection or amplification, optionally linked to a specialized sequence required by the selected amplification reaction or to facilitate detection.

As used herein, the terms "KIAA1840 gene" (or its synonyms: FLJ21439, ENSG00000104133 or SPG11) denotes a KIAA1840 gene of any species, especially human, but also other mammals or vertebrates to which the methods of the invention can apply. The human KIAA1840 gene encodes a large protein of 2443 amino-acids (aa) of unknown function that the inventors have named Spatacsin (SEQ ID NO: 2). *Homo sapiens* KIAA1840 gene is localized on chromosome 15 and its Coding Sequence (CDS) is deposited in Genebank under accession number NM_025137, or AB058743 (5'-3' forward strand shown SEQ ID NO: 1). Human KIAA1840 gene shares 85% identity with the homologous protein in dog, and 76% and 73% identity with the mouse and rat homologues and 59% with the chicken homologue. Homology is less than 25% with orthologous proteins, of smaller sizes, in *tetraodon* and *drosophila*. KIAA1840 homologous proteins at NCBI database are: dog XP_544657, gallus XP_413940.1, mouse BAE27954, rat XP_242139.3, and at Ensembl database; *drosophila* CG13531, *tetraodon* GSTENG00003909001. The human KIAA1840 gene contains 40 exons spanning 101 Kbases of genomic DNA on chromosome 15q21.1. The intron-exon structure of the complementary strand of the KIAA1840 gene is further indicated in Table 1 below and in FIG. 5.

TABLE 1

Exon-intron boundaries of the human KIAA 1840 gene (according to the Ensembl database)

| No | Exon/Intron | Position in SEQ ID NO: 1 | Length (bp) | Sequence |
|---|---|---|---|---|
| 1 | 5' upstream sequence ENSE00001183257 | 0 | 258 | .........cgacgcagtcagttccggcgaaagtgaccggaagtaaccgcggccaa ATGGGCTTCACCGACTGCTCTTGCTTCCGCGAGTGCTGCTTCCCGCCGGCAGGG CGGTTCCACCGATGCTGTTGGTCCAGTCCCCGCGGCGATGGGCAGCTCCCGGGCCAGCT GCCACACAGCCCGAGGCTCTGGGAGCCTCGCGGCAGCCTCCAAGCTGCTTTCTTTGACGCCTG GCAGCCGGGGCCGGGGTCGCTCTGCTCCTGAGGGCCCCTTCTGCA |
| 2 | Intro 1-2 ENSE00001183253 | 258 | 2,774 185 | gtaagtgctgagggaggagttgggc..........aataaatctaaacttttttcttag CTTTCTATGGGAGGAGATTCTCGTAACAGCAGCACATCCACCAACTGAAAAGCCAAACTGCTCGCTCTTGGTGAAAAT TATGAACTGCTTATCTATGAATTAATTGAAGATGAAGATGTGATGCAACCATTTTGTATAGCTGTAGTAGG GAGGCATTGCAAAGCTCATTGACGATCAAGATATCA |
| 3 | Intro 2-3 ENSE00001183250 | 443 | 1,128 225 | gtaagtatctacaggtgtctttca..........gaaataatatccttttgttttgtag GTATTTCCTTATTGTCTTTGAGAATCTGTCATTTCAATTCACAATAACACATCATGTTCATCAACAAATGTCAT CCTACACATATATTATTTCCTGAAAGAGATGCTCAATTAGAGTACTTCAACACTCTCTTGACACTTCCCTGCCTGCACA GGCATGGACACATGATTATTGACACGCCAGCTCTGCAGAGGAATTCTTTGTTTGAGTAGTTAGGCTGGATCT |
| 4 | Intro 3-4 ENSE00001183246 | 668 | 1,782 202 | gtatccttggtggtagaagtgttga..........attttctttaactctaactaaaag ACATTTTTGATGTTGTGAACAGAGCTACATATGTAGCACTTCACAAAGAGACATGTGTAAT GAGCAGCAACAGGAGCCAGCCAAGCACACTTCATTTCATTACTTGAAGAATCTCAAGACCTTCAAGACCTCGATGTTGCAGT GATTGTCAGCTCCTCCAACTCCGCAGTTGCTCTTAACTTAAATTGTATTCAG |
| 5 | Intro 4-5 ENSE00001183241 | 870 | 4,828 138 | gtatgtagatgactgcagtttca..........tgtctatcattatttttaaatgtag GCAACACCCAGGACACCTTACTGTGTGAAAGAATACTAGAAGATCTTCCTATTCAAGGACCTAAGGCGTAGAT GAAGATGATCCTTAACTGCTCCTACACATGAAACTGGCCAAGTTTCCTTCCAAATTGATAG |
| 6 | Intro 5-6 ENSE00001183238 | 1008 | 189 449 | gtacagaaacttcctttcatgtag..........aagttatatttttacctgttccag GTCTTGGAAGCCCAGCTATCATTCATTGAATGAATGAAACAATAAAGGAACTCCAAACTGGAGGTTTCCTGTTGTCTC CATGGTTCCAGGATATTTGCATTTGGAGTCCATGGTGAATCTGAATCTGCAACCACAAGTGTGCAGAGCTGGGC CTTCATTCCACAGGACATATGCATGGGACATCAGTGGCAATATAATGTTCTACACGAAAGATCATGCCAAGACCAGTGATCCAG GAAGATCATGAAGAAAATAATGCACATCAGTGAACAAGAGGAACCCATAGACCCATTACCCTGGATTGGACACCAGCCCATG CAGTGTTTTTCCCTTGGCACAAAGTGTATTCCTGTAGACAGTAGTGGAGACCAGCAGCTGTGCTTGTTTTGAC ATTCAC TGCCACTGTTACTTGGGAAGTGGAAAGGATGGGCTATACCATTACCCTGGGATTGGACACCAGCCCATG CAGTGTTTTTCCCTTGGCACAAAGTGTATTCCTGTAGACAGTAGTGGAGACCAGCAGCTGTGCTTGTTTTGAC AG |
| 7 | Intro 6-7 ENSE00001183236 | 1457 | 2,479 146 | gtgagactgtcttgtattagattga..........aagtaacttttatttttcctatag AGAATGGACTCTCTGTGGACACTCTTTGTCATCTCAATGGCTGGGAAGGTGCTCAATTCCCATACATGCACTAGAG GCCAGCACTGTGGACACTCTTTGTCATCTCAATGGCTGGGAAGGTGCTCAATTCCCATACATGCACTAGAG |
| 8 | Intro 7-8 ENSE00001105929 | 1603 | 15,288 133 | gtaacagaattaaatgccaagaac..........attttatttctctctcatttcag GCCGGATAGAAAATCGTCAGCTGGACACAGTAAATTCTTTTGAAGCAGAAATCTTTTAATCCATC CTCAAAATCTTCTGTATCTGATCAGTTGATCACTTGCATCCCATTATTATTAAGAA |
| 9 | Intro 8-9 | 1736 | 4,116 | gtaagtggaataaagatttctacat..........gttaatttcttgttcttcctccag |

TABLE 1-continued

Exon-intron boundaries of the human KIAA 1840 gene (according to the Ensembl database)

| No | Exon/Intron | Postition in SEQ ID NO: 1 | Length (bp) | Sequence |
|---|---|---|---|---|
| 9 | ENSE00001105933 | 1736 | 156 | ATGTGGAAGAGCTGATACCAGCATTGCTTCGGCAATTAGAGAAAGTTATTCTGAACCCCAAAGCAAACACTTTCAGAACATTGCTTAATCTTACTGTCTTCCTTAACAACCAAATAAAGGAGCTTTTCATTCACACTGAAG |
| 10 | Intro 9-10 ENSE00001105923 | 1892 | 388 176 | gtaagaatagcagctaggaagggg..........attggcacattgtatttccatagAACTAGATGAACATCTGCAAAAGGAGTGAACATTTTGACTAGCTACATTAATGAACTTCGAACCTTCATGATAAAGTTTCTTGGAAGCTAACAGATGCTATAGATGCTAGATGTACATGAAATGTCCCAAAGTAAAGGAGAGCAATATATGAAGAAACTCAGCTTTGAG |
| 11 | Intro 10-11 ENSE00001105941 | 2068 | 2,161 177 | gtaagtacgaataatcatcacttct..........aaggcaaacgttttctttcctagGAAGTTATTGCCAGCGCCATTTTAAACAACAAAATACCAGAGGCACAGACTTTCTTCAGGATTGATAGTCATTCTGCTCAAAAACTTGAGGAGCTTATTGGCATAGGCCTAAATTTGGTCTTTGACAATTTAAAAAGAACAATATAAAGGAAGCCTCTGAACTTTTGAAGAATATG |
| 12 | Intro 11-12 ENSE00001183220 | 2245 | 3,531 72 | gtgagtggtgtaatccataaagtct..........tttttgttttctatgttattttagGGGTTTGATGTAAAGGCCAATTGCTCAAGATCTGCTTCTATACAACTAATAAAAATATACGTGACTTTTG |
| 13 | Intro 12-13 ENSE00001183213 | 2317 | 380 128 | gtaggtaaagtgagactacatagt..........ctgctttaattacttttattcaagGTTGAAATTTTAAAGAAAAATTATTTTCTGAAAAAGAGAAAACATAGACTTCGTGCATCAAGTTGAGAAGCTTTATTGGGACATTTCCAAGAAAATATGCAAATCCAGTCATTTCCAG |
| 14 | Intro 13-14 ENSE00001183208 | 2445 | 285 176 | gtagtctcattagtcctcttttgat..........aaaaaatttatatcactgttttagGTACTGGATAAAGGAACAAGATTTTTTCAAGCACAAGTCTGTTTTGGACTCATTCTGAAATATGATTGTAAAGATGAATTTAACAACAGGACCATAGAATTGTGTTAAATTGGGCTCTGTGGTTTAAATGAGGTATCAACTAACACAAGAATCCATCCTTCTCCCCAGGATAAGTCCAGAAG |
| 15 | Intro 14-15 ENSE00001183204 | 2621 | 1,355 214 | gcaagtgtgagagagcctgaaatat..........ttaaaatgtgttttttcatgtagAATACAAATCATATTCCCCTGAAGCCCTCTGGAGATACCTCACAGCTCGCCATGATTGGTTAAACATTATCTTATGGATTGGAGAATTTCAAACCCAGCATAGTTATGCTTCACTTCAGCAGAACAAATGCCCCTTCTGACTGTTGATGTTATTAACCAGAATATCTTCCTGTAACAACTACATGAGGAATGAAATTTAGATAAGCTGGCCAG |
| 16 | Intro 15-16 ENSE00001047610 | 2835 | 4,623 204 | gtattataactgttgaactaatacc..........tgacatcctataaatcgtccatagGAATGGGGTTTTTTGGCATGTGAACTGGAAGACTTTGAAGACTTTGGAAGCTTCCTCCTAAGACTGAGCCCTATTGGAGTGTAATACAGGATACCCTCCCTGTTCAACAGACCAAGAAGGTGGGATTTCCATTCCAATTCATTCTCTATTGTTTGGAGACACAGTCTGCAGCATCTTCTTATGTCTACCTTGACTGTTACAA |
| 17 | Intro 16-17 ENSE00001287244 | 3039 | 1,826 107 | gtgagtactgagaatgcatttgtcc..........agttttgttgtttatatacagACTTAGTCTGAAAATTGCTCCTTTTTGAAAAAAAGAGTTACATGAAGCACACCCTTGGTTTGAATTTTTAGTTCAGTGTCGACAAGTTGCCAGTAACTTAACAG |
| 18 | Intro 17-18 ENSE00001047605 | 3146 | 2,444 146 | gtatgggtatactgttattaaacaca..........aaaaacactgtctttttatttcagATCCCAAACTGATCTTCCAGGCTAGCCTTGCAAATGCTCAGATTTTGATTCCCACCAATCAGGCCAGTGTAAGCAGTATGCTATTGGAAGGACATACCTCCTGGCCCTTGCTACTACAATGTATTCTCACTGTCAGTCAG |
| | Intro 18-19 | 3380 | 2,234 | gtatggtatactgtattatgacaaaa..........acctgttatctgtttttacttag |

TABLE 1 -continued

Exon-intron boundaries of the human KIAA 1840 gene (according to the Ensembl database)

| No | Exon/Intron | Position in SEQ ID NO: 1 | Length (bp) | Sequence |
|---|---|---|---|---|
| 19 | ENSE00001047617 | 3292 | 162 | GTTGTTCAGAATGAAGAAAATGAAAACTGTTGAAGAAAGTGGATCCCAGCTATTGAAGATGGCATTAACTCC TTACCCCAAGTCACTTAAAACTGCTCTCTTCCCACAGTGCACTCCTCCTGAGTGTCCTGCCATCTGATATTACAATCT ACCACCTTATTCAG |
| 20 | Intro 19-20 ENSE00001047612 | 3454 | 2,352 67 | gtacagtattaggtgccaatatt........ctgtttaacttttcccctttcag TCATTATCACCCTTTGATCCTAGCAGATTGTTTGGCTGGCAGTCTGCTAACACACTAGCTATAGGAG |
| 21 | Intro 20-21 ENSE00001047594 | 3521 | 5,392 166 | gtaagtcatcatggtactccttga........taatattgttacttccccctag ATGCGAGTCATCTCCACATTTCTAGCCCTGACCTGTAATAAATATGCTATAGTGAACGTCTGAAT TTTGCTTATTATTACATAATGGGCGGCCATCATTTGCATTTGTACTTTCTGCCAGGAATTAATCAAGAGC AAGACTCCCAAGCAGCT |
| 22 | Intro 21-22 ENSE00001047598 | 3687 | 1,630 206 | gtgagtattaaaatataattttgt........tgattttgattccttctttttcag GATCCAGCAAGTAGGCAATGAACCCTATGTTATAGGCTCTCTTCCTTCCACATACCTTCAATAGGACTGCA TGTGTTTGTTTTCTTAGAATTGCTTGGCCTTGACAGCCTCAGAGTTCAGAGTTGATATGAAGTGGCCAATATAAT TTTGAGCTACAAGTGCGAAAATGAAGATGCTCAGTACAGCTTATCAGAAGAGTCTGTAG |
| 23 | Intro 22-23 ENSE00001047622 | 3893 | 257 109 | gtacagcaccttttatctggcctgc........atttgttgttatattctacag CCGAAAAACTATCTAAACTAGCTGATGGTGAAAAGACAACCAGAAGAATTGCTTGTTCTCTTAGAAGAAGGT ACATGGAACAGCATTCAGCAACAGGAAATAAAGAG |
| 24 | Intro 23-24 ENSE00001047619 | 4002 | 1,321 160 | gtttgtgagttgcagtctcagcctc........cccccacctctaattctgattatag GTTATCCAGTGAATCTAGCAGCCAATGGGCATTAGTTGGTGCAGTTCTGCAGGCTACACAATATGAAACTAAGC ATATCTTACCTTAGAGAATGTCCAAAGCAATGATTGGCTGCAGTTCAGTTCATTATTCAGCAACTCCACAACTA CCACCCAGCAGAG |
| 25 | Intro 24-25 ENSE00001047603 | 4162 | 428 273 | gtaagcactaattgttagcagtca........tttaatcatctgatatgcctctag GTGAAATCCCTATCCAGTACTTCAGCCCAGTCATTCAGAACACTTAAGGCTGGCTTTTGAACTTGCCCTC AGTGCCCACCCTGCAAAATGGACAGCGATCAAGTCTGCAATAAGTGCCCCAGGAACTTCAAGGAAGCAAACAA GAGATGACCGATTTATTTGAAATTCTGCTCCAATGCTCAGAGGACCAAATGTAGTAGCAGTTGGCACTGCTTCTGGTTG AAGCAGTGAAACAACAGGCCCCTATCCTCCAGTGTTCTGGCCTCATGTCTCCAG |
| 26 | Intro 25-26 ENSE00001047590 | 4435 | 623 201 | gtgaggatcatgagaagcctgaagt........tgttattttattttatcccgtgcag GGTTCCAGTGCCATTCTTCGTCCTGTGTTTTGGATCATCACTTCTGTGGAGGACAATGTTGCAACTGAAGCAAT GGGACACACATTCAGACTCAACAGAGACCATACCTGGAACTTCATCAGAGGATCTTTCAGTCATCTGGAGAACATTA TTAACAGACAAAAGACCAAAACTCTCATCAGAGGTTTCCAGCTTTTCTTTAAG |
| 27 | Intro 26-27 ENSE00001047613 | 4636 | 2,820 108 | gtagtgatagttgcttcacttctt........atttttttcaaactcttttgtcaaag GATTCCCCGTTACTGGTGATGGAGATGTATGAACTGTGTTCTTCAGGAATTATAAAGAAGCTGAAGC TAAACTTCTGGAGTTTCAGAAGAGCCTTGAAACG |
| 28 | Intro 27-28 ENSE00001047595 | 4744 | 2,916 163 | gtaagttggaattatgtgctcttt........ctaagcttctcttttcttcatag CTTAACACAGCAGCCACCAAAGGTCCACCCTGTCATCCCTGCCATGTCGGAGGATCAGGTGTGTTCCTTT TGAAGCTTATGCTACACAGTGTAAGACCCCAGTATGAGCTGGGAAGCTTTTACAGCTCTTTGTTGAAAGAGA GCATCTCTTCTGATG |
| 29 | Intro 28-29 | 3,401 | | gtaagacaatcctacagtaagtt........ttatatccttttcttggcacag |

TABLE 1 -continued

Exon-intron boundaries of the human KIAA 1840 gene (according to the Ensembl database)

| No | Exon/Intron | Position in SEQ ID NO: 1 | Length (bp) | Sequence |
|---|---|---|---|---|
| 29 | ENSE00001047608 | 4907 | 215 | GTCCAGATGTGAAAAGCTTTGCATCCTTTGCCAGATTTGAAGGATACATCCATAGCCATTAATCATACAATTA<br>TTACCAGCTACGACATTGAGAATCTTCAGCATGAATGTGATCTATTTTGAAAGACTGCAGACAGATGGACAA<br>TTCGCTTTGGCCAGGAGGGTAGCAGAATTAGCTGAGTTACCTGTGGACAACTTGGTTATTAAAGAG |
| 30 | Intro 29-30<br>ENSE00001047607 | 5122 | 1,077<br>745 | gtatcatcggtctcttttttttttt...........aatctgctttgttaaatttcacag<br>ATAACACAGGAAATGCAGACCCTAAAACACATTGAACACAGTGGTCACTAAAACAAGCAAGAATTGACTTCTGAA<br>AAAATGCCATGACAGAATTTTAAGAAAAATTCAATTTCAAGCAAAAGCAGCTTCTTCCTTTTTCAACCCAGGCCCA<br>TGTGGCATGTGAGCACCCAACTGGATGGAGCAGCATGAGGAGCGCCATTCTGCTGCTCACCTTGGCAGGGC<br>ACTGGCTTGCCCAGGAGGACGTGTGCCCTTGGATAAGCTGGAGGAGCTGGAGGAAGCAGATCTGGCTGTGC<br>CGCATCACCCAGCACACTCTTGATAGTTTAGCCAGTGAGTTTTCCTTCTCCAAGTTGGCTCTGCTGAACACATCAAAA<br>GTGGTGAACTTTCCTTTGATAGTTTAGCCAGTGAGTTTTCCTTCTCCAAGTTGGCTCTGCTGAAAAGACCAGAGTCAC<br>TACTTAGAACTTAACAGCCTTCCATCCAAAGAGACATGCGAGAATAGATTGGATTGGAAAGAGACAGGAGTCAC<br>TAAACTTTTTGATTGGGCCTACTGGATGATGGCTGTGCATGAAGCAAGTAGAGTATGCCGTATTTTCAT<br>TTTTATAATCCAGATGTCGCCTTGGTATTGCACTGCACAGACACTGGCCTCAGGGAGAAGCTAGTATGGAGGATC<br>TGCACCCAGATCCATGCTCTCCTACAAAGTGCTGAGCTGCTTGAGGAGAAGCACCCGACATTCCCTAAG<br>GAGAGTCCACAGCA |
| 31 | Intro 30-31<br>ENSE00001047614 | 5867 | 8,772<br>140 | gtaagtgaaggagatcagatggccc..........ccctcagactgtattgcttccag<br>CTTCAAGTCTGATAGTCAGAGTTTGTGACAGTGCCCTCCAGTAATGAAGTGGTAACTAACCTGGAAGTGCT<br>GACAAGCAAATGCCTCCATGGGAAGACTACTGTCGACAGGTTCCTCTGTCTGTATGATCTTGCCAAG |
| 32 | Intro 31-32<br>ENSE00001123435 | 6007 | 1,156<br>199 | gtatgtgccaagggtgggctcct..........ttgactggctttgtcttcctctcag<br>GAGTTGGGCTGTTCCTACACAGATGTTGCTGCTCAGGATGGTGAAGCCATGCTCCGGAAAATCTTGGCCTCTC<br>AGCAGCCTGACCGATGCAAACAGCCCAGGCCTTCATCAGCACACAGGCCTTAAGCACAGATACTGTGGCTG<br>AACTCGTGCAGAAGAGGTGACGTGCCAGCTGCTTACTTCATCACAGGGAACAG |
| 33 | Intro 32-33<br>ENSE00001123426 | 6206 | 726<br>138 | gtgccctaccccgggattccaa..........cctgtcttcacacctctgtacag<br>GACATAAGCAGATGTTCAACCAACAGAGGAAAGCCAGACATTTCTTCAGCTGACCACTCTGTCAAGACCG<br>CACATTGGTAGGCATGAAGTTGTTGGATAAGAATTTCCTCCGTTCCCATGGGAACTGTCTTGCA |
| 34 | Intro 33-34<br>ENSE00001123415 | 6344 | 2,024<br>134 | gtaagttattgacctttcttaca..........atcttaccagtgccaccctccag<br>CCACAGAGCTCTGATCCTGGCCCATATTGTTCACCCTGACGTGCCACATGGAGGGCATCATCCGAGTCC<br>TACAGGCCGCCGCCACATGCTCACAGATAACCACCTGGGCCCAGTGAGGAGTATGGGCTGGTG |
| 35 | Intro 34-35<br>ENSE00001123405 | 6478 | 1,019<br>108 | gtaagtagccccctcaaccccagtc..........tgcgagctgtcctccacttcacag<br>GTACGGCTTCCTCACTGGCATTGAAGGTACACACGAGATGACATACATATTTGATTTGCTGCATAAAAAGCACTA<br>CTTTGAAGTGCTAATGAGGAAGAAGTTGGATCCG |
| 36 | Intro 35-36<br>ENSE00001123397 | 6586 | 1,805<br>169 | gtaggtgcaaagtaatgagctccag..........gctttttccctttattctggcag<br>AGTGGTACCCTGAAAACAAGCCCTGCTGACTACATCAAAACGCTGCCTCCTGGAGACAGTGAAAAGCACAAT<br>ATGATTGCCTGCTTCAGCATGTGCCGGAGATTGCGAGAACCACGAGGCAGCTGCCCGCATCCAACTG<br>AAATTGATTGAGTCTCAGCCTGG |
| | Intro 36-37 | | 1,118 | gtgagtgaggtcacagccacactac..........caaatcttctttattccccctacag |

TABLE 1 -continued

Exon-intron boundaries of the human KIAA 1840 gene (according to the Ensembl database)

| No | Exon/Intron | Position in SEQ ID NO: 1 | Length (bp) | Sequence |
|---|---|---|---|---|
| 37 | ENSE00000684756 | 6755 | 89 | AGGACAGCCTCAAGGATGGGCACCAGCTGAAACAACTGCTGCTGAAGGCCCTGACTCTGATGTTGGATGCAG<br>CAGAGAGTTATGCCAAG |
| 38 | Intro 37-38<br>ENSE00000684735 | 6844 | 207<br>156 | gtaaccaaaggcttttttcagact.........gtgcctctccaccctgttcctcag<br>GACTCCTGTGTGCGACAGGCCCAGCACTGTCAGCGGCTCACCAAGTTGATAACTCTGCAGATTCACTTTCTGA<br>ACACTGGCCAGAACACATGCTCATCAACTTGGGCCGCCACAAGCTGATGGACTGTATTCTGCCCTACCTCG<br>GTTCTACCAG |
| 39 | Intro 38-39<br>ENSE00000684706 | 7000 | 1,155<br>152 | gtgagcaagaaagcaaactgtagcc.........gtccttcttcacctctccttttaag<br>GCTTCTATTGTGCTGAGGCCTGACGATTTGTTCCAGATTGGGCTGAAATTTTATACCAGCAAGTGATTCTTAA<br>AGGAGACTTTAATTACTTGGAAGAATTAAGCAGCAAAGGTTATTAAAGTCCAGTATATTTGAAGAGATTCCAA<br>AAA |
| 40 | Intro 39-40<br>ENSE00000884381 | 7152 | 1,245<br>600 | gtaagtattaaaagttgactgtaaa.........ctgtacattatgtttctttatctag<br>ATATAAACAACATCAGCTACTGCATACGACATGGTCATGACAACAAGTTTATGGAAAATCTACCATATTGTGAAGAATGTTTA<br>CCTGTATTACAAGTTGGCATACGAACGACAAGTTGAAATTGTAAATGTCTTCTGAAGGACCCTCAGACAG<br>GTTGCTGTCTAAAGGACAATGCTAGCAGTCTAGCAGTTAGATGATTTCATAGGTGTCTGTTTTCTTGTACTGTTAGCAGATT<br>CTGACAGATGTGATGAGAAGAATGCATTGAAGTAGCAAGAATCCCGGTACTGTACCATA<br>TCAGTCCTTTGTGGGTAGTAGTGAGAAGTAAGAATGCATTGAAGGAGGAAATTCCTATTTAAAATAGATTGATTT<br>TAGATGATTGTTCATCCACACATTTATATAGATAGATACTCAAAAGCTTCCTCTTCCTCAGGACAG<br>CTTCTACTTTAGATGATCCAATAATGATTAAAGAATACCTGTACCTGCAGATTTCCAGTTTCAAGAAATTTAATTA<br>TTATTACACAGTTAAGAACAGGTGATACATTTCATTTGTTAGAACTGATCTTTCTGTAATAAAATAGATTTT<br>C |
| | 3' downstream sequence | | | aattcagtgtatgtcattattactgctgaaggaaatcttagccctgctg......... |

As used herein, the term "Spatacsin" denotes the SPAsticity with Thin or Corpus callosum Syndrom protein, which is encoded by the KIAA1840 gene. The sequence of the human form is shown in SEQ ID NO:2.

The terms "mutant" and "mutation" mean any detectable change in genetic material, e.g. DNA, RNA, cDNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. Generally a mutation is identified in a subject by comparing the sequence of a nucleic acid or polypeptide expressed by said subject with the corresponding nucleic acid or polypeptide expressed in a control population. A mutation in the genetic material may also be "silent", i.e. the mutation does not result in an alteration of the amino acid sequence of the expression product.

In the context of the instant application, mutations identified in KIAA1840 gene are designated pursuant to the nomenclature of Den Dunnen et al. 2001 (http://www.genomic.unimelb.edu.au/mdi/mutnomen/). As defined by Dunnen and Antonarakis at the nucleic acid level, substitutions are designated by "c.position(nt)>(nt)", e.g. "c.118C>G denotes that at nucleotide 118 of the reference sequence C is changed to a G. The mutation at the protein level is denoted p.Q40X: which means that a glutamine (Q) at position 40 encoded by CAG is replaced by a STOP (TAG) codon (Q40X). Deletions are designated by "del" after the deleted interval (followed by the deleted nucleotides). For instance 529_533delATATT denotes a ATATT deletion from nucleotides 529 to 533. The consequence of this deletion, p.I177_F178delfsX, is a deletion of aminoacids at positions 177 and 178 and a frameshift (fs) in the coding sequence leading to the appearance of a premature STOP codon (X). An alternative nomenclature is to indicate the position of the stop codon in the resulting protein after the X; p.I177_178 delfsX178 indicates that the stop codon resulting from the mutation is at codon 178. Insertions are designated by "ins," followed by the inserted nucleotides. For example, c.7029_7030 insT denotes that a T was inserted after nucleotide 7029. This leads to the replacement of valine (V) by cysteine (C) at position 2344 and to a frameshift of the coding sequence and a premature STOP codon at amino-acid 2349 (fsX): p.V2344CfsX or p.V2344CfsX2349. When a mutation is predicted to alter the splicing of the mRNA because the variant modifies a nucleotide of the consensus sequence for splicing (acceptor or donor site), the "r.?" denotes that the consequences of the mutation could not be checked at the RNA level, but is likely (as verified at http://rulai.cshl.edu/new_alt_exon_db2/HTML/score.html).

The term "hereditary spastic paraplegias (HSP)" denotes genetically heterogeneous Mendelian disorders characterized by weakness, spasticity and loss of vibratory sense in the lower limbs. The term "Autosomal Recessive Hereditary Spastic Paraplegia" or "AR-HSP" denotes spastic paraplegia that is transmitted as an autosomal recessive trait. Patients with HSP or AR-HSP can have a pure phenotype, or, more often, a complex phenotype that associates various neurological signs (cerebellar ataxia, mental retardation, peripheral neuropathy, etc). The term "AR-HSP-TCC" denotes an AR-HSP with Thin Corpus Callosum usually associated with, mental or cognitive deficit and peripheral neuropathy. Families without proved TCC can also be mutated in this gene either because of slow progression of the disease in the patient or because magnetic resonance imaging (MRI) couldn't be performed due to patient refusal or impossibility (patients leaving far from cities in North-Africa—this is the case for families FSP400, FSP393 and FSP343).

As used herein, the term "subject" denotes a mammal, such as a rodent, a feline, a canine, and a primate. Preferably a subject according to the invention is a human.

Mutations in the KIAA1840 Gene and Spatacsin Protein

The inventors identified various mutations in the KIAA1840 gene.

Fortythree different mutations on human KIAA1840 gene were indeed identified in 47 families, including the 16 linked ones, all at the homozygous state, except in 16 kindreds. They were either nonsense mutations (n=13), deletions (n=17), insertions (n=7), or splice site mutations (n=6) in the coding sequence, and resulted theoretically in an abnormally spliced mRNA or a truncated protein in all cases.

In one family, linked with a maximal 3.1 multipoint lod score to SPG11, a missense R945G mutation segregated at the homozygous state in both patients and was not detected in 150 control chromosomes. The mutation is probably not only affecting the nature of the amino-acid. Position of this variant was in the 5'-splice site consensus sequence (2 bases before the end of exon 15). The score of the 5'-splicing sequence changed from 4.9 for the wild type to 2.7 for the variant (Alternative Splicing Database: http://rulai.cshl.edu/new_at_exon_db2/HTML/score.html) suggesting that this variant could act at both the RNA level (splicing effect) and at the protein level (missense change). Indeed, this was confirmed by direct sequencing (using primers GCTCTGTGGTGGGATCAACT and TGCTTACACTGGCCTGATTG) on mRNA isolated from lymphoblasts of an affected family member (FSP670-5) in which an alternative splice site is generated downstream in intron 15 leading to a 65 bp insertion and a premature stop codon (c.2833A>G, r.2834+1_2834+65 ins, p.R945GfsX950). It cannot be excluded, however, that splicing occurs at its normal place in a small amount of messenger RNA and that a full length protein is generated with the G variant at position 945. Similarly, the mutation c.2444G>T, p.R815M likely affects not only the amino-acid but also splicing of exon 13 since the splice score down from 3.7 to 0.2 for the mutation. In addition, the c.869+1G>A, c.2316+1G>A, c.2444+1G>C and c.6477+4A>G, are all clearly affecting the acceptor splicing consensus sequence (see splice scores in table 2) and likely alter the splicing of exons 4, 12, 13 and 34, respectively. The mutations identified by the inventors are presented on the following Table 2.

TABLE 2

Mutations identified in the KIAA1840 CDS (SEQ ID NO: 1) and protein (SEQ ID NO:2)

| Exons | Nucleotide variants | mRNA or Protein variants | SEQ ID NO: | Family code (Origins) at the homozygous state | Family code (Origins) at the heterozygous state |
|---|---|---|---|---|---|
| 1 | c.118C>T, | p.Q40X | 149 | FSP672 (Israel) | |
| 3 | c.529_533delATATT | p.I177_F178>S177fsX178 | 150 | FSP386 (Portugal) FSP754 (Portugal) FSP831 (Portugal) | ITA17 (Brazil) |
| 4 | c.704_705delAT | p.H235RfsX246 | 166 | SPD199 (Turkey) | |
| 4 | c.733_734delAT, | p.M245VfsX246 | 151 | TUN2 (Tunisia) TUN3 (Tunisia) TUN4 (Tunisia) TUN22 (Tunisia) | FSP117 (France) |
| Intron 4 | c.869+1G>A | r.? Splice score down from 9.8 to −0.9 | | FSP847 (Argentina) | |
| 6 | c.1203delA, | p.K401KfsX415 | 152 | | PE (Italy) |
| 6 | cv.1235C>G, | p.S412X | 153 | FSP393 (Portugal) | |
| 6 | c.1282A>T | p.K428X | 167 | | FSP830 (Portugal) |
| 7 | c.1471_1472delCT | p.L491DfsX556 | 168 | | FSP522 (France) |
| 7 | c.1549_1550delCT, | p.L517LfsX556 | 154 | | FSP343 (Algeria) (non typical) |
| 8 | c.1668delT | p.F556LfsX577 | 169 | | SAL646 (France) |
| 8 | c.1679C>G | p.S560X | 170 | | ITA16SB (Italy) |
| 8 | c.1692delA | p.V564VfsX577 | 171 | | DKD (Italy) |
| 10 | c.1951C>T, | p.R651X | 155 | | MP (Italy) FSP683 (Romania) ITA28VAC (Italy) |
| 11 | c.2198T>G, | p.L733X | 156 | OS (Italy) | |
| Intron 12 | c.2316+1G>A | r.? Splice score down from 6.2 to −4.5 | | FSP892 (Norway) | |
| 13 | c.2444G>T | p.R815M and/or r.? Splice score down from 3.7 to 0.2 | 172 | | ITA28VAC (Italy) |
| Intron 13 | c.2444+1G>C | r.? Splice score down from 3.7 to −7 | | | ITA16 (Brazil) |
| 15 | c.2697G>A | p.W899X | 173 | ITA10 (Italy) | |
| 15 | c.2716delC | p.Q906SfsX920 | 174 | ITA9 (Italy) | |
| 15 | c.2833A>G, | r.2834+1_2834+65ins, p.R945G or p.R945GfsX950 Splice score down from 4.9 to 2.7 | 165 188 | FSP670 (Israel) | ITA14 (Italy) |
| 16 | c.2842_2843insG, | p.V948GfsX953 | 157 | | PE (Italy) |
| 16 | c.2850_2851insT, | p.L950FfsX953 | 158 | | MP (Italy) |
| 17 | c.3075_3076insA | p.E1026RfsX1029 | 175 | | ITA8 (Germany) |
| 22 | c.3741_3742insA | p.P1248TfsX1264 | 176 | | ITA17 (Brazil) |
| 25 | c.4307_4308delAA | p.Q1436RfsX1442 | 177 | | FSP398 (Israel) ITA16 (Brazil) |
| 30 | c.5470C>T | p.R1824X | 178 | | ITA8 (Germany) |
| 30 | c.5532_5533delCA | p.S1844SfsX1857 | 179 | | FSP522 (France) |
| 30 | c.5769delT | p.S1923RfsX1950 | 180 | FSP838(Saudi-Arabia) | |
| 31 | c.5870C>G | p.S1957X | 181 | | ITA16SB (Italy) |
| 31 | c.5974C>T, | p.R1992X | 159 | | FSP117 (France) |
| 31 | c.5982_5983insCTCT | p.L1995LfsX2000 | 182 | | DKD (Italy) |
| 31 | c.5986_5987insT | p.C1996LfsX1999 | 183 | | FSP398 (Israel) |
| 31 | c.5989_5992delCTGT | p.L1997_Y1998>M1997fsX2056 | 184 | | FSP683 (Romania) |
| 32 | c.6091C>T | p.R2031X | 185 | ITA1 (Turkey) | |
| 32 | c.6100C>T, | p.R2034X | 160 | FSP446 (Morocco), FSP221 (Algeria), FSP732 (Algeria), FSP400 (Algeria) FSP792 (Algeria) FSP845 (Morocco) TUN9 (Tunisia) TUN12 (Tunisia) TUN14 (Tunisia) | |
| 34 | c.6451delG, | p. A2151 P fsX2172 | 161 | SAL1608 (France) | |
| Intron 34 | c.6477+4 A>G | r.? Splice score down from 9.6 to 6.6 | | | FSP830 (Portugal) |
| 36 | c.6737_6740delTTGA, | p.I2246_E2247>S2246fsX2260 | 162 | FSP920 (Japan) | FSP343 (Algeria) |

TABLE 2-continued

Mutations identified in the KIAA1840 CDS (SEQ ID NO: 1) and protein (SEQ ID NO:2)

| Ex- ons | Nucleotide variants | Mutations mRNA or Protein variants | SEQ ID NO: | Family code (Origins) at the homozygous state | Family code (Origins) at the heterozygous state |
|---|---|---|---|---|---|
| 36 | c.6739__6742delGAGT | p.E2247__S2248>L2247fsX2260 | 186 | | SAL646 (France) |
| 37 | c.6832__6833delAG, | p.S2278LfsX2338 | 163 | FSP75 (Portugal) | |
| 38 | c.6856C>T | p.R2286X | 187 | | ITA14 (Italy) |
| 39 | c.7029__7030insT, | p.V2344CfsX2349 | 164 | FSP515 (Tunisia) | |

Each mutation are herein numbered according to human KIAA1840 CDS and amino acid sequence as shown in SEQ ID NO: 1 and SEQ ID NO:2.

Accordingly, the invention relates to an isolated nucleic acid specifically hybridizable to a region of KIAA1840 gene coding sequence (SEQ ID NO:1) that contains a mutation selected from the group consisting of the substitutions c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T and c.5974C>T, the deletions: c.529-533delATATT, c.6451delG, c.6832_6833 delAG, c.1203delA, c.1549_1550 delCT, c.6737_6740 delTTGA, c.1471_1472 delCT, c.1692delA, c.2716delC, c.1668delT, c.704_705delAT, c. 5989_5992delCTGT, c. 5532_5533delCA, c.5769delT, c.6739_6742delGAGT, c.4307_4308 delAA and c. 733_734delAT, and the insertions: c.7029_7030insT, c.2850_2851insT, c.3741_3742insA, c. 5982_5983insCTCT, c. 5986_5987insT, c. 3075_3076insA and c.2842_2843insG.

In one embodiment of this aspect of the invention, the isolated nucleic acid according to the invention consists of at least 10 nucleotides, preferably 20 nucleotides, more preferably 40 nucleotides.

In a preferred embodiment, such an isolated nucleic acid is specifically hybridizable to a region consisting of 10 nucleotides upstream and 10 nucleotides downstream of a mutation selected from the group consisting of the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T c.5974C>T, the deletions: c.529-533delATATT, c.6451delG, c.6832_6833 delAG, c.1203delA, c.1549_1550 delCT, c.6737_6740 delTTGA, c.1471_1472 delCT, c.1692delA, c.2716delC, c.1668delT, c.704_705delAT, c. 5989_5992delCTGT, c. 5532_5533delCA, c.5769delT, c.6739_6742delGAGT, c.4307_4308 delAA c. 733_734delAT, and the insertions: c.7029_7030insT, c.2850_2851insT, c.3741_3742insA, c. 5982_5983insCTCT, c. 5986_5987insT, c. 3075_3076insA c.2842_2843insG, of the KIAA1840 gene sequence.

Preferably, "specifically hybridizable" means "hybridizable under conditions at 68° C. in 0.2×SSC, at 42° C. in 50% formamide, 4×SSC, or under conditions that afford levels of hybridization equivalent to those observed under either of these two conditions".

In an alternative manner, a sequence "specifically hybridizable" to a target sequence means a sequence showing a percentage of sequence identity with the sequence complementary of said target sequence of at least about 70%, preferably at least about 80%, more preferably at least about 90%, most preferably at least about 95%.

Said nucleic acid according to the invention may be an oligonucleotide.

Preferably, said nucleic acid or oligonucleotide is complementary to a region of the KIAA1840 gene that contains at least one of the identified mutations.

In one embodiment of this aspect of the invention, the isolated nucleic acid according to the invention consists of at least 10 nucleotides, preferably 20 nucleotides, more preferably 40 nucleotides.

Such a nucleic acid according to the invention may advantageously be used as a primer or probe.

A further object of the present invention relates to an isolated nucleic acid, which comprises or consists in a KIAA1840 gene coding sequence (SEQ ID NO:1) that contains one or several mutation(s) selected from the group consisting of the substitutions: c.6100C>T, c.2198T>G, c.118C>T, c.1235C>G, c.2833A>G, c.1951C>T, c.869+1G>A, c.1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T c.5974C>T, the deletions: c.529-533delATATT, c.6451delG, c.6832_6833 delAG, c.1203delA, c.1549_1550 delCT, c.6737_6740 delTTGA, c.1471_1472 delCT, c.1692delA, c.2716delC, c.1668delT, c.704_705delAT, c. 5989_5992delCTGT, c. 5532_5533delCA, c.5769delT, c.6739_6742delGAGT, c.4307_4308 delAA c. 733_734delAT, and the insertions: c.7029_7030insT, c.2850_2851insT, c.3741_3742insA, c. 5982_5983insCTCT, c. 5986_5987insT, c. 3075_3076insA c.2842_2843insG or a sequence complementary thereto.

In one embodiment of this aspect of the invention, the isolated nucleic acid according to the invention consists of at least 10 nucleotides, preferably 20 nucleotides, more preferably 40 nucleotides.

In another embodiment, the invention relates to an isolated polypeptide which comprises the polypeptide sequence of KIAA1840 containing one or several mutation(s) selected from the group consisting of p.Q40X, p.I177_F178delfsX178, p.H235RfsX246, p.M245VfsX246, p.K401KfsX415, p.S412X, p.K428X, p.L491DfsX556, p.L517LfsX556, p.F556LfsX577, p.S560X, p.V564VfsX577, p.R651X, p.L733X, p.R815M, p.W899X, p.Q906SfsX920, p.R945G, p.R945GfsX950, p.L950FfsX953, p.V948GfsX953, p.E1026RfsX1029, p.P1248TfsX1264, p.Q1436RfsX1442, p.R1824X, p.S1844SfsX1857, p.S1923RfsX1950, p.S1957X, p.R1992X, p.L1995LfsX2000, p.C1996LfsX1999, p.L1997_1998 delfsX2056, p.R2031X, p.R2034X, p.A2151 PfsX2172, p.I2246_E2247delfsX2260, p.E2247_S2248delfsX2260, p.S2278LfsX2338, p.R2286X and p.V2344CfsX2349.

Diagnostic Method

The inventors have further shown that KIAA1840mutants are associated with a hereditary spastic paraplegias (HSP) which is characterized by weakness, spasticity and often loss of vibration sense in the lower limbs. More particular, the inventors have shown that KIAA1840 mutations as above described correlate in all patients with mild mental impairment, a thin corpus callosum (TCC) (AR-HSP-TCC) and frequent polyneuropathy (72% of the patients) in a series of 45 families with the full clinical criteria of SPG11. In the 2 other kindreds, cerebral imaging was not available to verify the presence of a thin corpus callosum (TUN2 and TUN14).

Therefore the invention provides an ex vivo method of diagnosing or predicting a hereditary spastic paraplegia (HSP) in a subject, which method comprises detecting a mutation in the KIAA1840 gene or protein (spatacsin), as compared to a control population, wherein the presence of a mutation is indicative of an hereditary spastic paraplegia (HSP).

Nucleic Acids Assays:

According to a first embodiment the mutations may be detected by analysing a KIAA1840 nucleic acid molecule. In the context of the invention, KIAA1840 nucleic acid molecules include mRNA, genomic DNA and cDNA derived from mRNA. DNA or RNA can be single stranded or double stranded. These may be utilized for detection by amplification and/or hybridization with a probe, for instance.

Thus the invention provides an ex vivo method of diagnosing or predicting a hereditary spastic paraplegia (HSP), in a subject, which method may comprise the step consisting of detecting a KIAA1840 mutation in a nucleic acid sample obtained from the subject, wherein the presence of a mutation is indicative of a hereditary spastic paraplegia (HSP).

The nucleic acid sample may be obtained from any cell source or tissue biopsy. Non-limiting examples of cell sources available include without limitation blood cells, buccal cells, epithelial cells, fibroblasts, or any cells present in a tissue obtained by biopsy or post-mortem. Cells may also be obtained from body fluids, such as blood, plasma, serum, lymph, etc. DNA may be extracted using any methods known in the art, such as described in Sambrook et al., 1989. RNA may also be isolated, for instance from tissue biopsy, using standard methods well known to the one skilled in the art such as guanidium thiocyanate-phenol-chloroform extraction (Chomocyznski et al., 1987).

A KIAA1840 mutation according to the invention may be found and located in many exons, including exon 1 and exon 39 (Table 2).

KIAA1840 mutations may be detected in a RNA or DNA sample, preferably after amplification. For instance, the isolated RNA may be subjected to coupled reverse transcription and amplification, such as reverse transcription and amplification by polymerase chain reaction (RT-PCR), using specific oligonucleotide primers that are specific for a mutated site or that enable amplification of a region containing the mutated site. According to a first alternative, conditions for primer annealing may be chosen to ensure specific reverse transcription (where appropriate) and amplification; so that the appearance of an amplification product be a diagnostic of the presence of a particular KIAA1840 mutation. Otherwise, RNA may be reverse-transcribed and amplified, or DNA may be amplified, after which a mutated site may be detected in the amplified sequence by hybridization with a suitable probe or by direct sequencing, or any other appropriate method known in the art. For instance, a cDNA obtained from RNA may be cloned and sequenced to identify a mutation in KIAA1840 sequence.

Actually numerous strategies for genotype analysis are available (Antonarakis et al., 1989 Cooper et al., 1991 Grompe, 1993). Briefly, the nucleic acid molecule may be tested for the presence or absence of a restriction site. When a base substitution mutation creates or abolishes the recognition site of a restriction enzyme, this allows a simple direct enzymatic test for the mutation. Further strategies include, but are not limited to, direct sequencing, restriction fragment length polymorphism (RFLP) analysis; hybridization with allele-specific oligonucleotides (ASO) that are short synthetic probes which hybridize only to a perfectly matched sequence under suitably stringent hybridization conditions; allele-specific PCR; PCR using mutagenic primers; ligase-PCR, HOT cleavage; denaturing gradient gel electrophoresis (DGGE), temperature denaturing gradient gel electrophoresis (TGGE), single-stranded conformational polymorphism (SSCP) and denaturing high performance liquid chromatography (DHPLC) (Kuklin et al., 1997). Direct sequencing may be accomplished by any method, including without limitation chemical sequencing, using the Maxam-Gilbert method by enzymatic sequencing, using the Sanger method mass spectrometry sequencing sequencing using a chip-based technology (see e.g. Little et al., 1996); and real-time quantitative PCR. Preferably, DNA from a subject is first subjected to amplification by polymerase chain reaction (PCR) using specific amplification primers. However several other methods are available, allowing DNA to be studied independently of PCR, such as the rolling circle amplification (RCA), the InvaderTMassay, or oligonucleotide ligation assay (OLA). OLA may be used for revealing base substitution mutations. According to this method, two oligonucleotides are constructed that hybridize to adjacent sequences in the target nucleic acid, with the join sited at the position of the mutation. DNA ligase will covalently join the two oligonucleotides only if they are perfectly hybridized (Nickerson et al., 1990).

The inventors designed a series of primers, manually or using Oligo6 (MBI, Cascade, Colo.), in order to amplify all coding exons of 18 genes from the candidate interval (primers and conditions available on request), including the mutated KIAA1840 gene (see Table 4). PCR-amplified fragments of genomic DNA were then purified using exonuclease 1 (New England Biolabs, 2 U/5 µl PCR product) and shrimp alkaline phosphatase (Roche, 1 U/5 µl of PCR product) and sequenced using the fluorescent dideoxy-terminator method (BigDye v3, Applied Biosystem) on an automated ABI-3730 sequencer according to the manufacturer's recommendations. With the use of the software package SeqScape (Applied Biosystems), sequences were aligned and compared to consensus sequences.

Protein Assays

According to a second embodiment said mutation may be detected in KIAA1840 protein or a truncated form of the KIAA1840 protein may be detected, as compared to a control population.

Figure 5:
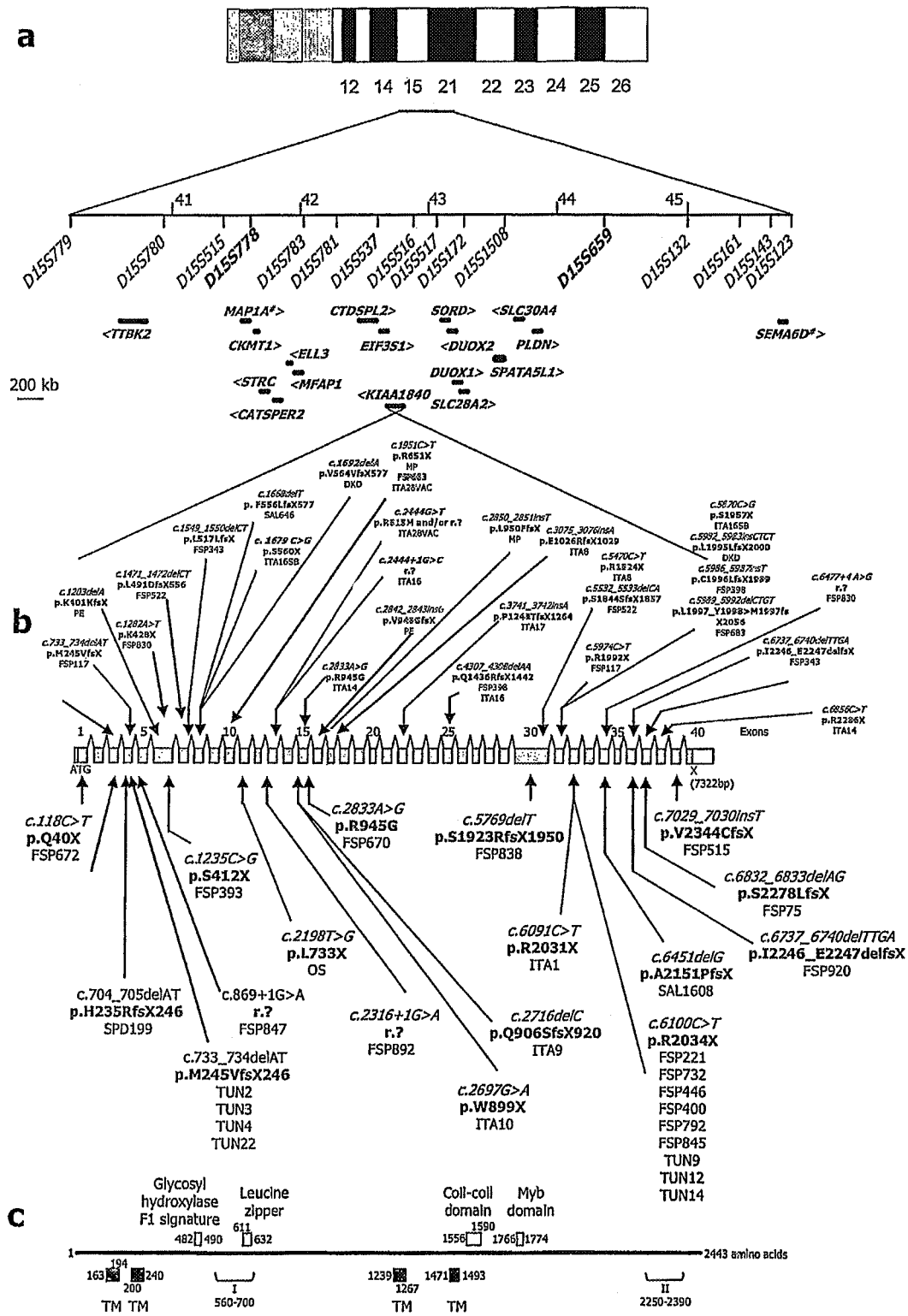

All of the identified mutations of the KIAA840 gene create some deletions of the C-terminal part of the spatacsin protein, in some cases because of aberrant splicing (FIG. 5). These deletions result in truncated proteins of sequences SEQ ID NO: 149 to SEQ ID NO:164 and SEQ ID NO:166 to SEQ ID NO:188, respectively. Those due to aberrant splicing, either very likely, could not be precised because the modification of the splicing could not be evidenced in mRNA directly, except in family FSP670 (r.2834+1_2834+ 65 ins, p.R945GfsX950). It can not be excluded, however, that a shorten protein fragment may be synthesized due to the activation of new ATGs after the stop codon.

Said mutation may be detected according to any appropriate method known in the art. In particular a sample, such as a tissue biopsy, obtained from a subject may be contacted with antibodies specific of the mutated form of KIAA1840 protein, i.e. antibodies that are capable of distinguishing between a mutated form of KIAA1840 and the wild-type protein (or any other protein), to determine the presence or absence of a KIAA1840 specified by the antibody. An antibody recognizing the wild type protein could also be used to check the presence of the protein or its abnormal location or size and could then be used as a diagnostic tool as well.

Antibodies that specifically recognize a mutated KIAA1840 protein also make part of the invention. The antibodies are specific of mutated KIAA1840 protein, that is to say they do not cross-react with the wild-type KIAA1840 protein.

A monoclonal or polyclonal antibody recognizing the wild-type KIAA1840 protein may be used to detect the presence of the wild-type protein or one of its truncated forms. For instance, an antibody recognizing the N-terminal part of the wild-type KIAA1840 protein may also recognize one or several truncated forms and can be used to reveal by immunoblotting, the different forms, wild-type and truncated, according to their molecular weights. An antibody recognizing the wild-type KIAA1840 protein, but not recognizing the truncated forms, can be used for immunoblotting or in immunoassay as ELISA; in that case, an absence of signal reveals the presence of a truncated form in the sample or the absence of synthesis of a stable protein as compared with a positive control comprising the wild-type KIAA1840 protein.

The antibodies of the present invention may be monoclonal or polyclonal antibodies, single chain or double chain, chimeric antibodies, humanized antibodies, or portions of an immunoglobulin molecule, including those portions known in the art as antigen binding fragments Fab, Fab', F(ab')$_2$ and F(v). They can also be immunoconjugated, e.g. with a toxin, or labelled antibodies.

Whereas polyclonal antibodies may be used, monoclonal antibodies are preferred for since they are more reproducible in the long run.

Procedures for raising "polyclonal antibodies" are also well known. Polyclonal antibodies can be obtained from serum of an animal immunized against the spatacsin complex, which may be produced by genetic engineering for example according to standard methods well-known by one skilled in the art. Typically, such antibodies can be raised by administering mutated KIAA1840 protein or peptides of this protein subcutaneously to New Zealand white rabbits which have first been bled to obtain pre-immune serum. The antigens can be injected at a total volume of 100 µl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al. (1988) which is hereby incorporated in the references.

A "monoclonal antibody" in its various grammatical forms refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Laboratory methods for preparing monoclonal antibodies are well known in the art (see, for example, Harlow et al., 1988). Monoclonal antibodies (mAbs) may be prepared by immunizing purified mutated KIAA1840 protein into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Antibodies raised against mutated KIAA1840 protein may be cross reactive with wild-type KIAA1840 protein. Accordingly a selection of antibodies specific for mutated KIAA1840 protein is required. This may be achieved by depleting the pool of antibodies from those that are reactive with the wild-type KIAA1840 protein, for instance by submitting the raised antibodies to an affinity chromatography against wild-type KIAA1840 protein.

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Kits

According to another aspect of the invention, the KIAA1840 mutation is detected by contacting the DNA of the subject with a nucleic acid probe, which is optionally labeled.

Primers may also be useful to amplify, analyse (dHPLC, Southern . . . ) or sequence the portion of the KIAA1840 gene containing the mutated positions of interest.

Such probes or primers are nucleic acids that are capable of specifically hybridizing with a portion of the KIAA1840 gene sequence containing the mutated positions of interest. That means that they are sequences that hybridize with the portion mutated KIAA1840 nucleic acid sequence to which they refer under conditions of high stringency.

The present invention further provides kits suitable for determining at least one of the mutations of the KIAA1840 gene.

The kits may include the following components:
(i) a probe, usually made of DNA, and that may be pre-labelled. Alternatively, the probe may be unlabelled and the ingredients for labelling may be included in the kit in separate containers; and
(ii) hybridization reagents: the kit may also contain other suitably packaged reagents and materials needed for the particular hybridization protocol, including solid-phase matrices, if applicable, and standards.

In another embodiment, the kits may include:
(i) sequence determination or amplification primers: sequencing primers may be pre-labelled or may contain an affinity purification or attachment moiety and
(2) sequence determination or amplification reagents: the kit may also contain other suitably packaged reagents and materials needed for the particular sequencing amplification protocol. In one preferred embodiment, the kit comprises a panel of sequencing or amplification primers, whose sequences correspond to sequences adjacent to at least one of the polymorphic positions, as well as a means for detecting the presence of each polymorphic sequence.

In a particular embodiment, it is provided a kit which comprises a pair of oligonucleotide primers specific for amplifying all or part of the KIAA1840 gene comprising at least one of the mutated positions that are identified above (see Table 2).

More preferably, the kits of the invention comprise a pair of primers selected from the pairs shown in Table 3 either for detection by direct sequencing or by screening by dHPLC when they could be set-up (second set of primer pairs).

TABLE 3

Primers used for PCR or for dHPLC (in parentheses)

| Exons | Mutations | For/Rev primers | SEQ ID NO: |
|---|---|---|---|
| 1 | c.118C>T, p.Q40X | ccacaggaaacgaatggaat/ggttctgtgaggaaaccacg | 3/4 |
| 3 | c.529_533delATATT, p.I177_F178delfsX | cagggacattgtaggccatc/tcccagctcccaaaactaaa (ccagttgtaaaattgtgacc)/(tcaatcaacacttctaccac) | 5/7 (6)/(8) |
| 4 | c.733_734delAT, p.M245VfsX c.704_705delAT, p.H235RfsX246 c.869+1G>A, r.? | caggttctttcttgtggcatca/cgaggatattttttaacctcttatca (gttaggcatacttacaaaactggc)/(cgaggatattttttaacctcttatca) | 9/10 (11)/(12) |
| 6 | c.1203delA, p.K401KfsX; c.1235C>G, p.S412X c.1282A>T, p.K428X | gaacatctttgccctggttt/caggcactgaggcagaagta (ctgtgacaggtgttaagtta)/(atctaatacaagacagtctc) | 13/15 (16) |
| 7 | c.1549_1550delCT, p.L517LfsX | aaaaatcaattcctaaatcataatcc/tcttttaaagccaaaaagggtaaa (tagtactgaagtattgagta)/(ttaagtaatgttcttgggca) | 17/19 (20) |
| 8 | c.1668delT, p.F556LfsX577 c.1679C>G, p.S560X c.1692delA, p.V564VfsX577 | cttgccccagattgcataat/tccaaaaagtacgtaaaatccca | 57/58 |
| 10 | c.1951C>T, p.R651X | cccaggactaatcatgaagga/atccccaaaccgataaaacc | 21/22 |
| 11 | c.2198T>G, p.L733X | cggtgtgtcttccactagctc/acccagccattctcagtgtt (gttacataaatgtataatccctg)/(cattttaagactttatggattac) | 23/25 (24)/(26) |
| 12 | c.2316+1G>A, r.? | tttgaaagagcagaaagctatgg/tgaagggggttgtcacacttttt | 61/62 |
| 13 | c.2444G>T, p.R815M and/or r.? c.2444+1G>C, r.? | ttgtggcaaaagaaaatttgtg/gagaatgcaggctcagttcc | 63/64 |

TABLE 3 -continued

Primers used for PCR or for dHPLC (in parentheses)

| Exons | Mutations | For/Rev primers | SEQ ID NO: |
|---|---|---|---|
| 15 | c.2833A>G, r.2834+1_2834+65ins, p.R945GfsX950 or p.R945G c.2697G>A, p.W899X c.2716delC, pQ906SfsX920 | cacagcgagatcctgtctca/cctcactgtaagatgatgccc | 27/28 |
| 16 | c.2842_2843insG, p.V948GfsX; c.2850_2851insT, p.L950FfsX | cctttaaatactacagtggtgcaga/ccaactgttgagatggagaaaa (tgtgggcatgatttggtcta)/(acctgctcaaggacaaatgc) | 29/31 (30)/(32) |
| 17 | c.3075_3076insA, p.E1026RfsX1029 | ttgtttccagatcatgaagaatatg/tcagatagctgaccacagcc | 67/68 |
| 22 | c.3741_3742insA, p.P1248TfsX1264 | agtcagcttaagggaagcgg/gaagataaccattttctcccca | 77/78 |
| 25 | c.4307_4308delAA, p.Q1436RfsX1442 | aaaaggcaccatacagctttg/ggaaacacatgctggaacct | 83/84 |
| 30 | c.5470C>T, p.R1824X c.5532_5533delCA, p.S1844SfsX1857 c.5769delT, p.S1923RfsX1950 | tgaggtgggaggatctcttg/gatgtgttcagagcagccaa and taagctggaggagctggaga/ttgttgtcccttaacttgg | 93/94 95/96 |
| 31 | c.5974C>T, p.R1992X c.5870C>G, p.S1957X c.5982_5983insCTCT, p.L1995LfsX2000 c.5986_5987insT, p.C1996LfsX1999 c.5989_5992delCTGT, p.L1997_Y1998>M1997fs X2056 | tttgaagtatcccagggtgg/ccaccattcccaaagataa | 33/34 |
| 32 | c.6100C>T, R2034X c.6091C>T, p.R2031X | ttacctggatttggctttgg/tgcaatccagaaacttgagaga (cctggcttctaaaagtggcc)/(aagcacaacatccaaatcctt) | 35/37 (36)(38) |
| 34 | c.6451delG, p.A2151PfsX c.6477+4 A>G, r.? | atgttggcaggaactccatc/ctcctttggagcaacctctg | 39/40 |
| 36 | c.6737_6740delTTGA, p.I2246_E2247delfsX c.6739_6742delGAGT, p.E2247_S2248>L2247fs X2260 | ttccaacaggaaagcacaca/cagctacttgggaggctgag (caacaggaaagcacacatgc)/(gtgtggctgtgacctcactc) | 41/43 (42)/(44) |
| 37 | c.6832_6833delAG, p.S2278LfxX | gcattagaaggggcactgaa/ctcacaacggtattcacccc (aacatggctgggatgtttct)/(ttcctggttggcctatgatg) | 45/47 (46)/(48) |
| 38 | c.6856C>T, p.R2286X | ttttgtccttgggctctttc/cctggttctgtcactagccc | 101/102 |
| 39 | c.7029_7030insT, p.V2344CfsX | aagggtttaagataatttgggga/ggattcttgatactgctttgcc (aatgccaaacacacacctga)/(ctcaaagcagaggcaaggag) | 49/51 (50)/(52) |

Therapeutic Methods

The inventors have demonstrated that the all, except one, mutations identified in the KIAA1840 gene cause truncation of the protein, suggesting that pathogenicity results from loss of function.

These results identify mutated KIAA1840 gene as target for the preventive or curative treatment of a hereditary spastic paraplegia.

Thus the invention further relates to a method of treatment of an HSP which comprises the step of administering a subject in need thereof with a KIAA1840 nucleic acid, i.e. a nucleic acid sequence that encodes a wild-type KIAA1840 protein, so that spatacsin is expressed in vivo by the cells of the subject that have been transfected with said nucleic acid. Accordingly, said method leads to an overexpression of wild-type spatacsin which compensates expression of defective mutated KIAA1840 protein.

The invention also relates to the use of a KIAA1840 nucleic acid for the manufacture of a medicament intended for the treatment of an HSP.

In the context of the invention, the term "treating" or "treatment", as used herein, means reversing, alleviating, inhibiting the progress of, or preventing the disorder or condition to which such term applies, or one or more symptoms of such disorder or condition.

Preferably said KIAA1840 nucleic acid is administered in a therapeutically effective amount. A "therapeutically effective amount" is intended for a minimal amount of active agent (e.g., KIAA1840 nucleic acid) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

The administered polynucleotide comprises the nucleotide sequence SEQ ID NO:1, or any homologous or similar sequence as defined below:

a) a sequence showing at least 70%, preferably at least 75% or 80% or 85% or 90% or 95% or 99%, sequence similarity with SEQ ID NO:1;

b) a sequence hybridizing with SEQ ID NO:1, or its complementary sequence, under stringent conditions;

c) a sequence encoding a protein of sequence SEQ ID NO:2, or any sequence substantially similar with SEQ ID NO:2.

The term "sequence similarity" in all its grammatical forms refers to the degree of identity or correspondence between nucleic acid or amino acid sequences of proteins that may or may not share a common evolutionary origin. Preferably the degree of sequence identity is calculated compared with the totality of a reference sequence.

In a specific embodiment, two DNA sequences are "substantially homologous" or "substantially similar" when at least 70%, preferably at least 75% or 80% or 85% or 90% or 95% or 99%, of the nucleotides match over the defined length of the DNA sequences, as determined by sequence comparison algorithms, such as BLAST, FASTA, DNA Strider, etc. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially similar" when greater than 80%, preferably than 85% or 90% or 95% or 99%, of the amino acids are similar (functionally identical). "Functionally identical" polypeptides are those in which a given amino acid residue has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Preferably, the similar sequences are identified by alignment using, for example, the GCG (Genetics Computer Group, Program Manual for the GCG Package, Version 7, Madison, Wis.) pileup program, or any of the programs described above (BLAST, FASTA, etc.).

Preferably the KIAA1840 nucleic acid sequence according to the invention is associated with elements that enable for regulation of its expression, such as a promoter sequence.

Such a nucleic acid may be in the form of a DNA vector. The terms "vector" means the vehicle by which a DNA or RNA sequence (e.g. a foreign gene) can be introduced into a host cell, so as to transform the host and promote expression (e.g. transcription and translation) of the introduced sequence. A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA.

The KIAA1840 nucleic acid may be introduced into a target cell by means of any procedure known for the delivery of nucleic acids to the nucleus of cells, ex vivo, on cells in culture or removed from an animal or a patient, or in vivo.

Ex vivo introduction may be performed by any standard method well known by one skilled in the art, e.g. transfection, electroporation, lipofection, microinjection, transduction, cell fusion, DEAE dextran, calcium phosphate precipitation, or use of a gene gun.

The above methods do not limit the scope of the invention and it is to be understood that the one skilled in the art may readily make use of any other known appropriate methods for delivering a nucleic acid to a cell in vivo or in vitro.

The invention also relates to the use of wild-type KIAA1840 protein (spatacsin) for the manufacture of a medicament intended for the treatment of an HSP.

Thus the invention further relates to a method of treatment of an HSP which comprises the step of administering a subject in need thereof with a therapeutically effective amount of wild-type KIAA1840 protein.

The KIAA1840 protein may be introduced to a target cell by means of any procedure known for the delivery of proteins to cells, ex vivo, on cells in culture or removed from an animal or a patient, or in vivo.

Protein delivery is the process by which a protein crosses the cell plasma membrane. Traditionally, methods to introduce antibodies, peptides or other membrane-impermeable molecules into cells include micro-injection and electroporation.

A number of protein-transduction domains (PTDs) have also been developed that mediate protein delivery into cells. These PTDs or signal peptide sequences are naturally occurring polypeptides of 15 to 30 amino acids, which normally mediate protein secretion in the cells. They are composed of a positively charged amino terminus, a central hydrophobic core and a carboxyl-terminal cleavage site recognized by a signal peptidase. Examples of such membrane-transducing peptides include Trojan peptides, human immunodeficiency virus (HIV)-1 transcriptional activator (TAT) protein or its functional domain peptides, and other peptides containing protein-transduction domains (PTDs) derived from translocation proteins such as *Drosophilia* homeotic transcription factor *Antennapedia* (Antp) and herpes simplex virus DNA-binding protein, VP22, and the like. Some commercially available peptides, for example, penetratin 1, Pep-1 (Chariot reagent, Active Motif Inc., CA) and HIV GP41 fragment (519-541), can be used for protein delivery.

Recently, the use of lipid liposomes or the like that can complex with a protein of interest and promote the delivery of the protein into the cell has also been demonstrated. Products available commercially can be used, such as Bio-PORTER (Gene Therapy Systems), or ProVectin (Imgenex, San Diego, Calif.).

The above methods do not limit the scope of the invention and it is to be understood that the one skilled in the art may readily make use of any other known appropriate methods for delivering a protein to a cell in vivo or in vitro.

The invention will be further illustrated by the following figures and examples.

FIGURES

FIGS. 1 and 2: Multipoint linkage analysis performed in 16 families for 34 microsatellite markers from chromosome 15q. cM=centimorgan.

(FIG. 1) Multipoint LOD score values for each family. *Relative position on the genetic map of chromosome 15 (according to http://research.marshfieldclinic.org/genetics).

(FIG. 2) Cumulative multipoint LOD scores in the 16 linked-families plotted according to the genetic map of chromosome 15.

Figure 3:
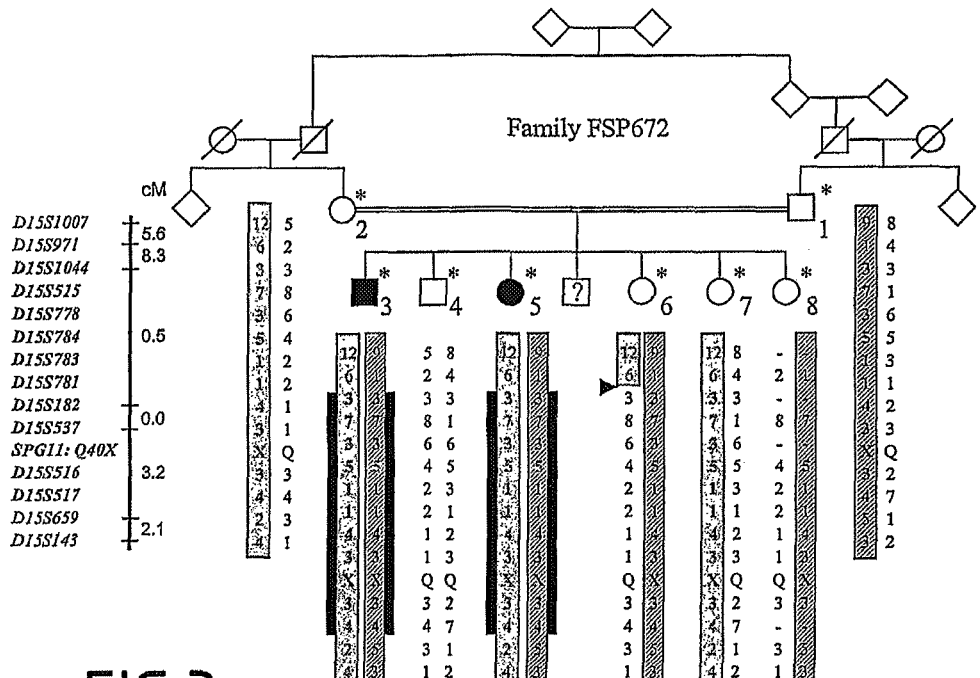
Figure 4:
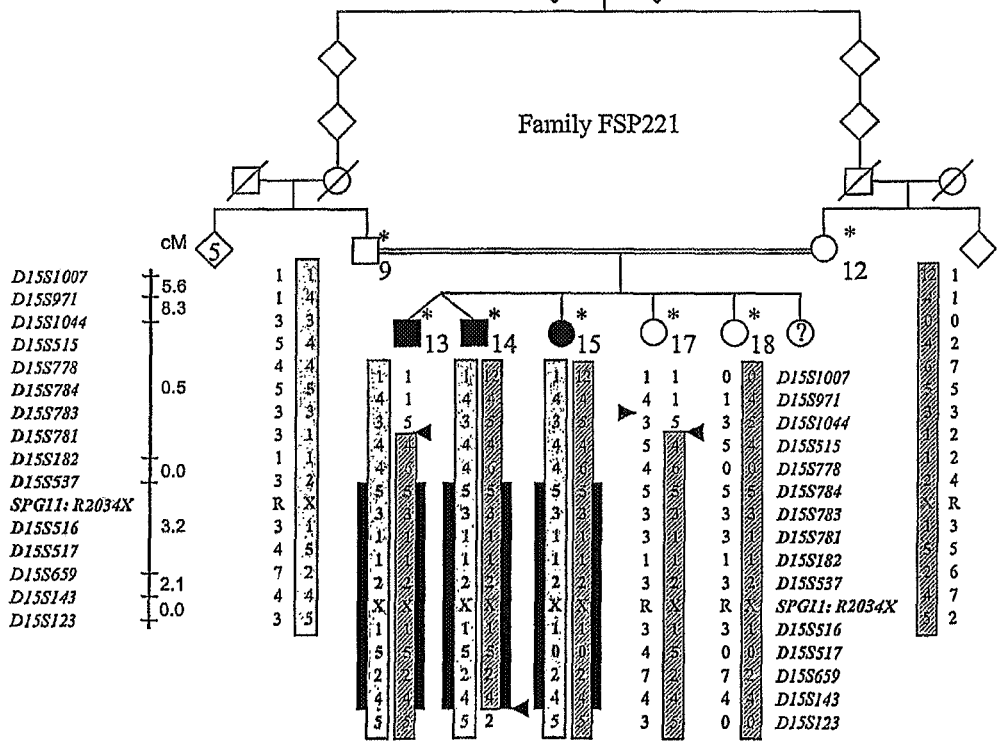

FIGS. 3 and 4: Pedigrees of 2 SPG11 families that reduced the candidate interval. Black circles (women) and squares (men) indicate affected members compared to previous publications. The numbers are an internal reference for each sampled individual. Asterisks indicate sampled subjects. Haplotype reconstruction for selected microsatellite markers positioned according to the human genome draft sequence (www.ncbi.nlm.nih.gov, www.ensembl.org) is shown. The homozygous haplotype, in which the mutated gene has been located, is flanked by black boxes. Arrowheads indicate the position of probable recombination events. cM=centimorgan (according to http://research-.marshfieldclinic.org/genetics).

FIG. 5: Critical region of SPG11. (a) Physical map of human chromosome 15q15-21 with selected genetic markers and candidate genes that were sequenced. Distances in megabases are indicated relative to chromosome 15 according to the Ensembl database. Markers defining the reduced candidate interval are in bold. # indicates that these genes (SEMA6D and MAP1A) were analyzed in a previous study (Stevanin et al, 2006). > and < indicate the orientation of the open reading frame (ORF) of each gene. (b) Exon-intron structure of the 101 Kb of the KIAA1840 gene, also known as FLJ21439, with positions of mutations identified in 17 SPG11 families. (c) Putative functional domains (boxes) and their positions on the protein sequence. TM=transmembrane domains. Regions I and II correspond to structurally similar domains based on their hydrophobicity status analysed with DomHCA software.

FIGS. 6 to 17: Pedigrees and segregation of the 17 mutations detected in KIAA1840. Square symbols are men, the circles are women. The filled symbols are affected individuals, grey or ? symbols indicate patients with an unknown status. The numbers are an internal reference for each sampled individual. Stars indicate sampled subjects. M or m=mutation; +=wild type. Electrophoregrams are shown for the homozygous mutations only. (6,7) Families with common origins sharing the same mutations. Haplotypes for three close microsatellites segregating with the mutations are highlighted. The correspondence between the numbering of alleles and their size in base pairs is indicated. (8, 10 to 14) Other homozygous mutations. (15) New homozygous mutations. (9, 16, 17) Compound heterozygous mutations.

Figure 18:
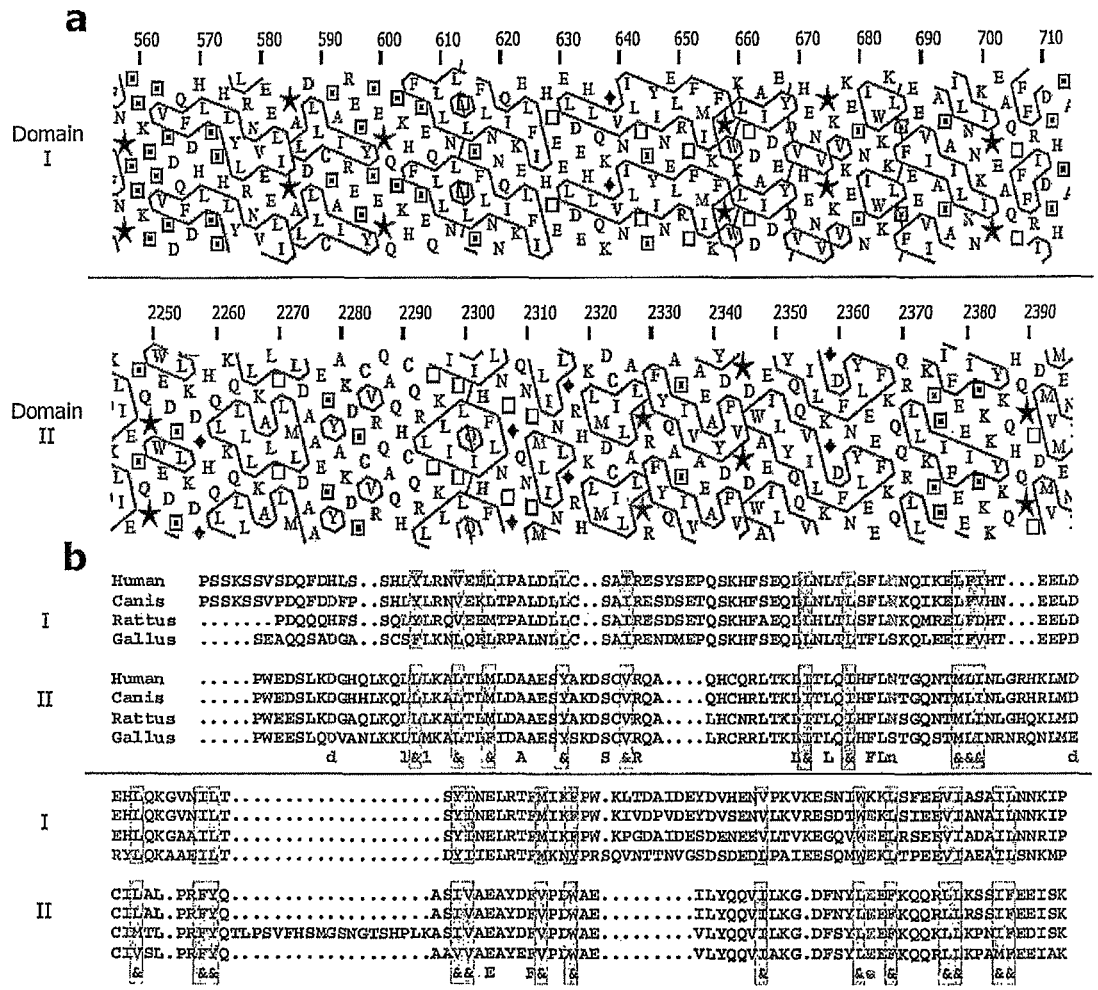

FIG. 18: Internal structural duplication in spatacsin (a) Hydrophobic cluster analysis (HCA) plots of the internal duplication of two regions in the human sequence. The HCA method is based on the use of a bidimensional plot (HCA plot) from the drawing of the 1D sequence on an alpha helix (3.6 residue/turn, connectivity distance of 4 residues separating two different clusters) which has been shown to offer the best correspondence between clusters and regular secondary structures. Examination of the HCA plot of a protein sequence enables globular regions to be easily distinguished from non globular ones and, in globular regions, secondary structures to be identified. This 2D signature, which is much more highly conserved than the 1D sequence and can be enriched from the comparison of families of highly divergent sequences, enables relevant similarities to be successfully detected at low levels of sequence identity. The form of the clusters is generally indicative of the type of secondary structures (vertical clusters are often associated with beta strands whereas horizontal ones often correspond to alpha helices). Dom-HCA software: http://www.lmcp.jussieu.fr/%7Emornon/hca.html. Special symbols are used for some amino acids: star for proline, square and dotted square for threonine and serine, diamond for glycine.

(b) Multiple alignment of the structural repeat domains (I and II, FIG. 3) corresponding to the HCA plots (DomHCA software). Under the multiple alignment, highly conserved residues are indicated by a capital letter when strictly conserved or in lower case if there is some homology. The character "&" means that this position is always occupied by a hydrophobic residue (amino acids FILMVW and Y).

Figure 19:
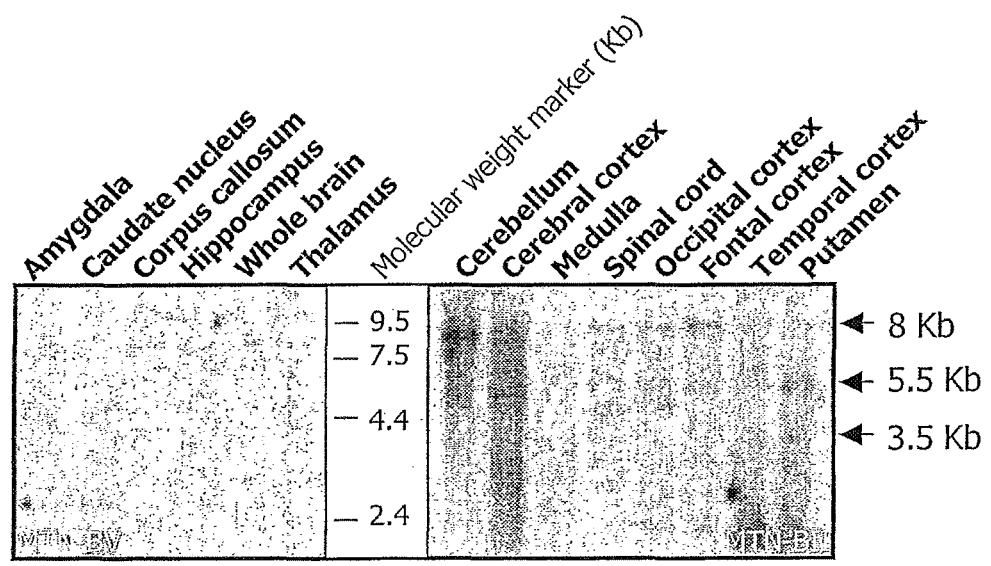

FIG. 19: Expression profile of KIAA1840 examined by northern blot in human adult brain. The transcripts were present in all brain tissues. Note the 8-Kb transcript more intensely expressed in the cerebellum while the 5.5-Kb transcript is mainly found in the cerebral cortex.

Table 1: Exon-intron boundaries in the KIAA1840 gene

Table 2: Mutations found in the KIAA1840 gene in families with AR-HSP-TCC.

Table 3: Primers used for detecting the mutations either by direct sequencing or by dHPLC Table 4: Primers used for the amplification of all exons of the KIAA1840 gene and PCR amplification conditions Table 5: PCR conditions and dHPLC conditions to analyze exons of KIAA1840.

Table 6: dHPLC primers to analyze exons of KIAA1840

EXAMPLE

Method

Subjects:

211 individuals, including 83 affected members and 44 non mutated members, from 91 families.

All patients were examined by a neurologist. They were selected among 216 families with hereditary spastic paraparesis compatible with recessive transmission collected in our neurogenetic reference center in collaboration with the SPATAX network. They presented a typical "SPG11" phenotype defined as the presence of progressive spastic paraparesis associated with thin corpus callosum on cerebral MRI and mental retardation and neuropathy.

Blood samples was obtained after written consent from all affected patients and their relatives with approval of the local Ethic committee of Paris-Necker (approval n° 03.12.07 of the comité Consultatif pour la Protection des Personnes et la Recherche Biomédicale, to A.D). Genomic DNA was extracted from leukocytes using standard procedures.

Linkage Analysis:

The genome scan in family FSP221 was performed using 400 microsatellites, regularly spaced on all chromosomes (ABI-Prism mapping set v2, Applied Biosystems, Foster City, Calif.) and 50 additional polymorphic markers were used to analyze the results. Genotypes were determined by PCR with a fluorescently-labeled primer, electrophoretic migration in an ABI-3730 sequencer (Applied Biosystems) and analysis with Genescan 3.5 (Applied Biosystems). Allegro 1.2c was used to calculate two-point and multipoint lod scores between the disease phenotype and each of the markers or the map of the markers assuming a complete penetrance, equal allele frequencies for the markers and a mutated allele frequency of 0.0005 (Gudbjartsson et al. 2000). Marker order and genetic distances were obtained from the Ensembl (http://www.ensembl.org) and Marshfield databases (http://research.marshfieldclinic.org/genetics), respectively.

Mutation Detection:

A series of primers was designed manually or using Oligo6 (MBI, Cascade, Colo.) in order to amplify all coding exons of 18 genes from the candidate interval (primers and conditions available on request). PCR-amplified fragments of genomic DNA were then purified using exonuclease 1 (New England Biolabs, 2 U/5 µl PCR product) and shrimp alkaline phosphatase (Roche, 1 U/5 µl of PCR product) and sequenced using the fluorescent dideoxy-terminator method (BigDye v3, Applied Biosystem) on an automated ABI-3730 sequencer according to the manufacturer's recommendations. With the use of the software package SeqScape (Applied Biosystems), sequences were aligned and compared to consensus sequences.

Primers used for the amplification of the KIAA1840 gene are listed in the following Table 4.

The conditions of the PCR programme are as follows:
95° C., 12 min
then 40 cycles of:
95° C., 30 s
Annealing Temperature (see Table 4), 30 s,
72° C., 30 s
then
72° C., 10 min, and
15° C., 15 min.

PCR were performed in 25 µl final volume using 10 pmol of each primer, at final concerntrations of 1.5 mM MgCl2 and 0.24 mM dNTP.

Taq pol, which is commercially available from Quiagen was used except for exons 6, 12 and 40B where Taq GOLD (Applied Biosystems) was used.

TABLE 4

| Exon | Annealing temperature | SEQ ID NO: | Forward primer | Reverse primer |
|---|---|---|---|---|
| ex1 | 60° C. | 3/4 | ccacaggaaacgaatggaat | ggttctgtgaggaaaccacg |
| ex2 | 60° C. | 53/54 | ctgagccccacattttttgtt | caagtgctcaatagccccat |
| ex3 | 60° C. | 5/7 | cagggacattgtaggccatc | tcccagctcccaaaactaaa |
| ex4 | 60° C. | 9/10 | caggttctttattgtggcatca | cgaggatattttttaacctcttatca |
| ex5 | 62° C. | 55/56 | gctaactgcccttaatagagtaaaa | aaagggtacagcgtcagcat |
| ex6 | TD62-58 | 13/15 | gaacatctttgccctggttt | caggcactgaggcagaagta |
| ex7 | 60° C. | 17/19 | aaaaatcaattcctaaatcataatcc | tcttttaaagccaaaaagggtaaa |
| ex8 | 60° C. | 57/58 | cttgccccagattgcataat | tccaaaaagtacgtaaaatccca |
| ex9 | 60° C. | 59/60 | cagcaaaagggtaatagcagtg | cccaaatgtagtaaatggcg |
| ex10 | 60° C. | 21/22 | cccaggactaatcatgaagga | atccccaaaccgataaaacc |
| ex11 | 60° C. | 23/25 | cggtgtgtcttccactagctc | acccagccattctcagtgtt |
| ex12 | TD62-58 | 61/62 | tttgaaagagcagaaagctatgg | tgaaggggttgtcacacttttt |
| ex13 | 60° C. | 63/64 | ttgtggcaaaagaaaatttgtg | gagaatgcaggctcagttcc |
| ex14 | 60° C. | 65/66 | atgtggaactgagcctgcat | cgacttgcatttttaaagaacctg |
| ex15 | 60° C. | 27/28 | cacagcgagatcctgtctca | cctcactgtaagatgatgccc |
| ex16 | 62° C. | 29/31 | cctttaaatactacagtggtgcaga | ccaactgttgagatggagaaaa |
| ex17 | 56° C. | 67/68 | ttgtttccagatcatgaagaatatg | tcagatagctgaccacagcc |
| ex18 | 60° C. | 69/70 | tccctcttaaggagaaaaacactg | accgggccgagatataaaat |
| ex19 | 60° C. | 71/72 | gctagtttgtcttagaaccagaaca | ttttggttgtctcactatcaca |
| ex20 | 60° C. | 73/74 | aaggaacatagccagttctgttttt | tgcgaactatttttcctttgg |
| ex21 | 60° C. | 75/76 | tgcaacttctcaggtacacatct | aggctagagtgcagtggcat |
| ex22 | 60° C. | 77/78 | agtcagcttaagggaagcgg | gaagataaccattttctcccca |
| ex23 | 60° C. | 79/80 | ttgtgagtgtttggggagaa | ggggatttagtgaaaacacca |
| ex24 | 64° C. | 81/82 | tttgttggagaatacactgtgctt | catgtctacacaacagaaagaatgc |
| ex25 | 60° C. | 83/84 | aaaaggcaccatacagctttg | ggaaacacatgctggaacct |
| ex26C | 55° C. | 85/86 | cttctgtctgcttcttggtctt | tatcatcattatctgttgttgg |

TABLE 4 -continued

| Exon | Annealing temperature | SEQ ID NO: | Forward primer | Reverse primer |
|---|---|---|---|---|
| ex27 | 60° C. | 87/88 | ttaggtgatcccactggctc | cccaggagttcaaggctgta |
| ex28 | 60° C. | 89/90 | ctgaggagggcttgtttttg | tctgtaacttgtttactcccagttg |
| ex29 | 60° C. | 91/92 | gatcacaccactgcattcca | ggcacctgtagtcccagcta |
| ex30A | 60° C. | 93/94 | tgaggtgggaggatctcttg | gatgtgttcagagcagccaa |
| ex30B | 60° C. | 95/96 | taagctggaggagctggaga | ttgttgtccccttaacttgg |
| ex31 | 60° C. | 33/34 | tttgaagtatcccagggtgg | ccaccattccccaaagataa |
| ex32 | 60° C. | 35/37 | ttacctggatttggcttttgg | tgcaatccagaaacttgagaga |
| ex33 | 60° C. | 97/98 | caataggccaagggtttcaa | tataactcctgctggagggc |
| ex34 | 62° C. | 39/40 | atgttggcaggaactccatc | ctcctttggagcaacctctg |
| ex35 | 60° C. | 99/100 | ggtagcctggaaattagccc | tgaaccagaatctgaagcca |
| ex36 | 62° C. | 41/43 | ttccaacaggaaagcacaca | cagctacttgggaggctgag |
| ex37 | 60° C. | 45/47 | gcattagaaggggcactgaa | ctcacaacggtattcacccc |
| ex38 | 60° C. | 101/102 | ttttgtccttgggctctttc | cctggttctgtcactagccc |
| ex39 | 60° C. | 49/51 | aagggtttaagataatttggggga | ggattcttgatactgctttgcc |
| ex40A | 60° C. | 103/104 | aattagccagggtggtgaca | cccacaaaggactgatatgg |
| ex40B | TD62-58 | 105/106 | aaggaccctcagacaggttg | tcctttaaggcagacaaggg |

TD = TouchDown 10 cycles decrease of annealing temperature, then 25 stable cycles. Temperatures in Celsius degrees.

For some exons, it was possible to set up dHPLC conditions to detect variants. Primers different from those used for direct sequencing were specifically designed but they can also be used for direct sequencing. The PCR conditions and dHPLC conditions are indicated on table 5.

TABLE 5 dHPLC conditions to analyze exons of KIAA1840. Temperature in Celsius degrees.

| Exon | Size | T° PCR | T° DHPLC |
|---|---|---|---|
| 2 | 323 | 62° - 1' - 35x | 55.3° |
| 3 | 305 | 58° - 1' - 35x | 55.1° |
| 4 | 320 | 62° - 1' - 35x | 54.8°-52.8° |
| 5 | 330 | 60° - 1' - 35x | 54.9° |
| 6 | 450 | 58° - 1' - 35x | 54°-53° |
| 7 | 275 | 58° - 1' - 35x | 50.6°-52.6° |
| 9 | 342 | 62° - 1' - 35x | 54.1 |
| 11 | 293 | 57° - 1' - 35x | 54.6° |
| 12 | 210 | 62° - 1' - 35x | 52.5° |
| 13 | 289 | 62° - 1' - 35x | 51.5° |
| 14 | 246 | 62° - 1' - 35x | 55.8° |
| 16 | 309 | 62° - 1' - 35x | 55.2° |
| 17 | 239 | 62° - 1' - 35x | 53.9° |
| 18 | 324 | 58° - 1' - 35x | 53°-50° |
| 20 | 311 | 62° - 1' - 35x | 52.3° |
| 22 | 383 | 62° - 1' - 35x | 55.8° |
| 23 | 356 | 62° - 1' - 35x | 53.1° |
| 24 | 267 | 60° - 1' - 35x | 57.1° |
| 25 | 361 | 60° - 1' - 35x | 56.6° |
| 27 | 330 | 62° - 1' - 35x | 53.6° |
| 28 | 329 | 62° - 1' - 35x | 53.5° |
| 29 | 330 | 56° - 1' - 35x | 54.2°-56.2° |
| 32 | 323 | 60° - 1' - 35x | 58.8° |
| 33 | 349 | 62° - 1' - 35x | 57.6° |
| 35 | 312 | 62° - 1' - 35x | 54° |
| 36 | 376 | 62° - 1' - 35x | 52° |
| 37 | 313 | 62° - 1' - 35x | 57.6° |
| 38 | 315 | 62° - 1' - 35x | 56.9° |
| 39 | 380 | 62° - 1' - 35x | 53.2° |
| 40 | 390 | 62° - 1' - 35x | 54.4° |
| 40 | 321 | 58° - 1' - 35x | 54.2° |

TABLE 6 dHPLC primers to analyze exons of KIAA1840

| Exon | PRIMERS F (5'-3')/R (5'-3') | SEQ ID NO: |
|---|---|---|
| 2 | accaggtcaactaaactgttctct/tatgctgaaagaccacctgtaga | 107/108 |
| 3 | ccagttgtaaaattgtgacc/tcaatcaacacttctaccac | |

TABLE 6 -continued dHPLC primers to analyze exons of KIAA1840

| Exon | PRIMERS F (5'-3')/R (5'-3') | SEQ ID NO: |
|---|---|---|
| 4 | gttaggcatacttacaaaactggc/cgaggatattttttaacctcttatca | 11/12 |
| 5 | caggagcagtagtaacacaa/aaagggtacagcgtcagcat | 109/110 |
| 6 | ctgtgacaggtgttaagtta/atctaatacaagacagtctc | 14/16 |
| 7 | tagtactgaagtattgagta/ttaagtaatgttcttgggca | 18/20 |
| 9 | gcaggtaataagcctgcagaa/cccccttcctagctgctatt | 111/112 |
| 11 | gttacataaatgtataatccctg/cattttaagactttatggattac | 24/26 |
| 12 | tgttcaaaatagttccattacaaaa/tttcttccaaggttttcttcca | 113/114 |
| 13 | tttgcaaaagtgcttgatttt/tgcaggctcagttccacata | 115/116 |
| 14 | ggaatgatgcctttttctcc/tctcacacttgccttctgga | 117/118 |
| 16 | tgtgggcatgatttggtcta/acctgctcaaggacaaatgc | 30/32 |
| 17 | aatcatcgcctgagcaaaat/ccagtgactgatccaaagca | 119/120 |
| 18 | ccctcttaaggagaaaaacac/cagccttatcctctgctctt | 121/122 |
| 20 | tggaaaaggggagcagacta/tgcgaactattttttcctttgg | 123/124 |
| 22 | gaggaggccacaaatcacat/gccttagacctcgtcacacc | 125/126 |
| 23 | tgctcaggttttgacttttttctc/tttcactgatggcaagatgc | 127/128 |
| 24 | accaccccacctctaattc/ctacacaacagaaagaatgc | 129/130 |
| 25 | ccagctgaaactgaaagttgg/ctgggtacttacttcaggct | 131/132 |
| 27 | cactgtgccctgccttatta/tgtgcctgagtaaccgagtg | 133/134 |
| 28 | tcccagatttggaggtttttg/tgcattttaatttcctaactaccc | 135/136 |
| 29 | gctgtagtggcattttattg/cctgggtgacagagcaagac | 137/138 |
| 32 | cctggcttctaaaagtggcc/aagcacaacatccaaatcctt | 36/38 |
| 33 | agctgcagagctccataagc/taggcatccagagcaggaac | 139/140 |
| 35 | ggcatctgaaagcaaccact/ccctccattttcccaagagt | 141/142 |
| 36 | caacaggaaagcacacatgc/gtgtggctgtgacctcactc | 42/44 |
| 37 | aacatggctgggatgtttct/ttcctggttggcctatgatg | 46/48 |
| 38 | ggggtgaataccgttgtgag/acctctgggttccatgagtg | 143/144 |
| 39 | aatgccaaacacacacctga/ctcaaagcagaggcaaggag | 50/52 |
| 40 | agactgctcctctgcactcc/ccgggattgttcaactttagc | 145/146 |
| 40 | cagtatcttaacctgtacat/ccgggattgttcaactttagc | 147/148 |

Overexpression Studies:

The KIAA1840 cDNA from clone pf01011 (Kazusa DNA research Institute, Japan) was excised from the pBluescript II SK(+) vector using XhoI/NotI restriction enzymes and cloned in fusion with EGFP in a SalI/Bsp120I digested pEGFP-C1 vector (Clontech). The construction was verified by direct sequencing after ligation, transformation and plasmid extraction using standard procedures.

COS-7 cells were maintained in DMEM (Invitrogen) supplemented with 10% fetal bovine serum, penicillin (100 UI/ml) and streptomycin (100 µg/ml). Cells were plated 24 h before transfection on cover slips coated with polyethylenimine and transfected with Lipofectamine-PLUS reagents according to the manufacturer's instructions (Invitrogen). For 6-well plates, 1-2 µg of plasmid DNA was used per well. Cells were analyzed by immunofluorescence 120 h post-transfection. The spatacsin-EGFP fusion protein was observed directly after fixation for 15 min with 4% formaldehyde. Immunocytochemistry was performed, using classical procedures with the following antibodies: rabbit anti-Cox2 (1/200, kind gift of A. Lombes, Paris) and rabbit anti-alpha-COP (1/1000$^e$; Affinity Bioreagent). Cells were counterstained with DAPI (1 µg/ml, Sigma) and mounted with Fluoromount-G (Southern Biotech). Samples were observed with a Leica SP1 confocal microscope. Leica confocal software was used to acquire the images.

Northern-Blot Analysis (Human):

Total RNA was extracted from the human post-mortem brain cortex of an healthy individual (Brain Bank of INSERM U679) using the RNAeasy Mini kit (Qiagen). The corresponding cDNAs were synthesized using random hexamers in the presence of Thermoscript reverse transcriptase as recommended by the supplier (Invitrogen). A series of 7 probes of 1.2 Kb covering the entire KIAA1840 cDNA was amplified by PCR at an annealing temperature of 60° C. (primer sequences available on request). Human multiple tissue northern blots (Clontech) were hybridized at 68° C. for 1 hour with a mix of these probes $aP^{32}$-labeled by random priming (Prime-it II Random Primer Labeling kit, Stratagene) and purified using ProbeQuant G-50 micro columns (Amersham Biosciences) in accordance to the manufacturer's recommendations to reach a specific activity of at least $1\times10^9$ cpm/μg. Membranes were then washed as recommended by Clontech then exposed to X-Ray film for autoradiography.

In Situ Hybridization (Rat):

Young (P1, P6, P15 and P21, n=1 each) and adult (P68, 200 g, n=2) Sprague Dawley rats (Charles River) were killed by decapitation and their brains were rapidly extracted and frozen in isopentane at −50° C. Sections were prepared with a cryostat at −20° C., from medulla to *striatum* (+1.7 from bregma) 600 μm-spaced, thaw-mounted on glass slides and stored at −80° C. until usage. KIAA1840 mRNA expression was analyzed using 3 antisens oligonucleotides designed using Helios ETC oligo design software (Helios Biosciences, Paris, France) on the mRNA sequence (XM-242139) of *Rattus norvegicus* similar to hypothetical protein FLJ21439 (LOC311372). Each oligonucleotide or a mix of the 3 oligonucleotides were used for the hybridization step and gave identical results. A mix of three sens oligonucleotides was used as a negative control.

In situ hybridization was performed as described in Moutsimilli et al. (2005) Briefly, oligonucleotides were labeled with [35S]-dATP (Amersham Biosciences) using terminal transferase (Amersham Biosciences) to a specific activity of $5\times10^8$ dpm/μg. The day of the experiment, slides were fixed in 4% formaldehyde in PBS, washed with PBS, rinsed with water, dehydrated in 70% ethanol and air-dried. Sections were then covered with 140 μl of hybridization medium (Helios Biosciences, Paris, France) containing $3-5\times10^5$ dpm of the labeled oligonucleotide mix. Slides were incubated overnight at 42° C., washed and exposed to a BAS-SR Fujifilm Imaging Plate for 5-10 days. The plates were scanned with a Fujifilm Biolmaging Analyzer BAS-5000 and analyzed with Multi Gauge Software (Fuji).

For double labeling experiments, brains were processed as for in situ hybridization. After the last wash step, sections were fixed in 4% paraformaldehyde in PBS and preincubated in PBS containing 6% goat serum and 0,1% triton. Sections were next incubated with mouse antibodies directed against Neu-N(Chemicon International, 1/250), in the same buffer, processed with biotinylated horse antimouse IgG antibodies and ABC reagents (Vector Laboratories, Burlingame, Calif.) and submitted to emulsion autoradiography. The labeling with the antisense probe in comparison with the Neu-N neuronal specific counterstaining was observed.

Bioinformatics:

Functional domains were searched using bioinformatics tools available online at BABEL (http://babel.infobiogen.fr: 1984/), Ressource Parisienne en Bioinformatique Structurale (http://bioserv.rpbs.jussieu.fr/RPBS) and PSORT (http://psort.nibb.ac.jp/). Psi-blast (www.ncbi.nlm.nih.gov) was used to look for homologous proteins or peptides. Alignment of homologous proteins was performed using CLUSTALW (http://www.ebi.ac.uk/clustalw/). Alteration of splicing sites was verified in the Alternative Splicing Database at http://rulai.cshl.edu/new_alt_exon_db2/HTML/score.html.

HCA is a method that allows to represent a protein sequence on a bidimensional scaffold that increases the density of the amino acids, and consequently, evidences local compacity of hydrophobic residues. They form clusters according to a connectivity that is the one of an alpha helix. It has been shown that the centers of the clusters and the centers of the secondary structures statistically match, (Woodcocks et al. 1992) and on the other hand the shape of a cluster is related to the nature of the secondary structure (Callebaut et al. 1997). HCA is a very efficient tool for recovery of highly divergent internal duplication of domains and for the detection of globular domain limits.

Results:

We selected a series of 91 families of European or North-African origins, all without mutations in the SPG7 gene and with a typical AR-HSP-TCC phenotype. Six of these families were previously reported as linked to SPG11 using a subset of polymorphic markers from the interval (Casali et al, 2004; Stevanin et al, 2006; Lossos et al, 2006). The other families were new. All available family members of 16 most informative families were genotyped using 34 microsatellite markers for linkage to three successive loci on chromosome 15 which have been associated with thin corpus callosum; SPG11, SPG21 and the locus for agenesis of corpus callosum with polyneuropathy (ACCPN). Positive multipoint LOD scores ranging from 0.60 to 3.85 and corresponding to the maximal expected values in the pedigrees were obtained in the 16 most informative families (FIGS. 1 and 2). Mutations in the ACCPN or SPG21 loci were excluded by direct sequencing in all families that showed positive linkage to these regions (data not shown). A significant combined multipoint LOD score of 28.1 was reached in the 3.3 cM interval flanked by markers D15S778 and D15S659 in the linked kindreds (FIGS. 1 and 2). Haplotype reconstructions identified two critical recombination events that allowed to restrict the candidate interval to 6.6 cM between markers D15S1044 and D15S123. The 3.2 cM of the D15S778-D15S659 interval was considered to be the region most likely containing the responsible gene on the basis of homozygosity in all consanguineous patients of two significantly linked families; family FSP221 linked to SPG11 with a maximal LOD score of 3.85 and family FSP672 linked to the same locus with a 2.6 LOD score value (FIGS. 3 and 4). In addition, a genome wide screen performed in family FSP221 at a resolution of 10 cM on all chromosomes only identified three other possible locations with multipoint lod scores of 2.2 to 2.5 that were excluded using 18 additional microsatellite markers (data not shown), therefore highly supporting linkage to SPG11.

The narrowed interval contained 40 genes in accordance with the National Center for Biotechnology Information (NCBI) and the Ensembl databases. Two were excluded in previous studies (SEMA6D and MAP1A, Stevanin et al, 2006). We evaluated 16 additional genes from the interval as candidates for SPG11, prioritizing those with a known or putative function in mitochondrial metabolism, intra-cellular trafficking or cytoskeleton integrity (FIG. 5). All coding and non-coding exons as well as their splicing sites with at least 50 bp of intronic sequences on each side were sequenced on genomic DNA of 5 index patients from 5 linked families. No mutations were found in 15 genes but sequence variations were found in the KIAA1840 gene. We then screened one affected member from the 16 linked families as well as of the uninformative kindreds and checked all other members of the families, when available, for sequence variations. 43 different mutations were identified in 47 families, including the 16 linked ones, 31 at the homozygous state, (FIGS. 5 to 9). They were either nonsense mutations (n=13), deletions (n=17), insertions (n=7) or splice site mutations (n=6) in the coding sequence, and resulted in an abnormally truncated protein or predicted to alter the splicing of the messenger RNA in all cases. In two families (FSP670 and ITA28 VAC, FIG. 8), we found a missense change (R945G or R815M) affecting a nucleotide of the 5'-splice site consensus and predicted to alter the splicing of the mRNA. This could be confirmed in family FSP670 by the analysis of mRNA from one patient (c.2833A>G, r.2834+1_2834+65 ins, p.R945GfsX950). Four mutations affected the intronic part of the consensus sequence for the acceptor splicing site (see Table 2) that also likely affect the splicing of the mRNA. The mutations segregated completely in the families with the disease and were not found on at least 140 chromosomes from unrelated control individuals of European and North-African origin suggesting that these mutations were not polymorphisms. Only 4 mutations were found in more than one pedigree (FIGS. 6 and 7). A c.6100C>T substitution that replaces an arginine by a stop codon in exon 32 (R2034X), shortening the protein from 2443 to 2034 amino acids (SEQ ID NO:160), was identified, in the homozygous state, in 4 Algerian, 3 Tunisian and 2 Moroccan consanguineous kindreds (FIG. 6). A 5 bp deletion in exon 3 (c.529_533delATATT) leading to a frameshift and a stop codon at aa 178 (SEQ ID NO:150) was found at the homozygous state in all patients of 3 Portuguese families and at the heterozygous state in one Brazilian kindred (FIG. 7). Interestingly, alleles at close flanking markers were partially similar in families with identical mutations (when it could be tested) suggesting founder effects in North-Africa and Portugal for these mutations. The c.733_734 del AT mutation was also found in 4 Tunisian pedigrees, sharing partial common haplotypes (data not shown) and one French kindred. Finally, the c.1951C>T variant was found at the heterozygous state in 2 Italian and one Kindred from Romania for which we are extending the pedigrees to check for haplotype conservation.

No mutations were found in 44 families, suggesting that the responsible mutations were either in non-coding regions of KIAA1840 or in another unidentified gene.

SPG11 mutations were thus found in the majority of the families with the typical AR-HSP-TCC studied here (47/91). Most families originated from the Mediterranean basin. Complete examination of 22 affected members (Stevanin et al, 2007), 12 men and 10 women, showed a mean age of 24.8±9.5 years ranging from 12 to 49. Onset of the disease always occurred before age 24 years (mean age 11.8±5.5 years; range 2-23) and consisted in either spastic gait (57%, 12/21) or cognitive impairment (19%, 4/21), sometimes diagnosed as mental retardation. After about 10 years of evolution, the full-blown clinical picture consisted in progressive and severe spastic paraplegia with distal wasting and cognitive problems. In several cases (n=6), cognitive dysfunction clearly worsened with disease progression. Cerebral imaging showed a thin corpus callosum, but also periventricular white matter changes and cortical atrophy, in the majority of the patients. Pseudo-bulbar dysarthria was frequent (54%, n=12) and dystonic voice was noted in one patient. Interestingly, although a few patients had normal electromyographic recordings, peripheral neuropathy was frequent (72%, 13 out of 18 patients) and was mostly associated with pure motor changes. Additional signs, such as optic atrophy, retinitis pigmentosa, mild cerebellar signs, cataract, and clinodactily were occasionally observed, a finding that expands the clinical spectrum of this entity.

The human KIAA1840 gene contains 40 exons spanning 101 Kbases of genomic DNA on chromosome 15q21.1. The full length transcript encodes a predicted protein of 2443 amino acids of unknown function called spatacsin for SPAsticity with Thin or Atrophied Corpus callosum Syndrome proteIN. The sequence of spatacsin is strongly conserved through evolution with orthologues in mammalians and other vertebrates: human KIAA1840 shares 85% identity with the homologous protein in dog, 76 and 73% with the mouse and rat homologues and 59% with the chicken homologue, all of similar sizes. Less similarity was found with homologous proteins of smaller sizes from fugu (44%), tetraodon (39%), and drosophila (22%).

Neither the gene nor the predicted protein it encodes in many species show any significant sequence similarity to known cDNA or protein sequences. We then looked for protein motifs and domains (FIG. 3). Four putative transmembrane domains were predicted by various algorithms (aa 163-194, 200-240, 1239-1267 and 1471-1493). A glycosyl hydrolase F1 signature was also detected (aa 482-490). This motif is based on a conserved glutamic acid residue which has been shown in the beta-glucosidase of various bacteria and plants and mammalian lactase-phlorizin hydrolase, an integral membrane glycoprotein that splits lactose in the small intestine. Interestingly, this protein is assigned to the aromatic compound dioxygenase superfamily because of a 22% identity with the consensus sequence between aa 2104-2381. A leucine zipper (aa 611 to 632), involved in dimerization of many gene-regulatory proteins (C/EBP, CREB, CRE-BP1, ATFs and Jun/AP1 family of transcription factors) and a Myb domain (aa 1766 to 1774), involved in the DNA-binding of drosophila and vertebrate myb and related proteins, were also identified. Interestingly, there is a 47% identity, over 44 aa, with thymosyl-like peptides, small peptides which play an important role in the organization of the cytoskeleton; these peptides, bind to and sequester actin monomers, thereby inhibiting actin polymerization (Low and Golstein 1985). Furthermore, a probable coiled-coil domain of 33 residues from 1556 to 1590 was also present and such domains are reported in structural or motor proteins such as spectrin, laminin, dynein or neurofilament proteins.

We then looked at the structure of the predicted protein. The level of hydrophobicity (34.2%) over the entire sequence was typical of a globular protein. Because of it's size, a succession of globular domains is likely and we tried to identify them by the identification of inter domain regions, corresponding to a low density of hydrophobic clusters with the DomHCA software (Prat-Albeau et al, 2006). Except a small linker located between positions 1410 and 1440, no domain separation was evidenced. From the HCA plots, one of the putative transmembrane regions was confirmed at amino acids 200 to 240 on spatacsin from 5 vertebrates, but it was lacking in the homologous sequences from tetraodon and drosophila, as these last two sequences presented a shortened N-terminal domain. A thorough analysis of putative duplication highlighted two structurally similar regions (aa 560-700 and 2250-2390) in all vertebrate homologues of the protein with 19% sequence identity in human sequences (FIG. 10). Amino acid proportion shows a non standard distribution in some cases: high amount of leucines (13.8% vs 9.6% in standard reference databases), a low level of methionines (1.9% instead of 2.38%) and glycines (3.9% vs 6.93% in Swiss Prot). The proportion of cysteins was over 2 fold higher (2.9%) compared to the mean in databases but did not gave rise to disulfide bridges, according to the predictions of the CysState software (Mucchielli-Girgi, 2002). Cluster shapes claim for a mainly helical behavior of this protein, which is confirmed by standard prediction tools.

The spatacsin protein, fused with GFP, had a diffuse cytosolic and nuclear distribution that sometimes excluded the nucleus of COS-7 cells. In rare cases (<5%), spatacsin formed small perinuclear dots or aggresome-like structures in cells with high expression levels after 4 days post-transfection that did not colocalized with the mitochondrial marker Cox2 or the Golgi marker alpha-COP.

Previous expression profiling of the SPG11 gene showed that it is expressed ubiquitously at low levels in mouse tissues, including the brain (Nagase et al, 2001). Ubiquitous low level expression, even in structures apparently not related to the phenotype, has been shown for other genes responsible for neurodegenerative diseases (Paisan-Ruiz et al, 2004). We successfully amplified seven overlapping cDNA fragments from the KIAA1840 mRNA extracted from human cerebral cortex and used them to probe human adult multiple-tissue northern blots. At least three alternative transcripts were detected in all structures of adult brain. The full-length transcript (~8 Kb) was most highly expressed in the cerebellum, the 5.5-Kb transcript in the cerebral cortex (FIG. 11).

When the temporal and regional expression of the mouse KIAA1840 mRNA was investigated by in situ hybridization in rat brain, it was undetectable in newborn rats (P1). It was detected in the cerebellum, however, from P6 to P21. At adulthood (P68), expression was found throughout the brain. Expression was generally low, but stronger signals were observed in the pineal gland, the edges of the lateral ventricles, the granular layer of the cerebellum and the hippocampus. In contrast to human adult northern blots, only a weak expression was detected in the cerebral cortex. Understanding the function of spatacsin in these structures would help to explain the major features of the disease phenotype: e.g., expression in the hippocampus could be related to the cognitive impairment observed in the patients. In addition, whether the labeling of the edges of the lateral ventricles, where oligodendrocyte progenitors are located, is related to the white matter changes in patients remains to be investigated.

Our study identified the gene responsible for spastic paraplegia with thin corpus callosum linked to SPG11, KIAA1840. This is supported by four pieces of evidence; first, we have excluded 17 out of the 40 genes assigned to the SPG11 candidate interval; second, we have identified 43 different mutations segregating in 47 families, 16 of which linked previously to the SPG11 locus, and not found in at least 140 control chromosomes; third, all, these mutations were leading to a truncated protein and/or abnormally spliced mRNA, and fourth all mutated families presented with the typical AR-HSP-TCC phenotype or at least a compatible phenotype in 2 families in which cerebral imaging was not available. Mutations in KIAA1840 affected 47 of 91 AR-HSP-TCC families in this study making this genetic entity very frequent among AR-HSP-TCC (52%), 75% was estimated in a previous study (Stevanin et al, 2006), but also among recessive spastic paraplegias. At least another gene might however exist as previously shown (Lossos et al, 2006; Stevanin et al, 2006; Casali et al, 2004).

This gene has a widespread low level expression, including in the brain where it is more strongly expressed in the cerebellum, the cerebral cortex, the hippocampus, the pineal gland and the edges of the ventricles. Spastic paraplegias are supposed to results from a dying back mechanism of the exons and mitochondrial metabolism or axonal transport has been implicated in several genetic entities of HSP (Crosby et al, 2002). Indeed, three causative genes identified in AR-HSP have been implicated in defective intracellular trafficking: mutations in the mitochondrial metalloprotease protein paraplegin impair axonal transport in SPG7; spartin (SPG20) mutations affect endosomal trafficking and microtubule dynamics; maspardin (SPG21) mutations may interfere with endosomal/trans-Golgi vesicle transportation. Although, the function of spatacsin remains unknown, given it's basal expression in all tissues and it's high conservation in all species, this protein might have a crucial function which might explain the degeneration of the corticospinal tracts which might rely on the post-translational modifications or modeling/carriage of other proteins involved in axonal transport, mitochondrial metabolism as well as cerebral development. The presence of at least one transmembrane domain suggests that spatacsin may act as a receptor of a transporter.

All mutations identified so far in the KIAA1840 gene cause or are predicted to cause truncation of the protein, suggesting that pathogenicity results from loss of function. They are located in many exons, including exon 1 and exon 39 suggesting that the C-terminal domain of the protein has also an important function or effect on the structure of the protein. It is also conceivable that, given its position in the 5'splice site consensus sequence, the missense mutation R815M would also affect the transcription of the gene as demonstrated for mutation c.2833A>G, r.2834+1_2834+65 ins, p.R945GfsX950. Similarly, the mutations found in the intronic part of the acceptor splicing sites in introns 4, 12, 13 and 34 (Table 2) are likely altering the splicing of the surrounding exons and therefore the synthesis and/or stability of the mRNA or protein. No tissues from patients were available yet, however, to validate this hypothesis.

The identification of the SPG11 gene will now improve the diagnostic procedure, as well as patient management, and permit more accurate genetic counseling. This is invaluable for patients and their families.

REFERENCES

The following are all incorporated herein by reference:

Antonarakis et al. (1989), N. Engl. J. Med. 320:153-163 Diagnosis of genetic disorders at the DNA level Barbas C F, Bain J D, Hoekstra D M, Lerner R A. (1992), Semisynthetic combinatorial antibody libraries: a chemical solution to the diversity problem. PNAS USA, 89, 4457-4461

Callebaut, I. et al. Deciphering protein sequence information through hydrophobic cluster analysis (HCA): current status and perspectives. Cell Mol. Life Sci. 53, 621-645 (1997).

Casali, C. et al. Clinical and genetic studies in hereditary spastic paraplegia with thin corpus callosum. Neurology 62, 262-268 (2004).

Casari, G. et al. Spastic paraplegia and OXPHOS impairment caused by mutations in paraplegin, a nuclear-encoded mitochondrial metalloprotease. Cell 93, 973-983 (1998).

Chomocyznski et al., Anal. Biochem., 162:156, 1987

Colas et al., 1996

Cooper et al. (1991) Diagnosis of genetic disease using recombinant DNA, 3rd edition, Hum. Genet, 87:519-560

Den Dunnen J. T., Antonarakis S. E.: Hum Genet 109(1): 121-124, 2001.

Engert, J. C. et al. ARSACS, a spastic ataxia common in northeastern Quebec, is caused by mutations in a new gene encoding an 11.5-kb ORF. Nat. Genet 24, 120-125 (2000).

Fink, J. K. Advances in the hereditary spastic paraplegias. Exp. Neurol 184 Suppl 1, S106-S110 (2003).

Fink, J. K. Hereditary spastic paraplegia. Curr. Neurol. Neurosci. Rep. 6, 65-76 (2006).

Grompe M. The rapid detection of unknown mutations in nucleic acids (1993) Nat. Genet. 5(2):111-7

Gudbjartsson, D. F., Jonasson, K., Frigge, M. L., & Kong, A. Allegro, a new computer program for multipoint linkage analysis. Nature Genet. 25, 12-13 (2000).

Harding, A. E. Classification of the hereditary ataxias and paraplegias. Lancet 1, 1151-1155 (1983).

Harlow E. et al., Antibodies: A Laboratory Manual, Cold Spring Harbor Laboratory, New York, (1988).

Hazan, J. et al. Spastin, a new AAA protein, is altered in the most frequent form of autosomal dominant spastic paraplegia. Nature Genet. 23, 296-303 (1999).

Kohler and Milstein (1975) Continuous cultures of fused cells secreting antibody of predefined specificity. Nature; 256, 495-7.

Kuklin et al. Detection of single-nucleotide polymorphisms with the WAVE DNA fragment analysis system Genet. Test (1997-98), 1(3):201-6

Lossos, A. et al. Hereditary spastic paraplegia with thin corpus callosum: reduction of the SPG11 interval and evidence for further heterogeneity. Arch Neurol 63(5): 756-60 (2006).

Martinez, M. F. et al. Genetic localization of a new locus for recessive familial spastic paraparesis to 15q13-15. Neurology 53, 50-56 (1999).

Moutsimilli, L. et al. Selective cortical VGLUT1 increase as a marker for antidepressant activity. Neuropharmacology 49, 890-900 (2005).

Nickerson et al., 1990

Olmez et al. Further Clinical and Genetic Characterization of SPG11: Hereditary Spastic Paraplegia with Thin Corpus Callosum. Neuropediatrics. 2006; 37:59-66.

Patel, H. et al. SPG20 is mutated in Troyer syndrome, an hereditary spastic paraplegia. Nature Genet. 31, 347-348 (2002).

Saiki et al., Science 1988, 239:487

Sambrook, Fritsch & Maniatis, Molecular Cloning: A Laboratory Manual, Second Edition (1989) Cold Spring Harbor Laboratory Press, Cold Spring Harbor, N.Y.

Shibasaki, Y. et al. Linkage of autosomal recessive hereditary spastic paraplegia with mental impairment and thin corpus callosum to chromosome 15A13-15. Ann Neurol 48, 108-112 (2000).

Simpson, M. A. et al. Maspardin is mutated in mast syndrome, a complicated form of hereditary spastic paraplegia associated with dementia. Am. J. Hum. Genet. 73, 1147-1156 (2003).

Stevanin, G. et al. Spastic paraplegia with thin corpus callosum: description of 20 new families, refinement of the SPG11 locus, candidate gene analysis and evidence of genetic heterogeneity. Neurogenetics, 7, 149-156 (2006).

Stevanin, G. et al., Mutations in SPG11, encoding spatacsin, are a major cause of spastic paraplegia with thin corpus callosum Nat Genet Mar; 39(3):366-72. Epub 2007 Feb. 18. (2007)

Tallaksen, C. M., Durr, A., & Brice, A. Recent advances in hereditary spastic paraplegia. Curr. Opin. Neurol. 14, 457-463 (2001).

Waterhouse P, Griffiths A D, Johnson K S, Winter G. (1993) Combinatorial infection and in vivo recombination: a strategy for making large phage antibody repertoires. Nucleic Acids Research, 21, 2265-2266.

Winner, B. et al. Clinical progression and genetic analysis in hereditary spastic paraplegia with thin corpus callosum in spastic gait gene 11 (SPG11). Arch. Neurol. 61, 117-121 (2004).

Winner, B. et al. Thin corpus callosum and amyotrophy in spastic paraplegia-Case report and review of literature. Clin. Neurol. Neurosurg. (2005).

Woodcock, S., Mornon, J. P., & Henrissat, B. Detection of secondary structure elements in proteins by hydrophobic cluster analysis. Protein Eng 5, 629-635 (1992).

Zhao, X. et al. Mutations in a newly identified GTPase gene cause autosomal dominant hereditary spastic paraplegia. Nature Genet. 29, 326-331 (2001).

Reid, E. Pure hereditary spastic paraplegia. J. Med. Genet. 34, 499-503 (1997).

What is claimed is:

1. A method for detecting the presence of a KIAA1840 nucleic acid mutation in a subject, which method comprises: (a) contacting a KIAA1840 nucleic acid from said subject with an oligonucleotide that specifically hybridizes to a KIAA1840 mutation, wherein said KIAA1840 nucleic acid is at least 90% identical to SEQ ID NO:1, and wherein said KIAA1840 mutation encodes a truncated form of the KIAA1840 protein, and (b) detecting hybridization of the oligonucleotide with said KIAA1840 nucleic acid from said subject, thereby detecting the presence of a KIAA1840 nucleic acid mutation in the subject.

2. The method of claim 1, wherein the KIAA 1840 mutation is a substitution selected from the group consisting of c.6100C>T, c.2198T>G, c.118C>T, c.1235C>G, c.2833A>G, c.1951C>T, c.869+1G>A, c. 1679 C>G, c.2316+1G>A, c.2444G>T, c.2444+1G>C, c.2697G>A, c.5470C>T, c.5870C>G, c.6091C>T, c.6477+4 A>G, c.6856C>T, c.1282A>T, and c.5974C>T, wherein said mutation is relative to SEQ ID NO:1.

3. The method of claim 1, wherein the KIAA 1840 mutation is a deletion selected from the group consisting of c.529-533delATATT, c.6451delG, c.6832_6833delAG, c.1203delA, c.1549_1550delCT, c.6737_6740delTTGA, c.1471_1472delCT, c.1692delA, c.2716delC, c.1668delT, c.704_705delAT, c.5989_5992delCTGT, c.5532_5533delCA, c.5769delT, c.6739_6742delGAGT, c.4307_4308delAA and c.733_734delAT, wherein said mutation is relative to SEQ ID NO:1.

4. The method of claim 1, wherein the KIAA 1840 mutation is an insertion selected from the group consisting of c.7029_7030insT, c.2850.sub_2851insT, c.3741_3742insA, c.5982_5983insCTCT, c.5986_5987insT, c.3075_3076insA and c.2842_2843insG, wherein said mutation is relative to SEQ ID NO:1.

5. The method of claim 1, wherein the encoded truncated KIAA1840 protein has an amino acid sequence selected from the group consisting of SEQ ID NO: 149 to SEQ ID NO:164 and SEQ ID NO:166 to SEQ ID NO:188.

6. The method of claim 1 wherein the KIAA1840 nucleic acid from the subject is obtained from a source selected from the group consisting of blood, blood cells, plasma, serum, lymph, buccal cells, epithelial cells, fibroblasts, and cells present in a tissue obtained by biopsy.

7. The method of claim 6, wherein the KIAA1840 nucleic acid from the subject is obtained from a DNA sample.

8. The method of claim 7, wherein the sample comprises genomic DNA and the nucleic acid in the sample is amplified using oligonucleotide primers that are specific for a mutated site in the KIAA 1840 nucleic acid or that are capable of amplifying a region containing the mutation.

9. The method of claim 8, wherein the method further comprises DNA sequencing.

10. The method of claim 6 wherein the KIAA1840 nucleic acid from the subject is obtained from an RNA sample.

11. The method of claim 10, wherein the sample is subjected to coupled reverse transcription and nucleic acid amplification using oligonucleotide primers specific for a mutated site in the KIAA 1840 nucleic acid or amplify a region containing the mutation.

12. The method of claim 11, wherein the method further comprises DNA sequencing.

13. The method of claim 1, wherein the KIAA1840 nucleic acid from the subject is assayed by at least one process selected from the group consisting of direct sequencing, hybridization with allele-specific oligonucleotides, allele-specific PCR, PCR using mutagenic primers, and ligase-PCR.

14. The method of claim 1, wherein the oligonucleotide is detectably labeled.

15. The method of claim 14, wherein the oligonucleotide is detectably labeled with a radiolabel, a fluorescent label, and/or an enzymatic label.

16. The method of claim 1, wherein the oligonucleotide is 10 to 100 nucleotides in length.

\* \* \* \* \*

SEQUENCE LISTING

```
<160> NUMBER OF SEQ ID NOS: 188

<210> SEQ ID NO 1
<211> LENGTH: 7751
<212> TYPE: DNA
<213> ORGANISM: homo sapiens

<400> SEQUENCE: 1
atggctgcag aggaaggggt cgcgagtgct gcttccgccg gcggtagctg gggcaccgcg      60
gccatggggc gggttctacc gatgctgttg gtgccagtcc ccgccgaggc gatggggcag     120
ctcggctccc gggcgcagct gcgcacacag ccggaggctc tggggagcct gacggctgcg     180
ggcagcctcc aagtgctttc tttgacgcct ggcagccggg gcggggtcg ctgctgcctg      240 gagggcccct tctggcactt tctatgggag gattctcgta acagcagcac accaactgaa     300
aagcccaaac tgctcgctct tggtgaaaat tatgaactgc ttatctatga atttaatttg     360
```

```
aaagatggaa gatgtgatgc aaccattttg tatagctgta gtagggaggc attgcaaaag      420
ctcattgacg atcaagatat cagtatttcc ttattgtctt tgagaatcct gtcatttcac      480
aataacacat cattactgtt catcaacaaa tgtgtcatcc tacatattat atttcctgaa      540
agagatgctg caattagagt actcaactgt ttcacacttc ccttgcctgc acaggcagtg      600
gacatgatta ttgacacgca gctctgcaga ggaattcttt ttgttttgag tagtttaggc      660
tggatctaca ttttgatgt tgtggatggt acatatgtag ctcatgtgga tttagcactt       720
cacaaagaag acatgtgtaa tgagcagcaa caggagccag ccaagatttc ttcatttact      780
tcactgaaag tttctcaaga cctcgatgtt gcagtgattg tcagctcctc caactccgca      840
gttgctctta acttaaattt gtatttcagg caacacccag acacctact gtgtgaaaga       900 atactagaag atcttcctat tcaaggacct aagggcgtag atgaagatga tcctgttaac      960
tctgcctaca acatgaaact ggccaagttt tccttccaaa ttgataggtc ttggaaagcc     1020
cagctatcat cattgaatga aacaataaag aactccaaac tggaggtttc ctgttgtgct     1080
ccatggttcc aggatatttt gcatttggag tcacctgaat ctggtaacca cagtacaagt     1140
gtgcagagct gggccttcat tccacaggac ataatgcatg gcaatataa tgttctacag      1200 aaagatcatg ccaagaccag tgatccagga agatcatgga aaataatgca catcagtgaa     1260
caagaggaac ccatagagct taaatgtgtg tctgtgacag gattcactgc actgtttact     1320
tgggaagtgg aaaggatggg ctataccatt accctctggg attggagac ccagggcatg      1380 cagtgttttt cccttggcac aaagtgtatt cctgtagaca gtagtggaga ccagcagctg     1440
tgctttgttt tgacagagaa tggactctct ctgattttgt ttggtttgac tcaagaagag     1500 ttttaaaca gactcatgat ccatggaagt gccagcactg tggacactct ttgtcatctc      1560
aatggctggg gaaggtgctc aattcccata catgcactag aggccgggat agaaaatcgt     1620
cagctggaca cagtaaattt cttttttgaag agcaaggaaa atcttttaa tccatcctca     1680 aaatcttctg tatctgatca gtttgatcac ttgtcatccc atttatattt aagaaatgtg     1740
gaagagctga taccagcatt ggatttactt tgctcggcaa ttagagaaag ttattctgaa     1800
ccccaaagca aacactttc agaacaattg cttaatctta cactgtcttt ccttaacaac      1860
caaataaagg agcttttcat tcacactgaa gaactagatg aacatctgca aaaaggagtg     1920
aacattttga ctagctacat taatgaactt cgaaccttca tgataaagtt tccttggaag     1980
ctaacagatg ctatagatga atatgatgta catgaaaatg tccccaaagt aaaggagagc     2040
aatatatgga agaaactcag ctttgaggaa gttattgcca gcgccatttt aaacaacaaa     2100
ataccagagg cacagacttt cttcaggatt gatagtcatt ctgctcaaaa acttgaggag     2160
cttattggca taggcctaaa tttggtcttt gacaatttaa aaagaacaa tataaaggaa      2220 gcctctgaac ttttgaagaa tatggggttt gatgtaaaag gccaattgct caagatctgc     2280
ttctatacaa ctaataaaaa tatacgtgac ttttggttg aaatttaaa agaaaaaat       2340 tatttttctg aaaagagaa aagaactata gacttcgtgc atcaagttga aagctttat      2400 ttgggacatt tccaagaaaa tatgcaaatc cagtcatttc ccaggtactg ataaaggaa      2460 caagattttt tcaagcacaa gtctgttttg gactcattcc tgaaatatga ttgtaaagat     2520
gaatttaaca aacaggacca tagaattgtg ttaaattggg ctctgtggtg ggatcaacta     2580
acacaagaat ccatccttct ccccaggata agtccagaag aatacaaatc atattcccct     2640
gaagccctct ggagatacct cacagctcgc catgattggt taaacattat cttatggatt     2700
ggagaatttc aaacccagca tagttatgct tcacttcagc agaacaaatg gcccttctg      2760
```

```
actgttgatg ttattaacca gaatacttcc tgtaacaact acatgaggaa tgaaatttta    2820
gataagctgg ccaggaatgg ggttttttg gcatctgaac tggaagactt tgaatgcttc    2880
ctcctaagac tgagccgtat tggaggtgta atacaggata ccctccctgt tcaaaactac    2940
aagaccaaag aaggttggga tttccattct caattcattc tctattgttt ggagcacagt    3000
ctgcagcatc ttctttatgt ctaccttgac tgttacaaac ttagtcctga aaattgtccc    3060 ttttggaaa aaaagagtt acatgaagca caccccttggt ttgaatttt agttcagtgt    3120 cgacaagttg ccagtaactt aacagatccc aaactgatct tccaggctag ccttgcaaat    3180
gctcagattt tgattcccac caatcaggcc agtgtaagca gtatgctatt ggaaggacat    3240
accctcctgg cccttgctac tacaatgtat tctcctgggg gtgtcagtca ggttgttcag    3300
aatgaagaaa atgaaaactg tttgaagaaa gtggatcccc agctattgaa gatggcatta    3360
actccttacc ccaagctaaa aactgctctc ttcccacagt gcactcctcc tagtgtcctg    3420
ccatctgata ttacaatcta ccaccttatt cagtcattat caccctttga tcctagcaga    3480
ttgtttggct ggcagtctgc taacacacta gctataggag atgcatggag tcatctccca    3540
catttctcta gccctgacct ggttaataaa tatgctatag tggaacgtct gaattttgct    3600
tattatttac ataatgggcg gccatcattt gcatttggta ctttctctggt ccaggaatta    3660 atcaagagca agactcccaa gcagctgatc cagcaagtag gcaatgaagc ctatgttata    3720
gggctctcct ccttccacat accttcaata ggagctgcat gtgtttgttt cttagaattg    3780
cttggccttg acagcctcaa gctcagagtt gatatgaaag tggccaatat aatttttgagc    3840 tacaagtgca gaaatgaaga tgctcagtac agctttatca gagagtctgt agccgaaaaa    3900
ctatctaaac tagctgatgg tgaaaagaca accacagaag aattgcttgt tctcttagaa    3960
gaaggtacat ggaacagcat tcagcaacag gaaataaaga ggttatccag tgaatctagc    4020
agccaatggg cattagtggt gcagttctgc aggctacaca atatgaaact aagcatatct    4080
taccttagag aatgtgccaa agcaaatgat tggctgcagt tcattattca cagccaactc    4140
cacaactacc acccagcaga ggtgaaatcc cttatccagt acttcagccc agtcattcaa    4200
gaccacttaa ggctggcttt tgagaacttg ccctcagtgc ccacctccaa aatggacagc    4260
gatcaagtct gcaataagtg cccccaggaa cttcaaggaa gcaaacaaga gatgaccgat    4320
ttatttgaaa ttctgctcca atgctcagag gagccagact cctggcactg gcttctggtt    4380
gaagcagtga acaacaggc ccctatcctc agtgttctgg cctcatgtct ccagggtgcc    4440
agtgccattt cttgtctctg tgtttggatc atcacttctg tggaggacaa tgttgcaact    4500
gaagcaatgg gacacattca ggactcaaca gaggaccata cctggaacct tgaggatctt    4560
tcagtcatct ggagaacatt attaacaaga caaaagagca aaactctcat cagaggtttc    4620 cagctttttct ttaaggattc cccgttacta ctggtgatgg agatgtatga actgtgtatg    4680
ttcttcagga attataaaga agctgaagct aaacttctgg agtttcagaa gagccttgaa    4740
acgcttaaca cagcagccac aaaggtccac cctgtcatcc ctgccatgtg gctggaggat    4800
caggtgtgtt tccttttgaa gcttatgcta cagcagtgta agaccagta tgagctgggg    4860 aagcttttac agctctttgt tgaaagagag catctcttct ctgatggtcc agatgtgaaa    4920
aagctttgca tcctttgcca gattttgaag gatacatcca tagccattaa tcatacaatt    4980
attaccagct acagcattga gaatcttcag catgaatgta gatctatttt ggaaagactt    5040
cagacagatg gacaattcgc tttggccagg agggtagcag aattagctga gttacctgtg    5100
```

```
gacaacttgg ttattaaaga gataacacag gaaatgcaga ccctaaaaca cattgaacag     5160
tggtcactaa aacaagcaag aattgacttc tggaaaaaat gccatgagaa ttttaagaaa     5220
aattcaattt caagcaaagc agcttcttcc tttttctcaa cccaggccca tgtggcatgt     5280
gagcacccaa ctggatggag cagcatggag gagcgccatc tgctgctcac cttggcaggg     5340
cactggcttg cccaggagga cgtggtgccc ttggataagc tggaggagct ggagaagcag     5400
atctggctgt gccgcatcac ccagcacact cttggaagaa atcaggagga aacagagccc     5460
agattttctc gacagatctc aactagtggt gaactttcct ttgatagttt agccagtgag     5520
ttttccttct ccaagttggc tgctctgaac acatcaaaat acttagaact taacagcctt     5580
ccatccaaag agacatgcga gaatagattg gattggaaag agcaggagtc actaaacttt     5640
ttgattgggc gcctactgga tgatggctgt gtgcatgaag caagtagagt atgccggtat     5700
tttcattttt ataatccaga tgtcgccttg gtattgcact gcagagcact ggcctcaggg     5760
gaagctagta tggaggatct gcacccagag atccatgctc tcctacaaag tgctgagctg     5820
cttgaggaag aagcacccga cattcccta aggagagtcc acagcacttc aagtctggat     5880
agtcagaagt ttgtgacagt gccctccagt aatgaagtgg taactaacct ggaagtgctg     5940
acaagcaaat gcctccatgg gaagaactac tgtcgacagg tcctctgtct gtatgatctt     6000
gccaaggagt tgggctgttc ctacacagat gttgctgctc aggatggtga agccatgctc     6060
cggaaaatct tggcctctca gcagcctgac cgatgcaaac gagcccaggc cttcatcagc     6120
acacagggcc ttaagccaga tactgtggct gaactcgtgg cagaagaggt gacacgggag     6180
ctgcttactt catcacaggg aacaggacat aagcagatgt tcaacccaac agaggaaagc     6240
cagacatttc ttcagctgac cactctgtgt caagaccgca cattggtagg catgaagttg     6300
ttggataaga tttcctccgt tccccatggg gaactgtctt gcaccacaga gctcctgatc     6360
ctggcccatc attgcttcac cctgacgtgc cacatggagg gcatcatccg agtcctacag     6420
gccgcccaca tgctcacaga taaccacctg gcccccagtg aggagtatgg gctggtggta     6480
cggctcctca ctggcattgg aaggtacaac gagatgacat acatatttga tttgctgcat     6540
aaaaagcact actttgaagt gctaatgagg aagaagttgg atccgagtgg taccctgaaa     6600
acagccctgc tggactacat caaacgctgc cgtcctggag acagtgaaaa gcacaatatg     6660
attgccctgt gcttcagcat gtgccgggag attggcgaga accacgaggc agctgcccgc     6720
atccaactga aattgattga gtctcagccc tgggaggaca gcctcaagga tgggcaccag     6780
ctgaaacaac tgctgctgaa ggccctgact ctgatgttgg atgcagcaga gagttatgcc     6840
aaggactcct gtgtgcgaca ggcccagcac tgtcagcggc tcaccaagtt gataactctg     6900
cagattcact ttctgaacac tggccagaac acaatgctca tcaacttggg ccgccacaag     6960
ctgatggact gtattctggc cctacctcgg ttctaccagg cttctattgt ggctgaggcc     7020
tacgattttg ttccagattg ggctgaaatt ttataccagc aagtgattct taaaggagac     7080
tttaattact tggaagaatt taagcagcaa aggttattaa agtccagtat atttgaagag     7140
atttccaaaa aatataaaca acatcagcct actgacatgg tcatggaaaa cctgaagaaa     7200
ttactcacat attgtgaaga tgtttacctg tattacaagt tggcatacga acacaagttt     7260
tatgaaattg taaatgtgct tctgaaggac cctcagacag gttgctgtct aaaggacatg     7320
ctagcaggtt agatgatttc ataggtgtct gttttcttgt actgttagca gattctgaca     7380
gatgtgatga gaagaagaat gcattggaga tctttgctaa agttgaacaa tcccggtact     7440
gtaccatatc agtccttgt gggtagtagg tagcaagtaa gaaactttc aggaggaaat      7500
```

-continued

```
tcctatttaa aatagattga ttttagatga ttgttcatcc acaccatttt atatagatac    7560
tagtattaag atcaaaagct tcctcttcct caggacagct tctactttag atgatccaat    7620
aatgattaaa gaatacctgt acctgcagat tccagtttca agaaattta attattattt     7680 acacagttaa ggaacaggtg atacattttc atttgttaga aactgatctt tctgtaataa    7740
aatagatttt c                                                          7751
```

<210> SEQ ID NO 2
<211> LENGTH: 2443
<212> TYPE: PRT
<213> ORGANISM: homo sapiens

<400> SEQUENCE: 2

```
Met Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Asp Pro Val Asn
305                 310                 315                 320
```

```
Ser Ala Tyr Asn Met Lys Leu Ala Lys Phe Ser Gln Ile Asp Arg
            325                 330                 335

Ser Trp Lys Ala Gln Leu Ser Ser Leu Asn Glu Thr Ile Lys Asn Ser
        340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Phe Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
            725                 730                 735

Asn Ile Lys Glu Ala Ser Glu Leu Leu Lys Asn Met Gly Phe Asp Val
```

-continued

```
                740                 745                 750
Lys Gly Gln Leu Leu Lys Ile Cys Phe Tyr Thr Thr Asn Lys Asn Ile
            755                 760                 765
Arg Asp Phe Leu Val Glu Ile Leu Lys Glu Lys Asn Tyr Phe Ser Glu
            770                 775                 780
Lys Glu Lys Arg Thr Ile Asp Phe Val His Gln Val Glu Lys Leu Tyr
785                 790                 795                 800
Leu Gly His Phe Gln Glu Asn Met Gln Ile Gln Ser Phe Pro Arg Tyr
                805                 810                 815
Trp Ile Lys Glu Gln Asp Phe Phe Lys His Lys Ser Val Leu Asp Ser
                820                 825                 830
Phe Leu Lys Tyr Asp Cys Lys Asp Glu Phe Asn Lys Gln Asp His Arg
            835                 840                 845
Ile Val Leu Asn Trp Ala Leu Trp Trp Asp Gln Leu Thr Gln Glu Ser
            850                 855                 860
Ile Leu Leu Pro Arg Ile Ser Pro Glu Tyr Lys Ser Tyr Ser Pro
865                 870                 875                 880
Glu Ala Leu Trp Arg Tyr Leu Thr Ala Arg His Asp Trp Leu Asn Ile
                885                 890                 895
Ile Leu Trp Ile Gly Glu Phe Gln Thr Gln His Ser Tyr Ala Ser Leu
                900                 905                 910
Gln Gln Asn Lys Trp Pro Leu Leu Thr Val Asp Val Ile Asn Gln Asn
            915                 920                 925
Thr Ser Cys Asn Asn Tyr Met Arg Asn Glu Ile Leu Asp Lys Leu Ala
            930                 935                 940
Arg Asn Gly Val Phe Leu Ala Ser Glu Leu Glu Asp Phe Glu Cys Phe
945                 950                 955                 960
Leu Leu Arg Leu Ser Arg Ile Gly Gly Val Ile Gln Asp Thr Leu Pro
                965                 970                 975
Val Gln Asn Tyr Lys Thr Lys Leu Gly Trp Asp Phe His Ser Gln Phe
            980                 985                 990
Ile Leu Tyr Cys Leu Glu His Ser  Leu Gln His Leu Leu  Tyr Val Tyr
            995                 1000                1005
Leu Asp Cys Tyr Lys Leu Ser  Pro Glu Asn Cys Pro  Phe Leu Glu
    1010                1015                1020
Lys Lys Glu Leu His Glu Ala  His Pro Trp Phe Glu  Phe Leu Val
    1025                1030                1035
Gln Cys Arg Gln Val Ala Ser  Asn Leu Thr Asp Pro  Lys Leu Ile
    1040                1045                1050
Phe Gln Ala Ser Leu Ala Asn  Ala Gln Ile Leu Ile  Pro Thr Asn
    1055                1060                1065
Gln Ala Ser Val Ser Ser Met  Leu Leu Glu Gly His  Thr Leu Leu
    1070                1075                1080
Ala Leu Ala Thr Thr Met Tyr  Ser Pro Gly Gly Val  Ser Gln Val
    1085                1090                1095
Val Gln Asn Glu Glu Asn Glu  Asn Cys Leu Lys Lys  Val Asp Pro
    1100                1105                1110
Gln Leu Leu Lys Met Ala Leu  Thr Pro Tyr Pro Lys  Leu Lys Thr
    1115                1120                1125
Ala Leu Phe Pro Gln Cys Thr  Pro Pro Ser Val Leu  Pro Ser Asp
    1130                1135                1140
Ile Thr Ile Tyr His Leu Ile  Gln Ser Leu Ser Pro  Phe Asp Pro
    1145                1150                1155
```

-continued

Ser Arg Leu Phe Gly Trp Gln Ser Ala Asn Thr Leu Ala Ile Gly
1160               1165               1170

Asp Ala Trp Ser His Leu Pro His Phe Ser Ser Pro Asp Leu Val
1175               1180               1185

Asn Lys Tyr Ala Ile Val Glu Arg Leu Asn Phe Ala Tyr Tyr Leu
1190               1195               1200

His Asn Gly Arg Pro Ser Phe Ala Phe Gly Thr Phe Leu Val Gln
1205               1210               1215

Glu Leu Ile Lys Ser Lys Thr Pro Lys Gln Leu Ile Gln Gln Val
1220               1225               1230

Gly Asn Glu Ala Tyr Val Ile Gly Leu Ser Ser Phe His Ile Pro
1235               1240               1245

Ser Ile Gly Ala Ala Cys Val Cys Phe Leu Glu Leu Leu Gly Leu
1250               1255               1260

Asp Ser Leu Lys Leu Arg Val Asp Met Lys Val Ala Asn Ile Ile
1265               1270               1275

Leu Ser Tyr Lys Cys Arg Asn Glu Asp Ala Gln Tyr Ser Phe Ile
1280               1285               1290

Arg Glu Ser Val Ala Glu Lys Leu Ser Lys Leu Ala Asp Gly Glu
1295               1300               1305

Lys Thr Thr Thr Glu Glu Leu Leu Val Leu Leu Glu Glu Gly Thr
1310               1315               1320

Trp Asn Ser Ile Gln Gln Gln Glu Ile Lys Arg Leu Ser Ser Glu
1325               1330               1335

Ser Ser Ser Gln Trp Ala Leu Val Val Gln Phe Cys Arg Leu His
1340               1345               1350

Asn Met Lys Leu Ser Ile Ser Tyr Leu Arg Glu Cys Ala Lys Ala
1355               1360               1365

Asn Asp Trp Leu Gln Phe Ile Ile His Ser Gln Leu His Asn Tyr
1370               1375               1380

His Pro Ala Glu Val Lys Ser Leu Ile Gln Tyr Phe Ser Pro Val
1385               1390               1395

Ile Gln Asp His Leu Arg Leu Ala Phe Glu Asn Leu Pro Ser Val
1400               1405               1410

Pro Thr Ser Lys Met Asp Ser Asp Gln Val Cys Asn Lys Cys Pro
1415               1420               1425

Gln Glu Leu Gln Gly Ser Lys Gln Glu Met Thr Asp Leu Phe Glu
1430               1435               1440

Ile Leu Leu Gln Cys Ser Glu Glu Pro Asp Ser Trp His Trp Leu
1445               1450               1455

Leu Val Glu Ala Val Lys Gln Ala Pro Ile Leu Ser Val Leu
1460               1465               1470

Ala Ser Cys Leu Gln Gly Ala Ser Ala Ile Ser Cys Leu Cys Val
1475               1480               1485

Trp Ile Ile Thr Ser Val Glu Asp Asn Val Ala Thr Glu Ala Met
1490               1495               1500

Gly His Ile Gln Asp Ser Thr Glu Asp His Thr Trp Asn Leu Glu
1505               1510               1515

Asp Leu Ser Val Ile Trp Arg Thr Leu Leu Thr Arg Gln Lys Ser
1520               1525               1530

Lys Thr Leu Ile Arg Gly Phe Gln Leu Phe Phe Lys Asp Ser Pro
1535               1540               1545

-continued

Leu Leu Leu Val Met Glu Met Tyr Glu Leu Cys Met Phe Phe Arg
1550             1555             1560

Asn Tyr Lys Glu Ala Glu Ala Lys Leu Leu Glu Phe Gln Lys Ser
1565             1570             1575

Leu Glu Thr Leu Asn Thr Ala Ala Thr Lys Val His Pro Val Ile
1580             1585             1590

Pro Ala Met Trp Leu Glu Asp Gln Val Cys Phe Leu Leu Lys Leu
1595             1600             1605

Met Leu Gln Gln Cys Lys Thr Gln Tyr Glu Leu Gly Lys Leu Leu
1610             1615             1620

Gln Leu Phe Val Glu Arg Glu His Leu Phe Ser Asp Gly Pro Asp
1625             1630             1635

Val Lys Lys Leu Cys Ile Leu Cys Gln Ile Leu Lys Asp Thr Ser
1640             1645             1650

Ile Ala Ile Asn His Thr Ile Ile Thr Ser Tyr Ser Ile Glu Asn
1655             1660             1665

Leu Gln His Glu Cys Arg Ser Ile Leu Glu Arg Leu Gln Thr Asp
1670             1675             1680

Gly Gln Phe Ala Leu Ala Arg Arg Val Ala Glu Leu Ala Glu Leu
1685             1690             1695

Pro Val Asp Asn Leu Val Ile Lys Glu Ile Thr Gln Glu Met Gln
1700             1705             1710

Thr Leu Lys His Ile Glu Gln Trp Ser Leu Lys Gln Ala Arg Ile
1715             1720             1725

Asp Phe Trp Lys Lys Cys His Glu Asn Phe Lys Lys Asn Ser Ile
1730             1735             1740

Ser Ser Lys Ala Ala Ser Ser Phe Phe Ser Thr Gln Ala His Val
1745             1750             1755

Ala Cys Glu His Pro Thr Gly Trp Ser Ser Met Glu Glu Arg His
1760             1765             1770

Leu Leu Leu Thr Leu Ala Gly His Trp Leu Ala Gln Glu Asp Val
1775             1780             1785

Val Pro Leu Asp Lys Leu Glu Glu Leu Glu Lys Gln Ile Trp Leu
1790             1795             1800

Cys Arg Ile Thr Gln His Thr Leu Gly Arg Asn Gln Glu Glu Thr
1805             1810             1815

Glu Pro Arg Phe Ser Arg Gln Ile Ser Thr Ser Gly Glu Leu Ser
1820             1825             1830

Phe Asp Ser Leu Ala Ser Glu Phe Ser Phe Ser Lys Leu Ala Ala
1835             1840             1845

Leu Asn Thr Ser Lys Tyr Leu Glu Leu Asn Ser Leu Pro Ser Lys
1850             1855             1860

Glu Thr Cys Glu Asn Arg Leu Asp Trp Lys Glu Gln Glu Ser Leu
1865             1870             1875

Asn Phe Leu Ile Gly Arg Leu Leu Asp Asp Gly Cys Val His Glu
1880             1885             1890

Ala Ser Arg Val Cys Arg Tyr Phe His Phe Tyr Asn Pro Asp Val
1895             1900             1905

Ala Leu Val Leu His Cys Arg Ala Leu Ala Ser Gly Glu Ala Ser
1910             1915             1920

Met Glu Asp Leu His Pro Glu Ile His Ala Leu Leu Gln Ser Ala
1925             1930             1935

Glu Leu Leu Glu Glu Glu Ala Pro Asp Ile Pro Leu Arg Arg Val

```
                1940                1945                1950
His Ser  Thr Ser Ser Leu Asp  Ser Gln Lys Phe Val  Thr Val Pro
     1955                1960                1965
Ser Ser  Asn Glu Val Val Thr  Asn Leu Glu Val Leu  Thr Ser Lys
     1970                1975                1980
Cys Leu  His Gly Lys Asn Tyr  Cys Arg Gln Val Leu  Cys Leu Tyr
     1985                1990                1995
Asp Leu  Ala Lys Glu Leu Gly  Cys Ser Tyr Thr Asp  Val Ala Ala
     2000                2005                2010
Gln Asp  Gly Glu Ala Met Leu  Arg Lys Ile Leu Ala  Ser Gln Gln
     2015                2020                2025
Pro Asp  Arg Cys Lys Arg Ala  Gln Ala Phe Ile Ser  Thr Gln Gly
     2030                2035                2040
Leu Lys  Pro Asp Thr Val Ala  Glu Leu Val Ala Glu  Glu Val Thr
     2045                2050                2055
Arg Glu  Leu Leu Thr Ser Ser  Gln Gly Thr Gly His  Lys Gln Met
     2060                2065                2070
Phe Asn  Pro Thr Glu Glu Ser  Gln Thr Phe Leu Gln  Leu Thr Thr
     2075                2080                2085
Leu Cys  Gln Asp Arg Thr Leu  Val Gly Met Lys Leu  Leu Asp Lys
     2090                2095                2100
Ile Ser  Ser Val Pro His Gly  Glu Leu Ser Cys Thr  Thr Glu Leu
     2105                2110                2115
Leu Ile  Leu Ala His His Cys  Phe Thr Leu Thr Cys  His Met Glu
     2120                2125                2130
Gly Ile  Ile Arg Val Leu Gln  Ala Ala His Met Leu  Thr Asp Asn
     2135                2140                2145
His Leu  Ala Pro Ser Glu Glu  Tyr Gly Leu Val Val  Arg Leu Leu
     2150                2155                2160
Thr Gly  Ile Gly Arg Tyr Asn  Glu Met Thr Tyr Ile  Phe Asp Leu
     2165                2170                2175
Leu His  Lys Lys His Tyr Phe  Glu Val Leu Met Arg  Lys Lys Leu
     2180                2185                2190
Asp Pro  Ser Gly Thr Leu Lys  Thr Ala Leu Leu Asp  Tyr Ile Lys
     2195                2200                2205
Arg Cys  Arg Pro Gly Asp Ser  Glu Lys His Asn Met  Ile Ala Leu
     2210                2215                2220
Cys Phe  Ser Met Cys Arg Glu  Ile Gly Glu Asn His  Glu Ala Ala
     2225                2230                2235
Ala Arg  Ile Gln Leu Lys Leu  Ile Glu Ser Gln Pro  Trp Glu Asp
     2240                2245                2250
Ser Leu  Lys Asp Gly His Gln  Leu Lys Gln Leu Leu  Leu Lys Ala
     2255                2260                2265
Leu Thr  Leu Met Leu Asp Ala  Ala Glu Ser Tyr Ala  Lys Asp Ser
     2270                2275                2280
Cys Val  Arg Gln Ala Gln His  Cys Gln Arg Leu Thr  Lys Leu Ile
     2285                2290                2295
Thr Leu  Gln Ile His Phe Leu  Asn Thr Gly Gln Asn  Thr Met Leu
     2300                2305                2310
Ile Asn  Leu Gly Arg His Lys  Leu Met Asp Cys Ile  Leu Ala Leu
     2315                2320                2325
Pro Arg  Phe Tyr Gln Ala Ser  Ile Val Ala Glu Ala  Tyr Asp Phe
     2330                2335                2340
```

-continued

| | | | | | | | | | | |
|---|---|---|---|---|---|---|---|---|---|---|
| Val | Pro | Asp | Trp | Ala | Glu | Ile | Leu | Tyr | Gln | Gln Val Ile Leu Lys |
| | 2345 | | | | 2350 | | | | 2355 | |
| Gly | Asp | Phe | Asn | Tyr | Leu | Glu | Glu | Phe | Lys | Gln Gln Arg Leu Leu |
| | 2360 | | | | 2365 | | | | 2370 | |
| Lys | Ser | Ser | Ile | Phe | Glu | Glu | Ile | Ser | Lys | Tyr Lys Gln His |
| | 2375 | | | | 2380 | | | | 2385 | |
| Gln | Pro | Thr | Asp | Met | Val | Met | Glu | Asn | Leu | Lys Lys Leu Leu Thr |
| | 2390 | | | | 2395 | | | | 2400 | |
| Tyr | Cys | Glu | Asp | Val | Tyr | Leu | Tyr | Tyr | Lys | Leu Ala Tyr Glu His |
| | 2405 | | | | 2410 | | | | 2415 | |
| Lys | Phe | Tyr | Glu | Ile | Val | Asn | Val | Leu | Leu | Lys Asp Pro Gln Thr |
| | 2420 | | | | 2425 | | | | 2430 | |
| Gly | Cys | Cys | Leu | Lys | Asp | Met | Leu | Ala | Gly | |
| | 2435 | | | | 2440 | | | | | |

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ccacaggaaa cgaatggaat                                             20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
ggttctgtga ggaaaccacg                                             20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
cagggacatt gtaggccatc                                             20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ccagttgtaa aattgtgacc                                             20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
tcccagctcc caaaactaaa                                              20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
tcaatcaaca cttctaccac                                              20

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
caggttcttt cttgtggcat ca                                           22

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
cgaggatatt tttaacctct tatca                                        25

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
gttaggcata cttacaaaac tggc                                         24

<210> SEQ ID NO 12
<211> LENGTH: 25
<212> TYPE: DNA
<213> ORGANISM: Artificial
<220> FEATURE:
<223> OTHER INFORMATION: primer

<400> SEQUENCE: 12
cgaggatatt tttaacctct tatca                                        25

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gaacatcttt gccctggttt                                              20

<210> SEQ ID NO 14
<211> LENGTH: 20
<212> TYPE: DNA

```
<213> ORGANISM: Artificial
<220> FEATURE:
<223> OTHER INFORMATION: primer

<400> SEQUENCE: 14
ctgtgacagg tgttaagtta                                              20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
caggcactga ggcagaagta                                              20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
atctaataca agacagtctc                                              20

<210> SEQ ID NO 17
<211> LENGTH: 26
<212> TYPE: DNA
<213> ORGANISM: Artificial
<220> FEATURE:
<223> OTHER INFORMATION: primer

<400> SEQUENCE: 17
aaaaatcaat tcctaaatca taatcc                                       26

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
tagtactgaa gtattgagta                                              20

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
tcttttaaag ccaaaaggg taaa                                          24

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
ttaagtaatg ttcttgggca                                              20
```

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
cccaggacta atcatgaagg a                                              21

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
atccccaaac cgataaaacc                                                20

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
cggtgtgtct tccactagct c                                              21

<210> SEQ ID NO 24
<211> LENGTH: 23
<212> TYPE: DNA
<213> ORGANISM: Artificial
<220> FEATURE:
<223> OTHER INFORMATION: primer

<400> SEQUENCE: 24
gttacataaa tgtataatcc ctg                                            23

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
acccagccat tctcagtgtt                                                20

<210> SEQ ID NO 26
<211> LENGTH: 23
<212> TYPE: DNA
<213> ORGANISM: Artificial
<220> FEATURE:
<223> OTHER INFORMATION: primer

<400> SEQUENCE: 26
cattttaaga ctttatggat tac                                            23

<210> SEQ ID NO 27
<211> LENGTH: 20
<212> TYPE: DNA
<213> ORGANISM: Artificial
<220> FEATURE:

<223> OTHER INFORMATION: primer

<400> SEQUENCE: 27
cacagcgaga tcctgtctca                                                    20

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
cctcactgta agatgatgcc c                                                  21

<210> SEQ ID NO 29
<211> LENGTH: 25
<212> TYPE: DNA
<213> ORGANISM: Artificial
<220> FEATURE:
<223> OTHER INFORMATION: primer

<400> SEQUENCE: 29
cctttaaata ctacagtggt gcaga                                              25

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
tgtgggcatg atttggtcta                                                    20

<210> SEQ ID NO 31
<211> LENGTH: 22
<212> TYPE: DNA
<213> ORGANISM: Artificial
<220> FEATURE:
<223> OTHER INFORMATION: primer

<400> SEQUENCE: 31
ccaactgttg agatggagaa aa                                                 22

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
acctgctcaa ggacaaatgc                                                    20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
tttgaagtat cccagggtgg                                                    20

```
<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
ccaccattcc ccaaagataa                                                 20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
ttacctggat ttggctttgg                                                 20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
cctggcttct aaaagtggcc                                                 20

<210> SEQ ID NO 37
<211> LENGTH: 22
<212> TYPE: DNA
<213> ORGANISM: Artificial
<220> FEATURE:
<223> OTHER INFORMATION: primer

<400> SEQUENCE: 37
tgcaatccag aaacttgaga ga                                              22

<210> SEQ ID NO 38
<211> LENGTH: 21
<212> TYPE: DNA
<213> ORGANISM: Artificial
<220> FEATURE:
<223> OTHER INFORMATION: primer

<400> SEQUENCE: 38
aagcacaaca tccaaatcct t                                               21

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
atgttggcag gaactccatc                                                 20

<210> SEQ ID NO 40
<211> LENGTH: 20
<212> TYPE: DNA
<213> ORGANISM: Artificial
<220> FEATURE:
<223> OTHER INFORMATION: primer
```

```
<400> SEQUENCE: 40
ctcctttgga gcaacctctg                                              20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
ttccaacagg aaagcacaca                                              20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
caacaggaaa gcacacatgc                                              20

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
cagctacttg ggaggctgag                                              20

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
gtgtggctgt gacctcactc                                              20

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
gcattagaag gggcactgaa                                              20

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
aacatggctg ggatgtttct                                              20

<210> SEQ ID NO 47
<211> LENGTH: 20
```

```
<212> TYPE: DNA
<213> ORGANISM: Artificial
<220> FEATURE:
<223> OTHER INFORMATION: primer

<400> SEQUENCE: 47
ctcacaacgg tattcacccc                                             20

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
ttcctggttg gcctatgatg                                             20

<210> SEQ ID NO 49
<211> LENGTH: 23
<212> TYPE: DNA
<213> ORGANISM: Artificial
<220> FEATURE:
<223> OTHER INFORMATION: primer

<400> SEQUENCE: 49
aagggtttaa gataatttgg gga                                         23

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
aatgccaaac acacacctga                                             20

<210> SEQ ID NO 51
<211> LENGTH: 22
<212> TYPE: DNA
<213> ORGANISM: Artificial
<220> FEATURE:
<223> OTHER INFORMATION: primer

<400> SEQUENCE: 51
ggattcttga tactgctttg cc                                          22

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
ctcaaagcag aggcaaggag                                             20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
```

-continued ctgagcccca cattttttgtt                                                    20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
caagtgctca atagccccat                                                     20

<210> SEQ ID NO 55
<211> LENGTH: 25
<212> TYPE: DNA
<213> ORGANISM: Artificial
<220> FEATURE:
<223> OTHER INFORMATION: primer

<400> SEQUENCE: 55
gctaactgcc cttaatagag taaaa                                               25

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
aaagggtaca gcgtcagcat                                                     20

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
cttgccccag attgcataat                                                     20

<210> SEQ ID NO 58
<211> LENGTH: 23
<212> TYPE: DNA
<213> ORGANISM: Artificial
<220> FEATURE:
<223> OTHER INFORMATION: primer

<400> SEQUENCE: 58
tccaaaaagt acgtaaaatc cca                                                 23

<210> SEQ ID NO 59
<211> LENGTH: 22
<212> TYPE: DNA
<213> ORGANISM: Artificial
<220> FEATURE:
<223> OTHER INFORMATION: primer

<400> SEQUENCE: 59
cagcaaaagg gtaatagcag tg                                                  22

<210> SEQ ID NO 60
<211> LENGTH: 20
<212> TYPE: DNA
<213> ORGANISM: Artificial

```
<220> FEATURE:
<223> OTHER INFORMATION: primer

<400> SEQUENCE: 60
cccaaatgta gtaaatggcg                                              20

<210> SEQ ID NO 61
<211> LENGTH: 23
<212> TYPE: DNA
<213> ORGANISM: Artificial
<220> FEATURE:
<223> OTHER INFORMATION: primer

<400> SEQUENCE: 61
tttgaaagag cagaaagcta tgg                                          23

<210> SEQ ID NO 62
<211> LENGTH: 21
<212> TYPE: DNA
<213> ORGANISM: Artificial
<220> FEATURE:
<223> OTHER INFORMATION: primer

<400> SEQUENCE: 62
tgaaggggtt gtcacacttt t                                            21

<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
ttgtggcaaa agaaaatttg tg                                           22

<210> SEQ ID NO 64
<211> LENGTH: 20
<212> TYPE: DNA
<213> ORGANISM: Artificial
<220> FEATURE:
<223> OTHER INFORMATION: primer

<400> SEQUENCE: 64
gagaatgcag gctcagttcc                                              20

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
atgtggaact gagcctgcat                                              20

<210> SEQ ID NO 66
<211> LENGTH: 23
<212> TYPE: DNA
<213> ORGANISM: Artificial
<220> FEATURE:
<223> OTHER INFORMATION: primer

<400> SEQUENCE: 66
cgacttgcat tttaaagaac ctg                                          23
```

```
<210> SEQ ID NO 67
<211> LENGTH: 25
<212> TYPE: DNA
<213> ORGANISM: Artificial
<220> FEATURE:
<223> OTHER INFORMATION: primer

<400> SEQUENCE: 67
ttgtttccag atcatgaaga atatg                                           25

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
tcagatagct gaccacagcc                                                 20

<210> SEQ ID NO 69
<211> LENGTH: 24
<212> TYPE: DNA
<213> ORGANISM: Artificial
<220> FEATURE:
<223> OTHER INFORMATION: primer

<400> SEQUENCE: 69
tccctcttaa ggagaaaaac actg                                            24

<210> SEQ ID NO 70
<211> LENGTH: 20
<212> TYPE: DNA
<213> ORGANISM: Artificial
<220> FEATURE:
<223> OTHER INFORMATION: primer

<400> SEQUENCE: 70
accgggccga gatataaaat                                                 20

<210> SEQ ID NO 71
<211> LENGTH: 25
<212> TYPE: DNA
<213> ORGANISM: Artificial
<220> FEATURE:
<223> OTHER INFORMATION: primer

<400> SEQUENCE: 71
gctagtttgt cttagaacca gaaca                                           25

<210> SEQ ID NO 72
<211> LENGTH: 23
<212> TYPE: DNA
<213> ORGANISM: Artificial
<220> FEATURE:
<223> OTHER INFORMATION: primer

<400> SEQUENCE: 72 ttttggggttg tctcactatc aca                                            23

<210> SEQ ID NO 73
<211> LENGTH: 24
<212> TYPE: DNA
<213> ORGANISM: Artificial
<220> FEATURE:
<223> OTHER INFORMATION: primer
```

```
<400> SEQUENCE: 73
aaggaacata gccagttctg tttt                                              24

<210> SEQ ID NO 74
<211> LENGTH: 21
<212> TYPE: DNA
<213> ORGANISM: Artificial
<220> FEATURE:
<223> OTHER INFORMATION: primer

<400> SEQUENCE: 74
tgcgaactat ttttcctttg g                                                 21

<210> SEQ ID NO 75
<211> LENGTH: 23
<212> TYPE: DNA
<213> ORGANISM: Artificial
<220> FEATURE:
<223> OTHER INFORMATION: primer

<400> SEQUENCE: 75
tgcaacttct caggtacaca tct                                               23

<210> SEQ ID NO 76
<211> LENGTH: 20
<212> TYPE: DNA
<213> ORGANISM: Artificial
<220> FEATURE:
<223> OTHER INFORMATION: primer

<400> SEQUENCE: 76
aggctagagt gcagtggcat                                                   20

<210> SEQ ID NO 77
<211> LENGTH: 20
<212> TYPE: DNA
<213> ORGANISM: Artificial
<220> FEATURE:
<223> OTHER INFORMATION: primer

<400> SEQUENCE: 77
agtcagctta agggaagcgg                                                   20

<210> SEQ ID NO 78
<211> LENGTH: 22
<212> TYPE: DNA
<213> ORGANISM: Artificial
<220> FEATURE:
<223> OTHER INFORMATION: primer

<400> SEQUENCE: 78
gaagataacc attttctccc ca                                                22

<210> SEQ ID NO 79
<211> LENGTH: 20
<212> TYPE: DNA
<213> ORGANISM: Artificial
<220> FEATURE:
<223> OTHER INFORMATION: primer

<400> SEQUENCE: 79
ttgtgagtgt ttggggagaa                                                   20

<210> SEQ ID NO 80
```

```
<211> LENGTH: 21
<212> TYPE: DNA
<213> ORGANISM: Artificial
<220> FEATURE:
<223> OTHER INFORMATION: primer

<400> SEQUENCE: 80 gggatttag tgaaaacacc a                                          21

<210> SEQ ID NO 81
<211> LENGTH: 24
<212> TYPE: DNA
<213> ORGANISM: Artificial
<220> FEATURE:
<223> OTHER INFORMATION: primer

<400> SEQUENCE: 81
tttgttggag aatacactgt gctt                                      24

<210> SEQ ID NO 82
<211> LENGTH: 25
<212> TYPE: DNA
<213> ORGANISM: Artificial
<220> FEATURE:
<223> OTHER INFORMATION: primer

<400> SEQUENCE: 82
catgtctaca caacagaaag aatgc                                     25

<210> SEQ ID NO 83
<211> LENGTH: 21
<212> TYPE: DNA
<213> ORGANISM: Artificial
<220> FEATURE:
<223> OTHER INFORMATION: primer

<400> SEQUENCE: 83
aaaaggcacc atacagcttt g                                         21

<210> SEQ ID NO 84
<211> LENGTH: 20
<212> TYPE: DNA
<213> ORGANISM: Artificial
<220> FEATURE:
<223> OTHER INFORMATION: primer

<400> SEQUENCE: 84
ggaaacacat gctggaacct                                           20

<210> SEQ ID NO 85
<211> LENGTH: 22
<212> TYPE: DNA
<213> ORGANISM: Artificial
<220> FEATURE:
<223> OTHER INFORMATION: primer

<400> SEQUENCE: 85
cttctgtctg cttcttggtc tt                                        22

<210> SEQ ID NO 86
<211> LENGTH: 22
<212> TYPE: DNA
<213> ORGANISM: Artificial
<220> FEATURE:
<223> OTHER INFORMATION: primer

<400> SEQUENCE: 86
```

```
tatcatcatt atctgttgtt gg                                              22

<210> SEQ ID NO 87
<211> LENGTH: 20
<212> TYPE: DNA
<213> ORGANISM: Artificial
<220> FEATURE:
<223> OTHER INFORMATION: primer

<400> SEQUENCE: 87
ttaggtgatc ccactggctc                                                 20

<210> SEQ ID NO 88
<211> LENGTH: 20
<212> TYPE: DNA
<213> ORGANISM: Artificial
<220> FEATURE:
<223> OTHER INFORMATION: primer

<400> SEQUENCE: 88
cccaggagtt caaggctgta                                                 20

<210> SEQ ID NO 89
<211> LENGTH: 20
<212> TYPE: DNA
<213> ORGANISM: Artificial
<220> FEATURE:
<223> OTHER INFORMATION: primer

<400> SEQUENCE: 89
ctgaggaggg cttgtttttg                                                 20

<210> SEQ ID NO 90
<211> LENGTH: 25
<212> TYPE: DNA
<213> ORGANISM: Artificial
<220> FEATURE:
<223> OTHER INFORMATION: primer

<400> SEQUENCE: 90
tctgtaactt gtttactccc agttg                                           25

<210> SEQ ID NO 91
<211> LENGTH: 20
<212> TYPE: DNA
<213> ORGANISM: Artificial
<220> FEATURE:
<223> OTHER INFORMATION: primer

<400> SEQUENCE: 91
gatcacacca ctgcattcca                                                 20

<210> SEQ ID NO 92
<211> LENGTH: 20
<212> TYPE: DNA
<213> ORGANISM: Artificial
<220> FEATURE:
<223> OTHER INFORMATION: primer

<400> SEQUENCE: 92
ggcacctgta gtcccagcta                                                 20

<210> SEQ ID NO 93
<211> LENGTH: 20
<212> TYPE: DNA
```

```
<213> ORGANISM: Artificial
<220> FEATURE:
<223> OTHER INFORMATION: primer

<400> SEQUENCE: 93
tgaggtggga ggatctcttg                                                 20

<210> SEQ ID NO 94
<211> LENGTH: 20
<212> TYPE: DNA
<213> ORGANISM: Artificial
<220> FEATURE:
<223> OTHER INFORMATION: primer

<400> SEQUENCE: 94
gatgtgttca gagcagccaa                                                 20

<210> SEQ ID NO 95
<211> LENGTH: 20
<212> TYPE: DNA
<213> ORGANISM: Artificial
<220> FEATURE:
<223> OTHER INFORMATION: primer

<400> SEQUENCE: 95
taagctggag gagctggaga                                                 20

<210> SEQ ID NO 96
<211> LENGTH: 20
<212> TYPE: DNA
<213> ORGANISM: Artificial
<220> FEATURE:
<223> OTHER INFORMATION: primer

<400> SEQUENCE: 96
ttgttgtccc cttaacttgg                                                 20

<210> SEQ ID NO 97
<211> LENGTH: 20
<212> TYPE: DNA
<213> ORGANISM: Artificial
<220> FEATURE:
<223> OTHER INFORMATION: primer

<400> SEQUENCE: 97
caataggcca agggtttcaa                                                 20

<210> SEQ ID NO 98
<211> LENGTH: 20
<212> TYPE: DNA
<213> ORGANISM: Artificial
<220> FEATURE:
<223> OTHER INFORMATION: primer

<400> SEQUENCE: 98
tataactcct gctggagggc                                                 20

<210> SEQ ID NO 99
<211> LENGTH: 20
<212> TYPE: DNA
<213> ORGANISM: Artificial
<220> FEATURE:
<223> OTHER INFORMATION: primer

<400> SEQUENCE: 99
ggtagcctgg aaattagccc                                                 20
```

<210> SEQ ID NO 100
<211> LENGTH: 20
<212> TYPE: DNA
<213> ORGANISM: Artificial
<220> FEATURE:
<223> OTHER INFORMATION: primer

<400> SEQUENCE: 100
tgaaccagaa tctgaagcca                                              20

<210> SEQ ID NO 101
<211> LENGTH: 20
<212> TYPE: DNA
<213> ORGANISM: Artificial
<220> FEATURE:
<223> OTHER INFORMATION: primer

<400> SEQUENCE: 101
ttttgtcctt gggctctttc                                              20

<210> SEQ ID NO 102
<211> LENGTH: 20
<212> TYPE: DNA
<213> ORGANISM: Artificial
<220> FEATURE:
<223> OTHER INFORMATION: primer

<400> SEQUENCE: 102
cctggttctg tcactagccc                                              20

<210> SEQ ID NO 103
<211> LENGTH: 20
<212> TYPE: DNA
<213> ORGANISM: Artificial
<220> FEATURE:
<223> OTHER INFORMATION: primer

<400> SEQUENCE: 103
aattagccag ggtggtgaca                                              20

<210> SEQ ID NO 104
<211> LENGTH: 20
<212> TYPE: DNA
<213> ORGANISM: Artificial
<220> FEATURE:
<223> OTHER INFORMATION: primer

<400> SEQUENCE: 104
cccacaaagg actgatatgg                                              20

<210> SEQ ID NO 105
<211> LENGTH: 20
<212> TYPE: DNA
<213> ORGANISM: Artificial
<220> FEATURE:
<223> OTHER INFORMATION: primer

<400> SEQUENCE: 105
aaggaccctc agacaggttg                                              20

<210> SEQ ID NO 106
<211> LENGTH: 20
<212> TYPE: DNA
<213> ORGANISM: Artificial
<220> FEATURE:

<223> OTHER INFORMATION: primer

<400> SEQUENCE: 106
tcctttaagg cagacaaggg                                                     20

<210> SEQ ID NO 107
<211> LENGTH: 24
<212> TYPE: DNA
<213> ORGANISM: Artificial
<220> FEATURE:
<223> OTHER INFORMATION: primer

<400> SEQUENCE: 107
accaggtcaa ctaaactgtt ctct                                                24

<210> SEQ ID NO 108
<211> LENGTH: 23
<212> TYPE: DNA
<213> ORGANISM: Artificial
<220> FEATURE:
<223> OTHER INFORMATION: primer

<400> SEQUENCE: 108
tatgctgaaa gaccacctgt aga                                                 23

<210> SEQ ID NO 109
<211> LENGTH: 20
<212> TYPE: DNA
<213> ORGANISM: Artificial
<220> FEATURE:
<223> OTHER INFORMATION: primer

<400> SEQUENCE: 109
caggagcagt agtaacacaa                                                     20

<210> SEQ ID NO 110
<211> LENGTH: 20
<212> TYPE: DNA
<213> ORGANISM: Artificial
<220> FEATURE:
<223> OTHER INFORMATION: primer

<400> SEQUENCE: 110
aaagggtaca gcgtcagcat                                                     20

<210> SEQ ID NO 111
<211> LENGTH: 21
<212> TYPE: DNA
<213> ORGANISM: Artificial
<220> FEATURE:
<223> OTHER INFORMATION: primer

<400> SEQUENCE: 111
gcaggtaata agcctgcaga a                                                   21

<210> SEQ ID NO 112
<211> LENGTH: 20
<212> TYPE: DNA
<213> ORGANISM: Artificial
<220> FEATURE:
<223> OTHER INFORMATION: primer

<400> SEQUENCE: 112
cccccttcct agctgctatt                                                     20

```
<210> SEQ ID NO 113
<211> LENGTH: 25
<212> TYPE: DNA
<213> ORGANISM: Artificial
<220> FEATURE:
<223> OTHER INFORMATION: primer

<400> SEQUENCE: 113
tgttcaaaat agttccatta caaaa                                          25

<210> SEQ ID NO 114
<211> LENGTH: 22
<212> TYPE: DNA
<213> ORGANISM: Artificial
<220> FEATURE:
<223> OTHER INFORMATION: primer

<400> SEQUENCE: 114
tttcttccaa ggttttcttc ca                                             22

<210> SEQ ID NO 115
<211> LENGTH: 21
<212> TYPE: DNA
<213> ORGANISM: Artificial
<220> FEATURE:
<223> OTHER INFORMATION: primer

<400> SEQUENCE: 115
tttgcaaaag tgcttgattt t                                              21

<210> SEQ ID NO 116
<211> LENGTH: 20
<212> TYPE: DNA
<213> ORGANISM: Artificial
<220> FEATURE:
<223> OTHER INFORMATION: primer

<400> SEQUENCE: 116
tgcaggctca gttccacata                                                20

<210> SEQ ID NO 117
<211> LENGTH: 20
<212> TYPE: DNA
<213> ORGANISM: Artificial
<220> FEATURE:
<223> OTHER INFORMATION: primer

<400> SEQUENCE: 117
ggaatgatgc cttttctcc                                                 20

<210> SEQ ID NO 118
<211> LENGTH: 20
<212> TYPE: DNA
<213> ORGANISM: Artificial
<220> FEATURE:
<223> OTHER INFORMATION: primer

<400> SEQUENCE: 118
tctcacactt gccttctgga                                                20

<210> SEQ ID NO 119
<211> LENGTH: 20
<212> TYPE: DNA
<213> ORGANISM: Artificial
<220> FEATURE:
<223> OTHER INFORMATION: primer
```

<400> SEQUENCE: 119
aatcatcgcc tgagcaaaat                                               20

<210> SEQ ID NO 120
<211> LENGTH: 20
<212> TYPE: DNA
<213> ORGANISM: Artificial
<220> FEATURE:
<223> OTHER INFORMATION: primer

<400> SEQUENCE: 120
ccagtgactg atccaaagca                                               20

<210> SEQ ID NO 121
<211> LENGTH: 21
<212> TYPE: DNA
<213> ORGANISM: Artificial
<220> FEATURE:
<223> OTHER INFORMATION: primer

<400> SEQUENCE: 121
ccctcttaag gagaaaaaca c                                             21

<210> SEQ ID NO 122
<211> LENGTH: 20
<212> TYPE: DNA
<213> ORGANISM: Artificial
<220> FEATURE:
<223> OTHER INFORMATION: primer

<400> SEQUENCE: 122
cagccttatc ctctgctctt                                               20

<210> SEQ ID NO 123
<211> LENGTH: 20
<212> TYPE: DNA
<213> ORGANISM: Artificial
<220> FEATURE:
<223> OTHER INFORMATION: primer

<400> SEQUENCE: 123
tggaaaaggg gagcagacta                                               20

<210> SEQ ID NO 124
<211> LENGTH: 21
<212> TYPE: DNA
<213> ORGANISM: Artificial
<220> FEATURE:
<223> OTHER INFORMATION: primer

<400> SEQUENCE: 124
tgcgaactat ttttcctttg g                                             21

<210> SEQ ID NO 125
<211> LENGTH: 20
<212> TYPE: DNA
<213> ORGANISM: Artificial
<220> FEATURE:
<223> OTHER INFORMATION: primer

<400> SEQUENCE: 125
gaggaggcca caaatcacat                                               20

<210> SEQ ID NO 126
<211> LENGTH: 20

```
<212> TYPE: DNA
<213> ORGANISM: Artificial
<220> FEATURE:
<223> OTHER INFORMATION: primer

<400> SEQUENCE: 126
gccttagacc tcgtcacacc                                              20

<210> SEQ ID NO 127
<211> LENGTH: 23
<212> TYPE: DNA
<213> ORGANISM: Artificial
<220> FEATURE:
<223> OTHER INFORMATION: primer

<400> SEQUENCE: 127
tgctcaggtt ttgactttt ctc                                           23

<210> SEQ ID NO 128
<211> LENGTH: 20
<212> TYPE: DNA
<213> ORGANISM: Artificial
<220> FEATURE:
<223> OTHER INFORMATION: primer

<400> SEQUENCE: 128
tttcactgat ggcaagatgc                                              20

<210> SEQ ID NO 129
<211> LENGTH: 20
<212> TYPE: DNA
<213> ORGANISM: Artificial
<220> FEATURE:
<223> OTHER INFORMATION: primer

<400> SEQUENCE: 129
accaccccca cctctaattc                                              20

<210> SEQ ID NO 130
<211> LENGTH: 20
<212> TYPE: DNA
<213> ORGANISM: Artificial
<220> FEATURE:
<223> OTHER INFORMATION: primer

<400> SEQUENCE: 130
ctacacaaca gaaagaatgc                                              20

<210> SEQ ID NO 131
<211> LENGTH: 21
<212> TYPE: DNA
<213> ORGANISM: Artificial
<220> FEATURE:
<223> OTHER INFORMATION: primer

<400> SEQUENCE: 131
ccagctgaaa ctgaaagttg g                                            21

<210> SEQ ID NO 132
<211> LENGTH: 20
<212> TYPE: DNA
<213> ORGANISM: Artificial
<220> FEATURE:
<223> OTHER INFORMATION: primer

<400> SEQUENCE: 132
```
ctgggtactt acttcaggct                                               20

<210> SEQ ID NO 133
<211> LENGTH: 20
<212> TYPE: DNA
<213> ORGANISM: Artificial
<220> FEATURE:
<223> OTHER INFORMATION: primer

<400> SEQUENCE: 133
cactgtgccc tgccttatta                                               20

<210> SEQ ID NO 134
<211> LENGTH: 20
<212> TYPE: DNA
<213> ORGANISM: Artificial
<220> FEATURE:
<223> OTHER INFORMATION: primer

<400> SEQUENCE: 134
tgtgcctgag taaccgagtg                                               20

<210> SEQ ID NO 135
<211> LENGTH: 20
<212> TYPE: DNA
<213> ORGANISM: Artificial
<220> FEATURE:
<223> OTHER INFORMATION: primer

<400> SEQUENCE: 135
tcccagattt ggaggttttg                                               20

<210> SEQ ID NO 136
<211> LENGTH: 24
<212> TYPE: DNA
<213> ORGANISM: Artificial
<220> FEATURE:
<223> OTHER INFORMATION: primer

<400> SEQUENCE: 136 tgcatttaa tttcctaact accc                                           24

<210> SEQ ID NO 137
<211> LENGTH: 20
<212> TYPE: DNA
<213> ORGANISM: Artificial
<220> FEATURE:
<223> OTHER INFORMATION: primer

<400> SEQUENCE: 137
gctgtagtgg cattttattg                                               20

<210> SEQ ID NO 138
<211> LENGTH: 20
<212> TYPE: DNA
<213> ORGANISM: Artificial
<220> FEATURE:
<223> OTHER INFORMATION: primer

<400> SEQUENCE: 138
cctgggtgac agagcaagac                                               20

<210> SEQ ID NO 139
<211> LENGTH: 20
<212> TYPE: DNA
<213> ORGANISM: Artificial

<220> FEATURE:
<223> OTHER INFORMATION: primer

<400> SEQUENCE: 139
agctgcagag ctccataagc          20

<210> SEQ ID NO 140
<211> LENGTH: 20
<212> TYPE: DNA
<213> ORGANISM: Artificial
<220> FEATURE:
<223> OTHER INFORMATION: primer

<400> SEQUENCE: 140
taggcatcca gagcaggaac          20

<210> SEQ ID NO 141
<211> LENGTH: 20
<212> TYPE: DNA
<213> ORGANISM: Artificial
<220> FEATURE:
<223> OTHER INFORMATION: primer

<400> SEQUENCE: 141
ggcatctgaa agcaaccact          20

<210> SEQ ID NO 142
<211> LENGTH: 20
<212> TYPE: DNA
<213> ORGANISM: Artificial
<220> FEATURE:
<223> OTHER INFORMATION: primer

<400> SEQUENCE: 142
ccctccattt tcccaagagt          20

<210> SEQ ID NO 143
<211> LENGTH: 20
<212> TYPE: DNA
<213> ORGANISM: Artificial
<220> FEATURE:
<223> OTHER INFORMATION: primer

<400> SEQUENCE: 143
ggggtgaata ccgttgtgag          20

<210> SEQ ID NO 144
<211> LENGTH: 20
<212> TYPE: DNA
<213> ORGANISM: Artificial
<220> FEATURE:
<223> OTHER INFORMATION: primer

<400> SEQUENCE: 144
acctctgggt tccatgagtg          20

<210> SEQ ID NO 145
<211> LENGTH: 20
<212> TYPE: DNA
<213> ORGANISM: Artificial
<220> FEATURE:
<223> OTHER INFORMATION: primer

<400> SEQUENCE: 145
agactgctcc tctgcactcc          20

```
<210> SEQ ID NO 146
<211> LENGTH: 21
<212> TYPE: DNA
<213> ORGANISM: Artificial
<220> FEATURE:
<223> OTHER INFORMATION: primer

<400> SEQUENCE: 146
ccgggattgt tcaactttag c                                              21

<210> SEQ ID NO 147
<211> LENGTH: 20
<212> TYPE: DNA
<213> ORGANISM: Artificial
<220> FEATURE:
<223> OTHER INFORMATION: primer

<400> SEQUENCE: 147
cagtatctta acctgtacat                                                20

<210> SEQ ID NO 148
<211> LENGTH: 21
<212> TYPE: DNA
<213> ORGANISM: Artificial
<220> FEATURE:
<223> OTHER INFORMATION: primer

<400> SEQUENCE: 148
ccgggattgt tcaactttag c                                              21

<210> SEQ ID NO 149
<211> LENGTH: 40
<212> TYPE: PRT
<213> ORGANISM: Homo sapiens
<220> FEATURE:
<221> NAME/KEY: misc_feature
<222> LOCATION: (40)..(40)
<223> OTHER INFORMATION: Xaa can be any naturally occurring amino acid

<400> SEQUENCE: 149
```

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Xaa
        35                  40

```
<210> SEQ ID NO 150
<211> LENGTH: 178
<212> TYPE: PRT
<213> ORGANISM: Homo sapiens
<220> FEATURE:
<221> NAME/KEY: misc_feature
<222> LOCATION: (178)..(178)
<223> OTHER INFORMATION: Xaa can be any naturally occurring amino acid

<400> SEQUENCE: 150
```

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln

```
Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ser Xaa
```

<210> SEQ ID NO 151
<211> LENGTH: 246
<212> TYPE: PRT
<213> ORGANISM: Homo sapiens
<220> FEATURE:
<221> NAME/KEY: misc_feature
<222> LOCATION: (246)..(246)
<223> OTHER INFORMATION: Xaa can be any naturally occurring amino acid

<400> SEQUENCE: 151

```
Met Ala Ala Glu Glu Gly Val Ala Ser Ala Ala Ser Ala Gly Gly Ser
 1               5                  10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220
```

Phe Asp Val Val Asp Gly Thr Tyr Val Ala His Val Asp Leu Ala Leu
225                 230                 235                 240

His Lys Glu Asp Val Xaa
                245

<210> SEQ ID NO 152
<211> LENGTH: 415
<212> TYPE: PRT
<213> ORGANISM: Homo sapiens
<220> FEATURE:
<221> NAME/KEY: misc_feature
<222> LOCATION: (415)..(415)
<223> OTHER INFORMATION: Xaa can be any naturally occurring amino acid

<400> SEQUENCE: 152

Met Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg

```
                        325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Ile Met Pro Arg Pro Val Ile Gln Glu Asp His Gly Lys Xaa
                405                 410                 415

<210> SEQ ID NO 153
<211> LENGTH: 412
<212> TYPE: PRT
<213> ORGANISM: Homo sapiens
<220> FEATURE:
<221> NAME/KEY: misc_feature
<222> LOCATION: (412)..(412)
<223> OTHER INFORMATION: Xaa can be any naturally occurring amino acid

<400> SEQUENCE: 153

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270
```

```
Ile Val Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Xaa
            405                 410

<210> SEQ ID NO 154
<211> LENGTH: 556
<212> TYPE: PRT
<213> ORGANISM: Homo sapiens
<220> FEATURE:
<221> NAME/KEY: misc_feature
<222> LOCATION: (556)..(556)
<223> OTHER INFORMATION: Xaa can be any naturally occurring amino acid

<400> SEQUENCE: 154

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205
```

```
Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Ser Ser Gln Trp Leu Gly Lys Val Leu Asn Ser
        515                 520                 525

His Thr Cys Thr Arg Gly Arg Asp Arg Lys Ser Ser Ala Gly His Ser
530                 535                 540

Lys Phe Leu Phe Glu Glu Gln Gly Lys Ser Phe Xaa
545                 550                 555

<210> SEQ ID NO 155
<211> LENGTH: 651
<212> TYPE: PRT
<213> ORGANISM: Homo sapiens
<220> FEATURE:
<221> NAME/KEY: misc_feature
<222> LOCATION: (651)..(651)
<223> OTHER INFORMATION: Xaa can be any naturally occurring amino acid

<400> SEQUENCE: 155

Met Ala Ala Glu Glu Gly Val Ala Ser Ala Ala Ser Ala Gly Gly Ser
```

-continued

```
  1               5                  10                 15
Trp Gly Thr Ala Ala Met Gly Arg Val Leu Pro Met Leu Leu Val Pro
                 20                 25                 30
Val Pro Ala Glu Ala Met Gly Gln Leu Gly Ser Arg Ala Gln Leu Arg
                 35                 40                 45
Thr Gln Pro Glu Ala Leu Gly Ser Leu Thr Ala Ala Gly Ser Leu Gln
                 50                 55                 60
Val Leu Ser Leu Thr Pro Gly Ser Arg Gly Gly Gly Arg Cys Cys Leu
 65                 70                 75                 80
Glu Gly Pro Phe Trp His Phe Leu Trp Glu Asp Ser Arg Asn Ser Ser
                 85                 90                 95
Thr Pro Thr Glu Lys Pro Lys Leu Leu Ala Leu Gly Glu Asn Tyr Glu
                100                105                110
Leu Leu Ile Tyr Glu Phe Asn Leu Lys Asp Gly Arg Cys Asp Ala Thr
                115                120                125
Ile Leu Tyr Ser Cys Ser Arg Glu Ala Leu Gln Lys Leu Ile Asp Asp
                130                135                140
Gln Asp Ile Ser Ile Ser Leu Leu Ser Leu Arg Ile Leu Ser Phe His
145                150                155                160
Asn Asn Thr Ser Leu Leu Phe Ile Asn Lys Cys Val Ile Leu His Ile
                165                170                175
Ile Phe Pro Glu Arg Asp Ala Ala Ile Arg Val Leu Asn Cys Phe Thr
                180                185                190
Leu Pro Leu Pro Ala Gln Ala Val Asp Met Ile Ile Asp Thr Gln Leu
                195                200                205
Cys Arg Gly Ile Leu Phe Val Leu Ser Ser Leu Gly Trp Ile Tyr Ile
                210                215                220
Phe Asp Val Val Asp Gly Thr Tyr Val Ala His Val Asp Leu Ala Leu
225                230                235                240
His Lys Glu Asp Met Cys Asn Glu Gln Gln Gln Glu Pro Ala Lys Ile
                245                250                255
Ser Ser Phe Thr Ser Leu Lys Val Ser Gln Asp Leu Asp Val Ala Val
                260                265                270
Ile Val Ser Ser Ser Asn Ser Ala Val Ala Leu Asn Leu Asn Leu Tyr
                275                280                285
Phe Arg Gln His Pro Gly His Leu Leu Cys Glu Arg Ile Leu Glu Asp
                290                295                300
Leu Pro Ile Gln Gly Pro Lys Gly Val Asp Glu Asp Pro Val Asn
305                310                315                320
Ser Ala Tyr Asn Met Lys Leu Ala Lys Phe Ser Phe Gln Ile Asp Arg
                325                330                335
Ser Trp Lys Ala Gln Leu Ser Ser Leu Asn Glu Thr Ile Lys Asn Ser
                340                345                350
Lys Leu Glu Val Ser Cys Cys Ala Pro Trp Phe Gln Asp Ile Leu His
                355                360                365
Leu Glu Ser Pro Glu Ser Gly Asn His Ser Thr Ser Val Gln Ser Trp
                370                375                380
Ala Phe Ile Pro Gln Asp Ile Met His Gly Gln Tyr Asn Val Leu Gln
385                390                395                400
Lys Asp His Ala Lys Thr Ser Asp Pro Gly Arg Ser Trp Lys Ile Met
                405                410                415
His Ile Ser Glu Gln Glu Pro Ile Glu Leu Lys Cys Val Ser Val
                420                425                430
```

```
Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Xaa
                645                 650

<210> SEQ ID NO 156
<211> LENGTH: 733
<212> TYPE: PRT
<213> ORGANISM: Homo sapiens
<220> FEATURE:
<221> NAME/KEY: misc_feature
<222> LOCATION: (733)..(733)
<223> OTHER INFORMATION: Xaa can be any naturally occurring amino acid

<400> SEQUENCE: 156

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125
```

```
Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
                420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
```

```
545                 550                 555                 560
Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
                595                 600                 605

Gln Leu Leu Asn Leu Thr Leu Ser Phe Leu Asn Gln Ile Lys Glu
                610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
                675                 680                 685

Glu Glu Val Ile Ala Ser Ala Ile Leu Asn Asn Lys Ile Pro Glu Ala
                690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Xaa
                725                 730

<210> SEQ ID NO 157
<211> LENGTH: 953
<212> TYPE: PRT
<213> ORGANISM: Homo sapiens
<220> FEATURE:
<221> NAME/KEY: misc_feature
<222> LOCATION: (953)..(953)
<223> OTHER INFORMATION: Xaa can be any naturally occurring amino acid

<400> SEQUENCE: 157

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
                50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
                130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175
```

-continued

```
Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Pro Ala Lys Ile
                245                 250                 255

Ser Ser Phe Thr Ser Leu Lys Val Ser Gln Asp Leu Val Ala Val
            260                 265                 270

Ile Val Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
            290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590
```

```
Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
        610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
930                 935                 940

Arg Asn Gly Gly Phe Phe Gly Ile Xaa
945                 950
```

<210> SEQ ID NO 158
<211> LENGTH: 953
<212> TYPE: PRT
<213> ORGANISM: Homo sapiens
<220> FEATURE:
<221> NAME/KEY: misc_feature
<222> LOCATION: (953)..(953)
<223> OTHER INFORMATION: Xaa can be any naturally occurring amino acid

<400> SEQUENCE: 158

```
Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415
```

```
His Ile Ser Glu Gln Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830
```

```
Phe Leu Lys Tyr Asp Cys Lys Asp Glu Phe Asn Lys Gln Asp His Arg
            835                 840                 845
Ile Val Leu Asn Trp Ala Leu Trp Trp Asp Gln Leu Thr Gln Glu Ser
        850                 855                 860
Ile Leu Leu Pro Arg Ile Ser Pro Glu Tyr Lys Ser Tyr Ser Pro
865                 870                 875                 880
Glu Ala Leu Trp Arg Tyr Leu Thr Ala Arg His Asp Trp Leu Asn Ile
                885                 890                 895
Ile Leu Trp Ile Gly Glu Phe Gln Thr Gln His Ser Tyr Ala Ser Leu
            900                 905                 910
Gln Gln Asn Lys Trp Pro Leu Leu Thr Val Asp Val Ile Asn Gln Asn
        915                 920                 925
Thr Ser Cys Asn Asn Tyr Met Arg Asn Glu Ile Leu Asp Lys Leu Ala
    930                 935                 940
Arg Asn Gly Val Phe Phe Gly Ile Xaa
945                 950

<210> SEQ ID NO 159
<211> LENGTH: 1992
<212> TYPE: PRT
<213> ORGANISM: Homo sapiens
<220> FEATURE:
<221> NAME/KEY: misc_feature
<222> LOCATION: (1992)..(1992)
<223> OTHER INFORMATION: Xaa can be any naturally occurring amino acid

<400> SEQUENCE: 159

Met Ala Ala Glu Glu Gly Val Ala Ser Ala Ser Ala Gly Gly Ser
1               5                   10                  15
Trp Gly Thr Ala Ala Met Gly Arg Val Leu Pro Met Leu Leu Val Pro
            20                  25                  30
Val Pro Ala Glu Ala Met Gly Gln Leu Gly Ser Arg Ala Gln Leu Arg
        35                  40                  45
Thr Gln Pro Glu Ala Leu Gly Ser Leu Thr Ala Ala Gly Ser Leu Gln
    50                  55                  60
Val Leu Ser Leu Thr Pro Gly Ser Arg Gly Gly Gly Arg Cys Cys Leu
65                  70                  75                  80
Glu Gly Pro Phe Trp His Phe Leu Trp Glu Asp Ser Arg Asn Ser Ser
                85                  90                  95
Thr Pro Thr Glu Lys Pro Lys Leu Leu Ala Leu Gly Glu Asn Tyr Glu
            100                 105                 110
Leu Leu Ile Tyr Glu Phe Asn Leu Lys Asp Gly Arg Cys Asp Ala Thr
        115                 120                 125
Ile Leu Tyr Ser Cys Ser Arg Glu Ala Leu Gln Lys Leu Ile Asp Asp
    130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
        195                 200                 205
Cys Arg Gly Ile Leu Phe Val Leu Ser Ser Leu Gly Trp Ile Tyr Ile
    210                 215                 220
Phe Asp Val Val Asp Gly Thr Tyr Val Ala His Val Asp Leu Ala Leu
```

```
                225                 230                 235                 240
His Lys Glu Asp Met Cys Asn Glu Gln Gln Gln Glu Pro Ala Lys Ile
                    245                 250                 255

Ser Ser Phe Thr Ser Leu Lys Val Ser Gln Asp Leu Asp Val Ala Val
                260                 265                 270

Ile Val Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
                595                 600                 605

Gln Leu Leu Asn Leu Thr Leu Ser Phe Leu Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655
```

```
Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
            850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
            930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Gly Trp Asp Phe His Ser Gln Phe
            980                 985                 990

Ile Leu Tyr Cys Leu Glu His Ser  Leu Gln His Leu Leu  Tyr Val Tyr
            995                 1000                1005

Leu Asp  Cys Tyr Lys Leu Ser  Pro Glu Asn Cys Pro  Phe Leu Glu
    1010                1015                1020

Lys Lys  Glu Leu His Glu Ala  His Pro Trp Phe Glu  Phe Leu Val
    1025                1030                1035

Gln Cys  Arg Gln Val Ala Ser  Asn Leu Thr Asp Pro  Lys Leu Ile
    1040                1045                1050

Phe Gln  Ala Ser Leu Ala Asn  Ala Gln Ile Leu Ile  Pro Thr Asn
    1055                1060                1065
```

```
Gln Ala Ser Val Ser Ser Met Leu Leu Glu Gly His Thr Leu Leu
    1070            1075                1080

Ala Leu Ala Thr Thr Met Tyr Ser Pro Gly Gly Val Ser Gln Val
    1085            1090                1095

Val Gln Asn Glu Glu Asn Glu Asn Cys Leu Lys Lys Val Asp Pro
    1100            1105                1110

Gln Leu Leu Lys Met Ala Leu Thr Pro Tyr Pro Lys Leu Lys Thr
    1115            1120                1125

Ala Leu Phe Pro Gln Cys Thr Pro Pro Ser Val Leu Pro Ser Asp
    1130            1135                1140

Ile Thr Ile Tyr His Leu Ile Gln Ser Leu Ser Pro Phe Asp Pro
    1145            1150                1155

Ser Arg Leu Phe Gly Trp Gln Ser Ala Asn Thr Leu Ala Ile Gly
    1160            1165                1170

Asp Ala Trp Ser His Leu Pro His Phe Ser Ser Pro Asp Leu Val
    1175            1180                1185

Asn Lys Tyr Ala Ile Val Glu Arg Leu Asn Phe Ala Tyr Tyr Leu
    1190            1195                1200

His Asn Gly Arg Pro Ser Phe Ala Phe Gly Thr Phe Leu Val Gln
    1205            1210                1215

Glu Leu Ile Lys Ser Lys Thr Pro Lys Gln Leu Ile Gln Gln Val
    1220            1225                1230

Gly Asn Glu Ala Tyr Val Ile Gly Leu Ser Ser Phe His Ile Pro
    1235            1240                1245

Ser Ile Gly Ala Ala Cys Val Cys Phe Leu Glu Leu Leu Gly Leu
    1250            1255                1260

Asp Ser Leu Lys Leu Arg Val Asp Met Lys Val Ala Asn Ile Ile
    1265            1270                1275

Leu Ser Tyr Lys Cys Arg Asn Glu Asp Ala Gln Tyr Ser Phe Ile
    1280            1285                1290

Arg Glu Ser Val Ala Glu Lys Leu Ser Lys Leu Ala Asp Gly Glu
    1295            1300                1305

Lys Thr Thr Thr Glu Glu Leu Leu Val Leu Leu Glu Glu Gly Thr
    1310            1315                1320

Trp Asn Ser Ile Gln Gln Gln Glu Ile Lys Arg Leu Ser Ser Glu
    1325            1330                1335

Ser Ser Ser Gln Trp Ala Leu Val Val Gln Phe Cys Arg Leu His
    1340            1345                1350

Asn Met Lys Leu Ser Ile Ser Tyr Leu Arg Glu Cys Ala Lys Ala
    1355            1360                1365

Asn Asp Trp Leu Gln Phe Ile Ile His Ser Gln Leu His Asn Tyr
    1370            1375                1380

His Pro Ala Glu Val Lys Ser Leu Ile Gln Tyr Phe Ser Pro Val
    1385            1390                1395

Ile Gln Asp His Leu Arg Leu Ala Phe Glu Asn Leu Pro Ser Val
    1400            1405                1410

Pro Thr Ser Lys Met Asp Ser Asp Gln Val Cys Asn Lys Cys Pro
    1415            1420                1425

Gln Glu Leu Gln Gly Ser Lys Gln Glu Met Thr Asp Leu Phe Glu
    1430            1435                1440

Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
```

```
              1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860
```

-continued

```
Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Xaa
    1985                1990

<210> SEQ ID NO 160
<211> LENGTH: 2034
<212> TYPE: PRT
<213> ORGANISM: Homo sapiens
<220> FEATURE:
<221> NAME/KEY: misc_feature
<222> LOCATION: (2034)..(2034)
<223> OTHER INFORMATION: Xaa can be any naturally occurring amino acid

<400> SEQUENCE: 160

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205
```

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
        340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
        420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
            565                 570                 575

Leu Arg Asn Val Glu Glu Leu Ile Pro Ala Leu Asp Leu Leu Cys Ser
        580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val

```
              625                 630                 635                 640
         Asn Ile Leu Thr Ser Tyr Ile Asn Glu Leu Arg Thr Phe Met Ile Lys
                         645                 650                 655

Phe Pro Trp Lys Leu Thr Asp Ala Ile Asp Glu Tyr Asp Val His Glu
                         660                 665                 670

Asn Val Pro Lys Val Lys Glu Ser Asn Ile Trp Lys Lys Leu Ser Phe
                         675                 680                 685

Glu Glu Val Ile Ala Ser Ala Ile Leu Asn Asn Lys Ile Pro Glu Ala
                         690                 695                 700

Gln Thr Phe Phe Arg Ile Asp Ser His Ser Ala Gln Lys Leu Glu Glu
         705                 710                 715                 720

Leu Ile Gly Ile Gly Leu Asn Leu Val Phe Asp Asn Leu Lys Lys Asn
                         725                 730                 735

Asn Ile Lys Glu Ala Ser Glu Leu Leu Lys Asn Met Gly Phe Asp Val
                         740                 745                 750

Lys Gly Gln Leu Leu Lys Ile Cys Phe Tyr Thr Thr Asn Lys Asn Ile
                         755                 760                 765

Arg Asp Phe Leu Val Glu Ile Leu Lys Glu Lys Asn Tyr Phe Ser Glu
                         770                 775                 780

Lys Glu Lys Arg Thr Ile Asp Phe Val His Gln Val Glu Lys Leu Tyr
         785                 790                 795                 800

Leu Gly His Phe Gln Glu Asn Met Gln Ile Gln Ser Phe Pro Arg Tyr
                         805                 810                 815

Trp Ile Lys Glu Gln Asp Phe Phe Lys His Lys Ser Val Leu Asp Ser
                         820                 825                 830

Phe Leu Lys Tyr Asp Cys Lys Asp Glu Phe Asn Lys Gln Asp His Arg
                         835                 840                 845

Ile Val Leu Asn Trp Ala Leu Trp Trp Asp Gln Leu Thr Gln Glu Ser
                         850                 855                 860

Ile Leu Leu Pro Arg Ile Ser Pro Glu Glu Tyr Lys Ser Tyr Ser Pro
         865                 870                 875                 880

Glu Ala Leu Trp Arg Tyr Leu Thr Ala Arg His Asp Trp Leu Asn Ile
                         885                 890                 895

Ile Leu Trp Ile Gly Glu Phe Gln Thr Gln His Ser Tyr Ala Ser Leu
                         900                 905                 910

Gln Gln Asn Lys Trp Pro Leu Thr Val Asp Val Ile Asn Gln Asn
                         915                 920                 925

Thr Ser Cys Asn Asn Tyr Met Arg Asn Glu Ile Leu Asp Lys Leu Ala
         930                 935                 940

Arg Asn Gly Val Phe Leu Ala Ser Glu Leu Glu Asp Phe Glu Cys Phe
         945                 950                 955                 960

Leu Leu Arg Leu Ser Arg Ile Gly Gly Val Ile Gln Asp Thr Leu Pro
                         965                 970                 975

Val Gln Asn Tyr Lys Thr Lys Leu Gly Trp Asp Phe His Ser Gln Phe
                         980                 985                 990

Ile Leu Tyr Cys Leu Glu His Ser  Leu Gln His Leu Leu  Tyr Val Tyr
                         995                 1000                1005

Leu Asp Cys Tyr Lys Leu Ser  Pro Glu Asn Cys Pro  Phe Leu Glu
         1010                1015                1020

Lys Lys  Glu Leu His Glu Ala  His Pro Trp Phe Glu  Phe Leu Val
         1025                1030                1035

Gln Cys  Arg Gln Val Ala Ser  Asn Leu Thr Asp Pro  Lys Leu Ile
         1040                1045                1050
```

```
Phe Gln Ala Ser Leu Ala Asn Ala Gln Ile Leu Ile Pro Thr Asn
    1055            1060            1065

Gln Ala Ser Val Ser Ser Met Leu Leu Glu Gly His Thr Leu Leu
    1070            1075            1080

Ala Leu Ala Thr Thr Met Tyr Ser Pro Gly Gly Val Ser Gln Val
    1085            1090            1095

Val Gln Asn Glu Glu Asn Glu Asn Cys Leu Lys Lys Val Asp Pro
    1100            1105            1110

Gln Leu Leu Lys Met Ala Leu Thr Pro Tyr Pro Lys Leu Lys Thr
    1115            1120            1125

Ala Leu Phe Pro Gln Cys Thr Pro Pro Ser Val Leu Pro Ser Asp
    1130            1135            1140

Ile Thr Ile Tyr His Leu Ile Gln Ser Leu Ser Pro Phe Asp Pro
    1145            1150            1155

Ser Arg Leu Phe Gly Trp Gln Ser Ala Asn Thr Leu Ala Ile Gly
    1160            1165            1170

Asp Ala Trp Ser His Leu Pro His Phe Ser Ser Asp Leu Val
    1175            1180            1185

Asn Lys Tyr Ala Ile Val Glu Arg Leu Asn Phe Ala Tyr Tyr Leu
    1190            1195            1200

His Asn Gly Arg Pro Ser Phe Ala Phe Gly Thr Phe Leu Val Gln
    1205            1210            1215

Glu Leu Ile Lys Ser Lys Thr Pro Lys Gln Leu Ile Gln Gln Val
    1220            1225            1230

Gly Asn Glu Ala Tyr Val Ile Gly Leu Ser Ser Phe His Ile Pro
    1235            1240            1245

Ser Ile Gly Ala Ala Cys Val Cys Phe Leu Glu Leu Leu Gly Leu
    1250            1255            1260

Asp Ser Leu Lys Leu Arg Val Asp Met Lys Val Ala Asn Ile Ile
    1265            1270            1275

Leu Ser Tyr Lys Cys Arg Asn Glu Asp Ala Gln Tyr Ser Phe Ile
    1280            1285            1290

Arg Glu Ser Val Ala Glu Lys Leu Ser Lys Leu Ala Asp Gly Glu
    1295            1300            1305

Lys Thr Thr Thr Glu Glu Leu Leu Val Leu Leu Glu Glu Gly Thr
    1310            1315            1320

Trp Asn Ser Ile Gln Gln Glu Ile Lys Arg Leu Ser Ser Glu
    1325            1330            1335

Ser Ser Ser Gln Trp Ala Leu Val Val Gln Phe Cys Arg Leu His
    1340            1345            1350

Asn Met Lys Leu Ser Ile Ser Tyr Leu Arg Glu Cys Ala Lys Ala
    1355            1360            1365

Asn Asp Trp Leu Gln Phe Ile Ile His Ser Gln Leu His Asn Tyr
    1370            1375            1380

His Pro Ala Glu Val Lys Ser Leu Ile Gln Tyr Phe Ser Pro Val
    1385            1390            1395

Ile Gln Asp His Leu Arg Leu Ala Phe Glu Asn Leu Pro Ser Val
    1400            1405            1410

Pro Thr Ser Lys Met Asp Ser Asp Gln Val Cys Asn Lys Cys Pro
    1415            1420            1425

Gln Glu Leu Gln Gly Ser Lys Gln Glu Met Thr Asp Leu Phe Glu
    1430            1435            1440
```

```
Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
```

```
                1835                1840                1845

Leu Asn Thr Ser Lys Tyr Leu Glu Leu Asn Ser Leu Pro Ser Lys
        1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
        1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
        1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
        1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
        1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
        2000                2005                2010

Gln Asp Gly Glu Ala Met Leu Arg Lys Ile Leu Ala Ser Gln Gln
    2015                2020                2025

Pro Asp Arg Cys Lys Xaa
    2030

<210> SEQ ID NO 161
<211> LENGTH: 2172
<212> TYPE: PRT
<213> ORGANISM: Homo sapiens
<220> FEATURE:
<221> NAME/KEY: misc_feature
<222> LOCATION: (2172)..(2172)
<223> OTHER INFORMATION: Xaa can be any naturally occurring amino acid

<400> SEQUENCE: 161

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140
```

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
        180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
        210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
            245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560
```

```
Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
```

-continued

```
                980             985             990
    Ile Leu Tyr Cys Leu Glu His Ser Leu Gln His Leu Leu Tyr Val Tyr
             995            1000            1005
    Leu Asp Cys Tyr Lys Leu Ser Pro Glu Asn Cys Pro Phe Leu Glu
            1010            1015            1020
    Lys Lys Glu Leu His Glu Ala His Pro Trp Phe Glu Phe Leu Val
            1025            1030            1035
    Gln Cys Arg Gln Val Ala Ser Asn Leu Thr Asp Pro Lys Leu Ile
            1040            1045            1050
    Phe Gln Ala Ser Leu Ala Asn Ala Gln Ile Leu Ile Pro Thr Asn
            1055            1060            1065
    Gln Ala Ser Val Ser Ser Met Leu Leu Glu Gly His Thr Leu Leu
            1070            1075            1080
    Ala Leu Ala Thr Thr Met Tyr Ser Pro Gly Gly Val Ser Gln Val
            1085            1090            1095
    Val Gln Asn Glu Glu Asn Glu Asn Cys Leu Lys Lys Val Asp Pro
            1100            1105            1110
    Gln Leu Leu Lys Met Ala Leu Thr Pro Tyr Pro Lys Leu Lys Thr
            1115            1120            1125
    Ala Leu Phe Pro Gln Cys Thr Pro Pro Ser Val Leu Pro Ser Asp
            1130            1135            1140
    Ile Thr Ile Tyr His Leu Ile Gln Ser Leu Ser Pro Phe Asp Pro
            1145            1150            1155
    Ser Arg Leu Phe Gly Trp Gln Ser Ala Asn Thr Leu Ala Ile Gly
            1160            1165            1170
    Asp Ala Trp Ser His Leu Pro His Phe Ser Ser Pro Asp Leu Val
            1175            1180            1185
    Asn Lys Tyr Ala Ile Val Glu Arg Leu Asn Phe Ala Tyr Tyr Leu
            1190            1195            1200
    His Asn Gly Arg Pro Ser Phe Ala Phe Gly Thr Phe Leu Val Gln
            1205            1210            1215
    Glu Leu Ile Lys Ser Lys Thr Pro Lys Gln Leu Ile Gln Gln Val
            1220            1225            1230
    Gly Asn Glu Ala Tyr Val Ile Gly Leu Ser Ser Phe His Ile Pro
            1235            1240            1245
    Ser Ile Gly Ala Ala Cys Val Cys Phe Leu Glu Leu Leu Gly Leu
            1250            1255            1260
    Asp Ser Leu Lys Leu Arg Val Asp Met Lys Val Ala Asn Ile Ile
            1265            1270            1275
    Leu Ser Tyr Lys Cys Arg Asn Glu Asp Ala Gln Tyr Ser Phe Ile
            1280            1285            1290
    Arg Glu Ser Val Ala Glu Lys Leu Ser Lys Leu Ala Asp Gly Glu
            1295            1300            1305
    Lys Thr Thr Thr Glu Glu Leu Leu Val Leu Leu Glu Glu Gly Thr
            1310            1315            1320
    Trp Asn Ser Ile Gln Gln Gln Glu Ile Lys Arg Leu Ser Ser Glu
            1325            1330            1335
    Ser Ser Ser Gln Trp Ala Leu Val Val Gln Phe Cys Arg Leu His
            1340            1345            1350
    Asn Met Lys Leu Ser Ile Ser Tyr Leu Arg Glu Cys Ala Lys Ala
            1355            1360            1365
    Asn Asp Trp Leu Gln Phe Ile Ile His Ser Gln Leu His Asn Tyr
            1370            1375            1380
```

```
His Pro Ala Glu Val Lys Ser Leu Ile Gln Tyr Phe Ser Pro Val
1385                1390                1395

Ile Gln Asp His Leu Arg Leu Ala Phe Glu Asn Leu Pro Ser Val
1400                1405                1410

Pro Thr Ser Lys Met Asp Ser Asp Gln Val Cys Asn Lys Cys Pro
1415                1420                1425

Gln Glu Leu Gln Gly Ser Lys Gln Glu Met Thr Asp Leu Phe Glu
1430                1435                1440

Ile Leu Leu Gln Cys Ser Glu Glu Pro Asp Ser Trp His Trp Leu
1445                1450                1455

Leu Val Glu Ala Val Lys Gln Gln Ala Pro Ile Leu Ser Val Leu
1460                1465                1470

Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
1520                1525                1530

Lys Thr Leu Ile Arg Gly Phe Gln Leu Phe Phe Lys Asp Ser Pro
1535                1540                1545

Leu Leu Leu Val Met Glu Met Tyr Glu Leu Cys Met Phe Phe Arg
1550                1555                1560

Asn Tyr Lys Glu Ala Glu Ala Lys Leu Leu Glu Phe Gln Lys Ser
1565                1570                1575

Leu Glu Thr Leu Asn Thr Ala Ala Thr Lys Val His Pro Val Ile
1580                1585                1590

Pro Ala Met Trp Leu Glu Asp Gln Val Cys Phe Leu Leu Lys Leu
1595                1600                1605

Met Leu Gln Gln Cys Lys Thr Gln Tyr Glu Leu Gly Lys Leu Leu
1610                1615                1620

Gln Leu Phe Val Glu Arg Glu His Leu Phe Ser Asp Gly Pro Asp
1625                1630                1635

Val Lys Lys Leu Cys Ile Leu Cys Gln Ile Leu Lys Asp Thr Ser
1640                1645                1650

Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770
```

```
Leu Leu Leu Thr Leu Ala Gly His Trp Leu Ala Gln Glu Asp Val
1775                1780                1785

Val Pro Leu Asp Lys Leu Glu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830

Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Glu Gln Glu Ser Leu
1865                1870                1875

Asn Phe Leu Ile Gly Arg Leu Leu Asp Asp Gly Cys Val His Glu
1880                1885                1890

Ala Ser Arg Val Cys Arg Tyr Phe His Phe Tyr Asn Pro Asp Val
1895                1900                1905

Ala Leu Val Leu His Cys Arg Ala Leu Ala Ser Gly Glu Ala Ser
1910                1915                1920

Met Glu Asp Leu His Pro Glu Ile His Ala Leu Leu Gln Ser Ala
1925                1930                1935

Glu Leu Leu Glu Glu Glu Ala Pro Asp Ile Pro Leu Arg Arg Val
1940                1945                1950

His Ser Thr Ser Ser Leu Asp Ser Gln Lys Phe Val Thr Val Pro
1955                1960                1965

Ser Ser Asn Glu Val Val Thr Asn Leu Glu Val Leu Thr Ser Lys
1970                1975                1980

Cys Leu His Gly Lys Asn Tyr Cys Arg Gln Val Leu Cys Leu Tyr
1985                1990                1995

Asp Leu Ala Lys Glu Leu Gly Cys Ser Tyr Thr Asp Val Ala Ala
2000                2005                2010

Gln Asp Gly Glu Ala Met Leu Arg Lys Ile Leu Ala Ser Gln Gln
2015                2020                2025

Pro Asp Arg Cys Lys Arg Ala Gln Ala Phe Ile Ser Thr Gln Gly
2030                2035                2040

Leu Lys Pro Asp Thr Val Ala Glu Leu Val Ala Glu Glu Val Thr
2045                2050                2055

Arg Glu Leu Leu Thr Ser Ser Gln Gly Thr Gly His Lys Gln Met
2060                2065                2070

Phe Asn Pro Thr Glu Glu Ser Gln Thr Phe Leu Gln Leu Thr Thr
2075                2080                2085

Leu Cys Gln Asp Arg Thr Leu Val Gly Met Lys Leu Leu Asp Lys
2090                2095                2100

Ile Ser Ser Val Pro His Gly Glu Leu Ser Cys Thr Thr Glu Leu
2105                2110                2115

Leu Ile Leu Ala His His Cys Phe Thr Leu Thr Cys His Met Glu
2120                2125                2130

Gly Ile Ile Arg Val Leu Gln Ala Ala His Met Leu Thr Asp Asn
2135                2140                2145

His Leu Pro Pro Val Arg Ser Met Gly Trp Trp Tyr Gly Ser Ser
2150                2155                2160

Leu Ala Leu Glu Gly Thr Thr Arg Xaa
```

```
                            2165                  2170

<210> SEQ ID NO 162
<211> LENGTH: 2260
<212> TYPE: PRT
<213> ORGANISM: Homo sapiens
<220> FEATURE:
<221> NAME/KEY: misc_feature
<222> LOCATION: (2260)..(2260)
<223> OTHER INFORMATION: Xaa can be any naturally occurring amino acid

<400> SEQUENCE: 162

Met Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
            50                  55                  60

Val Leu Ser Leu Thr Pro Gly Ser Arg Gly Gly Gly Arg Cys Cys Leu
65              70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
            130                 135                 140

Gln Asp Ile Ser Ile Ser Leu Leu Ser Leu Arg Ile Leu Ser Phe His
145             150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
            210                 215                 220

Phe Asp Val Val Asp Gly Thr Tyr Val Ala His Val Asp Leu Ala Leu
225             230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
            290                 295                 300

Leu Pro Ile Gln Gly Pro Lys Val Asp Glu Asp Pro Val Asn
305             310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350
```

```
Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
        610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765
```

```
Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
        980                 985                 990

Ile Leu Tyr Cys Leu Glu His Ser  Leu Gln His Leu Leu Tyr Val Tyr
            995                1000                1005

Leu Asp Cys Tyr Lys Leu Ser  Pro Glu Asn Cys Pro  Phe Leu Glu
       1010                1015                1020

Lys Lys Glu Leu His Glu Ala  His Pro Trp Phe Glu  Phe Leu Val
       1025                1030                1035

Gln Cys Arg Gln Val Ala Ser  Asn Leu Thr Asp Pro  Lys Leu Ile
       1040                1045                1050

Phe Gln Ala Ser Leu Ala Asn  Ala Gln Ile Leu Ile  Pro Thr Asn
       1055                1060                1065

Gln Ala Ser Val Ser Ser Met  Leu Leu Glu Gly His  Thr Leu Leu
       1070                1075                1080

Ala Leu Ala Thr Thr Met Tyr  Ser Pro Gly Gly Val  Ser Gln Val
       1085                1090                1095

Val Gln Asn Glu Glu Asn Glu  Asn Cys Leu Lys Lys  Val Asp Pro
       1100                1105                1110

Gln Leu Leu Lys Met Ala Leu  Thr Pro Tyr Pro Lys  Leu Lys Thr
       1115                1120                1125

Ala Leu Phe Pro Gln Cys Thr  Pro Pro Ser Val Leu  Pro Ser Asp
       1130                1135                1140

Ile Thr Ile Tyr His Leu Ile  Gln Ser Leu Ser Pro  Phe Asp Pro
       1145                1150                1155

Ser Arg Leu Phe Gly Trp Gln  Ser Ala Asn Thr Leu  Ala Ile Gly
       1160                1165                1170

Asp Ala Trp Ser His Leu Pro  His Phe Ser Ser Pro  Asp Leu Val
```

-continued

```
            1175                1180                1185

Asn Lys Tyr Ala Ile Val Glu Arg Leu Asn Phe Ala Tyr Tyr Leu
        1190                1195                1200

His Asn Gly Arg Pro Ser Phe Ala Phe Gly Thr Phe Leu Val Gln
        1205                1210                1215

Glu Leu Ile Lys Ser Lys Thr Pro Lys Gln Leu Ile Gln Gln Val
        1220                1225                1230

Gly Asn Glu Ala Tyr Val Ile Gly Leu Ser Ser Phe His Ile Pro
        1235                1240                1245

Ser Ile Gly Ala Ala Cys Val Cys Phe Leu Glu Leu Leu Gly Leu
        1250                1255                1260

Asp Ser Leu Lys Leu Arg Val Asp Met Lys Val Ala Asn Ile Ile
        1265                1270                1275

Leu Ser Tyr Lys Cys Arg Asn Glu Asp Ala Gln Tyr Ser Phe Ile
        1280                1285                1290

Arg Glu Ser Val Ala Glu Lys Leu Ser Lys Leu Ala Asp Gly Glu
        1295                1300                1305

Lys Thr Thr Thr Glu Glu Leu Leu Val Leu Leu Glu Glu Gly Thr
        1310                1315                1320

Trp Asn Ser Ile Gln Gln Gln Glu Ile Lys Arg Leu Ser Ser Glu
        1325                1330                1335

Ser Ser Ser Gln Trp Ala Leu Val Val Gln Phe Cys Arg Leu His
        1340                1345                1350

Asn Met Lys Leu Ser Ile Ser Tyr Leu Arg Glu Cys Ala Lys Ala
        1355                1360                1365

Asn Asp Trp Leu Gln Phe Ile Ile His Ser Gln Leu His Asn Tyr
        1370                1375                1380

His Pro Ala Glu Val Lys Ser Leu Ile Gln Tyr Phe Ser Pro Val
        1385                1390                1395

Ile Gln Asp His Leu Arg Leu Ala Phe Glu Asn Leu Pro Ser Val
        1400                1405                1410

Pro Thr Ser Lys Met Asp Ser Asp Gln Val Cys Asn Lys Cys Pro
        1415                1420                1425

Gln Glu Leu Gln Gly Ser Lys Gln Glu Met Thr Asp Leu Phe Glu
        1430                1435                1440

Ile Leu Leu Gln Cys Ser Glu Glu Pro Asp Ser Trp His Trp Leu
        1445                1450                1455

Leu Val Glu Ala Val Lys Gln Ala Pro Ile Leu Ser Val Leu
        1460                1465                1470

Ala Ser Cys Leu Gln Gly Ala Ser Ala Ile Ser Cys Leu Cys Val
        1475                1480                1485

Trp Ile Ile Thr Ser Val Glu Asp Asn Val Ala Thr Glu Ala Met
        1490                1495                1500

Gly His Ile Gln Asp Ser Thr Glu Asp His Thr Trp Asn Leu Glu
        1505                1510                1515

Asp Leu Ser Val Ile Trp Arg Thr Leu Thr Arg Gln Lys Ser
        1520                1525                1530

Lys Thr Leu Ile Arg Gly Phe Gln Leu Phe Phe Lys Asp Ser Pro
        1535                1540                1545

Leu Leu Leu Val Met Glu Met Tyr Glu Leu Cys Met Phe Phe Arg
        1550                1555                1560

Asn Tyr Lys Glu Ala Glu Ala Lys Leu Leu Glu Phe Gln Lys Ser
        1565                1570                1575
```

```
Leu Glu Thr Leu Asn Thr Ala  Ala Thr Lys Val His  Pro Val Ile
    1580             1585                 1590

Pro Ala Met Trp Leu Glu Asp  Gln Val Cys Phe Leu  Leu Lys Leu
    1595             1600                 1605

Met Leu Gln Gln Cys Lys Thr  Gln Tyr Glu Leu Gly  Lys Leu Leu
    1610             1615                 1620

Gln Leu Phe Val Glu Arg Glu  His Leu Phe Ser Asp  Gly Pro Asp
    1625             1630                 1635

Val Lys Lys Leu Cys Ile Leu  Cys Gln Ile Leu Lys  Asp Thr Ser
    1640             1645                 1650

Ile Ala Ile Asn His Thr Ile  Ile Thr Ser Tyr Ser  Ile Glu Asn
    1655             1660                 1665

Leu Gln His Glu Cys Arg Ser  Ile Leu Glu Arg Leu  Gln Thr Asp
    1670             1675                 1680

Gly Gln Phe Ala Leu Ala Arg  Arg Val Ala Glu Leu  Ala Glu Leu
    1685             1690                 1695

Pro Val Asp Asn Leu Val Ile  Lys Glu Ile Thr Gln  Glu Met Gln
    1700             1705                 1710

Thr Leu Lys His Ile Glu Gln  Trp Ser Leu Lys Gln  Ala Arg Ile
    1715             1720                 1725

Asp Phe Trp Lys Lys Cys His  Glu Asn Phe Lys Lys  Asn Ser Ile
    1730             1735                 1740

Ser Ser Lys Ala Ala Ser Ser  Phe Phe Ser Thr Gln  Ala His Val
    1745             1750                 1755

Ala Cys Glu His Pro Thr Gly  Trp Ser Ser Met Glu  Glu Arg His
    1760             1765                 1770

Leu Leu Leu Thr Leu Ala Gly  His Trp Leu Ala Gln  Glu Asp Val
    1775             1780                 1785

Val Pro Leu Asp Lys Leu Glu  Glu Leu Glu Lys Gln  Ile Trp Leu
    1790             1795                 1800

Cys Arg Ile Thr Gln His Thr  Leu Gly Arg Asn Gln  Glu Glu Thr
    1805             1810                 1815

Glu Pro Arg Phe Ser Arg Gln  Ile Ser Thr Ser Gly  Glu Leu Ser
    1820             1825                 1830

Phe Asp Ser Leu Ala Ser Glu  Phe Ser Phe Ser Lys  Leu Ala Ala
    1835             1840                 1845

Leu Asn Thr Ser Lys Tyr Leu  Glu Leu Asn Ser Leu  Pro Ser Lys
    1850             1855                 1860

Glu Thr Cys Glu Asn Arg Leu  Asp Trp Lys Glu Gln  Glu Ser Leu
    1865             1870                 1875

Asn Phe Leu Ile Gly Arg Leu  Leu Asp Asp Gly Cys  Val His Glu
    1880             1885                 1890

Ala Ser Arg Val Cys Arg Tyr  Phe His Phe Tyr Asn  Pro Asp Val
    1895             1900                 1905

Ala Leu Val Leu His Cys Arg  Ala Leu Ala Ser Gly  Glu Ala Ser
    1910             1915                 1920

Met Glu Asp Leu His Pro Glu  Ile His Ala Leu Leu  Gln Ser Ala
    1925             1930                 1935

Glu Leu Leu Glu Glu Glu Ala  Pro Asp Ile Pro Leu  Arg Arg Val
    1940             1945                 1950

His Ser Thr Ser Ser Leu Asp  Ser Gln Lys Phe Val  Thr Val Pro
    1955             1960                 1965
```

-continued

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp Arg Cys Lys Arg Ala Gln Ala Phe Ile Ser Thr Gln Gly
    2030                2035                2040

Leu Lys Pro Asp Thr Val Ala Glu Leu Val Ala Glu Glu Val Thr
    2045                2050                2055

Arg Glu Leu Leu Thr Ser Ser Gln Gly Thr Gly His Lys Gln Met
    2060                2065                2070

Phe Asn Pro Thr Glu Glu Ser Gln Thr Phe Leu Gln Leu Thr Thr
    2075                2080                2085

Leu Cys Gln Asp Arg Thr Leu Val Gly Met Lys Leu Leu Asp Lys
    2090                2095                2100

Ile Ser Ser Val Pro His Gly Glu Leu Ser Cys Thr Thr Glu Leu
    2105                2110                2115

Leu Ile Leu Ala His His Cys Phe Thr Leu Thr Cys His Met Glu
    2120                2125                2130

Gly Ile Ile Arg Val Leu Gln Ala Ala His Met Leu Thr Asp Asn
    2135                2140                2145

His Leu Ala Pro Ser Glu Glu Tyr Gly Leu Val Val Arg Leu Leu
    2150                2155                2160

Thr Gly Ile Gly Arg Tyr Asn Glu Met Thr Tyr Ile Phe Asp Leu
    2165                2170                2175

Leu His Lys Lys His Tyr Phe Glu Val Leu Met Arg Lys Lys Leu
    2180                2185                2190

Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ser Leu Ser Pro Gly Arg Thr Ala
    2240                2245                2250

Ser Arg Met Gly Thr Ser Xaa
    2255                2260

<210> SEQ ID NO 163
<211> LENGTH: 2338
<212> TYPE: PRT
<213> ORGANISM: Homo sapiens
<220> FEATURE:
<221> NAME/KEY: misc_feature
<222> LOCATION: (2338)..(2338)
<223> OTHER INFORMATION: Xaa can be any naturally occurring amino acid

<400> SEQUENCE: 163

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg

```
            35                  40                  45
Thr Gln Pro Glu Ala Leu Gly Ser Leu Thr Ala Ala Gly Ser Leu Gln
 50                  55                  60

Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
                130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
                210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
                290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
                355                 360                 365

Leu Glu Ser Pro Glu Ser Gly Asn His Ser Thr Ser Val Gln Ser Trp
                370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
                420                 425                 430

Thr Gly Phe Thr Ala Leu Phe Thr Trp Glu Val Glu Arg Met Gly Tyr
                435                 440                 445

Thr Ile Thr Leu Trp Asp Leu Glu Thr Gln Gly Met Gln Cys Ser Ser
                450                 455                 460
```

```
Leu Gly Thr Lys Cys Ile Pro Val Asp Ser Ser Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880
```

Glu Ala Leu Trp Arg Tyr Leu Thr Ala Arg His Asp Trp Leu Asn Ile
            885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
            930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
            965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
            995                 1000                1005

Leu Asp Cys Tyr Lys Leu Ser Pro Glu Asn Cys Pro Phe Leu Glu
        1010                1015                1020

Lys Lys Glu Leu His Glu Ala His Pro Trp Phe Glu Phe Leu Val
        1025                1030                1035

Gln Cys Arg Gln Val Ala Ser Asn Leu Thr Asp Pro Lys Leu Ile
        1040                1045                1050

Phe Gln Ala Ser Leu Ala Asn Ala Gln Ile Leu Ile Pro Thr Asn
        1055                1060                1065

Gln Ala Ser Val Ser Ser Met Leu Leu Glu Gly His Thr Leu Leu
        1070                1075                1080

Ala Leu Ala Thr Thr Met Tyr Ser Pro Gly Gly Val Ser Gln Val
        1085                1090                1095

Val Gln Asn Glu Glu Asn Glu Asn Cys Leu Lys Lys Val Asp Pro
        1100                1105                1110

Gln Leu Leu Lys Met Ala Leu Thr Pro Tyr Pro Lys Leu Lys Thr
        1115                1120                1125

Ala Leu Phe Pro Gln Cys Thr Pro Pro Ser Val Leu Pro Ser Asp
        1130                1135                1140

Ile Thr Ile Tyr His Leu Ile Gln Ser Leu Ser Pro Phe Asp Pro
        1145                1150                1155

Ser Arg Leu Phe Gly Trp Gln Ser Ala Asn Thr Leu Ala Ile Gly
        1160                1165                1170

Asp Ala Trp Ser His Leu Pro His Phe Ser Ser Pro Asp Leu Val
        1175                1180                1185

Asn Lys Tyr Ala Ile Val Glu Arg Leu Asn Phe Ala Tyr Tyr Leu
        1190                1195                1200

His Asn Gly Arg Pro Ser Phe Ala Phe Gly Thr Phe Leu Val Gln
        1205                1210                1215

Glu Leu Ile Lys Ser Lys Thr Pro Lys Gln Leu Ile Gln Gln Val
        1220                1225                1230

Gly Asn Glu Ala Tyr Val Ile Gly Leu Ser Ser Phe His Ile Pro
        1235                1240                1245

Ser Ile Gly Ala Ala Cys Val Cys Phe Leu Glu Leu Leu Gly Leu
        1250                1255                1260

Asp Ser Leu Lys Leu Arg Val Asp Met Lys Val Ala Asn Ile Ile
        1265                1270                1275

Leu Ser Tyr Lys Cys Arg Asn Glu Asp Ala Gln Tyr Ser Phe Ile

```
                  1280                1285                1290
Arg Glu Ser Val Ala Glu Lys Leu Ser Lys Leu Ala Asp Gly Glu
    1295                1300                1305
Lys Thr Thr Thr Glu Glu Leu Leu Val Leu Leu Glu Glu Gly Thr
    1310                1315                1320
Trp Asn Ser Ile Gln Gln Gln Glu Ile Lys Arg Leu Ser Ser Glu
    1325                1330                1335
Ser Ser Ser Gln Trp Ala Leu Val Val Gln Phe Cys Arg Leu His
    1340                1345                1350
Asn Met Lys Leu Ser Ile Ser Tyr Leu Arg Glu Cys Ala Lys Ala
    1355                1360                1365
Asn Asp Trp Leu Gln Phe Ile Ile His Ser Gln Leu His Asn Tyr
    1370                1375                1380
His Pro Ala Glu Val Lys Ser Leu Ile Gln Tyr Phe Ser Pro Val
    1385                1390                1395
Ile Gln Asp His Leu Arg Leu Ala Phe Glu Asn Leu Pro Ser Val
    1400                1405                1410
Pro Thr Ser Lys Met Asp Ser Asp Gln Val Cys Asn Lys Cys Pro
    1415                1420                1425
Gln Glu Leu Gln Gly Ser Lys Gln Glu Met Thr Asp Leu Phe Glu
    1430                1435                1440
Ile Leu Leu Gln Cys Ser Glu Glu Pro Asp Ser Trp His Trp Leu
    1445                1450                1455
Leu Val Glu Ala Val Lys Gln Ala Pro Ile Leu Ser Val Leu
    1460                1465                1470
Ala Ser Cys Leu Gln Gly Ala Ser Ala Ile Ser Cys Leu Cys Val
    1475                1480                1485
Trp Ile Ile Thr Ser Val Glu Asp Asn Val Ala Thr Glu Ala Met
    1490                1495                1500
Gly His Ile Gln Asp Ser Thr Glu Asp His Thr Trp Asn Leu Glu
    1505                1510                1515
Asp Leu Ser Val Ile Trp Arg Thr Leu Leu Thr Arg Gln Lys Ser
    1520                1525                1530
Lys Thr Leu Ile Arg Gly Phe Gln Leu Phe Phe Lys Asp Ser Pro
    1535                1540                1545
Leu Leu Leu Val Met Glu Met Tyr Glu Leu Cys Met Phe Phe Arg
    1550                1555                1560
Asn Tyr Lys Glu Ala Glu Ala Lys Leu Leu Glu Phe Gln Lys Ser
    1565                1570                1575
Leu Glu Thr Leu Asn Thr Ala Ala Thr Lys Val His Pro Val Ile
    1580                1585                1590
Pro Ala Met Trp Leu Glu Asp Gln Val Cys Phe Leu Leu Lys Leu
    1595                1600                1605
Met Leu Gln Gln Cys Lys Thr Gln Tyr Glu Leu Gly Lys Leu Leu
    1610                1615                1620
Gln Leu Phe Val Glu Arg Glu His Leu Phe Ser Asp Gly Pro Asp
    1625                1630                1635
Val Lys Lys Leu Cys Ile Leu Cys Gln Ile Leu Lys Asp Thr Ser
    1640                1645                1650
Ile Ala Ile Asn His Thr Ile Ile Thr Ser Tyr Ser Ile Glu Asn
    1655                1660                1665
Leu Gln His Glu Cys Arg Ser Ile Leu Glu Arg Leu Gln Thr Asp
    1670                1675                1680
```

```
Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp Arg Cys Lys Arg Ala Gln Ala Phe Ile Ser Thr Gln Gly
    2030                2035                2040

Leu Lys Pro Asp Thr Val Ala Glu Leu Val Ala Glu Glu Val Thr
    2045                2050                2055

Arg Glu Leu Leu Thr Ser Ser Gln Gly Thr Gly His Lys Gln Met
    2060                2065                2070
```

```
Phe Asn Pro Thr Glu Glu Ser Gln Thr Phe Leu Gln Leu Thr Thr
    2075                2080                2085

Leu Cys Gln Asp Arg Thr Leu Val Gly Met Lys Leu Leu Asp Lys
    2090                2095                2100

Ile Ser Ser Val Pro His Gly Glu Leu Ser Cys Thr Thr Glu Leu
    2105                2110                2115

Leu Ile Leu Ala His His Cys Phe Thr Leu Thr Cys His Met Glu
    2120                2125                2130

Gly Ile Ile Arg Val Leu Gln Ala Ala His Met Leu Thr Asp Asn
    2135                2140                2145

His Leu Ala Pro Ser Glu Glu Tyr Gly Leu Val Val Arg Leu Leu
    2150                2155                2160

Thr Gly Ile Gly Arg Tyr Asn Glu Met Thr Tyr Ile Phe Asp Leu
    2165                2170                2175

Leu His Lys Lys His Tyr Phe Glu Val Leu Met Arg Lys Lys Leu
    2180                2185                2190

Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ile Glu Ser Gln Pro Trp Glu Asp
    2240                2245                2250

Ser Leu Lys Asp Gly His Gln Leu Lys Gln Leu Leu Lys Ala
    2255                2260                2265

Leu Thr Leu Met Leu Asp Ala Ala Glu Leu Cys Gln Gly Leu Leu
    2270                2275                2280

Cys Ala Thr Gly Pro Ala Leu Ser Ala Ala His Gln Val Asp Asn
    2285                2290                2295

Ser Ala Asp Ser Leu Ser Glu His Trp Pro Glu His Asn Ala His
    2300                2305                2310

Gln Leu Gly Pro Pro Gln Ala Asp Gly Leu Tyr Ser Gly Pro Thr
    2315                2320                2325

Ser Val Leu Pro Gly Phe Tyr Cys Gly Xaa
    2330                2335

<210> SEQ ID NO 164
<211> LENGTH: 2349
<212> TYPE: PRT
<213> ORGANISM: Homo sapiens
<220> FEATURE:
<221> NAME/KEY: misc_feature
<222> LOCATION: (2349)..(2349)
<223> OTHER INFORMATION: Xaa can be any naturally occurring amino acid

<400> SEQUENCE: 164

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
```

-continued

```
                65                  70                  75                  80
Glu Gly Pro Phe Trp His Phe Leu Trp Glu Asp Ser Arg Asn Ser Ser
                    85                  90                  95

Thr Pro Thr Glu Lys Pro Lys Leu Leu Ala Leu Gly Glu Asn Tyr Glu
                    100                 105                 110

Leu Leu Ile Tyr Glu Phe Asn Leu Lys Asp Gly Arg Cys Asp Ala Thr
                    115                 120                 125

Ile Leu Tyr Ser Cys Ser Arg Glu Ala Leu Gln Lys Leu Ile Asp Asp
                    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                    165                 170                 175

Ile Phe Pro Glu Arg Asp Ala Ala Ile Arg Val Leu Asn Cys Phe Thr
                    180                 185                 190

Leu Pro Leu Pro Ala Gln Ala Val Asp Met Ile Ile Asp Thr Gln Leu
                    195                 200                 205

Cys Arg Gly Ile Leu Phe Val Leu Ser Ser Leu Gly Trp Ile Tyr Ile
                    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                    245                 250                 255

Ser Ser Phe Thr Ser Leu Lys Val Ser Gln Asp Leu Asp Val Ala Val
                    260                 265                 270

Ile Val Ser Ser Ser Asn Ser Ala Val Ala Leu Asn Leu Asn Leu Tyr
                    275                 280                 285

Phe Arg Gln His Pro Gly His Leu Leu Cys Glu Arg Ile Leu Glu Asp
                    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                    325                 330                 335

Ser Trp Lys Ala Gln Leu Ser Ser Leu Asn Glu Thr Ile Lys Asn Ser
                    340                 345                 350

Lys Leu Glu Val Ser Cys Cys Ala Pro Trp Phe Gln Asp Ile Leu His
                    355                 360                 365

Leu Glu Ser Pro Glu Ser Gly Asn His Ser Thr Ser Val Gln Ser Trp
                    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                    405                 410                 415

His Ile Ser Glu Gln Glu Glu Pro Ile Glu Leu Lys Cys Val Ser Val
                    420                 425                 430

Thr Gly Phe Thr Ala Leu Phe Thr Trp Glu Val Glu Arg Met Gly Tyr
                    435                 440                 445

Thr Ile Thr Leu Trp Asp Leu Glu Thr Gln Gly Met Gln Cys Ser Ser
                    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                    485                 490                 495
```

```
Thr Gln Glu Glu Phe Leu Asn Arg Leu Met Ile His Gly Ser Ala Ser
                500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
        610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
        770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
        850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910
```

```
Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
        930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
            995                 1000                1005

Leu Asp Cys Tyr Lys Leu Ser Pro Glu Asn Cys Pro Phe Leu Glu
        1010                1015                1020

Lys Lys Glu Leu His Glu Ala His Pro Trp Phe Glu Phe Leu Val
        1025                1030                1035

Gln Cys Arg Gln Val Ala Ser Asn Leu Thr Asp Pro Lys Leu Ile
        1040                1045                1050

Phe Gln Ala Ser Leu Ala Asn Ala Gln Ile Leu Ile Pro Thr Asn
        1055                1060                1065

Gln Ala Ser Val Ser Ser Met Leu Leu Glu Gly His Thr Leu Leu
        1070                1075                1080

Ala Leu Ala Thr Thr Met Tyr Ser Pro Gly Gly Val Ser Gln Val
        1085                1090                1095

Val Gln Asn Glu Glu Asn Asn Cys Leu Lys Lys Val Asp Pro
        1100                1105                1110

Gln Leu Leu Lys Met Ala Leu Thr Pro Tyr Pro Lys Leu Lys Thr
        1115                1120                1125

Ala Leu Phe Pro Gln Cys Thr Pro Pro Ser Val Leu Pro Ser Asp
        1130                1135                1140

Ile Thr Ile Tyr His Leu Ile Gln Ser Leu Ser Pro Phe Asp Pro
        1145                1150                1155

Ser Arg Leu Phe Gly Trp Gln Ser Ala Asn Thr Leu Ala Ile Gly
        1160                1165                1170

Asp Ala Trp Ser His Leu Pro His Phe Ser Ser Pro Asp Leu Val
        1175                1180                1185

Asn Lys Tyr Ala Ile Val Glu Arg Leu Asn Phe Ala Tyr Tyr Leu
        1190                1195                1200

His Asn Gly Arg Pro Ser Phe Ala Phe Gly Thr Phe Leu Val Gln
        1205                1210                1215

Glu Leu Ile Lys Ser Lys Thr Pro Lys Gln Leu Ile Gln Gln Val
        1220                1225                1230

Gly Asn Glu Ala Tyr Val Ile Gly Leu Ser Ser Phe His Ile Pro
        1235                1240                1245

Ser Ile Gly Ala Ala Cys Val Cys Phe Leu Glu Leu Leu Gly Leu
        1250                1255                1260

Asp Ser Leu Lys Leu Arg Val Asp Met Lys Val Ala Asn Ile Ile
        1265                1270                1275

Leu Ser Tyr Lys Cys Arg Asn Glu Asp Ala Gln Tyr Ser Phe Ile
        1280                1285                1290

Arg Glu Ser Val Ala Glu Lys Leu Ser Lys Leu Ala Asp Gly Glu
        1295                1300                1305

Lys Thr Thr Thr Glu Glu Leu Leu Val Leu Leu Glu Glu Gly Thr
```

-continued

```
                1310                1315                1320
Trp Asn Ser Ile Gln Gln Glu Ile Lys Arg Leu Ser Ser Glu
    1325                1330                1335
Ser Ser Ser Gln Trp Ala Leu Val Val Gln Phe Cys Arg Leu His
    1340                1345                1350
Asn Met Lys Leu Ser Ile Ser Tyr Leu Arg Glu Cys Ala Lys Ala
    1355                1360                1365
Asn Asp Trp Leu Gln Phe Ile Ile His Ser Gln Leu His Asn Tyr
    1370                1375                1380
His Pro Ala Glu Val Lys Ser Leu Ile Gln Tyr Phe Ser Pro Val
    1385                1390                1395
Ile Gln Asp His Leu Arg Leu Ala Phe Glu Asn Leu Pro Ser Val
    1400                1405                1410
Pro Thr Ser Lys Met Asp Ser Asp Gln Val Cys Asn Lys Cys Pro
    1415                1420                1425
Gln Glu Leu Gln Gly Ser Lys Gln Glu Met Thr Asp Leu Phe Glu
    1430                1435                1440
Ile Leu Leu Gln Cys Ser Glu Glu Pro Asp Ser Trp His Trp Leu
    1445                1450                1455
Leu Val Glu Ala Val Lys Gln Gln Ala Pro Ile Leu Ser Val Leu
    1460                1465                1470
Ala Ser Cys Leu Gln Gly Ala Ser Ala Ile Ser Cys Leu Cys Val
    1475                1480                1485
Trp Ile Ile Thr Ser Val Glu Asp Asn Val Ala Thr Glu Ala Met
    1490                1495                1500
Gly His Ile Gln Asp Ser Thr Glu Asp His Thr Trp Asn Leu Glu
    1505                1510                1515
Asp Leu Ser Val Ile Trp Arg Thr Leu Leu Thr Arg Gln Lys Ser
    1520                1525                1530
Lys Thr Leu Ile Arg Gly Phe Gln Leu Phe Phe Lys Asp Ser Pro
    1535                1540                1545
Leu Leu Leu Val Met Glu Met Tyr Glu Leu Cys Met Phe Phe Arg
    1550                1555                1560
Asn Tyr Lys Glu Ala Glu Ala Lys Leu Leu Glu Phe Gln Lys Ser
    1565                1570                1575
Leu Glu Thr Leu Asn Thr Ala Ala Thr Lys Val His Pro Val Ile
    1580                1585                1590
Pro Ala Met Trp Leu Glu Asp Gln Val Cys Phe Leu Leu Lys Leu
    1595                1600                1605
Met Leu Gln Gln Cys Lys Thr Gln Tyr Glu Leu Gly Lys Leu Leu
    1610                1615                1620
Gln Leu Phe Val Glu Arg Glu His Leu Phe Ser Asp Gly Pro Asp
    1625                1630                1635
Val Lys Lys Leu Cys Ile Leu Cys Gln Ile Leu Lys Asp Thr Ser
    1640                1645                1650
Ile Ala Ile Asn His Thr Ile Ile Thr Ser Tyr Ser Ile Glu Asn
    1655                1660                1665
Leu Gln His Glu Cys Arg Ser Ile Leu Glu Arg Leu Gln Thr Asp
    1670                1675                1680
Gly Gln Phe Ala Leu Ala Arg Arg Val Ala Glu Leu Ala Glu Leu
    1685                1690                1695
Pro Val Asp Asn Leu Val Ile Lys Glu Ile Thr Gln Glu Met Gln
    1700                1705                1710
```

```
Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Leu Glu Lys Gln Ile Trp Leu
    1790            1795                1800

Cys Arg Ile Thr Gln His Thr Leu Gly Arg Asn Gln Glu Glu Thr
    1805            1810                1815

Glu Pro Arg Phe Ser Arg Gln Ile Ser Thr Ser Gly Glu Leu Ser
    1820            1825                1830

Phe Asp Ser Leu Ala Ser Glu Phe Ser Phe Ser Lys Leu Ala Ala
    1835            1840                1845

Leu Asn Thr Ser Lys Tyr Leu Glu Leu Asn Ser Leu Pro Ser Lys
    1850            1855                1860

Glu Thr Cys Glu Asn Arg Leu Asp Trp Lys Gln Glu Ser Leu
    1865            1870                1875

Asn Phe Leu Ile Gly Arg Leu Leu Asp Asp Gly Cys Val His Glu
    1880            1885                1890

Ala Ser Arg Val Cys Arg Tyr Phe His Phe Tyr Asn Pro Asp Val
    1895            1900                1905

Ala Leu Val Leu His Cys Arg Ala Leu Ala Ser Gly Glu Ala Ser
    1910            1915                1920

Met Glu Asp Leu His Pro Glu Ile His Ala Leu Leu Gln Ser Ala
    1925            1930                1935

Glu Leu Leu Glu Glu Glu Ala Pro Asp Ile Pro Leu Arg Arg Val
    1940            1945                1950

His Ser Thr Ser Ser Leu Asp Ser Gln Lys Phe Val Thr Val Pro
    1955            1960                1965

Ser Ser Asn Glu Val Val Thr Asn Leu Glu Val Leu Thr Ser Lys
    1970            1975                1980

Cys Leu His Gly Lys Asn Tyr Cys Arg Gln Val Leu Cys Leu Tyr
    1985            1990                1995

Asp Leu Ala Lys Glu Leu Gly Cys Ser Tyr Thr Asp Val Ala Ala
    2000            2005                2010

Gln Asp Gly Glu Ala Met Leu Arg Lys Ile Leu Ala Ser Gln Gln
    2015            2020                2025

Pro Asp Arg Cys Lys Arg Ala Gln Ala Phe Ile Ser Thr Gln Gly
    2030            2035                2040

Leu Lys Pro Asp Thr Val Ala Glu Leu Val Ala Glu Glu Val Thr
    2045            2050                2055

Arg Glu Leu Leu Thr Ser Ser Gln Gly Thr Gly His Lys Gln Met
    2060            2065                2070

Phe Asn Pro Thr Glu Glu Ser Gln Thr Phe Leu Gln Leu Thr Thr
    2075            2080                2085

Leu Cys Gln Asp Arg Thr Leu Val Gly Met Lys Leu Leu Asp Lys
    2090            2095                2100
```

-continued

```
Ile Ser Ser Val Pro His Gly Glu Leu Ser Cys Thr Thr Glu Leu
    2105                2110                2115

Leu Ile Leu Ala His His Cys Phe Thr Leu Thr Cys His Met Glu
    2120                2125                2130

Gly Ile Ile Arg Val Leu Gln Ala Ala His Met Leu Thr Asp Asn
    2135                2140                2145

His Leu Ala Pro Ser Glu Glu Tyr Gly Leu Val Val Arg Leu Leu
    2150                2155                2160

Thr Gly Ile Gly Arg Tyr Asn Glu Met Thr Tyr Ile Phe Asp Leu
    2165                2170                2175

Leu His Lys Lys His Tyr Phe Glu Val Leu Met Arg Lys Lys Leu
    2180                2185                2190

Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ile Glu Ser Gln Pro Trp Glu Asp
    2240                2245                2250

Ser Leu Lys Asp Gly His Gln Leu Lys Gln Leu Leu Lys Ala
    2255                2260                2265

Leu Thr Leu Met Leu Asp Ala Ala Glu Ser Tyr Ala Lys Asp Ser
    2270                2275                2280

Cys Val Arg Gln Ala Gln His Cys Gln Arg Leu Thr Lys Leu Ile
    2285                2290                2295

Thr Leu Gln Ile His Phe Leu Asn Thr Gly Gln Asn Thr Met Leu
    2300                2305                2310

Ile Asn Leu Gly Arg His Lys Leu Met Asp Cys Ile Leu Ala Leu
    2315                2320                2325

Pro Arg Phe Tyr Gln Ala Ser Ile Val Ala Glu Ala Tyr Asp Phe
    2330                2335                2340

Cys Ser Arg Leu Gly Xaa
    2345

<210> SEQ ID NO 165
<211> LENGTH: 2443
<212> TYPE: PRT
<213> ORGANISM: homo sapiens

<400> SEQUENCE: 165

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110
```

```
Leu Leu Ile Tyr Glu Phe Asn Leu Lys Asp Gly Arg Cys Asp Ala Thr
        115                 120                 125
Ile Leu Tyr Ser Cys Ser Arg Glu Ala Leu Gln Lys Leu Ile Asp Asp
    130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
        195                 200                 205
Cys Arg Gly Ile Leu Phe Val Leu Ser Ser Leu Gly Trp Ile Tyr Ile
    210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Glu Pro Ala Lys Ile
                245                 250                 255
Ser Ser Phe Thr Ser Leu Lys Val Ser Gln Asp Leu Asp Val Ala Val
            260                 265                 270
Ile Val Ser Ser Ser Asn Ser Ala Val Ala Leu Asn Leu Asn Leu Tyr
        275                 280                 285
Phe Arg Gln His Pro Gly His Leu Leu Cys Glu Arg Ile Leu Glu Asp
    290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
        355                 360                 365
Leu Glu Ser Pro Glu Ser Gly Asn His Ser Thr Ser Val Gln Ser Trp
    370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
        435                 440                 445
Thr Ile Thr Leu Trp Asp Leu Glu Thr Gln Gly Met Gln Cys Ser Ser
    450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
        515                 520                 525
```

```
Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Gly Asn Gly Val Phe Leu Ala Ser Glu Leu Glu Asp Phe Glu Cys Phe
```

-continued

```
945                 950                 955                 960
Leu Leu Arg Leu Ser Arg Ile Gly Gly Val Ile Gln Asp Thr Leu Pro
                965                 970                 975
Val Gln Asn Tyr Lys Thr Lys Glu Gly Trp Asp Phe His Ser Gln Phe
                980                 985                 990
Ile Leu Tyr Cys Leu Glu His Ser Leu Gln His Leu Leu Tyr Val Tyr
                995                1000                1005
Leu Asp Cys Tyr Lys Leu Ser Pro Glu Asn Cys Pro Phe Leu Glu
   1010                1015                1020
Lys Lys Glu Leu His Glu Ala His Pro Trp Phe Glu Phe Leu Val
   1025                1030                1035
Gln Cys Arg Gln Val Ala Ser Asn Leu Thr Asp Pro Lys Leu Ile
   1040                1045                1050
Phe Gln Ala Ser Leu Ala Asn Ala Gln Ile Leu Ile Pro Thr Asn
   1055                1060                1065
Gln Ala Ser Val Ser Ser Met Leu Leu Glu Gly His Thr Leu Leu
   1070                1075                1080
Ala Leu Ala Thr Thr Met Tyr Ser Pro Gly Gly Val Ser Gln Val
   1085                1090                1095
Val Gln Asn Glu Glu Asn Glu Asn Cys Leu Lys Lys Val Asp Pro
   1100                1105                1110
Gln Leu Leu Lys Met Ala Leu Thr Pro Tyr Pro Lys Leu Lys Thr
   1115                1120                1125
Ala Leu Phe Pro Gln Cys Thr Pro Pro Ser Val Leu Pro Ser Asp
   1130                1135                1140
Ile Thr Ile Tyr His Leu Ile Gln Ser Leu Ser Pro Phe Asp Pro
   1145                1150                1155
Ser Arg Leu Phe Gly Trp Gln Ser Ala Asn Thr Leu Ala Ile Gly
   1160                1165                1170
Asp Ala Trp Ser His Leu Pro His Phe Ser Ser Pro Asp Leu Val
   1175                1180                1185
Asn Lys Tyr Ala Ile Val Glu Arg Leu Asn Phe Ala Tyr Tyr Leu
   1190                1195                1200
His Asn Gly Arg Pro Ser Phe Ala Phe Gly Thr Phe Leu Val Gln
   1205                1210                1215
Glu Leu Ile Lys Ser Lys Thr Pro Lys Gln Leu Ile Gln Gln Val
   1220                1225                1230
Gly Asn Glu Ala Tyr Val Ile Gly Leu Ser Ser Phe His Ile Pro
   1235                1240                1245
Ser Ile Gly Ala Ala Cys Val Cys Phe Leu Glu Leu Leu Gly Leu
   1250                1255                1260
Asp Ser Leu Lys Leu Arg Val Asp Met Lys Val Ala Asn Ile Ile
   1265                1270                1275
Leu Ser Tyr Lys Cys Arg Asn Glu Asp Ala Gln Tyr Ser Phe Ile
   1280                1285                1290
Arg Glu Ser Val Ala Glu Lys Leu Ser Lys Leu Ala Asp Gly Glu
   1295                1300                1305
Lys Thr Thr Thr Glu Glu Leu Leu Val Leu Leu Glu Glu Gly Thr
   1310                1315                1320
Trp Asn Ser Ile Gln Gln Gln Glu Ile Lys Arg Leu Ser Ser Glu
   1325                1330                1335
Ser Ser Ser Gln Trp Ala Leu Val Val Gln Phe Cys Arg Leu His
   1340                1345                1350
```

-continued

```
Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740
```

```
Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
    1790            1795                1800

Cys Arg Ile Thr Gln His Thr Leu Gly Arg Asn Gln Glu Glu Thr
    1805            1810                1815

Glu Pro Arg Phe Ser Arg Gln Ile Ser Thr Ser Gly Glu Leu Ser
    1820            1825                1830

Phe Asp Ser Leu Ala Ser Glu Phe Ser Phe Ser Lys Leu Ala Ala
    1835            1840                1845

Leu Asn Thr Ser Lys Tyr Leu Glu Leu Asn Ser Leu Pro Ser Lys
    1850            1855                1860

Glu Thr Cys Glu Asn Arg Leu Asp Trp Lys Glu Gln Glu Ser Leu
    1865            1870                1875

Asn Phe Leu Ile Gly Arg Leu Leu Asp Asp Gly Cys Val His Glu
    1880            1885                1890

Ala Ser Arg Val Cys Arg Tyr Phe His Phe Tyr Asn Pro Asp Val
    1895            1900                1905

Ala Leu Val Leu His Cys Arg Ala Leu Ala Ser Gly Glu Ala Ser
    1910            1915                1920

Met Glu Asp Leu His Pro Glu Ile His Ala Leu Leu Gln Ser Ala
    1925            1930                1935

Glu Leu Leu Glu Glu Glu Ala Pro Asp Ile Pro Leu Arg Arg Val
    1940            1945                1950

His Ser Thr Ser Ser Leu Asp Ser Gln Lys Phe Val Thr Val Pro
    1955            1960                1965

Ser Ser Asn Glu Val Val Thr Asn Leu Glu Val Leu Thr Ser Lys
    1970            1975                1980

Cys Leu His Gly Lys Asn Tyr Cys Arg Gln Val Leu Cys Leu Tyr
    1985            1990                1995

Asp Leu Ala Lys Glu Leu Gly Cys Ser Tyr Thr Asp Val Ala Ala
    2000            2005                2010

Gln Asp Gly Glu Ala Met Leu Arg Lys Ile Leu Ala Ser Gln Gln
    2015            2020                2025

Pro Asp Arg Cys Lys Arg Ala Gln Ala Phe Ile Ser Thr Gln Gly
    2030            2035                2040

Leu Lys Pro Asp Thr Val Ala Glu Leu Val Ala Glu Glu Val Thr
    2045            2050                2055

Arg Glu Leu Leu Thr Ser Ser Gln Gly Thr Gly His Lys Gln Met
    2060            2065                2070

Phe Asn Pro Thr Glu Glu Ser Gln Thr Phe Leu Gln Leu Thr Thr
    2075            2080                2085

Leu Cys Gln Asp Arg Thr Leu Val Gly Met Lys Leu Leu Asp Lys
    2090            2095                2100

Ile Ser Ser Val Pro His Gly Glu Leu Ser Cys Thr Thr Glu Leu
    2105            2110                2115

Leu Ile Leu Ala His His Cys Phe Thr Leu Thr Cys His Met Glu
    2120            2125                2130

Gly Ile Ile Arg Val Leu Gln Ala Ala His Met Leu Thr Asp Asn
```

2135                2140                2145

His Leu Ala Pro Ser Glu Glu Tyr Gly Leu Val Val Arg Leu Leu
        2150                2155                2160

Thr Gly Ile Gly Arg Tyr Asn Glu Met Thr Tyr Ile Phe Asp Leu
        2165                2170                2175

Leu His Lys Lys His Tyr Phe Glu Val Leu Met Arg Lys Lys Leu
        2180                2185                2190

Asp Pro Ser Gly Thr Leu Lys Thr Ala Leu Leu Asp Tyr Ile Lys
        2195                2200                2205

Arg Cys Arg Pro Gly Asp Ser Glu Lys His Asn Met Ile Ala Leu
        2210                2215                2220

Cys Phe Ser Met Cys Arg Glu Ile Gly Glu Asn His Glu Ala Ala
        2225                2230                2235

Ala Arg Ile Gln Leu Lys Leu Ile Glu Ser Gln Pro Trp Glu Asp
        2240                2245                2250

Ser Leu Lys Asp Gly His Gln Leu Lys Gln Leu Leu Lys Ala
        2255                2260                2265

Leu Thr Leu Met Leu Asp Ala Ala Glu Ser Tyr Ala Lys Asp Ser
        2270                2275                2280

Cys Val Arg Gln Ala Gln His Cys Gln Arg Leu Thr Lys Leu Ile
        2285                2290                2295

Thr Leu Gln Ile His Phe Leu Asn Thr Gly Gln Asn Thr Met Leu
        2300                2305                2310

Ile Asn Leu Gly Arg His Lys Leu Met Asp Cys Ile Leu Ala Leu
        2315                2320                2325

Pro Arg Phe Tyr Gln Ala Ser Ile Val Ala Glu Ala Tyr Asp Phe
        2330                2335                2340

Val Pro Asp Trp Ala Glu Ile Leu Tyr Gln Gln Val Ile Leu Lys
        2345                2350                2355

Gly Asp Phe Asn Tyr Leu Glu Glu Phe Lys Gln Gln Arg Leu Leu
        2360                2365                2370

Lys Ser Ser Ile Phe Glu Glu Ile Ser Lys Lys Tyr Lys Gln His
        2375                2380                2385

Gln Pro Thr Asp Met Val Met Glu Asn Leu Lys Lys Leu Leu Thr
        2390                2395                2400

Tyr Cys Glu Asp Val Tyr Leu Tyr Tyr Lys Leu Ala Tyr Glu His
        2405                2410                2415

Lys Phe Tyr Glu Ile Val Asn Val Leu Leu Lys Asp Pro Gln Thr
        2420                2425                2430

Gly Cys Cys Leu Lys Asp Met Leu Ala Gly
        2435                2440

<210> SEQ ID NO 166
<211> LENGTH: 245
<212> TYPE: PRT
<213> ORGANISM: homo sapiens

<400> SEQUENCE: 166

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
        35                  40                  45

```
Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala Arg Gly Phe Ser Thr Ser
225                 230                 235                 240

Gln Arg Arg His Val
            245

<210> SEQ ID NO 167
<211> LENGTH: 427
<212> TYPE: PRT
<213> ORGANISM: Homo sapiens

<400> SEQUENCE: 167

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175
```

-continued

```
Ile Phe Pro Glu Arg Asp Ala Ala Ile Arg Val Leu Asn Cys Phe Thr
                180                 185                 190
Leu Pro Leu Pro Ala Gln Ala Val Asp Met Ile Ile Asp Thr Gln Leu
            195                 200                 205
Cys Arg Gly Ile Leu Phe Val Leu Ser Ser Leu Gly Trp Ile Tyr Ile
210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Pro Ala Lys Ile
                245                 250                 255
Ser Ser Phe Thr Ser Leu Lys Val Ser Gln Asp Leu Val Ala Val
            260                 265                 270
Ile Val Ser Ser Asn Ser Ala Val Ala Leu Asn Leu Asn Leu Tyr
            275                 280                 285
Phe Arg Gln His Pro Gly His Leu Leu Cys Glu Arg Ile Leu Glu Asp
    290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
    370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Pro Ile Glu Leu
            420                 425

<210> SEQ ID NO 168
<211> LENGTH: 555
<212> TYPE: PRT
<213> ORGANISM: Homo sapiens

<400> SEQUENCE: 168

Met Ala Glu Glu Gly Val Ala Ser Ala Ser Ala Gly Gly Ser
1               5                   10                  15
Trp Gly Thr Ala Ala Met Gly Arg Val Leu Pro Met Leu Leu Val Pro
                20                  25                  30
Val Pro Ala Glu Ala Met Gly Gln Leu Gly Ser Arg Ala Gln Leu Arg
            35                  40                  45
Thr Gln Pro Glu Ala Leu Gly Ser Leu Thr Ala Ala Gly Ser Leu Gln
        50                  55                  60
Val Leu Ser Leu Thr Pro Gly Ser Arg Gly Gly Arg Cys Cys Leu
65                  70                  75                  80
Glu Gly Pro Phe Trp His Phe Leu Trp Glu Asp Ser Arg Asn Ser Ser
                85                  90                  95
Thr Pro Thr Glu Lys Pro Lys Leu Leu Ala Leu Gly Glu Asn Tyr Glu
            100                 105                 110
Leu Leu Ile Tyr Glu Phe Asn Leu Lys Asp Gly Arg Cys Asp Ala Thr
```

-continued

```
            115                 120                 125
Ile Leu Tyr Ser Cys Ser Arg Glu Ala Leu Gln Lys Leu Ile Asp Asp
        130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
        195                 200                 205
Cys Arg Gly Ile Leu Phe Val Leu Ser Ser Leu Gly Trp Ile Tyr Ile
    210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Glu Pro Ala Lys Ile
                245                 250                 255
Ser Ser Phe Thr Ser Leu Lys Val Ser Gln Asp Leu Asp Val Ala Val
            260                 265                 270
Ile Val Ser Ser Ser Asn Ser Ala Val Ala Leu Asn Leu Asn Leu Tyr
        275                 280                 285
Phe Arg Gln His Pro Gly His Leu Leu Cys Glu Arg Ile Leu Glu Asp
    290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
        355                 360                 365
Leu Glu Ser Pro Glu Ser Gly Asn His Ser Thr Ser Val Gln Ser Trp
    370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
        435                 440                 445
Thr Ile Thr Leu Trp Asp Leu Glu Thr Gln Gly Met Gln Cys Ser Ser
    450                 455                 460
Leu Gly Thr Lys Cys Ile Pro Val Asp Ser Ser Gly Asp Gln Leu
465                 470                 475                 480
Cys Phe Val Leu Thr Glu Asn Gly Leu Ser Asp Phe Val Trp Phe Asp
                485                 490                 495
Ser Arg Arg Val Phe Lys Gln Thr His Asp Pro Trp Lys Cys Gln His
            500                 505                 510
Cys Gly His Ser Leu Ser Ser Gln Trp Leu Gly Lys Val Leu Asn Ser
        515                 520                 525
His Thr Cys Thr Arg Gly Arg Asp Arg Lys Ser Ser Ala Gly His Ser
    530                 535                 540
```

```
Lys Phe Leu Phe Glu Glu Gln Gly Lys Ser Phe
545                 550                 555

<210> SEQ ID NO 169
<211> LENGTH: 576
<212> TYPE: PRT
<213> ORGANISM: Homo sapiens

<400> SEQUENCE: 169

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
```

-continued

```
                355                 360                 365
Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Leu Ile His Pro Gln
545                 550                 555                 560

Asn Leu Leu Tyr Leu Ile Ser Leu Ile Thr Cys His Pro Ile Tyr Ile
                565                 570                 575

<210> SEQ ID NO 170
<211> LENGTH: 559
<212> TYPE: PRT
<213> ORGANISM: Homo sapiens

<400> SEQUENCE: 170

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160
```

```
Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser
545                 550                 555

<210> SEQ ID NO 171
<211> LENGTH: 576
<212> TYPE: PRT
```

-continued

<213> ORGANISM: Homo sapiens

<400> SEQUENCE: 171

```
Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
            50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                    85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400
```

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Leu Ile Ser Leu Ile Thr Cys His Pro Ile Tyr Ile
            565                 570                 575

<210> SEQ ID NO 172
<211> LENGTH: 2443
<212> TYPE: PRT
<213> ORGANISM: Homo sapiens

<400> SEQUENCE: 172

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
            85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
            195                 200                 205

```
Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Gln Ile Lys Glu
    610                 615                 620
```

```
Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Met Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
835                 840                 845

Ile Val Leu Asn Trp Ala Leu Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Thr Val Asp Val Ile Asn Gln Asn
        915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Gly Trp Phe His Ser Gln Phe
            980                 985                 990

Ile Leu Tyr Cys Leu Glu His Ser Leu Gln His Leu Leu Tyr Val Tyr
        995                 1000                1005

Leu Asp Cys Tyr Lys Leu Ser Pro Glu Asn Cys Pro Phe Leu Glu
        1010                1015                1020

Lys Lys Glu Leu His Glu Ala His Pro Trp Phe Glu Phe Leu Val
        1025                1030                1035

Gln Cys Arg Gln Val Ala Ser Asn Leu Thr Asp Pro Lys Leu Ile
```

-continued

```
            1040                1045                1050
Phe Gln Ala Ser Leu Ala Asn Ala Gln Ile Leu Ile Pro Thr Asn
            1055                1060                1065
Gln Ala Ser Val Ser Ser Met Leu Leu Glu Gly His Thr Leu Leu
            1070                1075                1080
Ala Leu Ala Thr Thr Met Tyr Ser Pro Gly Gly Val Ser Gln Val
            1085                1090                1095
Val Gln Asn Glu Glu Asn Glu Asn Cys Leu Lys Lys Val Asp Pro
            1100                1105                1110
Gln Leu Leu Lys Met Ala Leu Thr Pro Tyr Pro Lys Leu Lys Thr
            1115                1120                1125
Ala Leu Phe Pro Gln Cys Thr Pro Pro Ser Val Leu Pro Ser Asp
            1130                1135                1140
Ile Thr Ile Tyr His Leu Ile Gln Ser Leu Ser Pro Phe Asp Pro
            1145                1150                1155
Ser Arg Leu Phe Gly Trp Gln Ser Ala Asn Thr Leu Ala Ile Gly
            1160                1165                1170
Asp Ala Trp Ser His Leu Pro His Phe Ser Ser Pro Asp Leu Val
            1175                1180                1185
Asn Lys Tyr Ala Ile Val Glu Arg Leu Asn Phe Ala Tyr Tyr Leu
            1190                1195                1200
His Asn Gly Arg Pro Ser Phe Ala Phe Gly Thr Phe Leu Val Gln
            1205                1210                1215
Glu Leu Ile Lys Ser Lys Thr Pro Lys Gln Leu Ile Gln Gln Val
            1220                1225                1230
Gly Asn Glu Ala Tyr Val Ile Gly Leu Ser Ser Phe His Ile Pro
            1235                1240                1245
Ser Ile Gly Ala Ala Cys Val Cys Phe Leu Glu Leu Leu Gly Leu
            1250                1255                1260
Asp Ser Leu Lys Leu Arg Val Asp Met Lys Val Ala Asn Ile Ile
            1265                1270                1275
Leu Ser Tyr Lys Cys Arg Asn Glu Asp Ala Gln Tyr Ser Phe Ile
            1280                1285                1290
Arg Glu Ser Val Ala Glu Lys Leu Ser Lys Leu Ala Asp Gly Glu
            1295                1300                1305
Lys Thr Thr Thr Glu Glu Leu Leu Val Leu Leu Glu Glu Gly Thr
            1310                1315                1320
Trp Asn Ser Ile Gln Gln Gln Glu Ile Lys Arg Leu Ser Ser Glu
            1325                1330                1335
Ser Ser Ser Gln Trp Ala Leu Val Val Gln Phe Cys Arg Leu His
            1340                1345                1350
Asn Met Lys Leu Ser Ile Ser Tyr Leu Arg Glu Cys Ala Lys Ala
            1355                1360                1365
Asn Asp Trp Leu Gln Phe Ile Ile His Ser Gln Leu His Asn Tyr
            1370                1375                1380
His Pro Ala Glu Val Lys Ser Leu Ile Gln Tyr Phe Ser Pro Val
            1385                1390                1395
Ile Gln Asp His Leu Arg Leu Ala Phe Glu Asn Leu Pro Ser Val
            1400                1405                1410
Pro Thr Ser Lys Met Asp Ser Asp Gln Val Cys Asn Lys Cys Pro
            1415                1420                1425
Gln Glu Leu Gln Gly Ser Lys Gln Glu Met Thr Asp Leu Phe Glu
            1430                1435                1440
```

-continued

Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
    1460            1465                1470

Ala Ser Cys Leu Gln Gly Ala Ser Ala Ile Ser Cys Leu Cys Val
    1475            1480                1485

Trp Ile Ile Thr Ser Val Glu Asp Asn Val Ala Thr Glu Ala Met
    1490            1495                1500

Gly His Ile Gln Asp Ser Thr Glu Asp His Thr Trp Asn Leu Glu
    1505            1510                1515

Asp Leu Ser Val Ile Trp Arg Thr Leu Leu Thr Arg Gln Lys Ser
    1520            1525                1530

Lys Thr Leu Ile Arg Gly Phe Gln Leu Phe Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
    1790            1795                1800

Cys Arg Ile Thr Gln His Thr Leu Gly Arg Asn Gln Glu Glu Thr
    1805            1810                1815

Glu Pro Arg Phe Ser Arg Gln Ile Ser Thr Ser Gly Glu Leu Ser
    1820            1825                1830

```
Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Gln Glu Ser Leu
1865                1870                1875

Asn Phe Leu Ile Gly Arg Leu Leu Asp Asp Gly Cys Val His Glu
1880                1885                1890

Ala Ser Arg Val Cys Arg Tyr Phe His Phe Tyr Asn Pro Asp Val
1895                1900                1905

Ala Leu Val Leu His Cys Arg Ala Leu Ala Ser Gly Glu Ala Ser
1910                1915                1920

Met Glu Asp Leu His Pro Glu Ile His Ala Leu Leu Gln Ser Ala
1925                1930                1935

Glu Leu Leu Glu Glu Glu Ala Pro Asp Ile Pro Leu Arg Arg Val
1940                1945                1950

His Ser Thr Ser Ser Leu Asp Ser Gln Lys Phe Val Thr Val Pro
1955                1960                1965

Ser Ser Asn Glu Val Val Thr Asn Leu Glu Val Leu Thr Ser Lys
1970                1975                1980

Cys Leu His Gly Lys Asn Tyr Cys Arg Gln Val Leu Cys Leu Tyr
1985                1990                1995

Asp Leu Ala Lys Glu Leu Gly Cys Ser Tyr Thr Asp Val Ala Ala
2000                2005                2010

Gln Asp Gly Glu Ala Met Leu Arg Lys Ile Leu Ala Ser Gln Gln
2015                2020                2025

Pro Asp Arg Cys Lys Arg Ala Gln Ala Phe Ile Ser Thr Gln Gly
2030                2035                2040

Leu Lys Pro Asp Thr Val Ala Glu Leu Val Ala Glu Glu Val Thr
2045                2050                2055

Arg Glu Leu Leu Thr Ser Ser Gln Gly Thr Gly His Lys Gln Met
2060                2065                2070

Phe Asn Pro Thr Glu Glu Ser Gln Thr Phe Leu Gln Leu Thr Thr
2075                2080                2085

Leu Cys Gln Asp Arg Thr Leu Val Gly Met Lys Leu Leu Asp Lys
2090                2095                2100

Ile Ser Ser Val Pro His Gly Glu Leu Ser Cys Thr Thr Glu Leu
2105                2110                2115

Leu Ile Leu Ala His His Cys Phe Thr Leu Thr Cys His Met Glu
2120                2125                2130

Gly Ile Ile Arg Val Leu Gln Ala Ala His Met Leu Thr Asp Asn
2135                2140                2145

His Leu Ala Pro Ser Glu Glu Tyr Gly Leu Val Val Arg Leu Leu
2150                2155                2160

Thr Gly Ile Gly Arg Tyr Asn Glu Met Thr Tyr Ile Phe Asp Leu
2165                2170                2175

Leu His Lys Lys His Tyr Phe Glu Val Leu Met Arg Lys Lys Leu
2180                2185                2190

Asp Pro Ser Gly Thr Leu Lys Thr Ala Leu Leu Asp Tyr Ile Lys
2195                2200                2205

Arg Cys Arg Pro Gly Asp Ser Glu Lys His Asn Met Ile Ala Leu
2210                2215                2220

Cys Phe Ser Met Cys Arg Glu Ile Gly Glu Asn His Glu Ala Ala
```

```
                     2225                2230                2235
Ala Arg Ile Gln Leu Lys Leu Ile Glu Ser Gln Pro Trp Glu Asp
    2240                2245                2250

Ser Leu Lys Asp Gly His Gln Leu Lys Gln Leu Leu Leu Lys Ala
    2255                2260                2265

Leu Thr Leu Met Leu Asp Ala Ala Glu Ser Tyr Ala Lys Asp Ser
    2270                2275                2280

Cys Val Arg Gln Ala Gln His Cys Gln Arg Leu Thr Lys Leu Ile
    2285                2290                2295

Thr Leu Gln Ile His Phe Leu Asn Thr Gly Gln Asn Thr Met Leu
    2300                2305                2310

Ile Asn Leu Gly Arg His Lys Leu Met Asp Cys Ile Leu Ala Leu
    2315                2320                2325

Pro Arg Phe Tyr Gln Ala Ser Ile Val Ala Glu Ala Tyr Asp Phe
    2330                2335                2340

Val Pro Asp Trp Ala Glu Ile Leu Tyr Gln Gln Val Ile Leu Lys
    2345                2350                2355

Gly Asp Phe Asn Tyr Leu Glu Glu Phe Lys Gln Gln Arg Leu Leu
    2360                2365                2370

Lys Ser Ser Ile Phe Glu Glu Ile Ser Lys Lys Tyr Lys Gln His
    2375                2380                2385

Gln Pro Thr Asp Met Val Met Glu Asn Leu Lys Lys Leu Leu Thr
    2390                2395                2400

Tyr Cys Glu Asp Val Tyr Leu Tyr Tyr Lys Leu Ala Tyr Glu His
    2405                2410                2415

Lys Phe Tyr Glu Ile Val Asn Val Leu Leu Lys Asp Pro Gln Thr
    2420                2425                2430

Gly Cys Cys Leu Lys Asp Met Leu Ala Gly
    2435                2440

<210> SEQ ID NO 173
<211> LENGTH: 898
<212> TYPE: PRT
<213> ORGANISM: Homo sapiens

<400> SEQUENCE: 173

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
                130                 135                 140
```

```
Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
            165                 170                 175

Ile Phe Pro Glu Arg Asp Ala Ala Ile Arg Val Leu Asn Cys Phe Thr
        180                 185                 190

Leu Pro Leu Pro Ala Gln Ala Val Asp Met Ile Ile Asp Thr Gln Leu
    195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
            245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
        340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Pro Ile Glu Leu Lys Cys Val Ser Val
        420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
```

```
                        565                 570                 575
Leu Arg Asn Val Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
                675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
                740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
            850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu

<210> SEQ ID NO 174
<211> LENGTH: 919
<212> TYPE: PRT
<213> ORGANISM: Homo sapiens

<400> SEQUENCE: 174

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
```

```
            35                  40                  45
Thr Gln Pro Glu Ala Leu Gly Ser Leu Thr Ala Ala Gly Ser Leu Gln
             50                  55                  60
Val Leu Ser Leu Thr Pro Gly Ser Arg Gly Gly Arg Cys Cys Leu
65                   70                  75                  80
Glu Gly Pro Phe Trp His Phe Leu Trp Glu Asp Ser Arg Asn Ser Ser
                 85                  90                  95
Thr Pro Thr Glu Lys Pro Lys Leu Leu Ala Leu Gly Glu Asn Tyr Glu
                100                 105                 110
Leu Leu Ile Tyr Glu Phe Asn Leu Lys Asp Gly Arg Cys Asp Ala Thr
                115                 120                 125
Ile Leu Tyr Ser Cys Ser Arg Glu Ala Leu Gln Lys Leu Ile Asp Asp
                130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
                180                 185                 190
Leu Pro Leu Pro Ala Gln Ala Val Asp Met Ile Ile Asp Thr Gln Leu
                195                 200                 205
Cys Arg Gly Ile Leu Phe Val Leu Ser Ser Leu Gly Trp Ile Tyr Ile
                210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Glu Pro Ala Lys Ile
                    245                 250                 255
Ser Ser Phe Thr Ser Leu Lys Val Ser Gln Asp Leu Asp Val Ala Val
                    260                 265                 270
Ile Val Ser Ser Asn Ser Ala Val Ala Leu Asn Leu Asn Leu Tyr
                275                 280                 285
Phe Arg Gln His Pro Gly His Leu Leu Cys Glu Arg Ile Leu Glu Asp
290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                    325                 330                 335
Ser Trp Lys Ala Gln Leu Ser Ser Leu Asn Glu Thr Ile Lys Asn Ser
                    340                 345                 350
Lys Leu Glu Val Ser Cys Cys Ala Pro Trp Phe Gln Asp Ile Leu His
                355                 360                 365
Leu Glu Ser Pro Glu Ser Gly Asn His Ser Thr Ser Val Gln Ser Trp
                370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                    405                 410                 415
His Ile Ser Glu Gln Glu Glu Pro Ile Glu Leu Lys Cys Val Ser Val
                420                 425                 430
Thr Gly Phe Thr Ala Leu Phe Thr Trp Glu Val Glu Arg Met Gly Tyr
                435                 440                 445
Thr Ile Thr Leu Trp Asp Leu Glu Thr Gln Gly Met Gln Cys Ser Ser
                450                 455                 460
```

-continued

```
Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
                675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
                755                 760                 765

Arg Asp Phe Leu Val Glu Ile Leu Lys Glu Lys Asn Tyr Phe Ser Glu
            770                 775                 780

Lys Glu Lys Arg Thr Ile Asp Phe Val His Gln Val Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Lys His Lys Ser Val Leu Asp Ser
            820                 825                 830

Phe Leu Lys Tyr Asp Cys Lys Asp Glu Phe Asn Lys Gln Asp His Arg
                835                 840                 845

Ile Val Leu Asn Trp Ala Leu Trp Trp Asp Gln Leu Thr Gln Glu Ser
        850                 855                 860

Ile Leu Leu Pro Arg Ile Ser Pro Glu Glu Tyr Lys Ser Tyr Ser Pro
865                 870                 875                 880
```

```
Glu Ala Leu Trp Arg Tyr Leu Thr Ala Arg His Asp Trp Leu Asn Ile
            885                 890                 895

Ile Leu Trp Ile Gly Glu Phe Gln Thr Ser Ile Val Met Leu His Phe
        900                 905                 910

Ser Arg Thr Asn Gly Pro Phe
        915

<210> SEQ ID NO 175
<211> LENGTH: 1028
<212> TYPE: PRT
<213> ORGANISM: Homo sapiens

<400> SEQUENCE: 175

Met Ala Ala Glu Glu Val Ala Ser Ala Ala Ser Ala Gly Gly Ser
 1               5                  10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
             35                  40                  45

Thr Gln Pro Glu Ala Leu Gly Ser Leu Thr Ala Ala Gly Ser Leu Gln
     50                  55                  60

Val Leu Ser Leu Thr Pro Gly Ser Arg Gly Gly Arg Cys Cys Leu
 65                  70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335
```

-continued

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
        450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
            485                 490                 495

Thr Gln Glu Glu Phe Leu Asn Arg Leu Met Ile His Gly Ser Ala Ser
        500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
        610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

-continued

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Lys His Lys Ser Val Leu Asp Ser
                820                 825                 830

Phe Leu Lys Tyr Asp Cys Lys Asp Glu Phe Asn Lys Gln Asp His Arg
                835                 840                 845

Ile Val Leu Asn Trp Ala Leu Trp Trp Asp Gln Leu Thr Gln Glu Ser
                850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
                915                 920                 925

Thr Ser Cys Asn Asn Tyr Met Arg Asn Glu Ile Leu Asp Lys Leu Ala
                930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
                980                 985                 990

Ile Leu Tyr Cys Leu Glu His Ser Leu Gln His Leu Leu Tyr Val Tyr
                995                 1000                1005

Leu Asp Cys Tyr Lys Leu Ser Pro Glu Asn Cys Pro Phe Leu Glu
        1010                1015                1020

Lys Lys Arg Val Thr
        1025

<210> SEQ ID NO 176
<211> LENGTH: 1263
<212> TYPE: PRT
<213> ORGANISM: Homo sapiens

<400> SEQUENCE: 176

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

```
Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
            130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
            210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
            290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510
```

-continued

Thr Val Asp Thr Leu Cys His Leu Asn Gly Trp Gly Arg Cys Ser Ile
    515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
                595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
                675                 680                 685

Glu Glu Val Ile Ala Ser Ala Ile Leu Asn Asn Lys Ile Pro Glu Ala
                690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
                740                 745                 750

Lys Gly Gln Leu Leu Lys Ile Cys Phe Tyr Thr Thr Asn Lys Asn Ile
                755                 760                 765

Arg Asp Phe Leu Val Glu Ile Leu Lys Glu Lys Asn Tyr Phe Ser Glu
                770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Lys His Lys Ser Val Leu Asp Ser
                820                 825                 830

Phe Leu Lys Tyr Asp Cys Lys Asp Glu Phe Asn Lys Gln Asp His Arg
                835                 840                 845

Ile Val Leu Asn Trp Ala Leu Trp Trp Asp Gln Leu Thr Gln Glu Ser
                850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
                915                 920                 925

Thr Ser Cys Asn Asn Tyr Met Arg Asn Glu Ile Leu Asp Lys Leu Ala

```
                930             935             940
Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
        995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Thr
    1235                1240                1245

Phe Asn Arg Ser Cys Met Cys Leu Phe Leu Arg Ile Ala Trp Pro
    1250                1255                1260

<210> SEQ ID NO 177
<211> LENGTH: 1441
<212> TYPE: PRT
<213> ORGANISM: Homo sapiens

<400> SEQUENCE: 177

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30
```

```
Val Pro Ala Glu Ala Met Gly Gln Leu Gly Ser Arg Ala Gln Leu Arg
             35                  40                  45

Thr Gln Pro Glu Ala Leu Gly Ser Leu Thr Ala Ala Gly Ser Leu Gln
 50                  55                  60

Val Leu Ser Leu Thr Pro Gly Ser Arg Gly Gly Gly Arg Cys Cys Leu
 65                  70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
            195                 200                 205

Cys Arg Gly Ile Leu Phe Val Leu Ser Ser Leu Gly Trp Ile Tyr Ile
            210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
            290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
```

```
              450             455             460
Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880
```

```
Glu Ala Leu Trp Arg Tyr Leu Thr Ala Arg His Asp Trp Leu Asn Ile
            885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
        930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
            965                 970                 975

Val Gln Asn Tyr Lys Thr Lys Glu Gly Trp Asp Phe His Ser Gln Phe
            980                 985                 990

Ile Leu Tyr Cys Leu Glu His Ser  Leu Gln His Leu Leu  Tyr Val Tyr
            995                 1000                1005

Leu Asp Cys Tyr Lys Leu Ser  Pro Glu Asn Cys Pro  Phe Leu Glu
    1010                1015                1020

Lys Lys Glu Leu His Glu Ala  His Pro Trp Phe Glu  Phe Leu Val
    1025                1030                1035

Gln Cys Arg Gln Val Ala Ser  Asn Leu Thr Asp Pro  Lys Leu Ile
    1040                1045                1050

Phe Gln Ala Ser Leu Ala Asn  Ala Gln Ile Leu Ile  Pro Thr Asn
    1055                1060                1065

Gln Ala Ser Val Ser Ser Met  Leu Leu Glu Gly His  Thr Leu Leu
    1070                1075                1080

Ala Leu Ala Thr Thr Met Tyr  Ser Pro Gly Gly Val  Ser Gln Val
    1085                1090                1095

Val Gln Asn Glu Glu Asn Glu  Asn Cys Leu Lys Lys  Val Asp Pro
    1100                1105                1110

Gln Leu Leu Lys Met Ala Leu  Thr Pro Tyr Pro Lys  Leu Lys Thr
    1115                1120                1125

Ala Leu Phe Pro Gln Cys Thr  Pro Pro Ser Val Leu  Pro Ser Asp
    1130                1135                1140

Ile Thr Ile Tyr His Leu Ile  Gln Ser Leu Ser Pro  Phe Asp Pro
    1145                1150                1155

Ser Arg Leu Phe Gly Trp Gln  Ser Ala Asn Thr Leu  Ala Ile Gly
    1160                1165                1170

Asp Ala Trp Ser His Leu Pro  His Phe Ser Ser Pro  Asp Leu Val
    1175                1180                1185

Asn Lys Tyr Ala Ile Val Glu  Arg Leu Asn Phe Ala  Tyr Tyr Leu
    1190                1195                1200

His Asn Gly Arg Pro Ser Phe  Ala Phe Gly Thr Phe  Leu Val Gln
    1205                1210                1215

Glu Leu Ile Lys Ser Lys Thr  Pro Lys Gln Leu Ile  Gln Gln Val
    1220                1225                1230

Gly Asn Glu Ala Tyr Val Ile  Gly Leu Ser Ser Phe  His Ile Pro
    1235                1240                1245

Ser Ile Gly Ala Ala Cys Val  Cys Phe Leu Glu Leu  Leu Gly Leu
    1250                1255                1260

Asp Ser Leu Lys Leu Arg Val  Asp Met Lys Val Ala  Asn Ile Ile
    1265                1270                1275
```

```
Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Arg Asp Asp Arg Phe Ile
    1430                1435                1440

<210> SEQ ID NO 178
<211> LENGTH: 1823
<212> TYPE: PRT
<213> ORGANISM: Homo sapiens

<400> SEQUENCE: 178

Met Ala Ala Glu Glu Gly Val Ala Ser Ala Ser Ala Gly Gly Ser
1               5                   10                  15

Trp Gly Thr Ala Ala Met Gly Arg Val Leu Pro Met Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
            195                 200                 205
```

-continued

```
Cys Arg Gly Ile Leu Phe Val Leu Ser Ser Leu Gly Trp Ile Tyr Ile
        210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Gln Ile Lys Glu
610                 615                 620
```

-continued

```
Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
            645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
835                 840                 845

Ile Val Leu Asn Trp Ala Leu Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Thr Val Asp Val Ile Asn Gln Asn
            915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Gly Trp Phe Ser Gln Phe
            980                 985                 990

Ile Leu Tyr Cys Leu Glu His Ser Leu Gln His Leu Leu Tyr Val Tyr
            995                 1000                1005

Leu Asp Cys Tyr Lys Leu Ser Pro Glu Asn Cys Pro Phe Leu Glu
     1010                1015                1020

Lys Lys Glu Leu His Glu Ala His Pro Trp Phe Glu Phe Leu Val
     1025                1030                1035

Gln Cys Arg Gln Val Ala Ser Asn Leu Thr Asp Pro Lys Leu Ile
```

-continued

```
            1040                1045                1050
Phe Gln Ala Ser Leu Ala Asn Ala Gln Ile Leu Ile Pro Thr Asn
            1055                1060                1065
Gln Ala Ser Val Ser Ser Met Leu Leu Glu Gly His Thr Leu Leu
            1070                1075                1080
Ala Leu Ala Thr Thr Met Tyr Ser Pro Gly Gly Val Ser Gln Val
            1085                1090                1095
Val Gln Asn Glu Glu Asn Glu Asn Cys Leu Lys Lys Val Asp Pro
            1100                1105                1110
Gln Leu Leu Lys Met Ala Leu Thr Pro Tyr Pro Lys Leu Lys Thr
            1115                1120                1125
Ala Leu Phe Pro Gln Cys Thr Pro Pro Ser Val Leu Pro Ser Asp
            1130                1135                1140
Ile Thr Ile Tyr His Leu Ile Gln Ser Leu Ser Pro Phe Asp Pro
            1145                1150                1155
Ser Arg Leu Phe Gly Trp Gln Ser Ala Asn Thr Leu Ala Ile Gly
            1160                1165                1170
Asp Ala Trp Ser His Leu Pro His Phe Ser Ser Pro Asp Leu Val
            1175                1180                1185
Asn Lys Tyr Ala Ile Val Glu Arg Leu Asn Phe Ala Tyr Tyr Leu
            1190                1195                1200
His Asn Gly Arg Pro Ser Phe Ala Phe Gly Thr Phe Leu Val Gln
            1205                1210                1215
Glu Leu Ile Lys Ser Lys Thr Pro Lys Gln Leu Ile Gln Gln Val
            1220                1225                1230
Gly Asn Glu Ala Tyr Val Ile Gly Leu Ser Ser Phe His Ile Pro
            1235                1240                1245
Ser Ile Gly Ala Ala Cys Val Cys Phe Leu Glu Leu Leu Gly Leu
            1250                1255                1260
Asp Ser Leu Lys Leu Arg Val Asp Met Lys Val Ala Asn Ile Ile
            1265                1270                1275
Leu Ser Tyr Lys Cys Arg Asn Glu Asp Ala Gln Tyr Ser Phe Ile
            1280                1285                1290
Arg Glu Ser Val Ala Glu Lys Leu Ser Lys Leu Ala Asp Gly Glu
            1295                1300                1305
Lys Thr Thr Thr Glu Glu Leu Leu Val Leu Leu Glu Glu Gly Thr
            1310                1315                1320
Trp Asn Ser Ile Gln Gln Glu Ile Lys Arg Leu Ser Ser Glu
            1325                1330                1335
Ser Ser Ser Gln Trp Ala Leu Val Val Gln Phe Cys Arg Leu His
            1340                1345                1350
Asn Met Lys Leu Ser Ile Ser Tyr Leu Arg Glu Cys Ala Lys Ala
            1355                1360                1365
Asn Asp Trp Leu Gln Phe Ile Ile His Ser Gln Leu His Asn Tyr
            1370                1375                1380
His Pro Ala Glu Val Lys Ser Leu Ile Gln Tyr Phe Ser Pro Val
            1385                1390                1395
Ile Gln Asp His Leu Arg Leu Ala Phe Glu Asn Leu Pro Ser Val
            1400                1405                1410
Pro Thr Ser Lys Met Asp Ser Asp Gln Val Cys Asn Lys Cys Pro
            1415                1420                1425
Gln Glu Leu Gln Gly Ser Lys Gln Glu Met Thr Asp Leu Phe Glu
            1430                1435                1440
```

Ile Leu Leu Gln Cys Ser Glu Glu Pro Asp Ser Trp His Trp Leu
1445                1450                1455

Leu Val Glu Ala Val Lys Gln Gln Ala Pro Ile Leu Ser Val Leu
1460                1465                1470

Ala Ser Cys Leu Gln Gly Ala Ser Ala Ile Ser Cys Leu Cys Val
1475                1480                1485

Trp Ile Ile Thr Ser Val Glu Asp Asn Val Ala Thr Glu Ala Met
1490                1495                1500

Gly His Ile Gln Asp Ser Thr Glu Asp His Thr Trp Asn Leu Glu
1505                1510                1515

Asp Leu Ser Val Ile Trp Arg Thr Leu Leu Thr Arg Gln Lys Ser
1520                1525                1530

Lys Thr Leu Ile Arg Gly Phe Gln Leu Phe Phe Lys Asp Ser Pro
1535                1540                1545

Leu Leu Leu Val Met Glu Met Tyr Glu Leu Cys Met Phe Phe Arg
1550                1555                1560

Asn Tyr Lys Glu Ala Glu Ala Lys Leu Leu Glu Phe Gln Lys Ser
1565                1570                1575

Leu Glu Thr Leu Asn Thr Ala Ala Thr Lys Val His Pro Val Ile
1580                1585                1590

Pro Ala Met Trp Leu Glu Asp Gln Val Cys Phe Leu Leu Lys Leu
1595                1600                1605

Met Leu Gln Gln Cys Lys Thr Gln Tyr Glu Leu Gly Lys Leu Leu
1610                1615                1620

Gln Leu Phe Val Glu Arg Glu His Leu Phe Ser Asp Gly Pro Asp
1625                1630                1635

Val Lys Lys Leu Cys Ile Leu Cys Gln Ile Leu Lys Asp Thr Ser
1640                1645                1650

Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770

Leu Leu Leu Thr Leu Ala Gly His Trp Leu Ala Gln Glu Asp Val
1775                1780                1785

Val Pro Leu Asp Lys Leu Glu Glu Leu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser
1820

<210> SEQ ID NO 179
<211> LENGTH: 1856
<212> TYPE: PRT
<213> ORGANISM: Homo sapiens

<400> SEQUENCE: 179

```
Met Ala Glu Glu Gly Val Ala Ser Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380
```

```
Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Glu Pro Ile Glu Leu Lys Cys Val Ser Val
        420                 425                 430

Thr Gly Phe Thr Ala Leu Phe Thr Trp Glu Val Glu Arg Met Gly Tyr
    435                 440                 445

Thr Ile Thr Leu Trp Asp Leu Glu Thr Gln Gly Met Gln Cys Ser Ser
450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800
```

```
Leu Gly His Phe Gln Glu Asn Met Gln Ile Gln Ser Phe Pro Arg Tyr
                805                 810                 815

Trp Ile Lys Glu Gln Asp Phe Lys His Lys Ser Val Leu Asp Ser
        820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
            885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
                980                 985                 990

Ile Leu Tyr Cys Leu Glu His Ser  Leu Gln His Leu Leu  Tyr Val Tyr
                995                1000                  1005

Leu Asp  Cys Tyr Lys Leu Ser  Pro Glu Asn Cys Pro  Phe Leu Glu
    1010                1015                1020

Lys Lys  Glu Leu His Glu Ala  His Pro Trp Phe Glu  Phe Leu Val
    1025                1030                1035

Gln Cys  Arg Gln Val Ala Ser  Asn Leu Thr Asp Pro  Lys Leu Ile
    1040                1045                1050

Phe Gln  Ala Ser Leu Ala Asn  Ala Gln Ile Leu Ile  Pro Thr Asn
    1055                1060                1065

Gln Ala  Ser Val Ser Ser Met  Leu Leu Glu Gly His  Thr Leu Leu
    1070                1075                1080

Ala Leu  Ala Thr Thr Met Tyr  Ser Pro Gly Gly Val  Ser Gln Val
    1085                1090                1095

Val Gln  Asn Glu Glu Asn Glu  Asn Cys Leu Lys Lys  Val Asp Pro
    1100                1105                1110

Gln Leu  Leu Lys Met Ala Leu  Thr Pro Tyr Pro Lys  Leu Lys Thr
    1115                1120                1125

Ala Leu  Phe Pro Gln Cys Thr  Pro Pro Ser Val Leu  Pro Ser Asp
    1130                1135                1140

Ile Thr  Ile Tyr His Leu Ile  Gln Ser Leu Ser Pro  Phe Asp Pro
    1145                1150                1155

Ser Arg  Leu Phe Gly Trp Gln  Ser Ala Asn Thr Leu  Ala Ile Gly
    1160                1165                1170

Asp Ala  Trp Ser His Leu Pro  His Phe Ser Ser Pro  Asp Leu Val
    1175                1180                1185

Asn Lys  Tyr Ala Ile Val Glu  Arg Leu Asn Phe Ala  Tyr Tyr Leu
    1190                1195                1200

His Asn  Gly Arg Pro Ser Phe  Ala Phe Gly Thr Phe  Leu Val Gln
```

-continued

```
            1205                1210                 1215

Glu Leu Ile Lys Ser Lys Thr Pro Lys Gln Leu Ile Gln Gln Val
            1220                1225                 1230

Gly Asn Glu Ala Tyr Val Ile Gly Leu Ser Ser Phe His Ile Pro
            1235                1240                 1245

Ser Ile Gly Ala Ala Cys Val Cys Phe Leu Glu Leu Leu Gly Leu
            1250                1255                 1260

Asp Ser Leu Lys Leu Arg Val Asp Met Lys Val Ala Asn Ile Ile
            1265                1270                 1275

Leu Ser Tyr Lys Cys Arg Asn Glu Asp Ala Gln Tyr Ser Phe Ile
            1280                1285                 1290

Arg Glu Ser Val Ala Glu Lys Leu Ser Lys Leu Ala Asp Gly Glu
            1295                1300                 1305

Lys Thr Thr Thr Glu Glu Leu Leu Val Leu Leu Glu Glu Gly Thr
            1310                1315                 1320

Trp Asn Ser Ile Gln Gln Gln Glu Ile Lys Arg Leu Ser Ser Glu
            1325                1330                 1335

Ser Ser Ser Gln Trp Ala Leu Val Val Gln Phe Cys Arg Leu His
            1340                1345                 1350

Asn Met Lys Leu Ser Ile Ser Tyr Leu Arg Glu Cys Ala Lys Ala
            1355                1360                 1365

Asn Asp Trp Leu Gln Phe Ile Ile His Ser Gln Leu His Asn Tyr
            1370                1375                 1380

His Pro Ala Glu Val Lys Ser Leu Ile Gln Tyr Phe Ser Pro Val
            1385                1390                 1395

Ile Gln Asp His Leu Arg Leu Ala Phe Glu Asn Leu Pro Ser Val
            1400                1405                 1410

Pro Thr Ser Lys Met Asp Ser Asp Gln Val Cys Asn Lys Cys Pro
            1415                1420                 1425

Gln Glu Leu Gln Gly Ser Lys Gln Glu Met Thr Asp Leu Phe Glu
            1430                1435                 1440

Ile Leu Leu Gln Cys Ser Glu Glu Pro Asp Ser Trp His Trp Leu
            1445                1450                 1455

Leu Val Glu Ala Val Lys Gln Gln Ala Pro Ile Leu Ser Val Leu
            1460                1465                 1470

Ala Ser Cys Leu Gln Gly Ala Ser Ala Ile Ser Cys Leu Cys Val
            1475                1480                 1485

Trp Ile Ile Thr Ser Val Glu Asp Asn Val Ala Thr Glu Ala Met
            1490                1495                 1500

Gly His Ile Gln Asp Ser Thr Glu Asp His Thr Trp Asn Leu Glu
            1505                1510                 1515

Asp Leu Ser Val Ile Trp Arg Thr Leu Leu Thr Arg Gln Lys Ser
            1520                1525                 1530

Lys Thr Leu Ile Arg Gly Phe Gln Leu Phe Phe Lys Asp Ser Pro
            1535                1540                 1545

Leu Leu Leu Val Met Glu Met Tyr Glu Leu Cys Met Phe Phe Arg
            1550                1555                 1560

Asn Tyr Lys Glu Ala Glu Ala Lys Leu Leu Glu Phe Gln Lys Ser
            1565                1570                 1575

Leu Glu Thr Leu Asn Thr Ala Ala Thr Lys Val His Pro Val Ile
            1580                1585                 1590

Pro Ala Met Trp Leu Glu Asp Gln Val Cys Phe Leu Leu Lys Leu
            1595                1600                 1605
```

Met Leu Gln Gln Cys Lys Thr Gln Tyr Glu Leu Gly Lys Leu Leu
1610                1615                1620

Gln Leu Phe Val Glu Arg Glu His Leu Phe Ser Asp Gly Pro Asp
1625                1630                1635

Val Lys Lys Leu Cys Ile Leu Cys Gln Ile Leu Lys Asp Thr Ser
1640                1645                1650

Ile Ala Ile Asn His Thr Ile Ile Thr Ser Tyr Ser Ile Glu Asn
1655                1660                1665

Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770

Leu Leu Leu Thr Leu Ala Gly His Trp Leu Ala Gln Glu Asp Val
1775                1780                1785

Val Pro Leu Asp Lys Leu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830

Phe Asp Ser Leu Ala Ser Glu Phe Ser Phe Ser Val Gly Cys Ser
1835                1840                1845

Glu His Ile Lys Ile Leu Arg Thr
1850                1855

<210> SEQ ID NO 180
<211> LENGTH: 1949
<212> TYPE: PRT
<213> ORGANISM: Homo sapiens

<400> SEQUENCE: 180

Met Ala Glu Glu Gly Val Ala Ser Ala Ala Ser Ala Gly Gly Ser
1               5                   10                  15

Trp Gly Thr Ala Ala Met Gly Arg Val Leu Pro Met Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu

```
                100                 105                 110
Leu Leu Ile Tyr Glu Phe Asn Leu Lys Asp Gly Arg Cys Asp Ala Thr
            115                 120                 125
Ile Leu Tyr Ser Cys Ser Arg Glu Ala Leu Gln Lys Leu Ile Asp Asp
            130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
            165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
            195                 200                 205
Cys Arg Gly Ile Leu Phe Val Leu Ser Ser Leu Gly Trp Ile Tyr Ile
            210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Glu Pro Ala Lys Ile
                245                 250                 255
Ser Ser Phe Thr Ser Leu Lys Val Ser Gln Asp Leu Asp Val Ala Val
                260                 265                 270
Ile Val Ser Ser Asn Ser Ala Val Ala Leu Asn Leu Asn Leu Tyr
            275                 280                 285
Phe Arg Gln His Pro Gly His Leu Leu Cys Glu Arg Ile Leu Glu Asp
            290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
            370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
            435                 440                 445
Thr Ile Thr Leu Trp Asp Leu Glu Thr Gln Gly Met Gln Cys Ser Ser
            450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
            515                 520                 525
```

```
Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gly Leu Thr Gln Glu Ser
    850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940
```

```
Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
        995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
```

|     |     |     |     |     |     |     |     |     |     |
| --- | --- | --- | --- | --- | --- | --- | --- | --- | --- |
|     |     |     |     | 1340 |     |     | 1345 |     | 1350 |
| Asn | Met | Lys | Leu | Ser | Ile | Ser | Tyr | Leu | Arg | Glu | Cys | Ala | Lys | Ala |
| 1355 |     |     |     | 1360 |     |     | 1365 |     |     |
| Asn | Asp | Trp | Leu | Gln | Phe | Ile | Ile | His | Ser | Gln | Leu | His | Asn | Tyr |
| 1370 |     |     |     | 1375 |     |     | 1380 |     |     |
| His | Pro | Ala | Glu | Val | Lys | Ser | Leu | Ile | Gln | Tyr | Phe | Ser | Pro | Val |
| 1385 |     |     |     | 1390 |     |     | 1395 |     |     |
| Ile | Gln | Asp | His | Leu | Arg | Leu | Ala | Phe | Glu | Asn | Leu | Pro | Ser | Val |
| 1400 |     |     |     | 1405 |     |     | 1410 |     |     |
| Pro | Thr | Ser | Lys | Met | Asp | Ser | Asp | Gln | Val | Cys | Asn | Lys | Cys | Pro |
| 1415 |     |     |     | 1420 |     |     | 1425 |     |     |
| Gln | Glu | Leu | Gln | Gly | Ser | Lys | Gln | Glu | Met | Thr | Asp | Leu | Phe | Glu |
| 1430 |     |     |     | 1435 |     |     | 1440 |     |     |
| Ile | Leu | Leu | Gln | Cys | Ser | Glu | Glu | Pro | Asp | Ser | Trp | His | Trp | Leu |
| 1445 |     |     |     | 1450 |     |     | 1455 |     |     |
| Leu | Val | Glu | Ala | Val | Lys | Gln | Gln | Ala | Pro | Ile | Leu | Ser | Val | Leu |
| 1460 |     |     |     | 1465 |     |     | 1470 |     |     |
| Ala | Ser | Cys | Leu | Gln | Gly | Ala | Ser | Ala | Ile | Ser | Cys | Leu | Cys | Val |
| 1475 |     |     |     | 1480 |     |     | 1485 |     |     |
| Trp | Ile | Ile | Thr | Ser | Val | Glu | Asp | Asn | Val | Ala | Thr | Glu | Ala | Met |
| 1490 |     |     |     | 1495 |     |     | 1500 |     |     |
| Gly | His | Ile | Gln | Asp | Ser | Thr | Glu | Asp | His | Thr | Trp | Asn | Leu | Glu |
| 1505 |     |     |     | 1510 |     |     | 1515 |     |     |
| Asp | Leu | Ser | Val | Ile | Trp | Arg | Thr | Leu | Leu | Thr | Arg | Gln | Lys | Ser |
| 1520 |     |     |     | 1525 |     |     | 1530 |     |     |
| Lys | Thr | Leu | Ile | Arg | Gly | Phe | Gln | Leu | Phe | Phe | Lys | Asp | Ser | Pro |
| 1535 |     |     |     | 1540 |     |     | 1545 |     |     |
| Leu | Leu | Leu | Val | Met | Glu | Met | Tyr | Glu | Leu | Cys | Met | Phe | Phe | Arg |
| 1550 |     |     |     | 1555 |     |     | 1560 |     |     |
| Asn | Tyr | Lys | Glu | Ala | Glu | Ala | Lys | Leu | Leu | Glu | Phe | Gln | Lys | Ser |
| 1565 |     |     |     | 1570 |     |     | 1575 |     |     |
| Leu | Glu | Thr | Leu | Asn | Thr | Ala | Ala | Thr | Lys | Val | His | Pro | Val | Ile |
| 1580 |     |     |     | 1585 |     |     | 1590 |     |     |
| Pro | Ala | Met | Trp | Leu | Glu | Asp | Gln | Val | Cys | Phe | Leu | Leu | Lys | Leu |
| 1595 |     |     |     | 1600 |     |     | 1605 |     |     |
| Met | Leu | Gln | Gln | Cys | Lys | Thr | Gln | Tyr | Glu | Leu | Gly | Lys | Leu | Leu |
| 1610 |     |     |     | 1615 |     |     | 1620 |     |     |
| Gln | Leu | Phe | Val | Glu | Arg | Glu | His | Leu | Phe | Ser | Asp | Gly | Pro | Asp |
| 1625 |     |     |     | 1630 |     |     | 1635 |     |     |
| Val | Lys | Lys | Leu | Cys | Ile | Leu | Cys | Gln | Ile | Leu | Lys | Asp | Thr | Ser |
| 1640 |     |     |     | 1645 |     |     | 1650 |     |     |
| Ile | Ala | Ile | Asn | His | Thr | Ile | Ile | Thr | Ser | Tyr | Ser | Ile | Glu | Asn |
| 1655 |     |     |     | 1660 |     |     | 1665 |     |     |
| Leu | Gln | His | Glu | Cys | Arg | Ser | Ile | Leu | Glu | Arg | Leu | Gln | Thr | Asp |
| 1670 |     |     |     | 1675 |     |     | 1680 |     |     |
| Gly | Gln | Phe | Ala | Leu | Ala | Arg | Arg | Val | Ala | Glu | Leu | Ala | Glu | Leu |
| 1685 |     |     |     | 1690 |     |     | 1695 |     |     |
| Pro | Val | Asp | Asn | Leu | Val | Ile | Lys | Glu | Ile | Thr | Gln | Glu | Met | Gln |
| 1700 |     |     |     | 1705 |     |     | 1710 |     |     |
| Thr | Leu | Lys | His | Ile | Glu | Gln | Trp | Ser | Leu | Lys | Gln | Ala | Arg | Ile |
| 1715 |     |     |     | 1720 |     |     | 1725 |     |     |
| Asp | Phe | Trp | Lys | Lys | Cys | His | Glu | Asn | Phe | Lys | Lys | Asn | Ser | Ile |
| 1730 |     |     |     | 1735 |     |     | 1740 |     |     |

-continued

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
    1790            1795                1800

Cys Arg Ile Thr Gln His Thr Leu Gly Arg Asn Gln Glu Glu Thr
    1805            1810                1815

Glu Pro Arg Phe Ser Arg Gln Ile Ser Thr Ser Gly Glu Leu Ser
    1820            1825                1830

Phe Asp Ser Leu Ala Ser Glu Phe Ser Phe Ser Lys Leu Ala Ala
    1835            1840                1845

Leu Asn Thr Ser Lys Tyr Leu Glu Leu Asn Ser Leu Pro Ser Lys
    1850            1855                1860

Glu Thr Cys Glu Asn Arg Leu Asp Trp Lys Glu Gln Glu Ser Leu
    1865            1870                1875

Asn Phe Leu Ile Gly Arg Leu Leu Asp Asp Gly Cys Val His Glu
    1880            1885                1890

Ala Ser Arg Val Cys Arg Tyr Phe His Phe Tyr Asn Pro Asp Val
    1895            1900                1905

Ala Leu Val Leu His Cys Arg Ala Leu Ala Ser Gly Glu Ala Arg
    1910            1915                1920

Trp Arg Ile Cys Thr Gln Arg Ser Met Leu Ser Tyr Lys Val Leu
    1925            1930                1935

Ser Cys Leu Arg Lys Lys His Pro Thr Phe Pro
    1940            1945

<210> SEQ ID NO 181
<211> LENGTH: 1956
<212> TYPE: PRT
<213> ORGANISM: Homo sapiens

<400> SEQUENCE: 181

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His

```
            145                 150                 155                 160
        Asn Asn Thr Ser Leu Leu Phe Ile Asn Lys Cys Val Ile Leu His Ile
                        165                 170                 175

Ile Phe Pro Glu Arg Asp Ala Ala Ile Arg Val Leu Asn Cys Phe Thr
                        180                 185                 190

Leu Pro Leu Pro Ala Gln Ala Val Asp Met Ile Ile Asp Thr Gln Leu
                        195                 200                 205

Cys Arg Gly Ile Leu Phe Val Leu Ser Ser Leu Gly Trp Ile Tyr Ile
                        210                 215                 220

Phe Asp Val Val Asp Gly Thr Tyr Val Ala His Val Asp Leu Ala Leu
        225                 230                 235                 240

His Lys Glu Asp Met Cys Asn Glu Gln Gln Glu Pro Ala Lys Ile
                        245                 250                 255

Ser Ser Phe Thr Ser Leu Lys Val Ser Gln Asp Leu Val Ala Val
                        260                 265                 270

Ile Val Ser Ser Ser Asn Ser Ala Val Ala Leu Asn Leu Asn Leu Tyr
                        275                 280                 285

Phe Arg Gln His Pro Gly His Leu Leu Cys Glu Arg Ile Leu Glu Asp
            290                 295                 300

Leu Pro Ile Gln Gly Pro Lys Gly Val Asp Glu Asp Pro Val Asn
        305                 310                 315                 320

Ser Ala Tyr Asn Met Lys Leu Ala Lys Phe Ser Phe Gln Ile Asp Arg
                        325                 330                 335

Ser Trp Lys Ala Gln Leu Ser Ser Leu Asn Glu Thr Ile Lys Asn Ser
                        340                 345                 350

Lys Leu Glu Val Ser Cys Cys Ala Pro Trp Phe Gln Asp Ile Leu His
                        355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
        385                 390                 395                 400

Lys Asp His Ala Lys Thr Ser Asp Pro Gly Arg Ser Trp Lys Ile Met
                        405                 410                 415

His Ile Ser Glu Gln Glu Pro Ile Glu Leu Lys Cys Val Ser Val
                        420                 425                 430

Thr Gly Phe Thr Ala Leu Phe Thr Trp Glu Val Glu Arg Met Gly Tyr
                        435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Leu
        465                 470                 475                 480

Cys Phe Val Leu Thr Glu Asn Gly Leu Ser Leu Ile Leu Phe Gly Leu
                        485                 490                 495

Thr Gln Glu Glu Phe Leu Asn Arg Leu Met Ile His Gly Ser Ala Ser
                        500                 505                 510

Thr Val Asp Thr Leu Cys His Leu Asn Gly Trp Gly Arg Cys Ser Ile
                        515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
        545                 550                 555                 560

Lys Ser Ser Val Ser Asp Gln Phe Asp His Leu Ser Ser His Leu Tyr
                        565                 570                 575
```

```
Leu Arg Asn Val Glu Leu Ile Pro Ala Leu Asp Leu Cys Ser
        580             585             590

Ala Ile Arg Glu Ser Tyr Ser Glu Pro Gln Ser Lys His Phe Ser Glu
        595             600             605

Gln Leu Leu Asn Leu Thr Leu Ser Phe Leu Asn Gln Ile Lys Glu
    610             615             620

Leu Phe Ile His Thr Glu Leu Asp Glu His Leu Gln Lys Gly Val
625             630             635             640

Asn Ile Leu Thr Ser Tyr Ile Asn Glu Leu Arg Thr Phe Met Ile Lys
            645             650             655

Phe Pro Trp Lys Leu Thr Asp Ala Ile Asp Gly Tyr Asp Val His Glu
        660             665             670

Asn Val Pro Lys Val Lys Glu Ser Asn Ile Trp Lys Lys Leu Ser Phe
        675             680             685

Glu Glu Val Ile Ala Ser Ala Ile Leu Asn Asn Lys Ile Pro Glu Ala
        690             695             700

Gln Thr Phe Phe Arg Ile Asp Ser His Ser Ala Gln Lys Leu Glu Glu
705             710             715             720

Leu Ile Gly Ile Gly Leu Asn Leu Val Phe Asp Asn Leu Lys Lys Asn
            725             730             735

Asn Ile Lys Glu Ala Ser Glu Leu Leu Lys Asn Met Gly Phe Asp Val
        740             745             750

Lys Gly Gln Leu Leu Lys Ile Cys Phe Tyr Thr Thr Asn Lys Asn Ile
        755             760             765

Arg Asp Phe Leu Val Glu Ile Leu Lys Glu Lys Asn Tyr Phe Ser Glu
        770             775             780

Lys Glu Lys Arg Thr Ile Asp Phe Val His Gln Val Glu Lys Leu Tyr
785             790             795             800

Leu Gly His Phe Gln Glu Asn Met Gln Ile Gln Ser Phe Pro Arg Tyr
            805             810             815

Trp Ile Lys Glu Gln Asp Phe Phe Lys His Lys Ser Val Leu Asp Ser
        820             825             830

Phe Leu Lys Tyr Asp Cys Lys Asp Glu Phe Asn Lys Gln Asp His Arg
        835             840             845

Ile Val Leu Asn Trp Ala Leu Trp Trp Asp Gln Leu Thr Gln Glu Ser
850             855             860

Ile Leu Leu Pro Arg Ile Ser Pro Glu Glu Tyr Lys Ser Tyr Ser Pro
865             870             875             880

Glu Ala Leu Trp Arg Tyr Leu Thr Ala Arg His Asp Trp Leu Asn Ile
            885             890             895

Ile Leu Trp Ile Gly Glu Phe Gln Thr Gln His Ser Tyr Ala Ser Leu
            900             905             910

Gln Gln Asn Lys Trp Pro Leu Leu Thr Val Asp Val Ile Asn Gln Asn
        915             920             925

Thr Ser Cys Asn Asn Tyr Met Arg Asn Glu Ile Leu Asp Lys Leu Ala
        930             935             940

Arg Asn Gly Val Phe Leu Ala Ser Glu Leu Glu Asp Phe Glu Cys Phe
945             950             955             960

Leu Leu Arg Leu Ser Arg Ile Gly Gly Val Ile Gln Asp Thr Leu Pro
            965             970             975

Val Gln Asn Tyr Lys Thr Lys Glu Gly Trp Asp Phe His Ser Gln Phe
        980             985             990
```

```
Ile Leu Tyr Cys Leu Glu His Ser Leu Gln His Leu Leu Tyr Val Tyr
        995                 1000                1005

Leu Asp Cys Tyr Lys Leu Ser Pro Glu Asn Cys Pro Phe Leu Glu
    1010                1015                1020

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
```

-continued

```
                1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785
```

-continued

```
Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr
    1955

<210> SEQ ID NO 182
<211> LENGTH: 1999
<212> TYPE: PRT
<213> ORGANISM: Homo sapiens

<400> SEQUENCE: 182

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
        35                  40                  45

Thr Gln Pro Glu Ala Leu Gly Ser Leu Thr Ala Ala Gly Ser Leu Gln
    50                  55                  60

Val Leu Ser Leu Thr Pro Gly Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
```

```
            180                 185                 190
Leu Pro Leu Pro Ala Gln Ala Val Asp Met Ile Ile Asp Thr Gln Leu
            195                 200                 205
Cys Arg Gly Ile Leu Phe Val Leu Ser Ser Leu Gly Trp Ile Tyr Ile
            210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Glu Pro Ala Lys Ile
            245                 250                 255
Ser Ser Phe Thr Ser Leu Lys Val Ser Gln Asp Leu Asp Val Ala Val
            260                 265                 270
Ile Val Ser Ser Ser Asn Ser Ala Val Ala Leu Asn Leu Asn Leu Tyr
            275                 280                 285
Phe Arg Gln His Pro Gly His Leu Leu Cys Glu Arg Ile Leu Glu Asp
            290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
            325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
            370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
            405                 410                 415
His Ile Ser Glu Gln Glu Glu Pro Ile Glu Leu Lys Cys Val Ser Val
            420                 425                 430
Thr Gly Phe Thr Ala Leu Phe Thr Trp Glu Val Glu Arg Met Gly Tyr
            435                 440                 445
Thr Ile Thr Leu Trp Asp Leu Glu Thr Gln Gly Met Gln Cys Ser Ser
            450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
            485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
            515                 520                 525
Pro Ile His Ala Leu Glu Ala Gly Ile Glu Asn Arg Gln Leu Asp Thr
            530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
            565                 570                 575
Leu Arg Asn Val Glu Glu Leu Ile Pro Ala Leu Asp Leu Leu Cys Ser
            580                 585                 590
Ala Ile Arg Glu Ser Tyr Ser Glu Pro Gln Ser Lys His Phe Ser Glu
            595                 600                 605
```

```
Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
    850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser Leu Gln His Leu Leu Tyr Val Tyr
        995                 1000                1005

Leu Asp Cys Tyr Lys Leu Ser Pro Glu Asn Cys Pro Phe Leu Glu
    1010                1015                1020
```

-continued

Lys Lys Glu Leu His Glu Ala His Pro Trp Phe Glu Phe Leu Val
    1025                1030                1035

Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro

-continued

```
            1415                1420                1425
Gln Glu Leu Gln Gly Ser Lys Gln Glu Met Thr Asp Leu Phe Glu
            1430                1435                1440
Ile Leu Leu Gln Cys Ser Glu Glu Pro Asp Ser Trp His Trp Leu
            1445                1450                1455
Leu Val Glu Ala Val Lys Gln Gln Ala Pro Ile Leu Ser Val Leu
            1460                1465                1470
Ala Ser Cys Leu Gln Gly Ala Ser Ala Ile Ser Cys Leu Cys Val
            1475                1480                1485
Trp Ile Ile Thr Ser Val Glu Asp Asn Val Ala Thr Glu Ala Met
            1490                1495                1500
Gly His Ile Gln Asp Ser Thr Glu Asp His Thr Trp Asn Leu Glu
            1505                1510                1515
Asp Leu Ser Val Ile Trp Arg Thr Leu Leu Thr Arg Gln Lys Ser
            1520                1525                1530
Lys Thr Leu Ile Arg Gly Phe Gln Leu Phe Phe Lys Asp Ser Pro
            1535                1540                1545
Leu Leu Leu Val Met Glu Met Tyr Glu Leu Cys Met Phe Phe Arg
            1550                1555                1560
Asn Tyr Lys Glu Ala Glu Ala Lys Leu Leu Glu Phe Gln Lys Ser
            1565                1570                1575
Leu Glu Thr Leu Asn Thr Ala Ala Thr Lys Val His Pro Val Ile
            1580                1585                1590
Pro Ala Met Trp Leu Glu Asp Gln Val Cys Phe Leu Leu Lys Leu
            1595                1600                1605
Met Leu Gln Gln Cys Lys Thr Gln Tyr Glu Leu Gly Lys Leu Leu
            1610                1615                1620
Gln Leu Phe Val Glu Arg Glu His Leu Phe Ser Asp Gly Pro Asp
            1625                1630                1635
Val Lys Lys Leu Cys Ile Leu Cys Gln Ile Leu Lys Asp Thr Ser
            1640                1645                1650
Ile Ala Ile Asn His Thr Ile Ile Thr Ser Tyr Ser Ile Glu Asn
            1655                1660                1665
Leu Gln His Glu Cys Arg Ser Ile Leu Glu Arg Leu Gln Thr Asp
            1670                1675                1680
Gly Gln Phe Ala Leu Ala Arg Arg Val Ala Glu Leu Ala Glu Leu
            1685                1690                1695
Pro Val Asp Asn Leu Val Ile Lys Glu Ile Thr Gln Glu Met Gln
            1700                1705                1710
Thr Leu Lys His Ile Glu Gln Trp Ser Leu Lys Gln Ala Arg Ile
            1715                1720                1725
Asp Phe Trp Lys Lys Cys His Glu Asn Phe Lys Lys Asn Ser Ile
            1730                1735                1740
Ser Ser Lys Ala Ala Ser Ser Phe Phe Ser Thr Gln Ala His Val
            1745                1750                1755
Ala Cys Glu His Pro Thr Gly Trp Ser Ser Met Glu Glu Arg His
            1760                1765                1770
Leu Leu Leu Thr Leu Ala Gly His Trp Leu Ala Gln Glu Asp Val
            1775                1780                1785
Val Pro Leu Asp Lys Leu Glu Glu Leu Glu Lys Gln Ile Trp Leu
            1790                1795                1800
Cys Arg Ile Thr Gln His Thr Leu Gly Arg Asn Gln Glu Glu Thr
            1805                1810                1815
```

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Ser Leu Ser
    1985                1990                1995

Val

<210> SEQ ID NO 183
<211> LENGTH: 1998
<212> TYPE: PRT
<213> ORGANISM: Homo sapiens

<400> SEQUENCE: 183

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

-continued

```
Ile Phe Pro Glu Arg Asp Ala Ala Ile Arg Val Leu Asn Cys Phe Thr
                180                 185                 190
Leu Pro Leu Pro Ala Gln Ala Val Asp Met Ile Ile Asp Thr Gln Leu
            195                 200                 205
Cys Arg Gly Ile Leu Phe Val Leu Ser Ser Leu Gly Trp Ile Tyr Ile
210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Pro Ala Lys Ile
                245                 250                 255
Ser Ser Phe Thr Ser Leu Lys Val Ser Gln Asp Leu Val Ala Val
            260                 265                 270
Ile Val Ser Ser Asn Ser Ala Val Ala Leu Asn Leu Asn Leu Tyr
            275                 280                 285
Phe Arg Gln His Pro Gly His Leu Leu Cys Glu Arg Ile Leu Glu Asp
    290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
            355                 360                 365
Leu Glu Ser Pro Glu Ser Gly Asn His Ser Thr Ser Val Gln Ser Trp
    370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Pro Ile Glu Leu Lys Cys Val Ser Val
            420                 425                 430
Thr Gly Phe Thr Ala Leu Phe Thr Trp Glu Val Glu Arg Met Gly Tyr
            435                 440                 445
Thr Ile Thr Leu Trp Asp Leu Glu Thr Gln Gly Met Gln Cys Ser Ser
    450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
            515                 520                 525
Pro Ile His Ala Leu Glu Ala Gly Ile Glu Asn Arg Gln Leu Asp Thr
    530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
                565                 570                 575
Leu Arg Asn Val Glu Glu Leu Ile Pro Ala Leu Asp Leu Leu Cys Ser
            580                 585                 590
```

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
    610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
    690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
    770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
        915                 920                 925

Thr Ser Cys Asn Asn Tyr Met Arg Asn Glu Ile Leu Asp Lys Leu Ala
    930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser  Leu Gln His Leu Leu  Tyr Val Tyr
        995                 1000                1005

Leu Asp  Cys Tyr Lys Leu Ser  Pro Glu Asn Cys Pro  Phe Leu Glu

```
            1010                1015                1020
Lys Lys Glu Leu His Glu Ala His Pro Trp Phe Glu Phe Leu Val
        1025                1030                1035
Gln Cys Arg Gln Val Ala Ser Asn Leu Thr Asp Pro Lys Leu Ile
        1040                1045                1050
Phe Gln Ala Ser Leu Ala Asn Ala Gln Ile Leu Ile Pro Thr Asn
        1055                1060                1065
Gln Ala Ser Val Ser Ser Met Leu Leu Glu Gly His Thr Leu Leu
        1070                1075                1080
Ala Leu Ala Thr Thr Met Tyr Ser Pro Gly Gly Val Ser Gln Val
        1085                1090                1095
Val Gln Asn Glu Glu Asn Glu Asn Cys Leu Lys Lys Val Asp Pro
        1100                1105                1110
Gln Leu Leu Lys Met Ala Leu Thr Pro Tyr Pro Lys Leu Lys Thr
        1115                1120                1125
Ala Leu Phe Pro Gln Cys Thr Pro Pro Ser Val Leu Pro Ser Asp
        1130                1135                1140
Ile Thr Ile Tyr His Leu Ile Gln Ser Leu Ser Pro Phe Asp Pro
        1145                1150                1155
Ser Arg Leu Phe Gly Trp Gln Ser Ala Asn Thr Leu Ala Ile Gly
        1160                1165                1170
Asp Ala Trp Ser His Leu Pro His Phe Ser Pro Asp Leu Val
        1175                1180                1185
Asn Lys Tyr Ala Ile Val Glu Arg Leu Asn Phe Ala Tyr Tyr Leu
        1190                1195                1200
His Asn Gly Arg Pro Ser Phe Ala Phe Gly Thr Phe Leu Val Gln
        1205                1210                1215
Glu Leu Ile Lys Ser Lys Thr Pro Lys Gln Leu Ile Gln Gln Val
        1220                1225                1230
Gly Asn Glu Ala Tyr Val Ile Gly Leu Ser Ser Phe His Ile Pro
        1235                1240                1245
Ser Ile Gly Ala Ala Cys Val Cys Phe Leu Glu Leu Leu Gly Leu
        1250                1255                1260
Asp Ser Leu Lys Leu Arg Val Asp Met Lys Val Ala Asn Ile Ile
        1265                1270                1275
Leu Ser Tyr Lys Cys Arg Asn Glu Asp Ala Gln Tyr Ser Phe Ile
        1280                1285                1290
Arg Glu Ser Val Ala Glu Lys Leu Ser Lys Leu Ala Asp Gly Glu
        1295                1300                1305
Lys Thr Thr Thr Glu Glu Leu Leu Val Leu Leu Glu Glu Gly Thr
        1310                1315                1320
Trp Asn Ser Ile Gln Gln Gln Glu Ile Lys Arg Leu Ser Ser Glu
        1325                1330                1335
Ser Ser Ser Gln Trp Ala Leu Val Val Gln Phe Cys Arg Leu His
        1340                1345                1350
Asn Met Lys Leu Ser Ile Ser Tyr Leu Arg Glu Cys Ala Lys Ala
        1355                1360                1365
Asn Asp Trp Leu Gln Phe Ile Ile His Ser Gln Leu His Asn Tyr
        1370                1375                1380
His Pro Ala Glu Val Lys Ser Leu Ile Gln Tyr Phe Ser Pro Val
        1385                1390                1395
Ile Gln Asp His Leu Arg Leu Ala Phe Glu Asn Leu Pro Ser Val
        1400                1405                1410
```

```
Pro Thr Ser Lys Met Asp Ser Asp Gln Val Cys Asn Lys Cys Pro
    1415            1420                1425

Gln Glu Leu Gln Gly Ser Lys Gln Glu Met Thr Asp Leu Phe Glu
    1430            1435                1440

Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
    1460            1465                1470

Ala Ser Cys Leu Gln Gly Ala Ser Ala Ile Ser Cys Leu Cys Val
    1475            1480                1485

Trp Ile Ile Thr Ser Val Glu Asp Asn Val Ala Thr Glu Ala Met
    1490            1495                1500

Gly His Ile Gln Asp Ser Thr Glu Asp His Thr Trp Asn Leu Glu
    1505            1510                1515

Asp Leu Ser Val Ile Trp Arg Thr Leu Leu Thr Arg Gln Lys Ser
    1520            1525                1530

Lys Thr Leu Ile Arg Gly Phe Gln Leu Phe Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665

Leu Gln His Glu Cys Arg Ser Ile Leu Glu Arg Leu Gln Thr Asp
    1670            1675                1680

Gly Gln Phe Ala Leu Ala Arg Arg Val Ala Glu Leu Ala Glu Leu
    1685            1690                1695

Pro Val Asp Asn Leu Val Ile Lys Glu Ile Thr Gln Glu Met Gln
    1700            1705                1710

Thr Leu Lys His Ile Glu Gln Trp Ser Leu Lys Gln Ala Arg Ile
    1715            1720                1725

Asp Phe Trp Lys Lys Cys His Glu Asn Phe Lys Lys Asn Ser Ile
    1730            1735                1740

Ser Ser Lys Ala Ala Ser Ser Phe Phe Ser Thr Gln Ala His Val
    1745            1750                1755

Ala Cys Glu His Pro Thr Gly Trp Ser Ser Met Glu Glu Arg His
    1760            1765                1770

Leu Leu Leu Thr Leu Ala Gly His Trp Leu Ala Gln Glu Asp Val
    1775            1780                1785

Val Pro Leu Asp Lys Leu Glu Glu Leu Glu Lys Gln Ile Trp Leu
    1790            1795                1800
```

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Leu Ser Val
    1985                1990                1995

<210> SEQ ID NO 184
<211> LENGTH: 2055
<212> TYPE: PRT
<213> ORGANISM: Homo sapiens

<400> SEQUENCE: 184

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Gly Ser Leu Gln
    50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

-continued

```
Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
        195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Pro Ala Lys Ile
                245                 250                 255

Ser Ser Phe Thr Ser Leu Lys Val Ser Gln Asp Leu Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590
```

-continued

```
Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Gln Ile Lys Glu
610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
            805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe
945                 950                 955                 960

Leu Leu Arg Leu Ser Arg Ile Gly Gly Val Ile Gln Asp Thr Leu Pro
                965                 970                 975

Val Gln Asn Tyr Lys Thr Lys Glu Gly Trp Asp Phe His Ser Gln Phe
            980                 985                 990

Ile Leu Tyr Cys Leu Glu His Ser  Leu Gln His Leu Leu  Tyr Val Tyr
            995                  1000                 1005

Leu Asp  Cys Tyr Lys Leu Ser  Pro Glu Asn Cys Pro  Phe Leu Glu
```

-continued

```
                1010                1015                1020
Lys Lys Glu Leu His Glu Ala His Pro Trp Phe Glu Phe Leu Val
        1025                1030                1035
Gln Cys Arg Gln Val Ala Ser Asn Leu Thr Asp Pro Lys Leu Ile
        1040                1045                1050
Phe Gln Ala Ser Leu Ala Asn Ala Gln Ile Leu Ile Pro Thr Asn
        1055                1060                1065
Gln Ala Ser Val Ser Ser Met Leu Leu Glu Gly His Thr Leu Leu
        1070                1075                1080
Ala Leu Ala Thr Thr Met Tyr Ser Pro Gly Gly Val Ser Gln Val
        1085                1090                1095
Val Gln Asn Glu Glu Asn Glu Asn Cys Leu Lys Lys Val Asp Pro
        1100                1105                1110
Gln Leu Leu Lys Met Ala Leu Thr Pro Tyr Pro Lys Leu Lys Thr
        1115                1120                1125
Ala Leu Phe Pro Gln Cys Thr Pro Pro Ser Val Leu Pro Ser Asp
        1130                1135                1140
Ile Thr Ile Tyr His Leu Ile Gln Ser Leu Ser Pro Phe Asp Pro
        1145                1150                1155
Ser Arg Leu Phe Gly Trp Gln Ser Ala Asn Thr Leu Ala Ile Gly
        1160                1165                1170
Asp Ala Trp Ser His Leu Pro His Phe Ser Pro Asp Leu Val
        1175                1180                1185
Asn Lys Tyr Ala Ile Val Glu Arg Leu Asn Phe Ala Tyr Tyr Leu
        1190                1195                1200
His Asn Gly Arg Pro Ser Phe Ala Phe Gly Thr Phe Leu Val Gln
        1205                1210                1215
Glu Leu Ile Lys Ser Lys Thr Pro Lys Gln Leu Ile Gln Gln Val
        1220                1225                1230
Gly Asn Glu Ala Tyr Val Ile Gly Leu Ser Ser Phe His Ile Pro
        1235                1240                1245
Ser Ile Gly Ala Ala Cys Val Cys Phe Leu Glu Leu Leu Gly Leu
        1250                1255                1260
Asp Ser Leu Lys Leu Arg Val Asp Met Lys Val Ala Asn Ile Ile
        1265                1270                1275
Leu Ser Tyr Lys Cys Arg Asn Glu Asp Ala Gln Tyr Ser Phe Ile
        1280                1285                1290
Arg Glu Ser Val Ala Glu Lys Leu Ser Lys Leu Ala Asp Gly Glu
        1295                1300                1305
Lys Thr Thr Thr Glu Glu Leu Leu Val Leu Leu Glu Glu Gly Thr
        1310                1315                1320
Trp Asn Ser Ile Gln Gln Gln Glu Ile Lys Arg Leu Ser Ser Glu
        1325                1330                1335
Ser Ser Ser Gln Trp Ala Leu Val Val Gln Phe Cys Arg Leu His
        1340                1345                1350
Asn Met Lys Leu Ser Ile Ser Tyr Leu Arg Glu Cys Ala Lys Ala
        1355                1360                1365
Asn Asp Trp Leu Gln Phe Ile Ile His Ser Gln Leu His Asn Tyr
        1370                1375                1380
His Pro Ala Glu Val Lys Ser Leu Ile Gln Tyr Phe Ser Pro Val
        1385                1390                1395
Ile Gln Asp His Leu Arg Leu Ala Phe Glu Asn Leu Pro Ser Val
        1400                1405                1410
```

-continued

```
Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800
```

-continued

```
Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Met Ile
    1985                1990                1995

Leu Pro Arg Ser Trp Ala Val Pro Thr Gln Met Leu Leu Leu Arg
    2000                2005                2010

Met Val Lys Pro Cys Ser Gly Lys Ser Trp Pro Leu Ser Ser Leu
    2015                2020                2025

Thr Asp Ala Asn Glu Pro Arg Pro Ser Ser Ala His Arg Ala Leu
    2030                2035                2040

Ser Gln Ile Leu Trp Leu Asn Ser Trp Gln Lys Arg
    2045                2050                2055

<210> SEQ ID NO 185
<211> LENGTH: 2030
<212> TYPE: PRT
<213> ORGANISM: Homo sapiens

<400> SEQUENCE: 185

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60

Val Leu Ser Leu Thr Pro Gly Ser Arg Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
            100                 105                 110
```

```
Leu Leu Ile Tyr Glu Phe Asn Leu Lys Asp Gly Arg Cys Asp Ala Thr
            115                 120                 125
Ile Leu Tyr Ser Cys Ser Arg Glu Ala Leu Gln Lys Leu Ile Asp Asp
        130                 135                 140
Gln Asp Ile Ser Ile Ser Leu Leu Ser Leu Arg Ile Leu Ser Phe His
145                 150                 155                 160
Asn Asn Thr Ser Leu Leu Phe Ile Asn Lys Cys Val Ile Leu His Ile
                165                 170                 175
Ile Phe Pro Glu Arg Asp Ala Ala Ile Arg Val Leu Asn Cys Phe Thr
            180                 185                 190
Leu Pro Leu Pro Ala Gln Ala Val Asp Met Ile Ile Asp Thr Gln Leu
        195                 200                 205
Cys Arg Gly Ile Leu Phe Val Leu Ser Ser Leu Gly Trp Ile Tyr Ile
    210                 215                 220
Phe Asp Val Val Asp Gly Thr Tyr Val Ala His Val Asp Leu Ala Leu
225                 230                 235                 240
His Lys Glu Asp Met Cys Asn Glu Gln Gln Gln Glu Pro Ala Lys Ile
                245                 250                 255
Ser Ser Phe Thr Ser Leu Lys Val Ser Gln Asp Leu Asp Val Ala Val
            260                 265                 270
Ile Val Ser Ser Ser Asn Ser Ala Val Ala Leu Asn Leu Asn Leu Tyr
        275                 280                 285
Phe Arg Gln His Pro Gly His Leu Leu Cys Glu Arg Ile Leu Glu Asp
    290                 295                 300
Leu Pro Ile Gln Gly Pro Lys Gly Val Asp Glu Asp Pro Val Asn
305                 310                 315                 320
Ser Ala Tyr Asn Met Lys Leu Ala Lys Phe Ser Phe Gln Ile Asp Arg
                325                 330                 335
Ser Trp Lys Ala Gln Leu Ser Ser Leu Asn Glu Thr Ile Lys Asn Ser
            340                 345                 350
Lys Leu Glu Val Ser Cys Cys Ala Pro Trp Phe Gln Asp Ile Leu His
        355                 360                 365
Leu Glu Ser Pro Glu Ser Gly Asn His Ser Thr Ser Val Gln Ser Trp
    370                 375                 380
Ala Phe Ile Pro Gln Asp Ile Met His Gly Gln Tyr Asn Val Leu Gln
385                 390                 395                 400
Lys Asp His Ala Lys Thr Ser Asp Pro Gly Arg Ser Trp Lys Ile Met
                405                 410                 415
His Ile Ser Glu Gln Glu Pro Ile Glu Leu Lys Cys Val Ser Val
            420                 425                 430
Thr Gly Phe Thr Ala Leu Phe Thr Trp Glu Val Glu Arg Met Gly Tyr
        435                 440                 445
Thr Ile Thr Leu Trp Asp Leu Glu Thr Gln Gly Met Gln Cys Ser Ser
    450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
        515                 520                 525
```

-continued

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
        610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
            660                 665                 670

Asn Val Pro Lys Val Lys Glu Ser Asn Ile Trp Lys Lys Leu Ser Phe
        675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
            820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
            900                 905                 910

Gln Gln Asn Lys Trp Pro Leu Thr Val Asp Val Ile Asn Gln Asn
        915                 920                 925

Thr Ser Cys Asn Asn Tyr Met Arg Asn Glu Ile Leu Asp Lys Leu Ala
930                 935                 940

Arg Asn Gly Val Phe Leu Ala Ser Glu Leu Glu Asp Phe Glu Cys Phe

```
                945                 950                 955                 960
Leu Leu Arg Leu Ser Arg Ile Gly Gly Val Ile Gln Asp Thr Leu Pro
                    965                 970                 975
Val Gln Asn Tyr Lys Thr Lys Glu Gly Trp Asp Phe His Ser Gln Phe
                        980                 985                 990
Ile Leu Tyr Cys Leu Glu His Ser Leu Gln His Leu Leu Tyr Val Tyr
                    995                 1000                1005
Leu Asp Cys Tyr Lys Leu Ser Pro Glu Asn Cys Pro Phe Leu Glu
    1010                1015                1020
Lys Lys Glu Leu His Glu Ala His Pro Trp Phe Glu Phe Leu Val
    1025                1030                1035
Gln Cys Arg Gln Val Ala Ser Asn Leu Thr Asp Pro Lys Leu Ile
    1040                1045                1050
Phe Gln Ala Ser Leu Ala Asn Ala Gln Ile Leu Ile Pro Thr Asn
    1055                1060                1065
Gln Ala Ser Val Ser Ser Met Leu Leu Glu Gly His Thr Leu Leu
    1070                1075                1080
Ala Leu Ala Thr Thr Met Tyr Ser Pro Gly Gly Val Ser Gln Val
    1085                1090                1095
Val Gln Asn Glu Glu Asn Glu Asn Cys Leu Lys Lys Val Asp Pro
    1100                1105                1110
Gln Leu Leu Lys Met Ala Leu Thr Pro Tyr Pro Lys Leu Lys Thr
    1115                1120                1125
Ala Leu Phe Pro Gln Cys Thr Pro Pro Ser Val Leu Pro Ser Asp
    1130                1135                1140
Ile Thr Ile Tyr His Leu Ile Gln Ser Leu Ser Pro Phe Asp Pro
    1145                1150                1155
Ser Arg Leu Phe Gly Trp Gln Ser Ala Asn Thr Leu Ala Ile Gly
    1160                1165                1170
Asp Ala Trp Ser His Leu Pro His Phe Ser Ser Pro Asp Leu Val
    1175                1180                1185
Asn Lys Tyr Ala Ile Val Glu Arg Leu Asn Phe Ala Tyr Tyr Leu
    1190                1195                1200
His Asn Gly Arg Pro Ser Phe Ala Phe Gly Thr Phe Leu Val Gln
    1205                1210                1215
Glu Leu Ile Lys Ser Lys Thr Pro Lys Gln Leu Ile Gln Gln Val
    1220                1225                1230
Gly Asn Glu Ala Tyr Val Ile Gly Leu Ser Ser Phe His Ile Pro
    1235                1240                1245
Ser Ile Gly Ala Ala Cys Val Cys Phe Leu Glu Leu Leu Gly Leu
    1250                1255                1260
Asp Ser Leu Lys Leu Arg Val Asp Met Lys Val Ala Asn Ile Ile
    1265                1270                1275
Leu Ser Tyr Lys Cys Arg Asn Glu Asp Ala Gln Tyr Ser Phe Ile
    1280                1285                1290
Arg Glu Ser Val Ala Glu Lys Leu Ser Lys Leu Ala Asp Gly Glu
    1295                1300                1305
Lys Thr Thr Thr Glu Glu Leu Leu Val Leu Leu Glu Glu Gly Thr
    1310                1315                1320
Trp Asn Ser Ile Gln Gln Gln Glu Ile Lys Arg Leu Ser Ser Glu
    1325                1330                1335
Ser Ser Ser Gln Trp Ala Leu Val Val Gln Phe Cys Arg Leu His
    1340                1345                1350
```

```
Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425

Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740
```

```
Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
    1820                1825                1830

Phe Asp Ser Leu Ala Ser Glu Phe Ser Phe Ser Lys Leu Ala Ala
    1835                1840                1845

Leu Asn Thr Ser Lys Tyr Leu Glu Leu Asn Ser Leu Pro Ser Lys
    1850                1855                1860

Glu Thr Cys Glu Asn Arg Leu Asp Trp Lys Glu Gln Glu Ser Leu
    1865                1870                1875

Asn Phe Leu Ile Gly Arg Leu Leu Asp Asp Gly Cys Val His Glu
    1880                1885                1890

Ala Ser Arg Val Cys Arg Tyr Phe His Phe Tyr Asn Pro Asp Val
    1895                1900                1905

Ala Leu Val Leu His Cys Arg Ala Leu Ala Ser Gly Glu Ala Ser
    1910                1915                1920

Met Glu Asp Leu His Pro Glu Ile His Ala Leu Leu Gln Ser Ala
    1925                1930                1935

Glu Leu Leu Glu Glu Glu Ala Pro Asp Ile Pro Leu Arg Arg Val
    1940                1945                1950

His Ser Thr Ser Ser Leu Asp Ser Gln Lys Phe Val Thr Val Pro
    1955                1960                1965

Ser Ser Asn Glu Val Val Thr Asn Leu Glu Val Leu Thr Ser Lys
    1970                1975                1980

Cys Leu His Gly Lys Asn Tyr Cys Arg Gln Val Leu Cys Leu Tyr
    1985                1990                1995

Asp Leu Ala Lys Glu Leu Gly Cys Ser Tyr Thr Asp Val Ala Ala
    2000                2005                2010

Gln Asp Gly Glu Ala Met Leu Arg Lys Ile Leu Ala Ser Gln Gln
    2015                2020                2025

Pro Asp
    2030

<210> SEQ ID NO 186
<211> LENGTH: 2259
<212> TYPE: PRT
<213> ORGANISM: Homo sapiens

<400> SEQUENCE: 186

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Ala Gly Ser Leu Gln
        50                  55                  60
```

-continued

```
Val Leu Ser Leu Thr Pro Gly Ser Arg Gly Gly Arg Cys Cys Leu
 65              70                  75                  80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
            130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190

Leu Pro Leu Pro Ala Gln Ala Val Asp Met Ile Ile Asp Thr Gln Leu
    195                 200                 205

Cys Arg Gly Ile Leu Phe Val Leu Ser Ser Leu Gly Trp Ile Tyr Ile
210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Pro Ala Lys Ile
                245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
            275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
            325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
            405                 410                 415

His Ile Ser Glu Gln Glu Pro Ile Glu Leu Lys Cys Val Ser Val
            420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480
```

```
Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
        530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
                580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
        610                 615                 620

Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                725                 730                 735

Asn Ile Lys Glu Ala Ser Glu Leu Leu Lys Asn Met Gly Phe Asp Val
            740                 745                 750

Lys Gly Gln Leu Leu Lys Ile Cys Phe Tyr Thr Thr Asn Lys Asn Ile
        755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                805                 810                 815

Trp Ile Lys Glu Gln Asp Phe Phe Lys His Lys Ser Val Leu Asp Ser
                820                 825                 830

Phe Leu Lys Tyr Asp Cys Lys Asp Glu Phe Asn Lys Gln Asp His Arg
        835                 840                 845

Ile Val Leu Asn Trp Ala Leu Trp Trp Asp Gln Leu Thr Gln Glu Ser
850                 855                 860

Ile Leu Leu Pro Arg Ile Ser Pro Glu Tyr Lys Ser Tyr Ser Pro
865                 870                 875                 880

Glu Ala Leu Trp Arg Tyr Leu Thr Ala Arg His Asp Trp Leu Asn Ile
                885                 890                 895

Ile Leu Trp Ile Gly Glu Phe Gln Thr Gln His Ser Tyr Ala Ser Leu
```

```
                900             905             910
Gln Gln Asn Lys Trp Pro Leu Leu Thr Val Asp Val Ile Asn Gln Asn
            915             920             925
Thr Ser Cys Asn Asn Tyr Met Arg Asn Glu Ile Leu Asp Lys Leu Ala
        930             935             940
Arg Asn Gly Val Phe Leu Ala Ser Glu Leu Glu Asp Phe Glu Cys Phe
945             950             955             960
Leu Leu Arg Leu Ser Arg Ile Gly Gly Val Ile Gln Asp Thr Leu Pro
                965             970             975
Val Gln Asn Tyr Lys Thr Lys Glu Gly Trp Asp Phe His Ser Gln Phe
            980             985             990
Ile Leu Tyr Cys Leu Glu His Ser Leu Gln His Leu Leu Tyr Val Tyr
        995             1000            1005
Leu Asp Cys Tyr Lys Leu Ser Pro Glu Asn Cys Pro Phe Leu Glu
    1010            1015            1020
Lys Lys Glu Leu His Glu Ala His Pro Trp Phe Glu Phe Leu Val
    1025            1030            1035
Gln Cys Arg Gln Val Ala Ser Asn Leu Thr Asp Pro Lys Leu Ile
    1040            1045            1050
Phe Gln Ala Ser Leu Ala Asn Ala Gln Ile Leu Ile Pro Thr Asn
    1055            1060            1065
Gln Ala Ser Val Ser Ser Met Leu Leu Glu Gly His Thr Leu Leu
    1070            1075            1080
Ala Leu Ala Thr Thr Met Tyr Ser Pro Gly Gly Val Ser Gln Val
    1085            1090            1095
Val Gln Asn Glu Glu Asn Glu Asn Cys Leu Lys Lys Val Asp Pro
    1100            1105            1110
Gln Leu Leu Lys Met Ala Leu Thr Pro Tyr Pro Lys Leu Lys Thr
    1115            1120            1125
Ala Leu Phe Pro Gln Cys Thr Pro Pro Ser Val Leu Pro Ser Asp
    1130            1135            1140
Ile Thr Ile Tyr His Leu Ile Gln Ser Leu Ser Pro Phe Asp Pro
    1145            1150            1155
Ser Arg Leu Phe Gly Trp Gln Ser Ala Asn Thr Leu Ala Ile Gly
    1160            1165            1170
Asp Ala Trp Ser His Leu Pro His Phe Ser Pro Asp Leu Val
    1175            1180            1185
Asn Lys Tyr Ala Ile Val Glu Arg Leu Asn Phe Ala Tyr Tyr Leu
    1190            1195            1200
His Asn Gly Arg Pro Ser Phe Ala Phe Gly Thr Phe Leu Val Gln
    1205            1210            1215
Glu Leu Ile Lys Ser Lys Thr Pro Lys Gln Leu Ile Gln Gln Val
    1220            1225            1230
Gly Asn Glu Ala Tyr Val Ile Gly Leu Ser Ser Phe His Ile Pro
    1235            1240            1245
Ser Ile Gly Ala Ala Cys Val Cys Phe Leu Glu Leu Leu Gly Leu
    1250            1255            1260
Asp Ser Leu Lys Leu Arg Val Asp Met Lys Val Ala Asn Ile Ile
    1265            1270            1275
Leu Ser Tyr Lys Cys Arg Asn Glu Asp Ala Gln Tyr Ser Phe Ile
    1280            1285            1290
Arg Glu Ser Val Ala Glu Lys Leu Ser Lys Leu Ala Asp Gly Glu
    1295            1300            1305
```

-continued

| | | | | | | | | | | | |
|---|---|---|---|---|---|---|---|---|---|---|---|
| Lys | Thr | Thr | Thr | Glu | Glu | Leu | Leu | Val | Leu | Leu | Glu |
| 1310 | | | | | 1315 | | | | 1320 | | |
| Glu | Gly | Thr | | | | | | | | | |
| Trp | Asn | Ser | Ile | Gln | Gln | Gln | Glu | Ile | Lys | Arg | Leu |
| 1325 | | | | | 1330 | | | | 1335 | | |
| Ser | Ser | Glu | | | | | | | | | |
| Ser | Ser | Ser | Gln | Trp | Ala | Leu | Val | Val | Gln | Phe | Cys |
| 1340 | | | | | 1345 | | | | 1350 | | |
| Arg | Leu | His | | | | | | | | | |
| Asn | Met | Lys | Leu | Ser | Ile | Ser | Tyr | Leu | Arg | Glu | Cys |
| 1355 | | | | | 1360 | | | | 1365 | | |
| Ala | Lys | Ala | | | | | | | | | |
| Asn | Asp | Trp | Leu | Gln | Phe | Ile | Ile | His | Ser | Gln | Leu |
| 1370 | | | | | 1375 | | | | 1380 | | |
| His | Asn | Tyr | | | | | | | | | |
| His | Pro | Ala | Glu | Val | Lys | Ser | Leu | Ile | Gln | Tyr | Phe |
| 1385 | | | | | 1390 | | | | 1395 | | |
| Ser | Pro | Val | | | | | | | | | |
| Ile | Gln | Asp | His | Leu | Arg | Leu | Ala | Phe | Glu | Asn | Leu |
| 1400 | | | | | 1405 | | | | 1410 | | |
| Pro | Ser | Val | | | | | | | | | |
| Pro | Thr | Ser | Lys | Met | Asp | Ser | Asp | Gln | Val | Cys | Asn |
| 1415 | | | | | 1420 | | | | 1425 | | |
| Lys | Cys | Pro | | | | | | | | | |
| Gln | Glu | Leu | Gln | Gly | Ser | Lys | Gln | Glu | Met | Thr | Asp |
| 1430 | | | | | 1435 | | | | 1440 | | |
| Leu | Phe | Glu | | | | | | | | | |
| Ile | Leu | Leu | Gln | Cys | Ser | Glu | Glu | Pro | Asp | Ser | Trp |
| 1445 | | | | | 1450 | | | | 1455 | | |
| His | Trp | Leu | | | | | | | | | |
| Leu | Val | Glu | Ala | Val | Lys | Gln | Ala | Pro | Ile | Leu | Ser |
| 1460 | | | | | 1465 | | | | 1470 | | |
| Val | Leu | | | | | | | | | | |
| Ala | Ser | Cys | Leu | Gln | Gly | Ala | Ser | Ala | Ile | Ser | Cys |
| 1475 | | | | | 1480 | | | | 1485 | | |
| Leu | Cys | Val | | | | | | | | | |
| Trp | Ile | Ile | Thr | Ser | Val | Glu | Asp | Asn | Val | Ala | Thr |
| 1490 | | | | | 1495 | | | | 1500 | | |
| Glu | Ala | Met | | | | | | | | | |
| Gly | His | Ile | Gln | Asp | Ser | Thr | Glu | Asp | His | Thr | Trp |
| 1505 | | | | | 1510 | | | | 1515 | | |
| Asn | Leu | Glu | | | | | | | | | |
| Asp | Leu | Ser | Val | Ile | Trp | Arg | Thr | Leu | Leu | Thr | Arg |
| 1520 | | | | | 1525 | | | | 1530 | | |
| Gln | Lys | Ser | | | | | | | | | |
| Lys | Thr | Leu | Ile | Arg | Gly | Phe | Gln | Leu | Phe | Phe | Lys |
| 1535 | | | | | 1540 | | | | 1545 | | |
| Asp | Ser | Pro | | | | | | | | | |
| Leu | Leu | Leu | Val | Met | Glu | Met | Tyr | Glu | Leu | Cys | Met |
| 1550 | | | | | 1555 | | | | 1560 | | |
| Phe | Phe | Arg | | | | | | | | | |
| Asn | Tyr | Lys | Glu | Ala | Glu | Ala | Lys | Leu | Leu | Glu | Phe |
| 1565 | | | | | 1570 | | | | 1575 | | |
| Gln | Lys | Ser | | | | | | | | | |
| Leu | Glu | Thr | Leu | Asn | Thr | Ala | Ala | Thr | Lys | Val | His |
| 1580 | | | | | 1585 | | | | 1590 | | |
| Pro | Val | Ile | | | | | | | | | |
| Pro | Ala | Met | Trp | Leu | Glu | Asp | Gln | Val | Cys | Phe | Leu |
| 1595 | | | | | 1600 | | | | 1605 | | |
| Leu | Lys | Leu | | | | | | | | | |
| Met | Leu | Gln | Gln | Cys | Lys | Thr | Gln | Tyr | Glu | Leu | Gly |
| 1610 | | | | | 1615 | | | | 1620 | | |
| Lys | Leu | Leu | | | | | | | | | |
| Gln | Leu | Phe | Val | Glu | Arg | Glu | His | Leu | Phe | Ser | Asp |
| 1625 | | | | | 1630 | | | | 1635 | | |
| Gly | Pro | Asp | | | | | | | | | |
| Val | Lys | Lys | Leu | Cys | Ile | Leu | Cys | Gln | Ile | Leu | Lys |
| 1640 | | | | | 1645 | | | | 1650 | | |
| Asp | Thr | Ser | | | | | | | | | |
| Ile | Ala | Ile | Asn | His | Thr | Ile | Ile | Thr | Ser | Tyr | Ser |
| 1655 | | | | | 1660 | | | | 1665 | | |
| Ile | Glu | Asn | | | | | | | | | |
| Leu | Gln | His | Glu | Cys | Arg | Ser | Ile | Leu | Glu | Arg | Leu |
| 1670 | | | | | 1675 | | | | 1680 | | |
| Gln | Thr | Asp | | | | | | | | | |
| Gly | Gln | Phe | Ala | Leu | Ala | Arg | Arg | Val | Ala | Glu | Leu |
| 1685 | | | | | 1690 | | | | 1695 | | |
| Ala | Glu | Leu | | | | | | | | | |

-continued

Pro Val Asp Asn Leu Val Ile Lys Glu Ile Thr Gln Glu Met Gln
1700                    1705                1710

Thr Leu Lys His Ile Glu Gln Trp Ser Leu Lys Gln Ala Arg Ile
1715                    1720                1725

Asp Phe Trp Lys Lys Cys His Glu Asn Phe Lys Lys Asn Ser Ile
1730                    1735                1740

Ser Ser Lys Ala Ala Ser Ser Phe Phe Ser Thr Gln Ala His Val
1745                    1750                1755

Ala Cys Glu His Pro Thr Gly Trp Ser Ser Met Glu Glu Arg His
1760                    1765                1770

Leu Leu Leu Thr Leu Ala Gly His Trp Leu Ala Gln Glu Asp Val
1775                    1780                1785

Val Pro Leu Asp Lys Leu Glu Glu Leu Glu Lys Gln Ile Trp Leu
1790                    1795                1800

Cys Arg Ile Thr Gln His Thr Leu Gly Arg Asn Gln Glu Glu Thr
1805                    1810                1815

Glu Pro Arg Phe Ser Arg Gln Ile Ser Thr Ser Gly Glu Leu Ser
1820                    1825                1830

Phe Asp Ser Leu Ala Ser Glu Phe Ser Phe Ser Lys Leu Ala Ala
1835                    1840                1845

Leu Asn Thr Ser Lys Tyr Leu Glu Leu Asn Ser Leu Pro Ser Lys
1850                    1855                1860

Glu Thr Cys Glu Asn Arg Leu Asp Trp Lys Glu Gln Glu Ser Leu
1865                    1870                1875

Asn Phe Leu Ile Gly Arg Leu Leu Asp Asp Gly Cys Val His Glu
1880                    1885                1890

Ala Ser Arg Val Cys Arg Tyr Phe His Phe Tyr Asn Pro Asp Val
1895                    1900                1905

Ala Leu Val Leu His Cys Arg Ala Leu Ala Ser Gly Glu Ala Ser
1910                    1915                1920

Met Glu Asp Leu His Pro Glu Ile His Ala Leu Leu Gln Ser Ala
1925                    1930                1935

Glu Leu Leu Glu Glu Glu Ala Pro Asp Ile Pro Leu Arg Arg Val
1940                    1945                1950

His Ser Thr Ser Ser Leu Asp Ser Gln Lys Phe Val Thr Val Pro
1955                    1960                1965

Ser Ser Asn Glu Val Val Thr Asn Leu Glu Val Leu Thr Ser Lys
1970                    1975                1980

Cys Leu His Gly Lys Asn Tyr Cys Arg Gln Val Leu Cys Leu Tyr
1985                    1990                1995

Asp Leu Ala Lys Glu Leu Gly Cys Ser Tyr Thr Asp Val Ala Ala
2000                    2005                2010

Gln Asp Gly Glu Ala Met Leu Arg Lys Ile Leu Ala Ser Gln Gln
2015                    2020                2025

Pro Asp Arg Cys Lys Arg Ala Gln Ala Phe Ile Ser Thr Gln Gly
2030                    2035                2040

Leu Lys Pro Asp Thr Val Ala Glu Leu Val Ala Glu Glu Val Thr
2045                    2050                2055

Arg Glu Leu Leu Thr Ser Ser Gln Gly Thr Gly His Lys Gln Met
2060                    2065                2070

Phe Asn Pro Thr Glu Glu Ser Gln Thr Phe Leu Gln Leu Thr Thr
2075                    2080                2085

Leu Cys Gln Asp Arg Thr Leu Val Gly Met Lys Leu Leu Asp Lys

```
                   2090                2095                2100
Ile Ser Ser Val Pro His Gly Glu Leu Ser Cys Thr Thr Glu Leu
    2105                2110                2115

Leu Ile Leu Ala His His Cys Phe Thr Leu Thr Cys His Met Glu
    2120                2125                2130

Gly Ile Ile Arg Val Leu Gln Ala Ala His Met Leu Thr Asp Asn
    2135                2140                2145

His Leu Ala Pro Ser Glu Glu Tyr Gly Leu Val Val Arg Leu Leu
    2150                2155                2160

Thr Gly Ile Gly Arg Tyr Asn Glu Met Thr Tyr Ile Phe Asp Leu
    2165                2170                2175

Leu His Lys Lys His Tyr Phe Glu Val Leu Met Arg Lys Lys Leu
    2180                2185                2190

Asp Pro Ser Gly Thr Leu Lys Thr Ala Leu Leu Asp Tyr Ile Lys
    2195                2200                2205

Arg Cys Arg Pro Gly Asp Ser Glu Lys His Asn Met Ile Ala Leu
    2210                2215                2220

Cys Phe Ser Met Cys Arg Glu Ile Gly Glu Asn His Glu Ala Ala
    2225                2230                2235

Ala Arg Ile Gln Leu Lys Leu Ile Leu Ser Pro Gly Arg Thr Ala
    2240                2245                2250

Ser Arg Met Gly Thr Ser
    2255

<210> SEQ ID NO 187
<211> LENGTH: 2285
<212> TYPE: PRT
<213> ORGANISM: Homo sapiens

<400> SEQUENCE: 187

Met Ala Ala Glu Glu Gly Val Ala Ser Ala Ala Ser Ala Gly Gly Ser
 1                5                  10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
            35                  40                  45

Thr Gln Pro Glu Ala Leu Gly Ser Leu Thr Ala Gly Ser Leu Gln
    50                  55                  60

Val Leu Ser Leu Thr Pro Gly Ser Arg Gly Gly Arg Cys Cys Leu
 65                 70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Leu Asn Tyr Glu
            100                 105                 110

Leu Leu Ile Tyr Glu Phe Asn Leu Lys Asp Gly Arg Cys Asp Ala Thr
        115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
            180                 185                 190
```

```
Leu Pro Leu Pro Ala Gln Ala Val Asp Met Ile Ile Asp Thr Gln Leu
        195                 200                 205

Cys Arg Gly Ile Leu Phe Val Leu Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Glu Pro Ala Lys Ile
                245                 250                 255

Ser Ser Phe Thr Ser Leu Lys Val Ser Gln Asp Leu Asp Val Ala Val
            260                 265                 270

Ile Val Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
    290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
            340                 345                 350

Lys Leu Glu Val Ser Cys Cys Ala Pro Trp Phe Gln Asp Ile Leu His
        355                 360                 365

Leu Glu Ser Pro Glu Ser Gly Asn His Ser Thr Ser Val Gln Ser Trp
    370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
            420                 425                 430

Thr Gly Phe Thr Ala Leu Phe Thr Trp Glu Val Glu Arg Met Gly Tyr
        435                 440                 445

Thr Ile Thr Leu Trp Asp Leu Glu Thr Gln Gly Met Gln Cys Ser Ser
    450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                485                 490                 495

Thr Gln Glu Glu Phe Leu Asn Arg Leu Met Ile His Gly Ser Ala Ser
            500                 505                 510

Thr Val Asp Thr Leu Cys His Leu Asn Gly Trp Gly Arg Cys Ser Ile
        515                 520                 525

Pro Ile His Ala Leu Glu Ala Gly Ile Glu Asn Arg Gln Leu Asp Thr
    530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                565                 570                 575

Leu Arg Asn Val Glu Glu Leu Ile Pro Ala Leu Asp Leu Leu Cys Ser
            580                 585                 590

Ala Ile Arg Glu Ser Tyr Ser Glu Pro Gln Ser Lys His Phe Ser Glu
        595                 600                 605

Gln Leu Leu Asn Leu Thr Leu Ser Phe Leu Asn Asn Gln Ile Lys Glu
```

-continued

```
              610                 615                 620
Leu Phe Ile His Thr Glu Glu Leu Asp Glu His Leu Gln Lys Gly Val
625                 630                 635                 640

Asn Ile Leu Thr Ser Tyr Ile Asn Glu Leu Arg Thr Phe Met Ile Lys
                    645                 650                 655

Phe Pro Trp Lys Leu Thr Asp Ala Ile Asp Glu Tyr Asp Val His Glu
                660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
        690                 695                 700

Gln Thr Phe Phe Arg Ile Asp Ser His Ser Ala Gln Lys Leu Glu Glu
705                 710                 715                 720

Leu Ile Gly Ile Gly Leu Asn Leu Val Phe Asp Asn Leu Lys Lys Asn
                    725                 730                 735

Asn Ile Lys Glu Ala Ser Glu Leu Leu Lys Asn Met Gly Phe Asp Val
                740                 745                 750

Lys Gly Gln Leu Leu Lys Ile Cys Phe Tyr Thr Thr Asn Lys Asn Ile
            755                 760                 765

Arg Asp Phe Leu Val Glu Ile Leu Lys Glu Lys Asn Tyr Phe Ser Glu
770                 775                 780

Lys Glu Lys Arg Thr Ile Asp Phe Val His Gln Val Glu Lys Leu Tyr
785                 790                 795                 800

Leu Gly His Phe Gln Glu Asn Met Gln Ile Gln Ser Phe Pro Arg Tyr
                    805                 810                 815

Trp Ile Lys Glu Gln Asp Phe Phe Lys His Lys Ser Val Leu Asp Ser
                820                 825                 830

Phe Leu Lys Tyr Asp Cys Lys Asp Glu Phe Asn Lys Gln Asp His Arg
            835                 840                 845

Ile Val Leu Asn Trp Ala Leu Trp Trp Asp Gln Leu Thr Gln Glu Ser
        850                 855                 860

Ile Leu Leu Pro Arg Ile Ser Pro Glu Glu Tyr Lys Ser Tyr Ser Pro
865                 870                 875                 880

Glu Ala Leu Trp Arg Tyr Leu Thr Ala Arg His Asp Trp Leu Asn Ile
                    885                 890                 895

Ile Leu Trp Ile Gly Glu Phe Gln Thr Gln His Ser Tyr Ala Ser Leu
                900                 905                 910

Gln Gln Asn Lys Trp Pro Leu Leu Thr Val Asp Val Ile Asn Gln Asn
            915                 920                 925

Thr Ser Cys Asn Asn Tyr Met Arg Asn Glu Ile Leu Asp Lys Leu Ala
        930                 935                 940

Arg Asn Gly Val Phe Leu Ala Ser Glu Leu Asp Phe Glu Cys Phe
945                 950                 955                 960

Leu Leu Arg Leu Ser Arg Ile Gly Gly Val Ile Gln Asp Thr Leu Pro
                    965                 970                 975

Val Gln Asn Tyr Lys Thr Lys Glu Gly Trp Asp Phe His Ser Gln Phe
                980                 985                 990

Ile Leu Tyr Cys Leu Glu His Ser  Leu Gln His Leu Leu  Tyr Val Tyr
            995                 1000                1005

Leu Asp  Cys Tyr Lys Leu Ser  Pro Glu Asn Cys Pro  Phe Leu Glu
    1010                1015                1020

Lys Lys  Glu Leu His Glu Ala  His Pro Trp Phe Glu  Phe Leu Val
    1025                1030                1035
```

-continued

```
Gln Cys Arg Gln Val Ala Ser Asn Leu Thr Asp Pro Lys Leu Ile
    1040                1045                1050

Phe Gln Ala Ser Leu Ala Asn Ala Gln Ile Leu Ile Pro Thr Asn
    1055                1060                1065

Gln Ala Ser Val Ser Ser Met Leu Leu Glu Gly His Thr Leu Leu
    1070                1075                1080

Ala Leu Ala Thr Thr Met Tyr Ser Pro Gly Gly Val Ser Gln Val
    1085                1090                1095

Val Gln Asn Glu Glu Asn Glu Asn Cys Leu Lys Lys Val Asp Pro
    1100                1105                1110

Gln Leu Leu Lys Met Ala Leu Thr Pro Tyr Pro Lys Leu Lys Thr
    1115                1120                1125

Ala Leu Phe Pro Gln Cys Thr Pro Pro Ser Val Leu Pro Ser Asp
    1130                1135                1140

Ile Thr Ile Tyr His Leu Ile Gln Ser Leu Ser Pro Phe Asp Pro
    1145                1150                1155

Ser Arg Leu Phe Gly Trp Gln Ser Ala Asn Thr Leu Ala Ile Gly
    1160                1165                1170

Asp Ala Trp Ser His Leu Pro His Phe Ser Ser Pro Asp Leu Val
    1175                1180                1185

Asn Lys Tyr Ala Ile Val Glu Arg Leu Asn Phe Ala Tyr Tyr Leu
    1190                1195                1200

His Asn Gly Arg Pro Ser Phe Ala Phe Gly Thr Phe Leu Val Gln
    1205                1210                1215

Glu Leu Ile Lys Ser Lys Thr Pro Lys Gln Leu Ile Gln Gln Val
    1220                1225                1230

Gly Asn Glu Ala Tyr Val Ile Gly Leu Ser Ser Phe His Ile Pro
    1235                1240                1245

Ser Ile Gly Ala Ala Cys Val Cys Phe Leu Glu Leu Leu Gly Leu
    1250                1255                1260

Asp Ser Leu Lys Leu Arg Val Asp Met Lys Val Ala Asn Ile Ile
    1265                1270                1275

Leu Ser Tyr Lys Cys Arg Asn Glu Asp Ala Gln Tyr Ser Phe Ile
    1280                1285                1290

Arg Glu Ser Val Ala Glu Lys Leu Ser Lys Leu Ala Asp Gly Glu
    1295                1300                1305

Lys Thr Thr Thr Glu Glu Leu Leu Val Leu Leu Glu Glu Gly Thr
    1310                1315                1320

Trp Asn Ser Ile Gln Gln Gln Glu Ile Lys Arg Leu Ser Ser Glu
    1325                1330                1335

Ser Ser Ser Gln Trp Ala Leu Val Val Gln Phe Cys Arg Leu His
    1340                1345                1350

Asn Met Lys Leu Ser Ile Ser Tyr Leu Arg Glu Cys Ala Lys Ala
    1355                1360                1365

Asn Asp Trp Leu Gln Phe Ile Ile His Ser Gln Leu His Asn Tyr
    1370                1375                1380

His Pro Ala Glu Val Lys Ser Leu Ile Gln Tyr Phe Ser Pro Val
    1385                1390                1395

Ile Gln Asp His Leu Arg Leu Ala Phe Glu Asn Leu Pro Ser Val
    1400                1405                1410

Pro Thr Ser Lys Met Asp Ser Asp Gln Val Cys Asn Lys Cys Pro
    1415                1420                1425
```

```
Gln Glu Leu Gln Gly Ser Lys Gln Glu Met Thr Asp Leu Phe Glu
    1430                1435                1440

Ile Leu Leu Gln Cys Ser Glu Glu Pro Asp Ser Trp His Trp Leu
    1445                1450                1455

Leu Val Glu Ala Val Lys Gln Gln Ala Pro Ile Leu Ser Val Leu
    1460                1465                1470

Ala Ser Cys Leu Gln Gly Ala Ser Ala Ile Ser Cys Leu Cys Val
    1475                1480                1485

Trp Ile Ile Thr Ser Val Glu Asp Asn Val Ala Thr Glu Ala Met
    1490                1495                1500

Gly His Ile Gln Asp Ser Thr Glu Asp His Thr Trp Asn Leu Glu
    1505                1510                1515

Asp Leu Ser Val Ile Trp Arg Thr Leu Leu Thr Arg Gln Lys Ser
    1520                1525                1530

Lys Thr Leu Ile Arg Gly Phe Gln Leu Phe Phe Lys Asp Ser Pro
    1535                1540                1545

Leu Leu Leu Val Met Glu Met Tyr Glu Leu Cys Met Phe Phe Arg
    1550                1555                1560

Asn Tyr Lys Glu Ala Glu Ala Lys Leu Leu Glu Phe Gln Lys Ser
    1565                1570                1575

Leu Glu Thr Leu Asn Thr Ala Ala Thr Lys Val His Pro Val Ile
    1580                1585                1590

Pro Ala Met Trp Leu Glu Asp Gln Val Cys Phe Leu Leu Lys Leu
    1595                1600                1605

Met Leu Gln Gln Cys Lys Thr Gln Tyr Glu Leu Gly Lys Leu Leu
    1610                1615                1620

Gln Leu Phe Val Glu Arg Glu His Leu Phe Ser Asp Gly Pro Asp
    1625                1630                1635

Val Lys Lys Leu Cys Ile Leu Cys Gln Ile Leu Lys Asp Thr Ser
    1640                1645                1650

Ile Ala Ile Asn His Thr Ile Ile Thr Ser Tyr Ser Ile Glu Asn
    1655                1660                1665

Leu Gln His Glu Cys Arg Ser Ile Leu Glu Arg Leu Gln Thr Asp
    1670                1675                1680

Gly Gln Phe Ala Leu Ala Arg Arg Val Ala Glu Leu Ala Glu Leu
    1685                1690                1695

Pro Val Asp Asn Leu Val Ile Lys Glu Ile Thr Gln Glu Met Gln
    1700                1705                1710

Thr Leu Lys His Ile Glu Gln Trp Ser Leu Lys Gln Ala Arg Ile
    1715                1720                1725

Asp Phe Trp Lys Lys Cys His Glu Asn Phe Lys Lys Asn Ser Ile
    1730                1735                1740

Ser Ser Lys Ala Ala Ser Ser Phe Phe Ser Thr Gln Ala His Val
    1745                1750                1755

Ala Cys Glu His Pro Thr Gly Trp Ser Ser Met Glu Glu Arg His
    1760                1765                1770

Leu Leu Leu Thr Leu Ala Gly His Trp Leu Ala Gln Glu Asp Val
    1775                1780                1785

Val Pro Leu Asp Lys Leu Glu Leu Glu Lys Gln Ile Trp Leu
    1790                1795                1800

Cys Arg Ile Thr Gln His Thr Leu Gly Arg Asn Gln Glu Glu Thr
    1805                1810                1815

Glu Pro Arg Phe Ser Arg Gln Ile Ser Thr Ser Gly Glu Leu Ser
```

-continued

```
              1820                1825                1830
Phe Asp Ser Leu Ala Ser Glu Phe Ser Phe Ser Lys Leu Ala Ala
     1835                1840                1845
Leu Asn Thr Ser Lys Tyr Leu Glu Leu Asn Ser Leu Pro Ser Lys
     1850                1855                1860
Glu Thr Cys Glu Asn Arg Leu Asp Trp Lys Glu Gln Glu Ser Leu
     1865                1870                1875
Asn Phe Leu Ile Gly Arg Leu Leu Asp Asp Gly Cys Val His Glu
     1880                1885                1890
Ala Ser Arg Val Cys Arg Tyr Phe His Phe Tyr Asn Pro Asp Val
     1895                1900                1905
Ala Leu Val Leu His Cys Arg Ala Leu Ala Ser Gly Glu Ala Ser
     1910                1915                1920
Met Glu Asp Leu His Pro Glu Ile His Ala Leu Leu Gln Ser Ala
     1925                1930                1935
Glu Leu Leu Glu Glu Glu Ala Pro Asp Ile Pro Leu Arg Arg Val
     1940                1945                1950
His Ser Thr Ser Ser Leu Asp Ser Gln Lys Phe Val Thr Val Pro
     1955                1960                1965
Ser Ser Asn Glu Val Val Thr Asn Leu Glu Val Leu Thr Ser Lys
     1970                1975                1980
Cys Leu His Gly Lys Asn Tyr Cys Arg Gln Val Leu Cys Leu Tyr
     1985                1990                1995
Asp Leu Ala Lys Glu Leu Gly Cys Ser Tyr Thr Asp Val Ala Ala
     2000                2005                2010
Gln Asp Gly Glu Ala Met Leu Arg Lys Ile Leu Ala Ser Gln Gln
     2015                2020                2025
Pro Asp Arg Cys Lys Arg Ala Gln Ala Phe Ile Ser Thr Gln Gly
     2030                2035                2040
Leu Lys Pro Asp Thr Val Ala Glu Leu Val Ala Glu Glu Val Thr
     2045                2050                2055
Arg Glu Leu Leu Thr Ser Ser Gln Gly Thr Gly His Lys Gln Met
     2060                2065                2070
Phe Asn Pro Thr Glu Glu Ser Gln Thr Phe Leu Gln Leu Thr Thr
     2075                2080                2085
Leu Cys Gln Asp Arg Thr Leu Val Gly Met Lys Leu Leu Asp Lys
     2090                2095                2100
Ile Ser Ser Val Pro His Gly Glu Leu Ser Cys Thr Thr Glu Leu
     2105                2110                2115
Leu Ile Leu Ala His His Cys Phe Thr Leu Thr Cys His Met Glu
     2120                2125                2130
Gly Ile Ile Arg Val Leu Gln Ala Ala His Met Leu Thr Asp Asn
     2135                2140                2145
His Leu Ala Pro Ser Glu Glu Tyr Gly Leu Val Val Arg Leu Leu
     2150                2155                2160
Thr Gly Ile Gly Arg Tyr Asn Glu Met Thr Tyr Ile Phe Asp Leu
     2165                2170                2175
Leu His Lys Lys His Tyr Phe Glu Val Leu Met Arg Lys Lys Leu
     2180                2185                2190
Asp Pro Ser Gly Thr Leu Lys Thr Ala Leu Leu Asp Tyr Ile Lys
     2195                2200                2205
Arg Cys Arg Pro Gly Asp Ser Glu Lys His Asn Met Ile Ala Leu
     2210                2215                2220
```

```
Cys Phe Ser Met Cys Arg Glu Ile Gly Glu Asn His Glu Ala Ala
    2225            2230                2235

Ala Arg Ile Gln Leu Lys Leu Ile Glu Ser Gln Pro Trp Glu Asp
    2240            2245                2250

Ser Leu Lys Asp Gly His Gln Leu Lys Gln Leu Leu Lys Ala
    2255            2260                2265

Leu Thr Leu Met Leu Asp Ala Ala Glu Ser Tyr Ala Lys Asp Ser
    2270            2275                2280

Cys Val
    2285

<210> SEQ ID NO 188
<211> LENGTH: 949
<212> TYPE: PRT
<213> ORGANISM: Homo sapiens

<400> SEQUENCE: 188

Met Ala Ala Glu Glu Gly Val Ala Ser Ala Ala Ser Gly Gly Ser
1               5                   10                  15

Trp Gly Thr Ala Ala Met Gly Arg Val Leu Pro Met Leu Leu Val Pro
                20                  25                  30

Val Pro Ala Glu Ala Met Gly Gln Leu Gly Ser Arg Ala Gln Leu Arg
                35                  40                  45

Thr Gln Pro Glu Ala Leu Gly Ser Leu Thr Ala Ala Gly Ser Leu Gln
    50                  55                  60

Val Leu Ser Leu Thr Pro Gly Ser Arg Gly Gly Gly Arg Cys Cys Leu
65                  70                  75                  80

Glu Gly Pro Phe Trp His Phe Leu Trp Glu Asp Ser Arg Asn Ser Ser
                85                  90                  95

Thr Pro Thr Glu Lys Pro Lys Leu Leu Ala Leu Gly Glu Asn Tyr Glu
                100                 105                 110

Leu Leu Ile Tyr Glu Phe Asn Leu Lys Asp Gly Arg Cys Asp Ala Thr
                115                 120                 125

Ile Leu Tyr Ser Cys Ser Arg Glu Ala Leu Gln Lys Leu Ile Asp Asp
    130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ile Arg Val Leu Asn Cys Phe Thr
                180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
    210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
                275                 280                 285

Phe Arg Gln His Pro Gly His Leu Leu Cys Glu Arg Ile Leu Glu Asp
```

```
                   290                 295                 300
Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                    325                 330                 335

Ser Trp Lys Ala Gln Leu Ser Ser Leu Asn Glu Thr Ile Lys Asn Ser
                    340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
            370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                    405                 410                 415

His Ile Ser Glu Gln Glu Glu Pro Ile Glu Leu Lys Cys Val Ser Val
                    420                 425                 430

Thr Gly Phe Thr Ala Leu Phe Thr Trp Glu Val Glu Arg Met Gly Tyr
            435                 440                 445

Thr Ile Thr Leu Trp Asp Leu Glu Thr Gln Gly Met Gln Cys Ser Ser
            450                 455                 460

Leu Gly Thr Lys Cys Ile Pro Val Asp Ser Ser Gly Asp Gln Gln Leu
465                 470                 475                 480

Cys Phe Val Leu Thr Glu Asn Gly Leu Ser Leu Ile Leu Phe Gly Leu
                    485                 490                 495

Thr Gln Glu Glu Phe Leu Asn Arg Leu Met Ile His Gly Ser Ala Ser
                    500                 505                 510

Thr Val Asp Thr Leu Cys His Leu Asn Gly Trp Gly Arg Cys Ser Ile
            515                 520                 525

Pro Ile His Ala Leu Glu Ala Gly Ile Glu Asn Arg Gln Leu Asp Thr
            530                 535                 540

Val Asn Phe Phe Leu Lys Ser Lys Glu Asn Leu Phe Asn Pro Ser Ser
545                 550                 555                 560

Lys Ser Ser Val Ser Asp Gln Phe Asp His Leu Ser Ser His Leu Tyr
                    565                 570                 575

Leu Arg Asn Val Glu Glu Leu Ile Pro Ala Leu Asp Leu Leu Cys Ser
                    580                 585                 590

Ala Ile Arg Glu Ser Tyr Ser Glu Pro Gln Ser Lys His Phe Ser Glu
            595                 600                 605

Gln Leu Leu Asn Leu Thr Leu Ser Phe Leu Asn Asn Gln Ile Lys Glu
            610                 615                 620

Leu Phe Ile His Thr Glu Leu Asp Glu His Leu Gln Lys Gly Val
625                 630                 635                 640

Asn Ile Leu Thr Ser Tyr Ile Asn Glu Leu Arg Thr Phe Met Ile Lys
                    645                 650                 655

Phe Pro Trp Lys Leu Thr Asp Ala Ile Asp Glu Tyr Asp Val His Glu
                    660                 665                 670

Asn Val Pro Lys Val Lys Glu Ser Asn Ile Trp Lys Lys Leu Ser Phe
            675                 680                 685

Glu Glu Val Ile Ala Ser Ala Ile Leu Asn Asn Lys Ile Pro Glu Ala
            690                 695                 700

Gln Thr Phe Phe Arg Ile Asp Ser His Ser Ala Gln Lys Leu Glu Glu
705                 710                 715                 720
```

```
Leu Ile Gly Ile Gly Leu Asn Leu Val Phe Asp Asn Leu Lys Lys Asn
                725                 730                 735
Asn Ile Lys Glu Ala Ser Glu Leu Leu Lys Asn Met Gly Phe Asp Val
            740                 745                 750
Lys Gly Gln Leu Leu Lys Ile Cys Phe Tyr Thr Thr Asn Lys Asn Ile
        755                 760                 765
Arg Asp Phe Leu Val Glu Ile Leu Lys Glu Lys Asn Tyr Phe Ser Glu
    770                 775                 780
Lys Glu Lys Arg Thr Ile Asp Phe Val His Gln Val Glu Lys Leu Tyr
785                 790                 795                 800
Leu Gly His Phe Gln Glu Asn Met Gln Ile Gln Ser Phe Pro Arg Tyr
                805                 810                 815
Trp Ile Lys Glu Gln Asp Phe Phe Lys His Lys Ser Val Leu Asp Ser
            820                 825                 830
Phe Leu Lys Tyr Asp Cys Lys Asp Glu Phe Asn Lys Gln Asp His Arg
        835                 840                 845
Ile Val Leu Asn Trp Ala Leu Trp Trp Asp Gln Leu Thr Gln Glu Ser
    850                 855                 860
Ile Leu Leu Pro Arg Ile Ser Pro Glu Glu Tyr Lys Ser Tyr Ser Pro
865                 870                 875                 880
Glu Ala Leu Trp Arg Tyr Leu Thr Ala Arg His Asp Trp Leu Asn Ile
                885                 890                 895
Ile Leu Trp Ile Gly Glu Phe Gln Thr Gln His Ser Tyr Ala Ser Leu
            900                 905                 910
Gln Gln Asn Lys Trp Pro Leu Leu Thr Val Asp Val Ile Asn Gln Asn
        915                 920                 925
Thr Ser Cys Asn Asn Tyr Met Arg Asn Glu Ile Leu Asp Lys Leu Ala
930                 935                 940
Gly Tyr Tyr Asn Cys
945
```

UNITED STATES PATENT AND TRADEMARK OFFICE
CERTIFICATE OF CORRECTION

| | | |
|---|---|---|
| PATENT NO. | : 9,546,402 B2 | Page 1 of 1 |
| APPLICATION NO. | : 14/206840 | |
| DATED | : January 17, 2017 | |
| INVENTOR(S) | : Azzedine et al. | |

It is certified that error appears in the above-identified patent and that said Letters Patent is hereby corrected as shown below:

On the Title Page

Item (71) delete:
"Institute National de la Sante Et de la Recherche Medicale (INSERM), Paris (FR)"

Insert:
-- Institut National de la Sante et de la Recherche Medicale (INSERM), Paris (FR) --

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*